US008541007B2

(12) United States Patent
Alderson et al.

(10) Patent No.: US 8,541,007 B2
(45) Date of Patent: Sep. 24, 2013

(54) VACCINES AGAINST CHLAMYDIAL INFECTION

(75) Inventors: Mark Alderson, Bainbridge Island, WA (US); Ajay Bhatia, Seattle, WA (US); Yves Lobet, Rixensart (BE); Brenda Maisonneuve, Federal Way, WA (US); Jean-Francois L Maisonneuve, Federal Way, WA (US); Martine Marchand, Rixensart (BE); Pascal Mettens, Rixensart (BE); Florence Bernadette Nozay, Rixensart (BE); Peter Probst, Seattle, WA (US); Yasir A Skeiky, Silver Spring, MD (US); Samira H Skeiky, legal representative, Silver Spring, MD (US)

(73) Assignees: GlaxoSmithKline Biologicals S.A., Rixensart (BE); Corixa Corporation, Wilmington, DE (US)

( * ) Notice: Subject to any disclaimer, the term of this patent is extended or adjusted under 35 U.S.C. 154(b) by 0 days.

(21) Appl. No.: 12/974,428

(22) Filed: Dec. 21, 2010
(Under 37 CFR 1.47)

(65) Prior Publication Data
US 2011/0300206 A1    Dec. 8, 2011

Related U.S. Application Data

(63) Continuation-in-part of application No. 11/909,992, filed as application No. PCT/US2006/010793 on Mar. 24, 2006, now abandoned.

(60) Provisional application No. 60/667,331, filed on Mar. 31, 2005.

(51) Int. Cl.
*A61K 39/118* (2006.01)

(52) U.S. Cl.
USPC ...................................... 424/263.1

(58) Field of Classification Search
None
See application file for complete search history.

(56) References Cited

U.S. PATENT DOCUMENTS

| | | | |
|---|---|---|---|
| 6,166,177 | A | 12/2000 | Probst |
| 6,432,916 | B1 | 8/2002 | Probst |
| 6,447,779 | B1 | 9/2002 | Probst |
| 6,448,234 | B1 | 9/2002 | Fling |
| 6,555,115 | B1 | 4/2003 | Probst |
| 6,565,856 | B1 | 5/2003 | Skeiky |
| 6,919,187 | B2 | 7/2005 | Bhatia |
| 7,384,638 | B2 | 6/2008 | Bhatia |
| 7,462,357 | B2 | 12/2008 | Bhatia |
| 2002/0061848 | A1 | 5/2002 | Bhatia |
| 2002/0146776 | A1 | 10/2002 | Bhatia et al. |
| 2004/0029129 | A1 | 2/2004 | Wang et al. |
| 2005/0065106 | A1 | 3/2005 | Murdin et al. |
| 2005/0106162 | A1 | 5/2005 | Grandi et al. |
| 2005/0239160 | A1 | 10/2005 | Shaw et al. |
| 2008/0305112 | A1 | 12/2008 | Grandi et al. |
| 2009/0098165 | A1 | 4/2009 | Arylanandam et al. |

FOREIGN PATENT DOCUMENTS

| | | |
|---|---|---|
| WO | WO96/31236 | 10/1996 |
| WO | WO96/33739 | 10/1996 |
| WO | WO98/28005 | 7/1998 |
| WO | WO99/27105 | 6/1999 |
| WO | WO99/28475 | 6/1999 |
| WO | WO01/40474 | 6/2001 |
| WO | WO01/46225 | 6/2001 |
| WO | WO02/08267 | 1/2002 |
| WO | WO02/48185 | 6/2002 |
| WO | WO02/062380 | 8/2002 |
| WO | WO02/077183 | 10/2002 |
| WO | WO02/079244 | 10/2002 |
| WO | WO02/082081 | 10/2002 |
| WO | WO03/041560 | 5/2003 |
| WO | WO03/049762 | 6/2003 |
| WO | WO03/068811 | 8/2003 |
| WO | WO2005/002619 | 1/2005 |
| WO | WO2005/0084305 | 9/2005 |
| WO | WO2006/045308 | 5/2006 |
| WO | WO2006/138004 | 12/2006 |
| WO | WO2007/027954 | 3/2007 |
| WO | WO2007/072214 | 6/2007 |
| WO | WO2007/110700 | 10/2007 |
| WO | WO2008/040757 | 4/2008 |
| WO | WO2008/134085 | 11/2008 |
| WO | WO2008/138999 | 11/2008 |

OTHER PUBLICATIONS

Brunham et al., Immunology of Chlamydia infection: Implication for a *Chlamydia trachomatis* Vaccine, Nature Reviews: Immunology, 5(2):149-161 (Feb. 2005).
Lu, Hang et al., GM-CSF Transgene based adjuvant allows the establishment of protective mucosal immunity following vaccination with inactivated *Chlamydia trachomatis*, J. Immunology, 169(11):6324-6331 (Dec. 2002).
Pal et al., Vaccination of newborn mice induces a strong protective immune response against respiratory and genital challenges with *Chlamydia trachomatis*, Vaccine, 23(46-47):5351-5358 (Nov. 2005).
Wyrick et al., Microb. Pathogen., 20:31-40 (1996).
Montigiani, et al., Infection and Immunity, 70(1):368-379 (2002).
Fields, et al., Molecular Microbiology, 38(5):1048-1060 (2000).
Igietseme, et al., Expert Review of Vaccines, 2(1):129-146 (2003).
Eko, et al., Journal of Immunology, 173(5):3375-3382 (2004).
Igietseme, et al., Infection and Immunity, 68(12):6798-6806 (2000).
Sambri, et al., Vaccine, 22(9-10):1131-1137 (2004).

*Primary Examiner* — Brian J Gangle
(74) *Attorney, Agent, or Firm* — Virginia G. Campen

(57) ABSTRACT

The present invention relates to compositions comprising proteins or polynucleotides of *Chlamydia* sp., in particular combinations of proteins or polynucleotides encoding them, and methods for the use of the proteins or polynucleotides in the treatment, prevention and diagnosis of *Chlamydia* infection.

14 Claims, 25 Drawing Sheets

Antigen combinations:

1: Momp, PmpD-pd, CT858, CT089, Swib

2: Momp, PmpD-pd, CT858, CT622, CT089

3: Momp, PmpD-pd, CT858, PmpG-pd, CT622, CT089

4: CT858, CT875, CT622, CT089

5: CT858, CT875, CT089

6: Momp PmpD-pd CT858- PmpG-pd CT089

Antigen combinations:

1: Momp, PmpD-pd, CT858, CT089, Swib

1': PmpD-pd, CT858, CT622, CT089

5: CT858, CT875, CT089

5': PmpD-pd, CT858, CT875, CT089

Antigen combinations:

1: Momp, PmpD-pd, CT858, CT089, Swib

1': PmpD-pd, CT858, CT622, CT089

5: CT858, CT875, CT089

5': PmpD-pd, CT858, CT875, CT089

Antigen combinations:

1: Momp, PmpD-pd, CT858, CT089, Swib

5: CT858, CT875, CT089

Antigen combinations:
1: Momp, PmpD-pd, CT858, CT089, Swib
5: CT858, CT875, CT089

Figure 6

CT089 amino acid sequences

```
                            *         20         *         40         *         60         *         80
CT089_A    : MTASGGAGGLGSTQTVDVARACAAAATCDAQEVIGSQEASEASMLKGCEDLINPAAATRIKKKEEKFFSLEARRKPTADKAEK :  83
CT089_B    : MTASGCAGCLGSTQTVDVARACAAAATCDAQEVICSQEASEASMLKGCEDLINPAAATRIKKKEBKFESLEARRKPTADKAEK :  83
CT089_D    : MTASGGAGGLGSTQTVDVARACAAAATCDAQEVIGSQEASEASMLKGCEDLINPAAATRIKKKGEKFFESLEARRKPTADKAEK :  83
CT089_E    : MTASGGAGGLGSTQTVDVARACAAAATCDAQEVIGSQEASEASMLKGCEDLINPAAATRIKKKEEKFESLEARGIPTADKAEK :  83
CT089_G    : MTASGGAGGLGSTQTVDVARACAAAATCDAQEVIGSQEASEASMLKGCEDLINPAAATRIKKKGEKFESLEARRKPTADKAEK :  83
CT089_H    : MTASGGAGGLGSTQTVDVARACAAAATCDAQEVIGSQEASEACMLKGCEDLINPAAATRIKKKGEKFESLEARRKPTADKAEK :  83
CT089_I    : MTASGCAGCLGSTQTVDVARACAAAATCDAQEVICSQEASEACMLKGCEDLINPAAATRIKKCGEKFESLEARRKPTADKAEK :  83
CT089_J    : MTASGGAGGLGSTQTVDVARACAAAATCDAQEVIGSQEASEASMLKECADLINPAAATRIKKKEEKFESLEARRKPTADKAEK :  83
CT089_K    : MTASGGAGGLGSTQTVDVARACAAAATCDAQEVIGSQEASEASMLKGCEDLINPAAATRIKKKGEKFESLEARRKPTADKAEK :  83
CT089_L2   : MTASGGAGGLGSTQTVDVARACAAAATCDAQEVIGSQEASEASMLKECEDLINPAAATRIKKKEEKFESLEARRKPTADKAEK :  83

*        100         *        120         *        140         *        160
CT089_A    : KSESTEEKGDTPLEDRFTEDLSEVSGEDFRGLKNSFDDDSSPEEILDALTSKFSDPTIKDLALDYLIQTAPSDRKLKSALTQA : 166
CT089_B    : KSESTEEKGDTPLEDRFTEDLSEVSGEDFRGLKNSFDDDSSPEEILDALTSKFSDPTIKDLALDYLIQTAPSDRKLKSALTQA : 166
CT089_D    : KSTSTEEKGDTPLEDRFTEDISEVSGEDFRGIKNSFDDDSPDEILDALTSKFSDPTIKDLALDYLIQTAPSDGKLKSTLTQA : 166
CT089_E    : KSESTEEKGDTPLEDRFTEDLSEVSGEDFRGLKNSFDDDSSPEEILDALTSKFSDPTIKDLALDYLIQTAPSDRKLKSALTQA : 166
CT089_G    : KSESTEEKGDTPLEDRFTEDLSEVSGEDFRGLKNSFDDDSSPDEILDALTSKFSDPTIKDLALDYLIQTAPSDGKLKSTLTQA : 166
CT089_H    : KSESTEEKGDTPLEDRFTEDLSEVSGEDFRGLKNSFDDDSSPDEILDALTSKFSDPTIKDLALDYLIQTAPSDGKLKSALTQA : 166
CT089_I    : KSESTEEKGDTPLEDRFTEDLSEVSGEDFRGLKNSFDDDSSPDEILDALTSKFSDPTIKDLALDYLIQTAPSDGKLKSTLTQA : 166
CT089_J    : KSESTEEKGDTPLEDRFTEDISEVSGEDFRGIKNSFDDDSPDEILDALTSKFSDPTIKDLALDYLIQTAPSDGKLKSTLTQA : 166
CT089_K    : KSESTEEKGDTPLEDRFTEDLSEVSGEDFRGLKNSFDDDSSPDEILDALTSKFSDPTIKDLALDYLIQTAPSDGKLKSTLTQA : 166
CT089_L2   : KSESTEEKGDTPLEDRFTEDLSEVSGEDFRGLKNSFDDDSSSDEILDALTSKFSDPTIKDLALDYLIQTAPSDGKLKSALTQA : 166

*        180         *        200         *        220         *        240
CT089_A    : KHQLMSQNPQATVGGRNVLLASETFASRANTSPSSTRSLYFQVTSSTSNCDNLRQMLASYSPSEKTAVMEFTLVNGMVADLKSE : 249
CT089_B    : KHQLMSQNPQATVGGRNVLLASETFASRANTSPSSLRSLYLQVTSSPSNCDNLRQMLASYSPSEKTAVMEFLVNGMVADLKSE : 249
CT089_D    : KHQLMSQNPQATVGGRNVLLASETFASRANTSPSSTRSLYLQVTSSPSNCANLHQMLASYLPSEKTAVMEFLVNGMVADLKSE : 249
CT089_E    : KHQLMSQNPQATVGGRNVLLASETFASRANTSPSSTRSLYLQVTSSPSNCDNLRQMLASYPSEKTAVMEFLVNGMVADLKSE : 249
CT089_G    : KHQLMSQNPQATVGGRNVLLASETFASRANTSPSSTRSLYFQVTSSPSNCANLIQMLASYLPSEKTAVMEFLVNGMVADLKSE : 249
CT089_H    : KHQLMSQNPQATVGGRNVLLASETFASRANTSPSSTRSLYFQVTSSPSNCANLHQMLASYLPSEKTAVMEFLVNGMVADLKSE : 249
CT089_I    : KHQLMSQNPQATVGGRNVLLASETFASRANTSPSSLRSLYLQVTSSPSNCANLHQMLASYLPSEKTAVMEFLVNGMVADLKSE : 249
CT089_J    : KHQLMSQNPQATVGGRNVLLASETFASRANTSPSSLRSLYFQVTSSPSNCDNLRQMLASYSPSEKTAVMEFLVNGMVADLKSE : 249
CT089_K    : KHQLMSQNPQATVGGRNVLLASETFASRANTSPSSTRSLYFQVTSSPSNCANLHQMLASYLPSEKTAVMEFLVNGMVADLKSE : 249
CT089_L2   : KHQLMSQNPQATVGGRNVLLASETFASRANTSPSSTRSLYFQVTSSPSNCANLIQMLASYSPSEKTAVMEFLVNGMVADLKSE : 249

*        260         *        280         *        300         *        320
CT089_A    : GPSTPPAKLQVYMTELSNLQALHSVDSFFDRNIGNLENSLKHEGEAPIPSLTTGNLKTFLQLVEDKFPSSSKAQKALNELVG : 332
CT089_B    : GPSTPPAKLQVYMTELSNLQALHSVDSFFDRNIGNLENSLKHEGEAPIPSLTTGNLKTFLQLVEDKFPSSSKAQKALNELVG : 332
CT089_D    : GPSTPPAKLQVYMTELSNLQALHSVNSFFDRNIGNLENSLKHEGEAPIPSLTTGNLKTFLQLVEDKFPSSSKAQKALNELVG : 332
CT089_E    : GPSTPPAKLQVYMELSNLQALHSVDSFFDRNIGNLENSLKHEGEAPIPSLTTGNLKTFLQLVEDKFPSSSKAQKALNELVG : 332
CT089_G    : GPSTPPAKLQVYMTELSNLQALHSVNSFFDRNIGNLENSLKHEGEAPIPSLTTGNLKTFLQLVEDKFPSSSKAQKALNELVG : 332
CT089_H    : GPSTPPAKLQVYMTELSNLQALHSVNSFFDRNIGNLENSLKHEGEAPIPSLTTGNLKTFLQLVEDKFPSSSKAQKALNELVG : 332
CT089_I    : GPSTPPAKLQVYMTELSNLQALHSVNSFFDRNIGNLENSLKHEGEAPIPSLTTGNLKTFLQLVEDKFPSSSKAQKALNELVG : 332
CT089_J    : GPSTPPAKLQVYMTELSNLQALHSVDSFFDRNIGNLENSLKHEGEAPIPSLTTGNLKTFLQLVEDKFPSSSKAQKALNELVG : 332
CT089_K    : GPSTPPAKLQVYMTELSNLQALHSVNSFFDRNIGNLENSLKHEGEAPIPSLTTGNLKTFLQLVEDKFPSSSKAQKALNELVG : 332
CT089_L2   : GPSTPPAKLQVYMTELSNLQALHSVDSFFDRNIGNLENSLKHEGEAPIPSLTTGNLKTFLQLVEDKFPSSSKAQKALNELVG : 332

*        340         *        360         *        380         *        400
CT089_A    : PDTGPQTEVLNLFFRALNGCSPRIFSGAEKKQQLASVITNTLDAINADNEDYPKPGDFPRSSFSSTPPHAPVPQSEIPTSPTS : 415
CT089_B    : PDTGPQTEVLNLFFRALNGCSPRIFSGAEKKQQLASVITNTLDAINADNEDYPKPGDFPRSSFSSTPPHAPVPQSEIPTSPTS : 415
CT089_D    : PDTGPQTEVLNLFFRALNGCSPRIFSGAEKKQQLASVITNTLDAINADNEDYPKPGDFPRSSFSSTPPHAPVPQSEIPTSPTS : 415
CT089_E    : PDTGPQTEVLNLFFRALNGCSPRIFSGAEKKQQLASVITNTLDAINADNEDYPKPGDFPRSSFSSTPPIIAPVPQSEIPTSPTS : 415
CT089_G    : PDTGPQTEVLNLFFRALNGCSPRIFSGAEKKQQLASVITNTLDAINADNEDYPKPGDFPRSSFSSTPPHAPVPQSEIPTSPTS : 415
CT089_H    : PDTGPQTEVLNLFFRALNGCSPRIFSGAEKKQQLASVITNTLDAINADNEDYPKPGDFPRSSFSSTPPHAPVPQSEIPTSPTS : 415
CT089_I    : PDTGPQTEVLNLFFRALNGCSPRIFSGAEKKQQLASVITNTLDAINADNEDYPKPGDFPRSSFSSTPPHAPVPQSEIPTSPTS : 415
CT089_J    : PDTGPQTEVLNLFFRALNGCSPRIFSGAEKKQQLASVITNTLDAINADNEDYPKPGDFPRSSFSSTPPHAPVPQSEIPTSPTS : 415
CT089_K    : PDTGPQTEVLNLFFRALNGCSPRIFSGAEKKQQLASVITNTLDAINADNEDYPKPGDFPRSSFSSTPPHAPVPQSEIPTSPTS : 415
CT089_L2   : PDTGPQTEVLNLFFRALNGCSPRIFSGAEKKQQLASVITNTLDAINADNEDYPKPGDFPRSSFSSTPPIIAPVPQSEIPTSPTS : 415

420
CT089_A    : TQPPSP : 421    SEQ ID NO:80
CT089_B    : TQPPSP : 421    SEQ ID NO:82
CT089_D    : TQPPSP : 421    SEQ ID NO:72
CT089_E    : TQPPSP : 421    SEQ ID NO:18
CT089_G    : TQPPSP : 421    SEQ ID NO:84
CT089_H    : TQPPSP : 421    SEQ ID NO:86
CT089_I    : TQPPSP : 421    SEQ ID NO:88
CT089_J    : TQPPSP : 421    SEQ ID NO:90
CT089_K    : TQPPSP : 421    SEQ ID NO:92
CT089_L2   : TQPPSP : 421    SEQ ID NO:94

!:          non-conservative amino acid change
-:          conservative amino acid change
Grey boxes: predicted HLA DRB1 epitope (serovar E)
```

Figure 7a

CT858 amino acid sequences

```
              *        20         *        40         *        60         *        80
CT858_A  : MVQGESLVCKNALQDLSFLEHLLQVKYAPKTWKEQYLGWDLVQSSVSAQQKLRTQENPSTSFCQQVLADFIGGLNDFHAGVTF :  83
CT858_B  : MVQGESLVCKNALQDLSFLEHLLQVKYAPKTWKEQYLGWDLVQSSVSAQQKLRTQENPSTSFCQQVLADFIGGLNDFHAGVTF :  83
CT858_D  : MVQGESLVCKNALQDLSFLEIILLQVKYAPKTWKEQYLGWDLVQSSVSAQQKLRTQENPSTSFCQQVLADFIGGLNDFHAGVTF :  83
CT858_E  : .................DLSFLEHLLQVKYAPKTWKEQY.........QKLRTQENPSTSFCQQ.........NDFHAGVTF :  83
CT858_G  : MVQGESLVCKNALQDLSFLEHLLQVKYAPKTWKEQYLGWDLVQSSVSAQQKLRTQENPSTSFCQQVLADFIGGLNDFHAGVTF :  83
CT858_H  : MVQGESLVCKNALQDLSFLEHLLQVKYAPKTWKEQYLGWDLVQSSVSAQQKLRTQENPSTSFCQQVLADFIGGLNDFHAGVTF :  83
CT858_I  : MVQGESLVCKNALQDLSFLEHLLQVKYAPKTWKEQYLGWDLVQSSVSAQQKLRTQENPSTSFCQQVLADFIGGLNDFHAGVTF :  83
CT858_J  : MVRGESLVCKNALQDLSFLEHLLQVKYAPKTWKEQYLGWDLVQSSVSAQQKLRTQENPSTSFCQQVLADFIGGLNDFHAGVTF :  83
CT858_K  : MVQGESLVCKNALQDLSFLEHLLQVKYAPKTWKEQYLGWDLVQSSVSAQQKLRTQENPSTSFCQQVLADFIGGLNDFHAGVTF :  83
CT858_L2 : MVRGESLVCKNALQDLSFLEHLLQVKYAPKTWKEQYLCWDLVQSSVSAQQKLRTQENPSTSFCQQVLADFIGGLNDFHACVTF :  83

*       100         *       120         *       140         *       160
CT858_A  : FAIESAYLPYIVQKSSDGRFYFVDIMTFSSEIRVGDELLEVDGAPVQDVLATLYGSNHKGTAAEESAALRTLFSRMASLGHKV : 166
CT858_B  : FAIESAYLPYIVQKSSDGRFYFVDIMTFSSEIRVGDELLEVDGAPVQDVLATLYGSNHKGTAAEESAALRTLFSRMASLGHKV : 166
CT858_D  : FAIESAYLPYIVQKSSDGRFYFVDIMTFSSEIRVGDELLEVDGAPVQDVLATLYGSNHKGTAAEESAALRTLFSRMASLGHKV : 166
CT858_E  : .........SDGR.........EIRVGDELLEVDGAPVQDVLATLYGSNHKGTAAEESAA.........LGHKV : 166
CT858_G  : FAIESAYLPYIVQKSSDGRFYFVDIMTFSSEIRVGDELLEVDGAPVQDVLATLYGSNHKGTAAEESAALRTLFSRMASLGHKV : 166
CT858_H  : FAIESAYLPYIVQKSSDGRFYFVDIMTFSSEIRVGDELLEVDGAPVQDVLATLYGSNHKGTAAEESAALRTLFSRMASLGHKV : 166
CT858_I  : FAIESAYLPYIVQKSSDGRFYFVDIMTFSSEIRVGDELLEVDGAPVQDVLATLYGSNHKGTAAEESAALRTLFSRMASLGHKV : 166
CT858_J  : FAIESAYLPYIVQKSSDGRFYFVDIMTFSSEIRVGDELLEVDGAPVQDVLATLYGSNHKGTAAEESAALRTLFSRMASLGHKV : 166
CT858_K  : FAIESAYLPYIVQKSSDGRFYFVDIMTFSSEIRVGDELLEVDGAPVQDVLATLYGSNIIKGTAAEESAALRTLFSRMASLGHKV : 166
CT858_L2 : FAIESAYLPYIVQKSSDGRFYFVDIMTFSSEIRVGDELLEVDGAPVQDVLATLYGSNHKGTAAEESAALRTLFSRMASLGHKV : 166

*       180         *       200         *       220         *       240
CT858_A  : PSGRTTLKIRRPFGTTREVRVKWRYVPEGVGDLATIAPSIRAPQLQKSMRSFFLKKDDAFHRSSSLFYSPMVPHFWAELRNHY : 249
CT858_B  : PSGRTTLKIRRPFGTTREVRVKWRYVPEGVGDLATIAPSIRAPQLQKSMRSFFPKKDDAFHRSSSLFYSPMVPHFWAELRNHY : 249
CT858_D  : PSGRTTLKIRRPFCTTREVRVKWRYVPEGVGDLATIAPSIRAPQLQKSMRSFFPKKDDAFHRSSSLFYSPMVPHFWAELRNHY : 249
CT858_E  : PSGRT.....TRE.........EGVGDLATIAPSIRAPQLQKSMRSFFPKKDDA.........SPMVPHFWAE..... : 249
CT858_G  : PSGRTTLKIRRPFGTTREVRVKWRYVPEGVGDLATIAPSIRAPQLQKSMRSFFPKKDDAFHRSSSLFYSPMVPHFWAELRNHY : 249
CT858_H  : PSGRTTLKIRRPFGTTREVRVKWRYVPEGVGDLATIAPSIRAPQLQKSMRSFFPKKDDAFHRSSSLFYSPMVPHFWAELRNHY : 249
CT858_I  : PSGRTTLKIRRPFGTTREVRVKWRYVPEGVGDLATIAPSIRAPQLQKSMRSFFPKKDDAFHRSSSLFYSPMVPHFWAELRNHY : 249
CT858_J  : PSGRTTLKIRRPFGTTREVRVKWRYVPEGVGDLATIAPSIRAPQLQKSMRSFFPKKDDAFHRSSSLFYSPMVPHFWAELRNHY : 249
CT858_K  : PSGRTTLKIRRPFGTTREVRVKWRYVPEGVGDLATIAPSIRAPQLQKSMRSFFPKKDAFHRSSSLFYSPMVPHFWAELRNHY : 249
CT858_L2 : PSGRTTLKIRRPFGTTREVRVKWRYVPEGVGDLATIAPSIRAPQLQKSMRSFFPKKDDAFHRSSSLFYSPMVPHFWAELRNHY : 249

*       260         *       280         *       300         *       320
CT858_A  : ATSGLKSGYNIGSTDGFLPVIGPVIWESEGLFRAYISSVTDGDGKSHKVGFLRIPTYSWQDMEDFDPSGPPWEEFAKIQVF : 332
CT858_B  : ATSGLKSGYNIGSTDGFLPVIGPVIWESEGLFRAYISSVTDGDGKSHKVGFLRIPTYSWQDMEDFDPSGPPWEEFAKIQVF : 332
CT858_D  : ATSGLKSGYNIGSTDGFLPVIGPVIWESEGLFRAYISSVTDGDGKSHKVGFLRIPTYSWQDMEDFDPSGPPWEEFAKIQVF : 332
CT858_E  : .....LKSGYNIGSTD.....WESEGL.........DGDGKSHKVGFLR..PTYSWQDMEDFDPSGPPWEEFAKIQVF : 332
CT858_G  : ATSGLKSGYNIGSTDGFLPVIGPVIWESEGLFRAYISSVTDGDGKSHKVGFLRIPTYSWQDMEDFDPSGPPWEEFAKIQVF : 332
CT858_H  : ATSGLKSGYNIGSTDGFLPVIGPVIWESEGLFRAYISSVTDGDGKSHKVGFLRIPTYSWQDMEDFDPSGPPWEEFAKIQVF : 332
CT858_I  : ATSGLKSGYNIGSTDGFLPVIGPVIWESEGLFRAYISSVTDGDGKSHKVGFLRIPTYSWQDMEDFDPSGPPWEEFAKIQVF : 332
CT858_J  : ATSGLKSGYNIGSTDGFLPVIGPVIWESEGLFRAYISSVTDGDGKSHKVGFLRIPTYSWQDMEDFDPSGPPWEEFAKIQVF : 332
CT858_K  : ATSGLKSGYNIGSTDGFLPVIGPVIWESEGLFRAYISSVTDGDGKSHKVGFLRIPTYSWQDMEDFDPSGPPWEEFAKIQVF : 332
CT858_L2 : ATSGLKSGYNIGSTDGFLPVIGPVIWESEGLFRAYISSVTDGDGKSHKVGFLRIPTYSWQDMEDFDPSGPPWEEFAKIQVF : 332

*       340         *       360         *       380         *       400
CT858_A  : SSNTEALIIDQTNNPGGSVLYLYALLSMLTDRPLELPKHRMILTQDEVVDALDWLTILENVDTNVESRLALGDNMEGYTVDIQ : 415
CT858_B  : SSNTEALIIDQTNNPGGSVLYLYALLSMLTDRPLELPKHRMILTQDEVVDALDWLTILENVDTNVESRLALGDNMEGYTVDIQ : 415
CT858_D  : SSNTEALIIDQTNNPGGSVLYLYALLSMLTDRPLELPKHRMILTQDEVVDALDWLTILENVDTNVESRLALGDNMEGYTVDIQ : 415
CT858_E  : SSNTEA......GGS.........PKHRMILTQDEVVDALDWLTILENVDTNVESRLALGDNMEGYTVDIQ : 415
CT858_G  : SSNTEALIIDQTNNPGGSVLYLYALLSMLTDRPLELPKHRMILTQDEVVDALDWLTILENVDTNVESRLALGDNMEGYTVDIQ : 415
CT858_H  : SSNTEALIIDQTNNPGGSVLYLYALLSMLTDRPLELPKHRMILTQDEVVDALDWLTILENVDTNVESRLALGDNMEGYTVDIQ : 415
CT858_I  : SSNTEALIIDQTNNPGGSVLYLYALLSMLTDRPLELPKHRMILTQDEVVDALDWLTILENVDTNVESRLALGDNMECYTVDIQ : 415
CT858_J  : SSNTEALIIDQTNNPGGSVLYLYALLSMLTDRPLELPKHRMILTQDEVVDALDWLTILENVDTNVESRLALGDNMEGYTVDIQ : 415
CT858_K  : SSNTEALIIDQTNNPGGSVLYLYALLSMLTDRPLELPKHRMILTQDEVVDALDWLTILENVDTNVESRLALGDNMEGYTVDIQ : 415
CT858_L2 : SSNTEALIIDQTNNPGGSVLYLYALLSMLTDRPLELPKHRMILTQDEVVDALDWLTILENVDTNVESRLALGDNMEGYTVDIQ : 415

420         *       440         *       460         *       480         *     5
CT858_A  : VAEYLKSFGRQVLNCWSKGDIELSTPIPLFGFEKIHPHPRVQYSKPICVLINEQDFSCADFFPVVLKNDRALIVGIRCAGAG : 498
CT858_B  : VAEYLKSFGRQVLNCWSKGDIELSTPIPLFGFEKIHDHPRVQYSKPICVLINEQDFSCADFFPVVLKNDRALIVGIRCAGAG : 498
CT858_D  : VAEYLKSFGRQVLNCWSKGDIELSTPIPLFGFEKIHPHPRVQYSKPICVLINEQDFSCADFFPVVLKNDRALIVGIRCAGAG : 498
CT858_E  : VAEY.........NCWSKG.........FGFEK.........INEQDFSCADFFPVVLKNDRAL.........AG : 498
CT858_G  : VADYLKSFGRQVLNCWSKGDIELSTPIPLFGFEKIHPIIPRVQYSKPICVLINEQDFSCADFFPVVLKNDRALIVGIRCAGAG : 498
CT858_H  : VAEYLKSFGRQVLNCWSKGDIELSTPIPLFGFEKIHPHPRVQYSKPICVLINEQDFSCADFFPVVLKNDRALIVGIRCAGAG : 498
CT858_I  : VAEYLKSFGRQVLNCWSKGDIELSTPIPLFGFEKIHPHPRVQYSKPICVLINEQDFSCADFFPVVLKNDRALIVGIRCAGAG : 498
CT858_J  : VAEYLKSFGRQVLNCWSKGDIELSTPIPLFGFEKIHPHPRVQYSKPICVLINEQDFSCADFFPVVLKNDRALIVGIRCAGAG : 498
CT858_K  : VAEYLKSFGRQVLNCWSKGDIELSTPIPLFGFEKIHPHPRVQYSKPICVLINEQDFSCADFFPVVLKNDRALIVGIRCAGAG : 498
CT858_L2 : VAEYLKSFGRQVLNCWSKGDIELSTPIPLFGFEKIHPHPRVQYSKPICVLINEQDFSCADFFPVVLKNDRALIVGIRCAGAG : 498
```

Figure 7b

```
            500         *        520         *        540         *        560         *        580
CT858_A  : GFVFNVQFPNRTGIKTCSLTGSLAVREEGAFIENIGVEPHIDLPFTANDIRYKGYSEYLDKVKKLVCQLINNDGTIILAEDGS : 581
CT858_B  : GFVFNVQFPNRTGIKTCSLTGSLAVREEGAFIENIGVEPHIDLPFTANDIRYKGYSEYLDKVKKLVCQLINNDGTIILADDGS : 581
CT858_D  : GFVFNVQFPNRTGIKTCSLTGSLAVREEGAFIENIGVEPHIDLPFTANDIRYKGYSEYLDKVKKLVCQLINNDGTIILADDGS : 581
CT858_E  : GFVFNVQFPNRTGIKTCSLTGSLAVREEGAFIENIGVEPHIDLPFTANDIRYKGYSEYLDKVKKLVCQLINNDGTIILAEDGS : 581
CT858_G  : GFVFNVQFPNRTGIKTCSLTGSLAVREEGAFIENIGVEPHIDLPFTANDIRYKGYSEYLDKVKKLVCQLINNDGTIILADDGS : 581
CT858_H  : GFVFNVQFPNRTGIKTCSLTGSLAVREEGAFIENIGVEPHIDLPFTANDIRYKGYSEYLDKVKKLVCQLINNDGTIILADDGS : 581
CT858_I  : GFVFNVQFPNRTGIKTCSLTGSLAVREEGAFIENIGVEPHIDLPFTANDIRYKGYSEYLDKVKKLVCQLINNDGTIILAEDGS : 581
CT858_J  : GFVFNVQFPNRTGIKTCSLTGSLAVREEGAFIENIGVEPHIDLPFTANDIRYKGYSEYLDKVKKLVCQLINNDGTIILAEDGS : 581
CT858_K  : GFVFNVQFPNRTGIKTCSLTGSLAVREEGAFIENIGVEPHIDLPFTANDIRYKGYSEYLDKVKKLVCQLINNDGTIILAEDGS : 581
CT858_L2 : GFVFNVQFPNRTGIKTCSLTGSLAVREEGAFIENIGVEPHIDLPFTANDIRYKGYSEYLDKVKKLVCQLINNDGTIILAEDGS : 581
```

```
CT858_A  : D : 582    SEQ ID NO:96
CT858_B  : F : 582    SEQ ID NO:98
CT858_D  : F : 582    SEQ ID NO:34
CT858_E  : D : 582    SEQ ID NO:6
CT858_G  : D : 582    SEQ ID NO:100
CT858_H  : F : 582    SEQ ID NO:102
CT858_I  : F : 582    SEQ ID NO:104
CT858_J  : F : 582    SEQ ID NO:106
CT858_K  : D : 582    SEQ ID NO:108
CT858_L2 : F : 582    SEQ ID NO:110
```

+: non-conservative amino acid change
−: conservative amino acid change
Grey boxes: predicted HLA DRB1 epitopes (serovar E)

Amino acids with charged polar groups (D,E,K,R,H)
Amino acids with uncharged polar R groups (G,S,T,C,Y,N,Q)
Amino acids nonpolars R groups (A,V,L,I,P,F,W,M)

Figure 8a

CT875 amino acid sequences

Figure 8b

```
              00         *         520        *         540        *         560        *         580
CT875_A   : LPRASDYDLPRSFYFTPPLPPRYQLQNMDVEAGFREAVYASFVAGMYNYVVTQFQERIPNSQCVEGILRDMLTNGSQTFRDLM : 579
CT875_B   : LPRASDYDLPRSFYFTPPLPPRYQLQNMDVEAGFREAVYASFVAGMYNYVVTQFQERIPNSQCVFRILRDMLTNGSQTFRDLM : 579
CT875_D   : LPRASDYDLPRSFYFTPPLPPRYQLQNMDVEAGFREAVYASFVAGMYNYVVTQFQERIPNSQCVEGILRDMLTNGSQTFRDLM : 581
CT875_E   : LPRASDYDLPRSFYFTPPLPPRYQLQNMDVEAGFREAVYASFVAGM          IPNSQCVEG          QTFRDLM : 581
CT875_G   : LPRASDYDLPRSFYFTPPLPPRYQLQNMDVEAGFREAVYASFVAGMYNYVVTQFQERIPNSQCVEGILRDMLTNGSQTFRDLM : 581
CT875_H   : LPRASDYDLPRSFYFTPPLPPRYQLQNMDVEAGFREAVYASFVAGMYNYVVTQFQERIPNSQCVEGILRDMLTNGSQTFRDLM : 581
CT875_I   : LPRASDYDLPRSFYFTPPLPPRYQLQNMDVEAGFREAVYASFVAGMYNYVVTQFQERIPNSQCVFGILRDMLTNGSQTFRDLM : 581
CT875_J   : LPRASDYDLPRSFYFTPPLPSRYQLQNMDVEAGFREAVYASFVAGMYNYVVTQFQERIPNSQCVEGILRDMLTNGSQTFSDLM : 580
CT875_K   : LPRASDYDLPRSFYFTPPLPPRYQLQNMDVEAGFREAVYASFVAGMYNYVVTQFQERIPNSQCVEGILRDMLTNGSQTFRDLM : 581
CT875_L2  : LPRASDYDLPRSFYFTPPLPSRYQLQNMDVEAGFREAVYASFVAGMYNYVVTQFQERIPNSQCVEGILRDMLTNGSQTFSNLM : 580

CT875_A   : KRWNREVDRE-  : 589     SEQ ID NO:112
CT875_B   : KRWNREVDRE-  : 589     SEQ ID NO:114
CT875_D   : RRWNREVDRE-  : 591     SEQ ID NO:22
CT875_E   : KRWNREVDRE-  : 591     SEQ ID NO:8
CT875_G   : RRWNREVDRE-  : 591     SEQ ID NO:116
CT875_H   : KRWNREVDRE-  : 591     SEQ ID NO:118
CT875_I   : KRWNREVDRE-  : 591     SEQ ID NO:120
CT875_J   : KRWDREVDRE-  : 590     SEQ ID NO:122
CT875_K   : RRWNREVDRE-  : 591     SEQ ID NO:124
CT875_L2  : QRWDREVDRE-  : 590     SEQ ID NO:126
```

+:         non-conservative amino acid change
-:         conservative amino acid change
Grey boxes: predicted HLA DRB1 epitopes (serovar E)

Amino acids with charged polar groups (D,E,K,R,H)
Amino acids with uncharged polar R groups (G,S,T,C,Y,N,Q)
Amino acids nonpolar R groups (A,V,L,I,P,F,W,M)

Figure 12

```
CT089-SerE  MTASGGAGGLGSTQTVDVARAQAAAATQDAQEVIGSQEASEASMLKGCED          50
CT089 serD  MTASGGAGGLGSTQTVDVARAQAAAATQDAQEVIGSQEASEASMLKGCED          50
CT089 Cpn   MAASGGTGGLGGTQGVNLAAVEAAAAKADAAEVVASQEGSEMNMIQQSQD          50
CT089 Mopn  MTASGGAGGLGGTQTVNVAQAQAAAATQDAQEIIGSQEASEASLIKGSED          50

CT089-SerE  LINPAAATRIKKKEEKFESLEARRKPTADKAEKKSESTEEKGDTPLEDRF         100
CT089 serD  LINPAAATRIKKKGEKFESLEARRKPTADKAEKKSESTEEKGDTPLEDRF         100
CT089 Cpn   LTNPAAATRTKKKEEKFQTLESRKKGEAGKAEKKSESTEEKPDTDLADKY         100
CT089 Mopn  LANPAAATRIKKKEDKFQSLEARRKTTS-KSEKKSESTEEKSDSSLEERF          99

CT089-SerE  TEDLSEVSGEDFRGLKNSFDDDSSPEEILDALTSKFSDPTIKDLALDYLI         150
CT089 serD  TEDLSEVSGEDFRGLKNSFDDDSSPDEILDALTSKFSDPTIKDLALDYLI         150
CT089 Cpn   ASGNSEISGQELRGLRDAIGDDASPEDILALVQEKIKDPALQSTALDYLV         150
CT089 Mopn  TENLSDVSGEDFRGLKDSLSEDSSPEEILEKLSGKFSDPTIKDLALDFLI         149

CT089-SerE  QTAPS-DRKLKSALIQAKHQLMSQNPQAIVGGRNVLLASETFASRANTSP         199
CT089 serD  QTAPS-DGKLKSTLIQAKHQLMSQNPQAIVGGRNVLLASETFASRANTSP         199
CT089 Cpn   QTTPPSQGKLKEALIQARNTHTEQFGRTAIGAKNILFASQEYADQLNVSP         200
CT089 Mopn  QSSPP-DGKLRASLIQAKQTLFQQNPQAVKGGRNVLLASEAFASKANTSP         198

CT089-SerE  SSLRSLYLQVTSSPSNCDNLRQMLAS-YLPSEKTAVMEFLVNGMVADLKS         248
CT089 serD  SSLRSLYFQVTSSPSNCANLHQMLAS-YLPSEKTAVMEFLVNGMVADLKS         248
CT089 Cpn   SGLRSLYLEVTGDTHTCDQLLSMLQDRYTYQDMAIVSSFLMKGMATELKR         250
CT089 Mopn  ASLRALYTQVTSSPANCASLSQMLSS-YSPTEKAAVIDFLTNGMVSDLKS         247

CT089-SerE  EGPSIPPAKLQVYMTELSNLQALHSVDSFFDRNIGNLENSLKHEGHAPIP         298
CT089 serD  EGPSIPPAKLQVYMTELSNLQALHSVNSFFDRNIGNLENSLKHEGHAPIP         298
CT089 Cpn   QGPYVPSAQLQVLMTETRNLQAVLTSYDYIESRVPILLDSLKAEGIQTPS         300
CT089 Mopn  GGPSIPAPQLQVYMTELSNLQALNSVDSFFDKNTKGLEDNLKAEGHTLPP         297

CT089-SerE  SLTTGNLTKTFLQLVEDKFPSSSKAQKALNELVGPDTGPQTEVLNLFFRA         348
CT089 serD  SLTTGNLTKTFLQLVEDKFPSSSKAQKALNELVGPDTGPQTEVLNLFFRA         348
CT089 Cpn   DLNFVKVAESYHKIINDKFPTASKVEREVRNLLGDDVDSVIGVLNLFFSA         350
CT089 Mopn  SLTPSNLAQTFLKLVEDKFPSSQKAQKLLDGLVGSDVTPQTEVLNLFYRA         347

CT089-SerE  LNGCSPRIFSGAEKKQQLASVITNTLDAINADNEDYPKPGDFPRSSFSST         398
CT089 serD  LNGCSPRIFSGAEKKQQLASVITNTLDAINADNEDYPKPGDFPRSSFSST         398
CT089 Cpn   LRQTSSRLFSSADKRQQLGAMIANALDAVNINNEDYPKASDFPKPY----         396
CT089 Mopn  LNGCSPRIFGNAEKKQQLATVITNTLDTVNADNEDYPKPSDFPKPSFHGT         397

CT089-SerE  PPHAPVPQSEIPTSPTSTQPPSP    SEQ ID NO:16                    421
CT089 serD  PPHAPVPQSEIPTSPTSTQPPSP    SEQ ID NO:72                    421
CT089 Cpn   ------------------PWS      SEQ ID NO:78                    399
CT089 Mopn  PPHAPVSLSDLPSA--TTNSADQ    SEQ ID NO:74                    418
```

Decoration 'Decoration #1': Shade (with solid black) residues that match CT089-SerE exactly.

Figure 13

(Sequence alignment figure)

Decoration 'Decoration #1': Shade (with solid black) residues that match Ct858-E exactly.

Cp = CpN

Figure 14

```
                   *        20         *        40         *        60
CT875_E.pr : ---------MSIRGVGGNGNS--RIPSHNGDGSNRRSQNTKGNNKVEDRVCSLYS---SR :  46
CT875_D.pr : ---------MSIRGVGGNGNS--RIPSHNGDGSNRRSQNTKGNNKVEDRVCSLYS---SR :  46
CT875_MOPN : MFYFLGWFVMGIKGVGGSGHSDYPIPSHNGDGESEKNSSDSTSSKVNAKVTSSLQGAPST :  60

*        80         *       100         *       120
CT875_E.pr : SNENRESPYAVVDVSSMIESTPTSGETTR--------------------ASRGVLSRFQR :  86
CT875_D.pr : SNENRESPYAVVDVSSMIESTPTSGETTR--------------------ASRGVFSRFQR :  86
CT875_MOPN : NDENSVSPYSVVDVTDLIESGESSRHVIKKSIETEEAAHRESSVEGAGHSSRGIFGRLQA : 120

*       140         *       160         *       180
CT875_E.pr : GLVRIADKVRRAVQCAWSSVSTSRSSATRAAESGSSSRTARGASSGYREYSPSAARGLRL : 146
CT875_D.pr : GLVRVADKVRRAVQCAWSSVSTRRSSATRAAESGSSSRTARGASSGYREYSPSAARGLRL : 146
CT875_MOPN : GLGRLARRVGEAVRNTVGSIFPQR--------AGAEQRTGKAR-T---KYSPSASRGLRL : 168

*       200         *       220         *       240
CT875_E.pr : MFTDFWRTRVLRQTSPMAGVFGNLDVNEARLMAAYTSECADHLEAKELAGPDGVAAAREI : 206
CT875_D.pr : MFTDFWRTRVLRQTSPMAGVFGNLDVNEARLMAAYTSECADHLEANKLAGPDGVAAAREI : 206
CT875_MOPN : MFTDFWRYRVLHRNEPMDGLEAKLDADEAEDMAAYTKEYVSNLEKRGAADRETIEHCQMV : 228

*       260         *       280         *       300
CT875_E.pr : AKRWEKRVRDLQDKGAARKLLNDPLGRRTPNYCSKNPGEYTVGNSMFYDGPQVANLQNVD : 266
CT875_D.pr : AKRWDQRVRDLQDKGAARKLLNDPLGRRTPNYCSKNPGEYTVGNSMFYDGPQVANLQNVD : 266
CT875_MOPN : AKNWEKRARDLRDMGAAKKFLRDPFGKSDPKYKGTLPGEYTVGNTMFYDGPGVSKLSEVD : 288

*       320         *       340         *       360
CT875_E.pr : TGFWLDMSNLSDVVLSREIQTGLRARATLEESMPMLENLEERFRRLQETCDAARTEIEES : 326
CT875_D.pr : TGFWLDMSNLSDVVLSREIQTGLRARATLEESMPMLENLEERFRRLQETCDAARTEIEES : 326
CT875_MOPN : TGFWLDMEKLSDAVLSANIQKGLRARFVLNQSIPQLESLEERFRKLESACDEARASLKEA : 348

*       380         *       400         *       420
CT875_E.pr : GWTRESASRMEGDEAQGPSRVQQAFQSFVNECNSIEFSFGSFGEIVRVLCARVSRGLAAA : 386
CT875_D.pr : GWTRESASRMEGDEAQGPSRAQQAFQSFVNECNSIEFSFGSFGEHVRVLCARVSRGLAAA : 386
CT875_MOPN : GWIKE------GKE---PNKAQRAFRREVEESRNLELSFGSFGESARRLSARVSQGLAAA : 399

*       440         *       460         *       480
CT875_E.pr : GEAIRRCFSCCKGSTHRYAPRDDLSPEGASLAETLARFADDMGIERGADCTYDIPLVDDW : 446
CT875_D.pr : GEAIRRCFSCCKGSTHRYAPRDDLSPEGASLAETLARFADDMGIERGADGTYDIPLVDDW : 446
CT875_MOPN : GEATRRCFDCRKG---KYSTKKDLSSPELNLAFFITRFTDFMGIERDPDGNYNIPWVENW : 456

*       500         *       520         *       540
CT875_E.pr : RRGVPSIEGEGSDSIYEIMMP-------IYEVMNMDLETRRSFAVQQGHYQDPRAS--DY : 497
CT875_D.pr : RRGVPSIEGEGSDSIYEIMMP-------IYEVMDMDLETRRSFAVQQGHYQDPRAS--DY : 497
CT875_MOPN : RTGVPVIEGEGAEHIYETMMPVQESFEQVYEVMDMGLPERRDFAVSQQHYQVPRSSLNY : 516

*       560         *       580         *       600
CT875_E.pr : DLPRASDYDLPR----SPYPTPPLPPRYQLQNMDVEAGFREAVYASFVAGMYNYVVTQPQ : 553
CT875_D.pr : DLPRASDYDLPR----SPYPTPPLPPRYQLQNMDVEAGFREAVYASFVAGMYNYVVTQPQ : 553
CT875_MOPN : ETPRFREYDVPRNSARSYIDVPRVPEQNEVEEMHVTKGMRSSVYACFVAGMRNYIVSQPQ : 576

*       620         *
CT875_E.pr : ERIPNSQQVEGILRDMLTNGSQTFRDLMKRWNREVDRE : 591    SEQ ID NO:8
CT875_D.pr : ERIPNSQQVEGILRDMLTNGSQTFRDLMRRWNREVDRE : 591    SEQ ID NO:22
CT875_MOPN : EQIPNSEQVEQLFQELINDGDQIIQELMKIWNEELDNQ : 614    SEQ ID NO:24
```

S/N = signal to noise

VACCINES AGAINST CHLAMYDIAL INFECTION

CROSS REFERENCE TO RELATED APPLICATIONS

The present application is a continuation-in-part of U.S. application Ser. No. 11/909,992 (now abandoned), which is the National Stage of International Patent Application No. PCT/US2006/010793, filed 24 Mar. 2006, now lapsed, which claims priority benefit to U.S. Provisional Application No. 60/667,331, filed 31 Mar. 2005, each of which is hereby incorporated by reference in its entirety.

FIELD OF THE INVENTION

The present invention relates generally to the treatment or prevention of Chlamydial infection. In particular, the invention is related to compositions of polypeptides comprising a *Chlamydia* antigen and combinations thereof, and to compositions of polynucleotides encoding a *Chlamydia* antigen and combinations thereof, and to the use of such compositions for prophylactic or therapeutic treatment of Chlamydial infection.

BACKGROUND OF THE INVENTION

Chlamydiae are intracellular bacterial pathogens that are responsible for a wide variety of important human and animal infections.

*Chlamydia trachomatis* is transmitted between human beings through social or sexual contact. A number of *Chlamydia trachomatis* serovars exist, and although the identification and classification of serovars continues to evolve, at least 18 have been reported to date. Serovars A to C are primarily associated with ocular trachoma, serovars D to K with oculogenital disease and serovars L1 to L3 with lymphogranuloma venereum (LGV) (Brunham, R C et al. *J. Nat. Rev. Immunol.* 2005 5:149-161).

*Chlamydia trachomatis* is one of the most common causes of sexually transmitted diseases and can lead to pelvic inflammatory disease (PID), resulting in tubal obstruction and infertility. *Chlamydia trachomatis* may also play a role in male infertility. In 1990, the cost of treating PID in the US was estimated to be $4 billion. The World Health Organisation estimated that in 1999 over 90 million new cases of sexually transmitted *Chlamydia trachomatis* occurred worldwide (Global Prevalence and Incidence of Selected Curable Sexually Transmitted Infections, World Health Organisation, Geneva, 2001). Furthermore, ulcerative sexually transmitted diseases such as *Chlamydia trachomatis* infection are a major risk factor for HIV acquisition (Brunham, R C et al. *J. Nat. Rev. Immunol.* 2005 5:149-161; Igietseme, J U et al. *Expert Rev. Vaccines* 2003 2(1):129-146).

Trachoma, due to ocular infection with *Chlamydia trachomatis*, is the leading cause of preventable blindness worldwide and is estimated to affect 300-500 million people (West, S K *Prog. Ret. Eye Res.* 2004 23:381-401). Current treatment involves the use of antibiotics such as tetracycline (daily, for a period of 4 to 6 weeks) or azithromycin (single dose). Although effective in combating infection, re-infection generally occurs due to the endemic nature of the infection. Repeated infection over many years leads to scarring of the eyelid, distortion of the lid margin and rubbing of the eye lashes against the cornea (trichiasis). Constant trauma to the cornea is both painful and leads to corneal opacity and blindness (Mabey, D C W et al. *The Lancet* 2003 362:223-229).

*Chlamydia pneumoniae* is a major cause of acute respiratory tract infections in humans and is also believed to play a role in the pathogenesis of atherosclerosis and, in particular, coronary heart disease. Individuals with a high titer of antibodies to *Chlamydia pneumoniae* have been shown to be at least twice as likely to suffer from coronary heart disease as seronegative individuals.

Often chlamydial infection is asymptomatic and subclinical, such that severe and often irreversible complications may present as the first symptoms of genital infection. Infants born from a mother with a genital chlamydial infection may develop pneumonia and *Chlamydia trachomatis* is considered the most common causative agent of pneumonia during the first six months of life (de la Maza, L M et al. *Curr. Opin. Investig. Drugs* 2002 3(7):980-986).

Chlamydial infections thus constitute a significant health problem both in developed and developing countries. In light of the public health concerns, and the fact that the cost of current treatments is excessive in many developing countries, the development of vaccines for *Chlamydia* species has been an important research target. As the genomic make-up of *Chlamydia trachomatis* is relatively stable, and since the presence of animal reservoirs is negligible, even vaccines with limited efficacy may have a significant impact on the prevalence of infections.

There thus remains a need in the art for improved vaccines and pharmaceutical compositions for the prevention and treatment of *Chlamydia* infections. There also remains a need in the art for multivalent vaccines for the prevention and treatment of *Chlamydia trachomatis* infections which are effective against a range of serovars. The present invention fulfills these needs and further provides other related advantages.

SUMMARY OF THE INVENTION

The present invention relates to compositions comprising antigens of bacterial pathogens of *Chlamydia*. Such bacterial pathogens include *Chlamydia trachomatis, Chlamydia psitacci, Chlamydia pneumonia,* and *Chlamydia muridarum*. The *Chlamydia* antigens may be derived from any number of serovars within a *Chlamydia* species.

It should be noted that *Chlamydia muridarum* was previously known as *Chlamydia trachomatis* mouse pneumonitis strain (MoPn), both names are still in common use, although they refer to the same bacterium. For consistency, only the name *Chlamydia muridarum* is used herein.

The present invention is based, in part, on the inventors' discovery that *Chlamydia* polypeptides possess immunogenic and antigenic properties and can offer protection against chlamydial infection when administered as prophylactic vaccines. Some level of cross reactivity may be seen between antigens of different serovars and species, and therefore *Chlamydia* antigens are predicted to provide a protective immune response against a species or serovar other than the one from which the antigen was obtained.

More specifically, the inventors have discovered that certain combinations of *Chlamydia* polypeptides provide a good immune response. Certain combinations of *Chlamydia* polypeptides have been shown to provide protection against *Chlamydia* infection in mouse models.

In a specific embodiment, the isolated or purified *Chlamydia* polypeptides of the invention may be formulated as pharmaceutical compositions for administration into a subject in the prevention and/or treatment of *Chlamydia* infection. The immunogenicity of the protein composition may be enhanced by the inclusion of an adjuvant.

In a specific embodiment, the isolated or purified *Chlamydia* polypeptides are administered as combinations of individual antigens, optionally in combination with an adjuvant. Alternatively, the *Chlamydia* polypeptides are administered in the form of a fusion protein, optionally in combination with an adjuvant.

In another aspect of the invention, isolated or purified polynucleotides are used to produce recombinant polypeptide antigens in vitro. Alternatively, the polynucleotides may be administered into a subject as polynucleotide vaccines to cause antigen expression in the subject, and the subsequent induction of an anti-*Chlamydia* immune response.

In a further aspect of the invention, certain combinations of *Chlamydia* polypeptides according to the present invention, immunogenic fragments thereof or polynucleotides encoding them which are derived from a first *Chlamydia trachomatis* serovar may be administered to a subject for the treatment or prevention of *Chlamydia* infection from a second *Chlamydia trachomatis* serovar.

It is also an object of the invention that the polypeptides be used in in vitro assays for detecting humoral antibodies or cell-mediated immunity against *Chlamydia* for diagnosis of infection or monitoring of disease progression. Alternatively, the polypeptides may be used as immunogens to generate anti-Chlamydia antibodies in a non-human animal. The antibodies can be used to detect the target antigens in vivo and in vitro.

BRIEF DESCRIPTION OF THE FIGURES

FIG. 6 shows the sequence alignment for Ct-089 from *Chlamydia trachomatis* serovar E (SEQ ID NO. 16) with Ct-089 from a range of other *Chlamydia trachomatis* serovars (i.e. A (SEQ ID NO. 80), B (SEQ ID NO. 82), D (SEQ ID NO. 72), G (SEQ ID NO. 84), H (SEQ ID NO. 86), I (SEQ ID NO. 88), J (SEQ ID NO. 90), K (SEQ ID NO. 92), and L2 (SEQ ID NO. 94)).

FIGS. 7a and 7b show the sequence alignment for Ct-858 from *Chlamydia trachomatis* serovar E (SEQ ID NO:6) with Ct-858 from a range of other *Chlamydia trachomatis* serovars (i.e., A (SEQ ID NO:96), B (SEQ ID NO:98), D (SEQ ID NO:34), G (SEQ ID NO:100), H (SEQ ID NO:102), I (SEQ ID NO:104), J (SEQ ID NO:106), K (SEQ ID NO:108), and L2 (SEQ ID NO:110)).

Figure 8A:
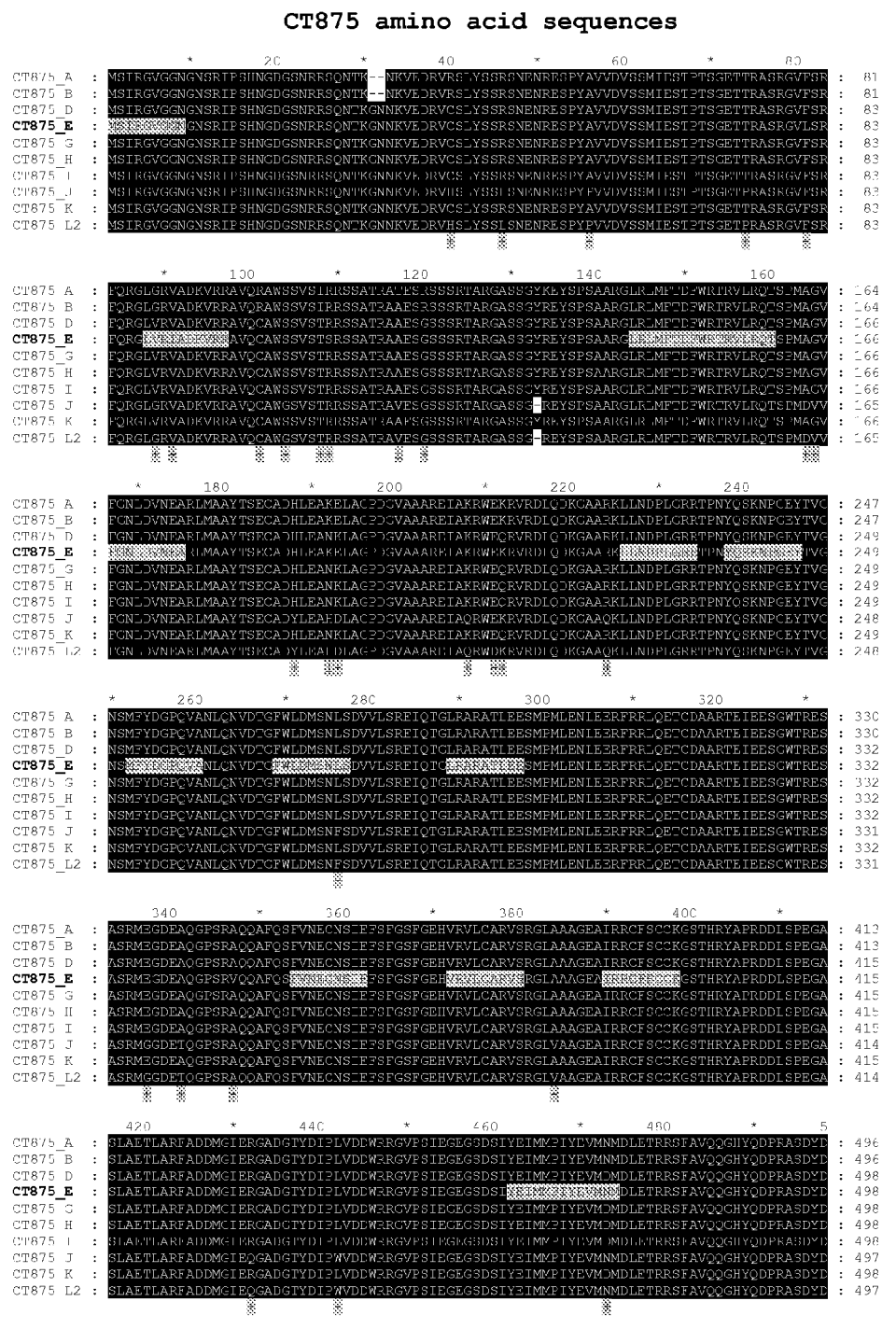

FIGS. 8a and 8b show the sequence alignment for Ct-875 from *Chlamydia trachomatis* serovar E (SEQ ID NO:8) with Ct-875 from a range of other *Chlamydia trachomatis* serovars (i.e., A (SEQ ID NO:112), (SEQ ID NO:114), D (SEQ ID NO:22), G (SEQ ID NO:116), H (SEQ ID NO:118), I (SEQ ID NO:120), J (SEQ ID NO:122), K (SEQ ID NO:124), and L2 (SEQ ID NO:126)).

FIG. 12 shows the sequence alignment for Ct-089 from *Chlamydia trachomatis* serovar E (SEQ ID NO:16) with equivalent proteins from other *Chlamydia trachomatis* serovars (i.e., D (SEQ ID NO:72) and *Chlamydia* species (i.e., Cpn—*C. pneumoniae* (SEQ ID NO:78), and Mopn—*C. muridarum* (SEQ ID NO:74)).

FIG. 13 shows the sequence alignment for Ct-858 from *Chlamydia trachomatis* serovar E (SEQ ID NO:6) with equivalent proteins from other *Chlamydia trachomatis* serovars (i.e., D (SEQ ID NO:34) and L2 (SEQ ID NO:110)) and *Chlamydia* species (i.e., Cp—*C. pneumoniae* (SEQ ID NO:40), and Mopn—*C. muridarum* (SEQ ID NO:36)).

FIG. 14 shows the sequence alignment for Ct-875 from *Chlamydia trachomatis* serovar E (SEQ ID NO:8) with equivalent proteins from other *Chlamydia trachomatis* serovars (i.e., D (SEQ ID NO:22)) and *Chlamydia* species (i.e., Mopn—*C. muridarum* (SEQ ID NO:24)).

Figure 1:
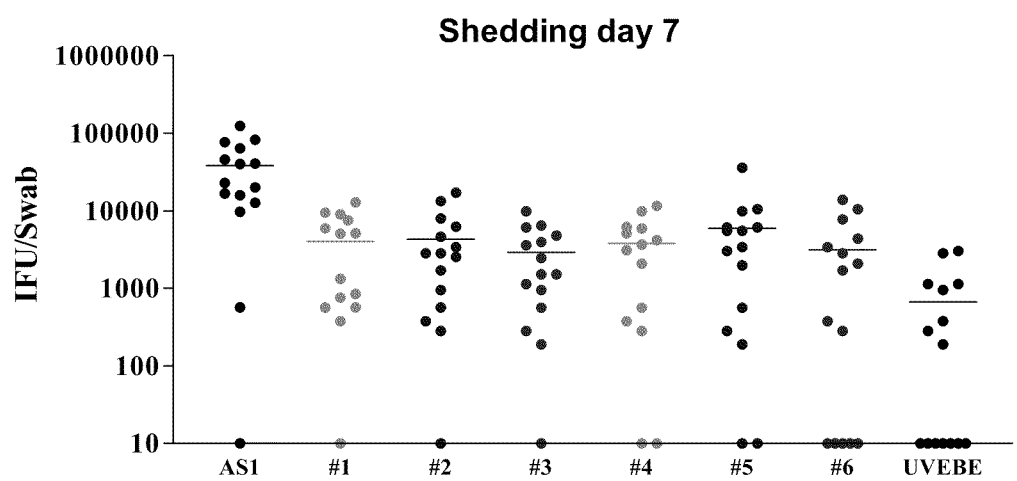
FIG. 1 shows Day 7 bacterial shedding data in Balb/c mice, representing data from three experiments in which groups of 5 Balb/c mice were immunized with the indicated combinations of antigens in AS01B. Graph represents data from three experiments in which groups of 5 Balb/c mice were immunized with the indicated combination of antigens in AS01B adjuvant. UVEB from serovar E formulated with AS01B served as a positive control of protection, and AS01B sham-immunized mice were used as positive control of infection. Progesterone-treated mice were challenged with an intra-vaginal dose of $5\times10^5$ IFU of serovar K. Bacterial shedding was quantified by taking swabs on day 7 post infection and determining the IFU using McCoy cells. Data from one back to back experiment were pooled.
Figure 2:
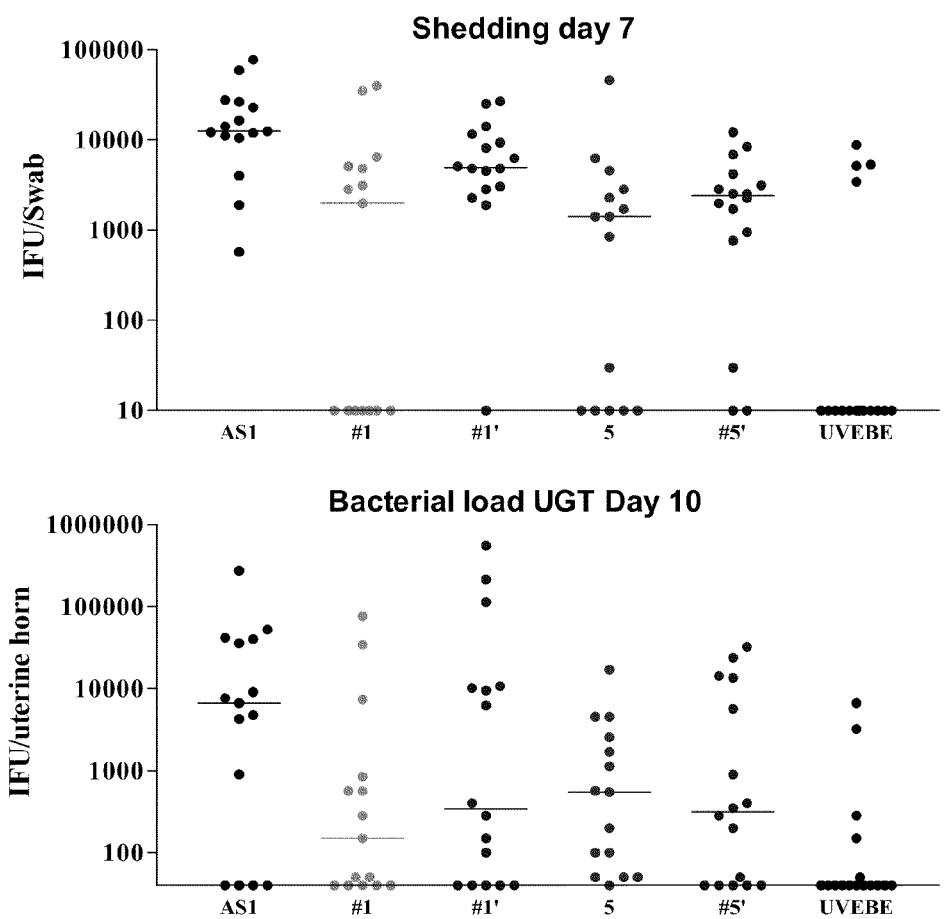
FIG. 2 shows Chlamydial shedding in the LGT and chlamydial load post challenge with *Chlamydia trachomatis* serovar K in the UGT of Balb/c mice immunized with antigen combinations. Graphs represent data from back to back experiments in which groups of 8 balb/c mice were immunized with the indicated combination of antigens in AS01B adjuvant. UVEB from serovar E formulated with AS01B served as a positive control of protection, and AS01B sham-immunized mice were used as control of infection. Progesterone-treated mice were challenged with an intra-vaginal dose of $5\times10^5$ IFU of serovar K. Bacterial shedding was quantified by taking swabs on day 7 post challenge and determining the IFU using McCoy cells. Mice were sacrificed 10 days post infection to determine the chlamydial load in the upper genital tract by homogenizing half of the UGT and determining IFU using McCoy cells. It should be noted that the limit of detection was 10 in respect of both of the above plots.
Figure 3:
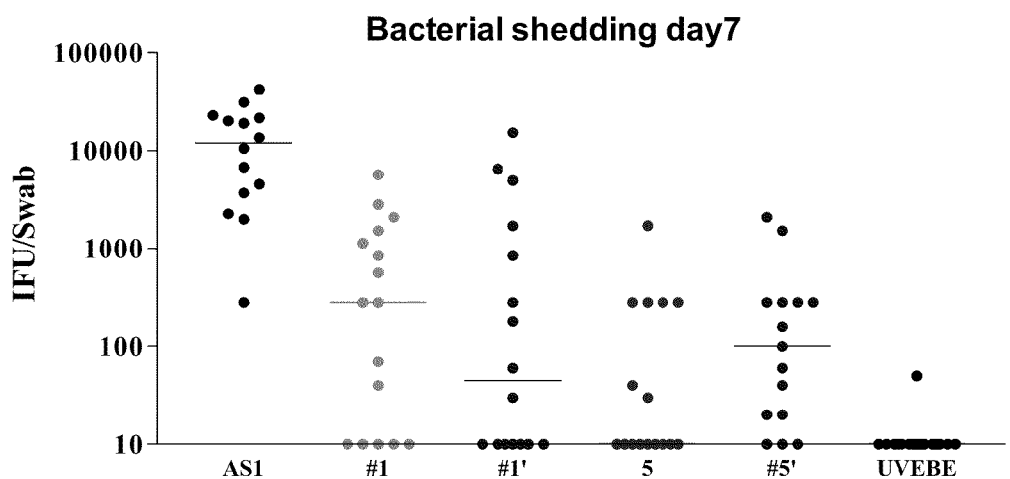
FIG. 3 shows Day 7 bacterial shedding data in C57Bl/6 mice immunized with the indicated combinations of antigens in AS01B. Graphs represent data from back to back experiments in which groups of 8 C57Bl/6 mice were immunized with the indicated combination of antigens in AS01B. UVEB from serovar E formulated with AS01B served as a positive control of protection, and AS01B sham-immunized mice were used as control of infection. Progesterone-treated mice were challenged with an intra-vaginal dose of $5\times10^5$ IFU of serovar K. Bacterial shedding was quantified by taking swabs on day 7 post challenge and determining the IFU using McCoy cells.
Figure 4:
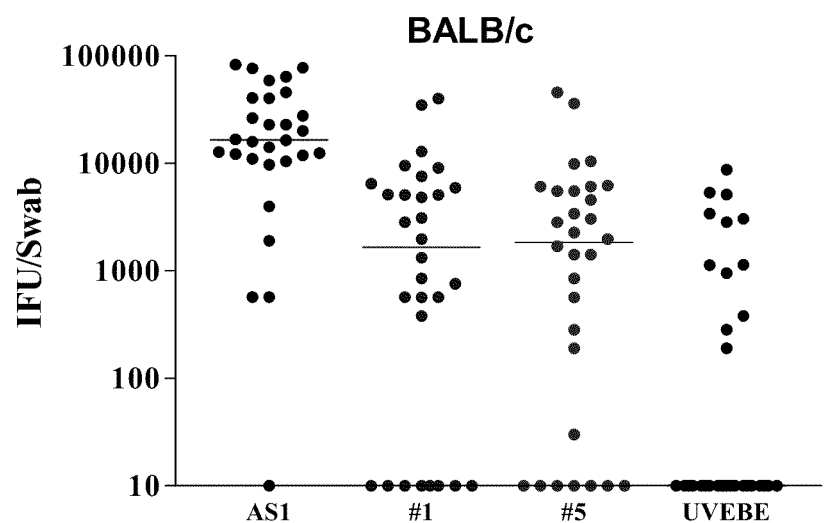
FIG. 4 shows Day 7 bacterial shedding data in Balb/c mice immunized with the indicated combinations of antigens in AS01B. Graphs represent pooled data from 5 experiments in which groups of 5-8 Balb/c mice were immunized with the indicated combination of antigens in AS01B. UVEB from serovar E formulated with AS01B served as a positive control of protection, and AS01B sham-immunized mice were used as control of infection. Progesterone-treated mice were challenged with an intra-vaginal dose of $5\times10^5$ IFU of serovar K. Bacterial shedding was quantified by taking swabs on day 7 post challenge and determining the IFU using McCoy cells.
Figure 5:
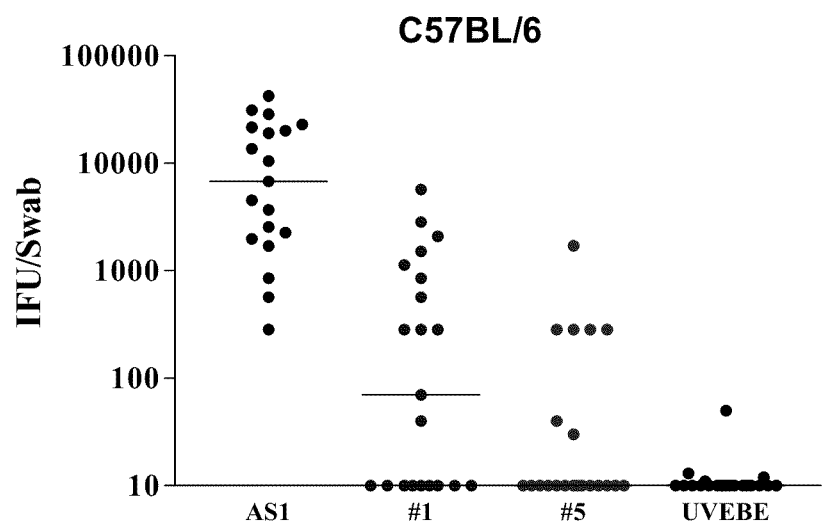
FIG. 5 shows Day 7 bacterial shedding data in C57Bl/6 mice immunized with the indicated combinations of antigens in AS01B. Graphs represent pooled data from 3 experiments in which groups of 5-8 C57Bl/6 mice were immunized with the indicated combination of antigens in AS01B. UVEB from serovar E formulated with AS01B served as a positive control of protection, and AS01B sham-immunized mice were used as control of infection. Progesterone-treated mice were challenged with an intra-vaginal dose of $5\times10^5$ IFU of serovar K. Bacterial shedding was quantified by taking swabs on day 7 post challenge and determining the IFU using McCoy cells.

In a further set of examples, the composition of the present invention comprises one of the following combinations, provided that all of the combinations comprise Ct-875 and Ct-858:
1c. Five out of: Swib, Momp, PmpDpd, Ct-858, PmpGpd and Ct-875
1c'. Three out of: PmpDpd, Ct-858, Ct-0875, Swib
2c. Five out of: Momp, PmpDpd, Ct-858, Ct-622, Ct-875 and Swib
3c. Five out of: Momp, PmpDpd, Ct-858, PmpGpd, Ct-622 and Ct-875
4c. Three out of: Ct-858, Ct-875, Ct-622 and Ct-089
5c'. Three out of: PmpDpd, Ct-858, Ct-875, Ct-089
6c. Four out of: Momp, PmpD, Ct-858, PmpGpd and Ct-875

The compositions according to the invention comprise two or more *Chlamydia* proteins or immunogenic fragments, for example 3, 4, 5, 6, 7, 8, 9 or 10 proteins or immunogenic fragments. For a composition comprising each of the combinations listed above under numbers 1-6, 1a-6a, 1b-6b and 1c-6c (e.g. 1-6 and 1a-6a) the combination may include further *Chlamydia* antigens, for example one further *Chlamydia* antigen, or it may contain no more *Chlamydia* antigens than those listed. For example, composition 1a" may contain only five antigens which are a combination of those *Chlamydia* antigens as listed and no other antigens, or composition 1a" may comprise a combination of five of the *Chlamydia* antigens as listed (such as all six antigens listed, or five of the six antigens listed plus one other *Chlamydia* antigen), and so forth for compositions 2-6, 2a-6a, 1b-6b and 1c-6c (e.g. 2-6 and 2a-6a).

It will be evident that in the case of the passenger domains of PmpD and PmpG, these may be present in the context of a larger portion of the PmpD or PmpG antigen or polynucleotide, for example full length PmpD or PmpG or a fragment thereof, provided that the fragment comprises the passenger domain.

The Momp and Swib proteins or immunogenic fragments may be for example from *Chlamydia trachomatis*, or they may be from other species of *Chlamydia*. The antigens above designated "Ct" may be *Chlamydia trachomatis* proteins or immunogenic fragments, or, where possible, they may be the equivalent proteins from different species of *Chlamydia* (i.e. a *Chlamydia* species other than *Chlamydia trachomatis*). In one example, all of the antigens in the composition according to the invention are from *Chlamydia trachomatis*.

Compositions of the present invention may alternatively comprise polynucleotides encoding the combination of two or more *Chlamydia* proteins or immunogenic fragments which may be selected from Swib (also known as Ct-460), Momp (major outer membrane protein also known as Ct-681), Ct-858, Ct-875, Ct-622, Ct-089, passenger domain of PmpG (PmpGpd, also known as Ct-871) and passenger domain of PmpD (PmpDpd, also known as Ct-812), for example the combinations of antigens listed above as 1-6, 1a-6a, 1b-6b and 1c-6c (e.g. 1-6). The compositions of polynucleotides according to the invention include those which encode the combinations of antigens according to the invention as described herein (for example Ct-858 and Ct-875). The polynucleotides encoding the different antigens may be present as separate nucleic acids or they may be present together in a single nucleic acid, or a combination of separate and combined nucleic acids.

The following provides polynucleotide and polypeptide sequences for some of the antigens, which may be used in the compositions of the invention and which have been listed above.

BRIEF DESCRIPTION OF SEQUENCE IDENTIFIERS

SEQ ID NO:1 is the cDNA sequence of Ct-460, also known as Swib from *Chlamydia trachomatis*, serovar LGVII (serovar LGVII is also referred to as serovar LII).

SEQ ID NO:2 is the protein sequence of Ct-460, also known as Swib from *Chlamydia trachomatis*, serovar LGVII, which protein is encoded by SEQ ID NO:1.

SEQ ID NO:3 is the cDNA sequence of the *Chlamydia* antigen known as Major Outer Membrane Protein (Momp) from *Chlamydia trachomatis*, serovar F.

SEQ ID NO:4 is the protein sequence of the chlamydia antigen known as Major Outer Membrane Protein (Momp) from *Chlamydia trachomatis*, serovar F, which protein is encoded by SEQ ID NO:3.

SEQ ID NO:5 is the cDNA sequence of Ct-858 from *Chlamydia trachomatis*, serovar E.

SEQ ID NO:6 is the protein sequence of Ct-858 *Chlamydia trachomatis*, serovar E, which protein is encoded by SEQ ID NO:5.

SEQ ID NO:7 is the cDNA sequence of Ct-875 from *Chlamydia trachomatis*, serovar E.

SEQ ID NO: 8 is the protein sequence of Ct-875 from *Chlamydia trachomatis*, serovar E, which protein is encoded by SEQ ID NO: 7.

SEQ ID NO: 9 is the cDNA sequence of Ct-622 from *Chlamydia trachomatis*, serovar E.

SEQ ID NO: 10 is the protein sequence of Ct-622 from *Chlamydia trachomatis*, serovar E, which protein is encoded by SEQ ID NO: 9.

SEQ ID NO: 11 is the cDNA sequence of the passenger domain of PmpG also known as Ct-871 from *Chlamydia trachomatis*, serovar LGVII.

SEQ ID NO: 12 is the protein sequence of the passenger domain of PmpG, also known as Ct-871 from *Chlamydia trachomatis*, serovar LGVII, which protein is encoded by SEQ ID NO: 11.

SEQ ID NO: 13 is the cDNA sequence of the passenger domain of PmpD, also known as Ct-812, from *Chlamydia trachomatis*, serovar LGVII.

SEQ ID NO: 14 is the protein sequence of the passenger domain of PmpD, also known as Ct-812, from *Chlamydia trachomatis*, serovar LGVII, which protein is encoded by SEQ ID NO: 13.

SEQ ID NO: 15 is the cDNA sequence of the Ct-089 from *Chlamydia trachomatis*, serovar E.

SEQ ID NO: 16 is the protein sequence of Ct-089 from *Chlamydia trachomatis*, serovar E, which protein is encoded by SEQ ID NO: 15.

SEQ ID NO: 17 is the cDNA sequence of the chlamydia antigen known as Major Outer Membrane Protein (Momp) from *Chlamydia psitacci*.

SEQ ID NO: 18 is the protein sequence of the chlamydia antigen known as Major Outer Membrane Protein (Momp) from *Chlamydia* psitacci, which protein is encoded by SEQ ID NO: 17.

SEQ ID NO: 19 is the cDNA sequence of the *Chlamydia* antigen known as Major Outer Membrane Protein (Momp) from *Chlamydia pneumoniae*.

SEQ ID NO: 20 is the protein sequence of the chlamydia antigen known as Major Outer Membrane Protein (Momp) from *Chlamydia pneumoniae*, which protein is encoded by SEQ ID NO: 19.

SEQ ID NO: 21 is the cDNA sequence of Ct-875 from *Chlamydia trachomatis*, serovar D.

SEQ ID NO: 22 is the protein sequence of Ct-875 from *Chlamydia trachomatis*, serovar D which protein is encoded by SEQ ID NO: 21.

SEQ ID NO: 23 is the cDNA sequence of Ct-875 from *Chlamydia muridarum*.

SEQ ID NO: 24 is the protein sequence of Ct-875 from *Chlamydia muridarum*, which protein is encoded by SEQ ID NO:23.

SEQ ID NO: 25 is the cDNA sequence of Ct-875 from *Chlamydia psitacci*

SEQ ID NO: 26 is the protein sequence of Ct-875 from *Chlamydia psitacci*, which protein is encoded by SEQ ID NO:25.

SEQ ID NO: 27 is the cDNA sequence PmpG also known as Ct-871 from *Chlamydia trachomatis*, serovar D.

SEQ ID NO: 28 is the protein sequence of PmpG, also known as Ct-871 from *Chlamydia trachomais*, serovar D, which protein is encoded by SEQ ID NO:27.

SEQ ID NO: 29 is the cDNA sequence PmpG also known as Ct-871 from *Chlamydia muridarum*.

SEQ ID NO: 30 is the protein sequence of PmpG, also known as Ct-871 from *Chlamydia muridarum*, which protein is encoded by SEQ ID NO:29.

SEQ ID NO: 31 is the cDNA sequence PmpG also known as Ct-871 from *Chlamydia psitacci*.

SEQ ID NO: 32 is the protein sequence of PmpG, also known as Ct-871 from *Chlamydia psitacci*, which protein is encoded by SEQ ID NO:31.

SEQ ID NO: 33 is the cDNA sequence of Ct-858 from *Chlamydia trachomatis*, serovar D.

SEQ ID NO: 34 is the protein sequence of Ct-858 *Chlamydia trachomatis*, serovar D, which protein is encoded by SEQ ID NO: 33.

SEQ ID NO: 35 is the cDNA sequence of Ct-858 from *Chlamydia muridarum*.

SEQ ID NO: 36 is the protein sequence of Ct-858 *Chlamydia muridarum*, which protein is encoded by SEQ ID NO: 35.

SEQ ID NO: 37 is the cDNA sequence of Ct-858 from *Chlamydia psitacci*.

SEQ ID NO: 38 is the protein sequence of Ct-858 *Chlamydia psitacci*, which protein is encoded by SEQ ID NO: 37.

SEQ ID NO: 39 is the cDNA sequence of Ct-858 from *Chlamydia pneumoniae*.

SEQ ID NO: 40 is the protein sequence of Ct-858 *Chlamydia pneumoniae*, which protein is encoded by SEQ ID NO: 39.

SEQ ID NO: 41 is the cDNA sequence of PmpD, also known as Ct-812, from *Chlamydia trachomatis*, serovar D.

SEQ ID NO: 42 is the protein sequence of PmpD, also known as Ct-812, from *Chlamydia trachomatis*, serovar D, which protein is encoded by SEQ ID NO: 41. The passenger domain spans amino acids 31 to 1203.

SEQ ID NO: 43 is the cDNA sequence of PmpD, also known as Ct-812, from *Chlamydia muridarum*.

SEQ ID NO: 44 is the protein sequence of PmpD, also known as Ct-812, from *Chlamydia muridarum*, which protein is encoded by SEQ ID NO: 43.

SEQ ID NO: 45 is the cDNA sequence of PmpD, also known as Ct-812, from *Chlamydia psitacci*.

SEQ ID NO: 46 is the protein sequence of PmpD, also known as Ct-812, from *Chlamydia psitacci*, which protein is encoded by SEQ ID NO: 45.

SEQ ID NO: 47 is the cDNA sequence of the *Chlamydia* antigen known as Major Outer Membrane Protein (Momp), also known as Ct-681 from *Chlamydia trachomatis*, serovar LGVII.

SEQ ID NO: 48 is the protein sequence of the chlamydia antigen known as Major Outer Membrane Protein (Momp), also known as Ct-681 from *Chlamydia trachomatis*, serovar LGVII, which protein is encoded by SEQ ID NO: 47.

SEQ ID NO: 49 is the cDNA sequence of the *Chlamydia* antigen known as Major Outer Membrane Protein (Momp), also known as Ct-681 from *Chlamydia trachomatis*, serovar J.

SEQ ID NO: 50 is the protein sequence of the chlamydia antigen known as Major Outer Membrane Protein (Momp), also known as Ct-681 from *Chlamydia trachomatis*, serovar J, which protein is encoded by SEQ ID NO: 49.

SEQ ID NO: 51 is the cDNA sequence of the *Chlamydia* antigen known as Major Outer Membrane Protein (Momp), also known as Ct-681 from *Chlamydia trachomatis*, serovar H.

SEQ ID NO: 52 is the protein sequence of the chlamydia antigen known as Major Outer Membrane Protein (Momp), also known as Ct-681 from *Chlamydia trachomatis*, serovar H, which protein is encoded by SEQ ID NO: 51.

SEQ ID NO: 53 is the cDNA sequence of the *Chlamydia* antigen known as Major Outer Membrane Protein (Momp), also known as Ct-681 from *Chlamydia trachomatis*, serovar E.

SEQ ID NO: 54 is the protein sequence of the chlamydia antigen known as Major Outer Membrane Protein (Momp), also known as Ct-681 from *Chlamydia trachomatis*, serovar E, which protein is encoded by SEQ ID NO: 53.

SEQ ID NO: 55 is the cDNA sequence of the *Chlamydia* antigen known as Major Outer Membrane Protein (Momp), also known as Ct-681 from *Chlamydia trachomatis*, serovar D.

SEQ ID NO: 56 is the protein sequence of the chlamydia antigen known as Major Outer Membrane Protein (Momp), also known as Ct-681 from *Chlamydia trachomatis*, serovar D, which protein is encoded by SEQ ID NO: 55.

SEQ ID NO: 57 is the cDNA sequence of Ct-622 from *Chlamydia trachomatis*, serovar D.

SEQ ID NO: 58 is the protein sequence of Ct-622 from *Chlamydia trachomatis*, serovar D, which protein is encoded by SEQ ID NO: 57.

SEQ ID NO: 59 is the cDNA sequence of Ct-622 from *Chlamydia psitacci*.

SEQ ID NO: 60 is the protein sequence of Ct-622 from *Chlamydia psitacci*, which protein is encoded by SEQ ID NO: 59.

SEQ ID NO: 61 is the cDNA sequence of Ct-622 from *Chlamydia pneumoniae*.

SEQ ID NO: 62 is the protein sequence of Ct-622 from *Chlamydia pneumoniae*, which protein is encoded by SEQ ID NO: 61.

SEQ ID NO: 63 is the cDNA sequence of Ct-460, also known as Swib from *Chlamydia trachomatis*, serovar D.

SEQ ID NO: 64 is the protein sequence of Ct-460, also known as Swib from *Chlamydia trachomatis*, serovar D, which protein is encoded by SEQ ID NO: 63.

SEQ ID NO: 65 is the cDNA sequence of Ct-460, also known as Swib from *Chlamydia muridarum*.

SEQ ID NO: 66 is the protein sequence of Ct-460, also known as Swib from *Chlamydia muridarum*, which protein is encoded by SEQ ID NO: 65.

SEQ ID NO: 67 is the cDNA sequence of Ct-460, also known as Swib from *Chlamydia psitacci*.

SEQ ID NO: 68 is the protein sequence of Ct-460, also known as Swib from *Chlamydia psitacci*, which protein is encoded by SEQ ID NO: 67.

SEQ ID NO: 69 is the cDNA sequence of Ct-460, also known as Swib from *Chlamydia pneumoniae*.

SEQ ID NO: 70 is the protein sequence of Ct-460, also known as Swib from *Chlamydia pneumoniae*, which protein is encoded by SEQ ID NO:69.

SEQ ID NO: 71 is the cDNA sequence of the Ct-089 from *Chlamydia trachomatis*, serovar D.

SEQ ID NO: 72 is the protein sequence of Ct-089 from *Chlamydia trachomatis*, serovar D, which protein is encoded by SEQ ID NO: 71.

SEQ ID NO: 73 is the cDNA sequence of the Ct-089 from *Chlamydia muridarum*.

SEQ ID NO: 74 is the protein sequence of Ct-089 from *Chlamydia muridarum*, which protein is encoded by SEQ ID NO: 73.

SEQ ID NO: 75 is the cDNA sequence of the Ct-089 from *Chlamydia psitacci*.

SEQ ID NO: 76 is the protein sequence of Ct-089 from *Chlamydia psitacci*, which protein is encoded by SEQ ID NO: 75.

SEQ ID NO: 77 is the cDNA sequence of the Ct-089 from *Chlamydia pneumoniae*.

SEQ ID NO: 78 is the protein sequence of Ct-089 from *Chlamydia pneumoniae*, which protein is encoded by SEQ ID NO: 77.

SEQ ID NO: 79 is the cDNA sequence of the Ct-089 from *Chlamydia trachomatis*, serovar A.

SEQ ID NO: 80 is the protein sequence of Ct-089 from *Chlamydia trachomatis*, serovar A, which protein is encoded by SEQ ID NO: 79.

SEQ ID NO: 81 is the cDNA sequence of the Ct-089 from *Chlamydia trachomatis*, serovar B.

SEQ ID NO: 82 is the protein sequence of Ct-089 from *Chlamydia trachomatis*, serovar B, which protein is encoded by SEQ ID NO: 81.

SEQ ID NO: 83 is the cDNA sequence of the Ct-089 from *Chlamydia trachomatis*, serovar G.

SEQ ID NO: 84 is the protein sequence of Ct-089 from *Chlamydia trachomatis*, serovar G, which protein is encoded by SEQ ID NO: 83.

SEQ ID NO: 85 is the cDNA sequence of the Ct-089 from *Chlamydia trachomatis*, serovar H.

SEQ ID NO: 86 is the protein sequence of Ct-089 from *Chlamydia trachomatis*, serovar H, which protein is encoded by SEQ ID NO: 85.

SEQ ID NO: 87 is the cDNA sequence of the Ct-089 from *Chlamydia trachomatis*, serovar I.

SEQ ID NO: 88 is the protein sequence of Ct-089 from *Chlamydia trachomatis*, serovar I, which protein is encoded by SEQ ID NO: 87.

SEQ ID NO: 89 is the cDNA sequence of the Ct-089 from *Chlamydia trachomatis*, serovar J.

SEQ ID NO: 90 is the protein sequence of Ct-089 from *Chlamydia trachomatis*, serovar J, which protein is encoded by SEQ ID NO: 89.

SEQ ID NO: 91 is the cDNA sequence of the Ct-089 from *Chlamydia trachomatis*, serovar K.

SEQ ID NO: 92 is the protein sequence of Ct-089 from *Chlamydia trachomatis*, serovar K, which protein is encoded by SEQ ID NO: 91.

SEQ ID NO: 93 is the cDNA sequence of the Ct-089 from *Chlamydia trachomatis*, serovar L2.

SEQ ID NO: 94 is the protein sequence of Ct-089 from *Chlamydia trachomatis*, serovar L2, which protein is encoded by SEQ ID NO: 93.

SEQ ID NO: 95 is the cDNA sequence of the Ct-858 from *Chlamydia trachomatis*, serovar A.

SEQ ID NO: 96 is the protein sequence of Ct-858 from *Chlamydia trachomatis*, serovar A, which protein is encoded by SEQ ID NO: 95.

SEQ ID NO: 97 is the cDNA sequence of the Ct-858 from *Chlamydia trachomatis*, serovar B.

SEQ ID NO: 98 is the protein sequence of Ct-858 from *Chlamydia trachomatis*, serovar B, which protein is encoded by SEQ ID NO: 97.

SEQ ID NO: 99 is the cDNA sequence of the Ct-858 from *Chlamydia trachomatis*, serovar G.

SEQ ID NO: 100 is the protein sequence of Ct-858 from *Chlamydia trachomatis*, serovar G, which protein is encoded by SEQ ID NO: 99.

SEQ ID NO: 101 is the cDNA sequence of the Ct-858 from *Chlamydia trachomatis*, serovar H.

SEQ ID NO: 102 is the protein sequence of Ct-858 from *Chlamydia trachomatis*, serovar H, which protein is encoded by SEQ ID NO: 101.

SEQ ID NO: 103 is the cDNA sequence of the Ct-858 from *Chlamydia trachomatis*, serovar I.

SEQ ID NO: 104 is the protein sequence of Ct-858 from *Chlamydia trachomatis*, serovar I, which protein is encoded by SEQ ID NO: 103.

SEQ ID NO: 105 is the cDNA sequence of the Ct-858 from *Chlamydia trachomatis*, serovar J.

SEQ ID NO: 106 is the protein sequence of Ct-858 from *Chlamydia trachomatis*, serovar J, which protein is encoded by SEQ ID NO: 105.

SEQ ID NO: 107 is the cDNA sequence of the Ct-858 from *Chlamydia trachomatis*, serovar K.

SEQ ID NO: 108 is the protein sequence of Ct-858 from *Chlamydia trachomatis*, serovar K, which protein is encoded by SEQ ID NO: 107.

SEQ ID NO: 109 is the cDNA sequence of the Ct-858 from *Chlamydia trachomatis*, serovar L2.

SEQ ID NO: 110 is the protein sequence of Ct-858 from *Chlamydia trachomatis*, serovar L2, which protein is encoded by SEQ ID NO: 109.

SEQ ID NO: 111 is the cDNA sequence of the Ct-875 from *Chlamydia trachomatis*, serovar A.

SEQ ID NO: 112 is the protein sequence of Ct-875 from *Chlamydia trachomatis*, serovar A, which protein is encoded by SEQ ID NO: 111.

SEQ ID NO: 113 is the cDNA sequence of the Ct-875 from *Chlamydia trachomatis*, serovar B.

SEQ ID NO: 114 is the protein sequence of Ct-875 from *Chlamydia trachomatis*, serovar B, which protein is encoded by SEQ ID NO: 113.

SEQ ID NO: 115 is the cDNA sequence of the Ct-875 from *Chlamydia trachomatis*, serovar G.

SEQ ID NO: 116 is the protein sequence of Ct-875 from *Chlamydia trachomatis*, serovar G, which protein is encoded by SEQ ID NO: 115.

SEQ ID NO: 117 is the cDNA sequence of the Ct-875 from *Chlamydia trachomatis*, serovar H.

SEQ ID NO: 118 is the protein sequence of Ct-875 from *Chlamydia trachomatis*, serovar H, which protein is encoded by SEQ ID NO: 117.

SEQ ID NO: 119 is the cDNA sequence of the Ct-875 from *Chlamydia trachomatis*, serovar I.

SEQ ID NO: 120 is the protein sequence of Ct-875 from *Chlamydia trachomatis*, serovar I, which protein is encoded by SEQ ID NO: 119.

SEQ ID NO: 121 is the cDNA sequence of the Ct-875 from *Chlamydia trachomatis*, serovar J.

SEQ ID NO: 122 is the protein sequence of Ct-875 from *Chlamydia trachomatis*, serovar J, which protein is encoded by SEQ ID NO: 121.

SEQ ID NO: 123 is the cDNA sequence of the CT875 from *Chlamydia trachomatis*, serovar K.

SEQ ID NO: 124 is the protein sequence of Ct-875 from *Chlamydia trachomatis*, serovar K, which protein is encoded by SEQ ID NO: 123.

SEQ ID NO: 125 is the cDNA sequence of the Ct-875 from *Chlamydia trachomatis*, serovar L2.

SEQ ID NO: 126 is the protein sequence of Ct-875 from *Chlamydia trachomatis*, serovar L2, which protein is encoded by SEQ ID NO: 125.

Certain of the above sequences and other related *Chlamydia* polypeptides and polynucleotides from a number of serovars are known and available in the art. Further related sequences can be found in issued U.S. Pat. Nos. 6,447,779, 6,166,177, 6,565,856, 6,555,115, 6,432,916, and 6,448,234 and are also disclosed in U.S. patent application Ser. Nos. 10/197,220, 10/762,058 and 10/872,155, each of which is herein incorporated by reference.

The sequence of Ct-089 from serovar D and the potential application of this protein as an antigen has been publicly disclosed, for example in WO02/08267 (Corixa Corporation). The sequence of Ct-089 from serovar L2 was disclosed in WO99/28475 (Genset). The role of CopN (also known as Ct-089) as a putative exported regulator of type III protein secretion systems is discussed in Fields, K A and Hackstadt, *T Mol. Microbiol.* 2000 38(5):1048-1060.

The sequences of Ct-858 and Ct-875 from serovar D are available from the Swiss-Prot database, primary accession numbers 084866 and 084883 respectively. For further information see Stephens, R S et al. *Science* 1998 282:754-759.

The use of Ct-858 as an antigen is disclosed, for example, in WO02/08267 (Corixa Corporation).

The sequence of Ct-875 from serovar E (incorporating a His-tag) and its use as an antigen is disclosed, for example, in US 20040137007. However, the document incorrectly refers to Sequence 139 as being Ct-875, when it is in fact Sequence 140 therein.

Individuals who have been exposed to *Chlamydia trachomatis* have been shown to develop some degree of natural immunity to reinfection, at least in the case of the same serovar (Katz, B P et al. *Sex. Transm. Dis.* 1987 14:160-164), although the extent of protection may depend upon the time elapsed since the prior infection occurred. Age has also been shown to be important in the duration of infection, with older individuals demonstrating a shorter duration of infection by ocular *Chlamydia trachomatis* (Bailey, R et al. *Epidemiol. Infect.* 1999 123:479-486), again suggesting the existence of adaptive immunological protection. It has been suggested that the use of antibiotics may in fact hamper the development of natural immunity to *Chlamydia trachomatis* (Brunham, R C et al. *J. Nat. Rev. Immunol.* 2005 5:149-161).

The major outer membrane protein (Momp) constitutes approximately 60% of the protein mass of the bacterial outer membrane and is believed to be important in the determination of serotype specificity. The amino acid sequence contains four regions which are externally exposed and in which the majority of sequence variations occur. Of the ca. 400 amino acids in the Momp sequence, up to 70 amino acids differ between Momp from different serovars. Particularly surprising is the finding that serovar grouping based on amino acid sequence identity does not correspond to the serovar grouping based on disease state (i.e. ocular, oculogenital and LGV) (Stothard, D R et al. *Infect. Immun.* 1998 66(8):3618-3625). Similarly, nucleotide sequence identity comparisons for the ompA gene which encodes Momp do not correspond to disease states (Meijer, A et al. *J. Bateriol.* 1999 181(15):4469-4475; Lysen, M et al. *J. Clin. Microbiol.* 2004 42(4):1641-1647). Monoclonal antibodies for Momp are effective in culture and in some animal models, however, protection can be limited and is generally serovar specific.

Mice immunised subcutaneously or orally with a monoclonal anti-idiotypic body to the exoglycolipid antigen developed a protective response to serovar C, though remained susceptible to challenge with serovar K (Whittum-Hudson, J A et al. *Nat. Med.* 1996 2(10):1116-1121).

One protein which has been disclosed to date and which shows a high level of sequence homology among different serovars, namely class I accessible protein-1 (referred to as Cap1, or Ct-529), such proteins have potential use in the development of vaccines which stimulate protection against more than one serovar (Fling, S P et al. *PNAS* 2001 98(3): 1160-1165). However, in addition to the requirement for high levels of sequence homology between serovars, proteins of use in vaccines must also elicit sufficient immune response.

Surprisingly, it has been found that *Chlamydia trachomatis* proteins Ct-089, Ct-858 and Ct-875 in particular are both highly antigenic and have a high degree of sequence identity across the different *Chlamydia trachomatis* serovars. There is particularly high conservation in the region of the predicted epitopes. In light of this finding, the possibility exists for the development of *Chlamydia* vaccines which are effective against a broad range of *Chlamydia trachomatis* serovars (i.e. which may be of use in cross-protection).

According to this aspect of the present invention there is provided the use of one or more Chlamydial proteins, immunogenic fragments thereof or polynucleotides encoding them, selected from the list consisting of Ct-089, Ct-858 and Ct-875, and which are derived from a first *Chlamydia trachomatis* serovar, in the manufacture of a vaccine for the treatment or prevention of Chlamydial infection by a second *Chlamydia trachomatis* serovar.

In a further aspect of the present invention there is provided a method for the treatment or prevention of Chlamydial infection by a second *Chlamydia trachomatis* serovar, comprising the administration of a vaccine comprising one or more Chlamydial proteins, immunogenic fragments thereof or polynucleotides encoding them, selected from the list consisting of Ct-089, Ct-858 and Ct-875, and which are derived from a first *Chlamydia trachomatis* serovar.

In one embodiment of the invention the cross-protection vaccine comprises one protein, immunogenic fragment thereof or polynucleotide encoding them, selected from the list consisting of Ct-089, Ct-858 and Ct-875. Vaccines which comprise only one protein, immunogenic fragment thereof or polynucleotide encoding them, selected from the list consisting of Ct-089, Ct-858 and Ct-875 will suitably further comprise at least one additional Chlamydial antigen (for example 1 or 2 additional antigens).

In a second embodiment of the invention the cross-protection vaccine comprises two proteins, immunogenic fragments thereof or polynucleotides encoding them, selected from the list consisting of Ct-089, Ct-858 and Ct-875. For example: Ct-089 and Ct-858; Ct-089 and Ct-875; or Ct-858 and Ct-875.

In a third embodiment of the invention the cross-protection vaccine comprises Ct-089, Ct-858 and Ct-875, immunogenic fragments thereof or polynucleotides encoding them.

The first *Chlamydia trachomatis* serovar may be any *Chlamydia trachomatis* serovar. The second *Chlamydia trachomatis* serovar may be any *Chlamydia trachomatis* serovar, excluding that of the first *Chlamydia trachomatis* serovar.

In one embodiment of the invention the first *Chlamydia trachomatis* serovar is selected from the list consisting of *Chlamydia trachomatis* serovars A, B, Ba, C, D, Da, E, F, G, H, I, Ia, J, Ja, K, L1, L2 and L3. In a second embodiment of the invention the first *Chlamydia trachomatis* serovar is selected from the *Chlamydia trachomatis* ocular serovars (for example A, B, Ba and C). In another embodiment of the invention the first *Chlamydia trachomatis* serovar is selected from the *Chlamydia trachomatis* oculogenital serovars (for example D, Da, E, F, G, H, I, Ia, J, Ja and K). In a further embodiment of the invention the first *Chlamydia trachomatis* serovar is selected from the *Chlamydia trachomatis* LGV serovars (for example L1, L2 and L3).

In one embodiment of the invention the second *Chlamydia trachomatis* serovar is selected from the list consisting of *Chlamydia trachomatis* serovars A, B, Ba, C, D, Da, E, F, G, H, I, Ia, J, Ja, K, L1, L2 and L3. In a second embodiment of the invention the second *Chlamydia trachomatis* serovar is selected from the *Chlamydia trachomatis* ocular serovars (for example A, B, Ba and C). In another embodiment of the invention the second *Chlamydia trachomatis* serovar is selected from the *Chlamydia trachomatis* oculogenital serovars (for example D, Da, E, F, G, H, I, Ia, J, Ja and K). In a further embodiment of the invention the second *Chlamydia trachomatis* serovar is selected from the *Chlamydia trachomatis* LGV serovars (for example L1, L2 and L3).

In order to maximise the breadth of action of the method and use of the present invention, it may be desirable that the first *Chlamydia trachomatis* serovar is selected such that there is a high level of sequence identity (for example at least 90%, especially 95%, in particular 98%, more particularly 99% sequence identity) with the majority of other *Chlamydia trachomatis* serovars (for example at least 50%, especially 70%, in particular 80%, more particularly 90% of other *Chlamydia trachomatis* serovars).

In order to maximise the practical application of the method and use of the present invention, it may be desirable that the first *Chlamydia trachomatis* serovar is selected such that there is a high level of sequence identity (for example at least 90%, especially 95%, in particular 98%, more particularly 99% sequence identity) with the majority (for example at least 50%, especially 70%, in particular 80%, more particularly 90%) of common *Chlamydia trachomatis* serovars (such as the common ocular serovars, the common oculogenital serovars, the common LGV serovars, or a combination of any two of these serovar groups, for example, the common ocular and oculogentical serovars). Common *Chlamydia trachomatis* ocular serovars include A and B. Common *Chlamydia trachomatis* oculogenital serovars include D, E, F and I (Lan, J et al. *J. Clin. Microbiol.* 1995 33(12):3194-3197; Singh, V et al. *J. Clin. Microbiol.* 2003 41(6):2700-2702). Common *Chlamydia trachomatis* LGV serovars include L2.

In one embodiment of the present invention the first *Chlamydia trachomatis* serovar is *Chlamydia trachomatis* serovar E. In a second embodiment of the invention the first *Chlamydia trachomatis* serovar is *Chlamydia trachomatis* serovar K.

In one embodiment of the invention the second *Chlamydia trachomatis* serovar is selected from *Chlamydia trachomatis* serovars D, J and K (for example *Chlamydia trachomatis* serovar K or J).

In another embodiment of the invention the first *Chlamydia trachomatis* serovar is *Chlamydia trachomatis* serovar E and the second *Chlamydia trachomatis* serovar is selected from *Chlamydia trachomatis* serovars D, J and K (for example *Chlamydia trachomatis* serovar K or J).

In one example of the present invention, where the vaccine comprises Ct-089, an immunogenic fragment thereof or polynucleotide encoding it, derived from *Chlamydia trachomatis* serovar E, the vaccine may be used in the treatment or prophylaxis of infections arising from *Chlamydia trachomatis* serovars A, B, D, G, H, I, J, K or L2; in particular A, B, D, G, H, I or K; especially A or B.

In a second example of the present invention, where the vaccine comprises Ct-858, an immunogenic fragment thereof or polynucleotide encoding it, derived from *Chlamydia trachomatis* serovar E, the vaccine may be used in the treatment or prophylaxis of infections arising from *Chlamydia trachomatis* serovars A, B, D, G, H, I, J, K or L2; in particular J or L2.

In a further example of the present invention, where the vaccine comprises Ct-875, an immunogenic fragment thereof or polynucleotide encoding it, derived from *Chlamydia trachomatis* serovar E, the vaccine may be used in the treatment or prophylaxis of infections arising from *Chlamydia trachomatis* serovars A, B, D, G, H, I, J, K or L2; in particular A, B, D, G, H, I or K.

The first and second *Chlamydia trachomatis* serovars may be associated with the same disease state (for example they may both be ocular serovars or both be oculogenital serovars), or the first and second *Chlamydia trachomatis* serovars may be associated with different disease states (for example the first *Chlamydia trachomatis* serovar may an oculogenital serovar and the second *Chlamydia trachomatis* serovar may be an ocular serovar, or vice versa).

In the event that the vaccine of use in the present invention comprises more than one protein, immunogenic fragment thereof or polynucleotide encoding them, selected from the list consisting of Ct-089, Ct-858 and Ct-875, it should be noted that each protein, immunogenic fragment thereof or polynucleotide encoding them, may optionally be derived from a different first *Chlamydia trachomatis* serovar which may be independently selected.

Cross-protection vaccines of use in the present invention may also comprise additional *Chlamydia* antigens (i.e. antigens other than Ct-089, Ct-858 and Ct-875 proteins, immunogenic fragments thereof or polynucleotides encoding them), for example 1, 2, 3, 4 or 5 other antigens (selected for example from Momp, Ct-622, PmpGpd and PmpDpd). Additional antigens in cross-protection vaccines may also include Ct-089, Ct-858 and Ct-875 proteins, immunogenic fragments thereof or polynucleotides encoding them which are derived from the second serovar.

In a further embodiment of the invention *Chlamydia* polypeptides and polynucleotides that may be used in accordance with the invention include those from serovars associated with trachoma such as serovars A, B, Ba and C.

Thus the compositions according to the invention may employ the polypeptide sequences given above or immunogenic fragments of these, or polynucleotide sequences encoding these which may be for example the polynucleotide sequences given above or fragments of these encoding immunogenic fragments of the polypeptides.

In particular embodiments:

(i) the Ct-089 and Ct-858 components of the composition according to the invention may be a polypeptide having at least 95% homology to the polypeptide of SEQ ID NO: 16 (*C. trachomatis* serovar E) or an immunogenic fragment thereof, or a polypeptide having at least 95% homology to the polypeptide of SEQ ID NO: 6 (*C. trachomatis* serovar E) or an immunogenic fragment thereof, respectively, or polynucleotides encoding these. Alternatively the Ct-089 and Ct-858 components of the composition may show at least 95% homology to any one of the Ct-089 and Ct-858 polypeptide and polynucleotide sequences from other *C. trachomatis* serovars which are described herein.

(ii) A Ct-875 component may be a polypeptide having at least 95% homology to the polypeptide of SEQ ID NO: 8 (*C. trachomatis* serovar E) or an immunogenic fragment thereof, or polynucleotides encoding these.
Alternatively the Ct-875 component of the composition may show at least 95% homology to any one of the Ct-875 polypeptide and polynucleotide sequences from other *C. trachomatis* serovars which are described herein.

(iii) A PmpDpd component may be a polypeptide having at least 95% homology to the polypeptide of SEQ ID NO: 14 (*C. trachomatis* serovar LII) or an immunogenic fragment thereof, or polynucleotides encoding these.

(iv) A PmpGpd component may be a polypeptide having at least 95% homology to the polypeptide of SEQ ID NO: 12 (*C. trachomatis* serovar LII) or an immunogenic fragment thereof, or polynucleotides encoding these.

(v) A Momp component may be a polypeptide having at least 95% homology to the polypeptide of SEQ ID NO: 4 (*C. trachomatis* serovar F) or an immunogenic fragment thereof, or polynucleotides encoding these.

(vi) A Swib component may be a polypeptide having at least 95% homology to the polypeptide of SEQ ID NO: 8 (*C. trachomatis* serovar LII) or an immunogenic fragment thereof, or polynucleotides encoding these.

The antigens described herein include polymorphic variants and conservatively modified variations, as well as interstrain and interspecies *Chlamydia* homologues. In addition, the antigens described herein include subsequences or truncated sequences.

The antigens described herein may be in the form of fusion proteins. The fusion proteins may also contain additional polypeptides, optionally heterologous peptides from *Chlamydia* or other sources. These antigens may be modified, for example, by adding linker peptide sequences as described below. These linker peptides may be inserted between one or more polypeptides which make up each of the fusion proteins.

The antigens described herein may also be in the form of chemical conjugates.

The invention further relates to immunogenic compositions and vaccine compositions comprising the compositions of *Chlamydia* antigens according to the invention, together with a pharmaceutically acceptable carrier and optionally an immunostimulant. The compositions of the present invention may further comprise other components designed to enhance the antigenicity of the antigens or to improve these antigens in other aspects, for example, the isolation of these antigens through addition of a stretch of histidine residues at one end of the antigen. The addition of a stretch of histidine residues at one end of the antigen may also improve expression. The compositions of the invention can comprise additional copies of antigens, or additional polypeptides or polynucleotides from *Chlamydia* sp. The compositions of the invention can also comprise additional heterologous polypeptides or polynucleotides from other non-Chlamydia sources. For example, the compositions of the invention can include polypeptides or nucleic acids encoding polypeptides, wherein the polypeptide enhances expression of the antigen, e.g., NS1, an influenza virus protein, or an immunogenic portion thereof (see, e.g. WO99/40188 and WO93/04175). The nucleic acids of the invention can be engineered based on codon preference in a species of choice, e.g., humans.

The compositions of the invention may further comprise adjuvants, e.g., MPL, 3D-MPL, IFA, ENHANZYN (Detox), QS21, CWS, TDM, AGP, CPG, Leif, saponin, and saponin mimetics, and derivatives thereof. Alternatively or in addition, the compositions of the invention can comprise BCG or Pvac as an adjuvant.

DEFINITIONS

"Fusion polypeptide" or "fusion protein" refers to a protein having at least two *Chlamydia* polypeptides (which may be the same, or may be different) covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. This term also refers to conservatively modified variants, polymorphic variants, alleles, mutants, subsequences, interspecies homologs, and immunogenic fragments of the antigens that make up the fusion protein. Fusion proteins of the invention can also comprise additional copies of a component antigen or immunogenic fragment thereof.

A polynucleotide sequence encoding a fusion protein of the invention hybridizes under stringent conditions to at least two nucleotide sequences, each encoding an antigen polypeptide selected from the group consisting of Ct-681 (Momp) or an immunogenic fragment thereof, Ct-871 (PmpG) or an immunogenic fragment thereof, Ct-812 (PmpD) or an immunogenic fragment thereof, Ct-089 or an immunogenic fragment thereof, Ct-858 or an immunogenic fragment thereof, Ct-875 or an immunogenic fragment thereof, Ct-460 (swib) or an immunogenic fragment thereof, and Ct-622 or an immunogenic fragment thereof. The polynucleotide sequences encoding the individual antigens of the fusion polypeptide therefore include conservatively modified variants, polymorphic variants, alleles, mutants, subsequences, immunogenic fragments, and interspecies homologs of Ct-681 (Momp), Ct-871 (PmpG), Ct-812 (PmpD), Ct-089, Ct-858, Ct-875, Ct-460 (swib), and Ct-622. The polynucleotide sequences encoding the individual polypeptides of the fusion protein can be in any order.

In some embodiments, the individual polypeptides of the fusion protein are in order (N- to C-terminus) from large to small. Large antigens are approximately 30 to 150 kD in size, medium antigens are approximately 10 to 30 kD in size, and small antigens are approximately less than 10 kD in size. The sequence encoding the individual polypeptide may be as small as, e.g., an immunogenic fragment such as an individual CTL epitope encoding about 8 to 9 amino acids, or, e.g., an HTL or B cell epitope. The fragment may also include multiple epitopes.

A fusion polypeptide of the invention specifically binds to antibodies raised against at least two antigen polypeptides selected from Ct-681 (Momp) or an immunogenic fragment thereof, Ct-871 (PmpG) or an immunogenic fragment thereof, Ct-812 (PmpD) or an immunogenic fragment thereof, Ct-089 or an immunogenic fragment thereof, Ct-858 or an immunogenic fragment thereof, Ct-875 or an immunogenic fragment thereof, Ct-460 (swib) or an immunogenic fragment thereof, and Ct-622 or an immunogenic fragment thereof. The antibodies can be polyclonal or monoclonal. Optionally, the fusion polypeptide specifically binds to antibodies raised against the fusion junction of the antigens, which antibodies do not bind to the antigens individually, i.e., when they are not part of a fusion protein. The fusion polypeptides optionally comprise additional polypeptides, e.g., three, four, five, six, or more polypeptides, up to about 25 polypeptides, optionally heterologous polypeptides or repeated homologous polypeptides, fused to the at least two antigens. The additional polypeptides of the fusion protein are optionally derived from *Chlamydia* as well as other sources, such as other bacterial, viral, or invertebrate, vertebrate, or mammalian sources. The individual polypeptides of the fusion protein can be in any order. As described herein, the fusion protein can also be linked to other molecules, including additional polypeptides. The compositions of the invention can also comprise additional polypeptides that are unlinked to the fusion proteins of the invention. These additional polypeptides may be heterologous or homologous polypeptides.

The term "fused" refers to the covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

"FL" refers to full-length, i.e., a polypeptide that is the same length as the wild-type polypeptide.

The term "immunogenic fragment thereof" refers to a polypeptide comprising an epitope that is recognized by cytotoxic T lymphocytes, helper T lymphocytes or B cells. Methods of determining epitope regions of a sequence are described elsewhere herein. Suitably, the immunogenic fragment will comprise at least 30%, suitably at least 50%, especially at least 75% and in particular at least 90% (e.g. 95% or 98%) of the amino acids in the reference sequence. The immunogenic fragment will suitably comprise all of the epitope regions of the reference sequence.

An adjuvant refers to the components in a vaccine or therapeutic composition that increase the specific immune response to the antigen (see, e.g., Edelman, *AIDS Res. Hum Retroviruses* 8:1409-1411 (1992)). Adjuvants induce immune responses of the Th1-type and Th-2 type response. Th1-type cytokines (e.g., IFN-γ, IL-2, and IL-12) tend to favor the induction of cell-mediated immune response to an administered antigen, while Th-2 type cytokines (e.g., IL-4, IL-5, Il-6, IL-10 and TNF-β) tend to favor the induction of humoral immune responses. Any of a variety of adjuvants may be employed in the vaccines of this invention to enhance the immune response. Some adjuvants contain a substance designed to protect the antigen from rapid catabolism, such as aluminum hydroxide or mineral oil, and a specific or nonspecific stimulator of immune responses, such as lipid A, *Bortadella pertussis* or *Mycobacterium tuberculosis*. Suitable adjuvants are commercially available and include, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A, quil A, SBAS1c, SBAS2 (Ling et al., 1997, Vaccine 15:1562-1567), SBAS7, Al(OH)$_3$ and CpG oligonucleotide (WO96/02555). Suitable adjuvants for use in the invention are discussed in more detail below.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

A polynucleotide of the invention may contain a number of silent variations (for example, 1-5, in particular 1 or 2, and especially 1 codon(s) may be altered) when compared to the reference sequence. A polynucleotide of the invention may contain a number of non-silent conservative variations (for example, 1-5, in particular 1 or 2, and especially 1 codon(s) may be altered) when compared to the reference sequence. Those skilled in the art will recognise that a particular polynucleotide sequence may contain both silent and non-silent conservative variations.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

A polypeptide of the invention may contain a number of conservative variations (for example, 1-5, in particular 1 or 2, and especially 1 amino acid residue(s) may be altered) when compared to the reference sequence. In general, such conservative substitutions will fall within one of the amino-acid groupings specified below, though in some circumstances other substitutions may be possible without substantially affecting the immunogenic properties of the antigen. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Suitably amino-acid substitutions are restricted to non-epitope regions of an antigen.

Polypeptide sequence variants may also include those wherein additional amino acids are inserted compared to the reference sequence, for example, such insertions may occur at 1 or 2 locations (suitably 1) and may involve the addition of 50 or fewer amino acids (such as 20 or fewer, in particular 10 or fewer, especially 5 or fewer) at each location. Suitably such insertions so not occur in the region of an epitope, and do not therefore have a significant impact on the immunogenic properties of the antigen. One example of insertions includes a short stretch of histidine residues (e.g. 1-6 residues) to aid expression and/or purification of the antigen in question.

Other polypeptide sequence variants include those wherein amino acids have been deleted compared to the reference sequence, for example, such deletions may occur at 1 or 2 locations (suitably 1) and may, for example, involve the deletion of 50 or fewer amino acids (such as 20 or fewer, in particular 10 or fewer, especially 5 or fewer) at each location. Suitably such insertions so not occur in the region of an epitope, and do not therefore have a significant impact on the immunogenic properties of the antigen.

Methods of determining the epitope regions of an antigen are described and exemplified elsewhere herein.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes, "Overview of principles of hybridization and the strategy of nucleic acid assays"* (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to fusion proteins can be selected to obtain only those polyclonal antibodies that are specifically immunoreactive with fusion protein and not with individual components of the fusion proteins. This selection may be achieved by subtracting out antibodies that cross-react with the individual antigens. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

Polynucleotides may comprise a native sequence (i.e., an endogenous sequence that encodes an individual antigen or a portion thereof) or may comprise a variant of such a sequence. Polynucleotide variants may contain one or more substitutions, additions, deletions and/or insertions such that the biological activity of the encoded fusion polypeptide is not diminished, relative to a fusion polypeptide comprising native antigens. Variants preferably exhibit at least about 70% identity, more preferably at least about 80% identity and most preferably at least about 90% identity to a polynucleotide sequence that encodes a native polypeptide or a portion thereof.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, or 95% (e.g. 98%) identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 25 to about 50 amino acids or nucleotides in length, or optionally over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 25 to 500, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted by, for example, the local homology algorithm of Smith & Waterman, *Adv. Appl. Math.* 2:482 (1981), by the homology alignment algorithm of Needleman & Wunsch, *J.*

*Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, $M=5$, $N=-4$, and a comparison of both strands.

The BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

The terms "isolated," "purified," or "biologically pure" therefore refer to material that is substantially or essentially free from components that normally accompany it as found in its native state. Of course, this refers to the DNA segment as originally isolated, and does not exclude other isolated proteins, genes, or coding regions later added to the composition by the hand of man. Purity and homogeneity are typically determined using analytical chemistry techniques such as polyacrylamide gel electrophoresis or high performance liquid chromatography. A protein that is the predominant species present in a preparation is substantially purified. An isolated nucleic acid is separated from other open reading frames that flank the gene and encode proteins other than the gene.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a *Chlamydia* antigen or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotide Identification and Characterization

Polynucleotides may be identified, prepared and/or manipulated using any of a variety of well-established techniques. For example, a polynucleotide may be identified, as described in more detail below, by screening a microarray of cDNAs. Such screens may be performed, for example, using a Synteni microarray (Palo Alto, Calif.) according to the manufacturer's instructions (and essentially as described by Schena et al., *Proc. Natl. Acad. Sci. USA* 93:10614-10619 (1996) and Heller et al., *Proc. Natl. Acad. Sci. USA* 94:2150-2155 (1997)). Alternatively, polynucleotides may be amplified from cDNA prepared from cells expressing the proteins described herein, such as *C. trachomatis* cells. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a full-length gene from a suitable library (e.g., a *C. trachomatis* cDNA library) using well-known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well-known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual* (1989)). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full-length cDNA molecule can be generated by ligating suitable fragments, using well-known techniques.

Alternatively, there are numerous amplification techniques for obtaining a full-length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22-30 nucleotides in length have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186 (1988)), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR*

*Methods Applic.* 1:111-19 (1991)) and walking PCR (Parker et al., *Nucl. Acids. Res.* 19:3055-60 (1991)). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life that is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al., *Nucl. Acids Res. Symp. Ser.* pp. 215-223 (1980), Horn et al., *Nucl. Acids Res. Symp. Ser.* pp. 225-232 (1980)). Alternatively, the protein itself may be produced using chemical methods to synthesize the amino acid sequence of a polypeptide, or a portion thereof. For example, peptide synthesis can be performed using various solid-phase techniques (Roberge et al., *Science* 269:202-204 (1995)) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, *Proteins, Structures and Molecular Principles* (1983)) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector that contains the necessary elements for the transcription and translation of the inserted coding sequence. Methods that are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning, A Laboratory Manual* (1989), and Ausubel et al., *Current Protocols in Molecular Biology* (1989).

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke &Schuster, *J. Biol. Chem.* 264:5503-5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. Other vectors containing constitutive or inducible promoters include GAP, PGK, GAL and ADH. For reviews, see Ausubel et al. (supra), Grant et al., *Methods Enzymol.* 153:516-544 (1987) and Romas et al. *Yeast* 8 423-88 (1992).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in *McGraw Hill Yearbook of Science and Technology pp.* 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers that are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines that stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-32 (1977)) and adenine phosphoribosyltransferase (Lowy et al., *Cell* 22:817-23 (1990)) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques that include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences that direct secretion of the encoded polypeptide through a prokaryotic or eukaryotic cell membrane. Other recombinant constructions may be used to join sequences encoding a polypeptide of interest to nucleotide sequence encoding a polypeptide domain that will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath et al., *Prot. Exp. Purif.* 3:263-281 (1992) while the enterokinase cleavage site provides a means for purifying the desired polypeptide from the fusion protein. A discussion of vectors which contain fusion proteins is provided in Kroll et al., *DNA Cell Biol.* 12:441-453 (1993)).

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

In Vivo Polynucleotide Delivery Techniques

In additional embodiments, genetic constructs comprising the compositions of polynucleotides of the invention are introduced into cells in vivo. This may be achieved using any of a variety or well-known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus & Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, U K) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus & Horwitz, 1992; Graham & Prevec, 1992). Recently, animal studies suggested that recombinant adenovirus could be used for gene therapy (Stratford-Perricaudet & Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993).

2. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas & Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

3. Adeno-Associated Viruses

AAV (Ridgeway, 1988; Hermonat & Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka & McLaughlin, 1988).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat & Muzyczka, 1984).

There are several factors that prompted researchers to study the possibility of using rAAV as an expression vector. One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., 1988), lentiviruses, polioviruses and herpes viruses may be employed. They offer several attractive features for various mammalian cells (Friedmann, 1989; Ridgeway, 1988; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Additional 'viral' vectors include virus like particles (VLPs) and phages.

5. Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984)

successfully injected polyomavirus DNA in the form of calcium phosphate precipitates into liver and spleen of adult and newborn mice demonstrating active viral replication and acute infection. Benvenisty & Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

Polypeptide Compositions

The present invention provides polypeptide compositions as described herein. Generally, a polypeptide composition of the invention will be a combination of isolated polypeptides or immunogenic fragments thereof. Alternatively, some or all of the polypeptide antigens in an inventive composition may be within a fusion protein. For example, in an inventive composition comprising three antigens: (i) the antigens may be provided in the form of three isolated polypeptides (ii) all three polypeptides antigens may be provided in a single fusion protein (iii) two of the antigens may be provided in a fusion protein, with the third provided in isolated form. The polypeptides of the combination may be encoded by a polynucleotide sequence or sequences disclosed herein or a sequence or sequences that hybridize under moderately stringent conditions to a polynucleotide sequence or sequences disclosed herein. Alternatively, the polypeptides may be defined as polypeptides each comprising a contiguous amino acid sequence from an amino acid sequence disclosed herein, or which polypeptides each comprise an entire amino acid sequence disclosed herein.

Immunogenic portions may generally be identified using well-known techniques, such as those summarized in Paul, Fundamental Immunology, 3rd ed., 243-247 (1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques. An immunogenic portion of a Chlamydia sp. protein is a portion that reacts with such antisera and/or T-cells at a level that is not substantially less than the reactivity of the full-length polypeptide (e.g., in an ELISA and/or T-cell reactivity assay). Such immunogenic portions may react within such assays at a level that is similar to or greater than the reactivity of the full-length polypeptide. Such screens may generally be performed using methods well known to those of ordinary skill in the art, such as those described in Harlow & Lane, Antibodies: A Laboratory Manual (1988). For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Polypeptides may be prepared using any of a variety of well-known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are E. coli, yeast or a mammalian cell line such as COS or CHO. Supernatants from suitable host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Polypeptides of the invention, immunogenic fragments thereof which may have for example less than about 100 amino acids, or less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146 (1963). Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known protein. Such a fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Thus, a fusion protein may be expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides. Typically fusion proteins comprising two or more antigens may omit the initiation codon (Met) from the second and subsequent antigens.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46 (1985); Murphy et al., *Proc. Natl. Acad. Sci. USA* 83:8258-8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Thus the compositions according to the invention may comprise one or more fusion proteins. Such proteins comprise a polypeptide component of the composition as described herein together with an unrelated immunogenic protein. The immunogenic protein may for example be capable of eliciting a recall response. Examples of such proteins include tetanus, tuberculosis and hepatitis proteins (see, e.g., Stoute et al., *New Engl. J. Med.* 336:86-91 (1997)).

Within certain embodiments, an immunological fusion partner is derived from protein D, a surface protein of the gram-negative bacterium *Haemophilus influenza* B (WO 91/18926). A protein D derivative may comprise approximately the first third of the protein (e.g., the first N-terminal 100-110 amino acids), and a protein D derivative may be lipidated. Within certain embodiments, the first 109 residues of a lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798 (1992)). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

T Cells

Immunotherapeutic compositions may also, or alternatively, comprise T cells specific for a *Chlamydia* antigen. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide of the invention, polynucleotide encoding such a polypeptide, and/or an antigen presenting cell (APC) that expresses such a polypeptide. Such stimulation is performed under conditions and for a time sufficient to permit the generation of T cells that are specific for the polypeptide. Preferably, the polypeptide or polynucleotide is present within a delivery vehicle, such as a microsphere, to facilitate the generation of specific T cells.

T cells are considered to be specific for a polypeptide of the invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070 (1994)). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the invention (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., *Current Protocols in Immunology*, vol. 1 (1998)). T cells that have been activated in response to a polypeptide, polynucleotide or polypeptide-expressing APC may be CD4+ and/or CD8+. Protein-specific T cells may be expanded using standard techniques. Within preferred embodiments, the T cells are derived from a patient, a related donor or an unrelated donor, and are administered to the patient following stimulation and expansion.

For therapeutic purposes, CD4+ or CD8+ T cells that proliferate in response to a polypeptide, polynucleotide or APC can be expanded in number either in vitro or in vivo. Proliferation of such T cells in vitro may be accomplished in a variety of ways. For example, the T cells can be re-exposed to a polypeptide, or a short peptide corresponding to an immunogenic portion of such a polypeptide, with or without the addition of T cell growth factors, such as interleukin-2, and/or stimulator cells that synthesize the polypeptide. Alternatively, one or more T cells that proliferate in the presence of the protein can be expanded in number by cloning. Methods for cloning cells are well known in the art, and include limiting dilution.

Diagnostic Methods

Prior infection of an individual by *Chlamydia* will often be detectable by ELISA. Individuals carrying *Chlamydia* specific antibodies ('seropositive') having been infected previously. However, it is not uncommon for individuals who have been infected by *Chlamydia* previously to be found to be seronegative upon testing, i.e. no *Chlamydia* specific antibodies may be detected. As a result of the prior infection, despite testing seronegative, such individuals respond strongly to restimulation by Chlamydial antigens (relative to seronegative individuals which have not previously been infected), in particular to the various Chlamydial antigen combinations which have been described previously herein.

Therefore, in a further aspect of the present invention there is provided a method for determining prior Chlamydial infection in an individual comprising:

(i) obtaining a sample from the individual;
(ii) contacting said sample with a combination of two or more *Chlamydia* proteins or immunogenic fragments thereof or a polynucleotide or polynucleotides encoding them, said two or more proteins or immunogenic fragments selected from Swib, Momp, Ct-858, Ct-875, Ct-622, Ct-089, passenger domain of PmpG (PmpGpd) and passenger domain of PmpD (PmpDpd);
(iii) quantifying the sample response.

The sample may for example be whole blood or purified cells. Suitably the sample will contain peripheral blood mononucleated cells (PBMC). In one embodiment of the invention the individual will be seropositive. In a second embodiment of the invention the individual will be seronegative.

The sample response may be quantified by a range of means known to those skilled in the art, including the monitoring of lymphocyte proliferation or the production of specific cytokines or antibodies in the presence of the combination of Chlamydial antigens. For example, T-cell ELISPOT may be used to monitor cytokines such as interferon gamma (IFNγ), interleukin 2 (IL2) and interleukin 5 (IL5). B-cell ELLISPOT may be used to monitor the stimulation of *Chlamydia* specific antigens.

Methods of quantifying sample response are illustrated in the Examples herein (specifically Example 9). When using such method, a positive response to an antigen may be defined by a signal to noise ratio (S/N ratio) of at least 2:1 (for example, at least 3:1).

In a further aspect of the present invention methods are provided for using one or more of the antigen combinations (or immunogenic fragments thereof or nucleotides encoding them) described above to diagnose prior Chlamydial infection using a skin test. As used herein, a "skin test" is any assay performed directly on a patient in which a delayed-type hypersensitivity (DTH) reaction (such as swelling, reddening or dermatitis) is measured following intradermal injection of an antigen combination (or immunogenic fragments thereof or nucleotides encoding them) as described above. Such injection may be achieved using any suitable device sufficient to contact the antigen combinations with dermal cells of the patient, such as a tuberculin syringe or 1 mL syringe. The reaction is measured after a period of time, for example at least 48 hours after injection, especially 48-72 hours.

The DTH reaction is a cell-mediated immune response, which is greater in patients that have been exposed previously to the test antigen. The response may be measured visually, using a ruler. In general, a response that is greater than about 0.5 cm in diameter, especially greater than about 1.0 cm in diameter, is a positive response, indicative of prior Chlamydial infection, which may or may not be manifested as an active disease.

For use in a skin test, the combinations of this invention are suitably formulated as pharmaceutical compositions containing a physiologically acceptable carrier. Suitably, the carrier employed in such pharmaceutical compositions is a saline solution with appropriate preservatives, such as phenol and/or Tween 80™.

Pharmaceutical Compositions

In additional embodiments, the present invention concerns formulation of the polynucleotide, polypeptide, T-cell and/or antibody compositions disclosed herein in pharmaceutically-acceptable or physiologically-acceptable solutions for administration to a cell or an animal, either alone, or in combination with one or more other modalities of therapy. Such compositions are also useful for diagnostic uses.

It will also be understood that, if desired, the nucleic acid segments, RNA, DNA or PNA compositions that express a composition of polypeptides as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation. Other routes of administration include via the mucosal surfaces, for example intravaginal administration.

1. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In certain circumstances it will be desirable to deliver the pharmaceutical compositions disclosed herein parenterally, intravenously, intramuscularly, or even intraperitoneally as described in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Mucosal Delivery (i) Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

(ii) Intravaginal Delivery

In other embodiments of the invention the pharmaceutical compositions may be formulated for intravaginal delivery. Such formulations may be prepared as liquids, semi-solids or solids (including for example, creams, ointments, gels etc), or may be contained within a physical delivery system such as a pessary, sponge, vaginal ring or film.

(iii) Ocular Delivery

In further embodiments of the invention the pharmaceutical compositions may be formulated for ocular delivery. Such formulations will desirably be clear and colorless.

5. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon & Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath & Martin, 1986; Heath et al., 1986; Balazsovits et al., 1989; Fresta & Puglisi, 1996), radiotherapeutic agents (Pikul et al., 1987), enzymes (Imaizumi et al., 1990a; Imaizumi et al., 1990b), viruses (Faller & Baltimore, 1984), transcription factors and allosteric effectors (Nicolau & Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori & Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention. Such particles may be are easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety).

Vaccines

In certain preferred embodiments of the present invention, vaccines are provided. The vaccines will generally comprise one or more pharmaceutical compositions, such as those discussed above, in combination with an immunostimulant. An immunostimulant may be any substance that enhances or potentiates an immune response (including antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., *Vaccine Design* (the subunit and adjuvant approach) (1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

Illustrative vaccines may contain DNA encoding two or more of the polypeptides as described above, such that the polypeptides are generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198 (1998), and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317-321 (1989); Flexner et al., Ann. N.Y. Acad. Sci. 569:86-103 (1989); Flexner et al., *Vaccine* 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627 (1988); Rosenfeld et al., *Science* 252:431-434 (1991); Kolls et al., *Proc. Natl. Acad. Sci. USA* 91:215-219 (1994); Kass-Eisler et al., *Proc. Natl. Acad. Sci. USA* 90:11498-11502 (1993); Guzman et al., *Circulation* 88:2838-2848 (1993); and Guzman et al., *Cir. Res.* 73:1202-1207 (1993). Techniques for incorporating DNA into such expression systems are well known to those of ordinary skill in the art. The DNA may also be "naked," as described, for example, in Ulmer et al., *Science* 259:1745-1749 (1993) and reviewed by Cohen, *Science* 259:1691-1692 (1993). The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

It will be apparent that a vaccine may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the vaccine compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium* species or *Mycobacterium* derived proteins. For example, delipidated, deglycolipidated *M. vaccae* ("pVac") can be used. In another embodiment, BCG is used as an adjuvant. In addition, the vaccine can be administered to a subject previously exposed to BCG. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition may be designed to induce an immune response predominantly of the Th1 type. High levels of Th1-type cytokines (e.g., IFN-γ, TNFα, IL-2 and IL-12) tend to favor the induction of cell-mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within one embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann & Coffman, *Ann. Rev. Immunol.* 7:145-173 (1989).

Suitable adjuvants for use in eliciting a predominantly Th1-type response include, for example, a combination of monophosphoryl lipid A, for example 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352 (1996). Another suitable adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other suitable formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol containing liposomes, as described in WO 96/33739. Other suitable formulations comprise an oil-in-water emulsion and tocopherol. Another suitable adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 as disclosed in WO 00/09159. Preferably the formulation additionally comprises an oil in water emulsion and tocopherol.

Other suitable adjuvants include Montanide ISA 720 (Seppic, France), SAF (Chiron, Calif., United States), ISCOMS (CSL), MF-59 (Chiron), the SBAS series of adjuvants (SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other suitable adjuvants include adjuvant molecules of the general formula (I):

wherein, n is 1-50, A is a bond or —C(O)—, R is $C_{1\text{-}50}$ alkyl or Phenyl $C_{1\text{-}50}$ alkyl.

A further adjuvant of interest is shiga toxin b chain, used for example as described in WO2005/112991.

One embodiment of the present invention consists of a vaccine formulation comprising a polyoxyethylene ether of general formula (I), wherein n is between 1 and 50, preferably 4-24, most preferably 9; the R component is $C_{1\text{-}50}$, preferably $C_4$-$C_{20}$ alkyl and most preferably $C_{1\text{-}2}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

Any vaccine provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429-1438 (1996)) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see, e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain embodiments of the present invention use dendritic cells or progenitors thereof as antigen-presenting cells. Dendritic cells are highly potent APCs (Banchereau & Steinman, *Nature* 392:245-251 (1998)) and have been shown to be effective as a physiological adjuvant for eliciting prophylactic or therapeutic antitumor immunity (see Timmerman & Levy, *Ann. Rev. Med.* 50:507-529 (1999)). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600 (1998)).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allow a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1 BB).

APCs may generally be transfected with a polynucleotide encoding a protein (or portion or other variant thereof) such that the polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and Cell Biology* 75:456-460 (1997). Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a protein in a biological sample. Such kits generally comprise at least one oligonucleotide probe or primer, as described above, that hybridizes to a polynucleotide encoding a protein. Such an oligonucleotide may be used, for example, within a PCR or hybridization assay. Additional components that may be present within such kits include a second oligonucleotide and/or a diagnostic reagent or container to facilitate the detection of a polynucleotide encoding a protein of the invention.

Other diagnostics kits include those designed for the detection of cell mediated responses (which may, for example, be of use in the diagnostic methods of the present invention). Such kits will typically comprise:
 (i) apparatus for obtaining an appropriate cell sample from a subject;
 (ii) means for stimulating said cell sample with a combination of *Chlamydia* antigens according to the present invention (or immunogenic fragments thereof, or DNA encoding such antigens or fragments);
 (iii) means for detecting or quantifying the cellular response to stimulation.

Suitable means for quantifying the cellular response include a B-cell ELISPOT kit or alternatively a T-cell ELISPOT kit, which are known to those skilled in the art.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1

Expression and Purification of *Chlamydia trachomatis* Recombinant Proteins

Several *Chlamydia trachomatis* genes were cloned into plasmid incorporating a 6× histidine tag at the N-terminal to allow for expression and purification of recombinant protein.

Two full-length recombinant proteins, Ct-622 and Ct-875, were expressed in *E. coli*. Both of these genes were identified using CtL2 and CtE expression screening and the serovar E homologues were expressed. The primers used to amplify these genes were based on serovar L2/E sequences. The genes were amplified using serovar E genomic DNA as the template. Once amplified, the fragments were cloned in pET-17b with a N-terminal 6×-His Tag. After transforming the recombinant plasmid in XL-I blue cells, the DNA was prepared and the clones fully sequenced. The DNA was then transformed into the expression host BL21-pLysS (Novagen) for production of the recombinant proteins. The proteins were induced with IPTG and purified on Ni-NTA agarose using standard methods. The DNA sequences for CTE622 and CTE875 are disclosed in SEQ ID NO: 9 and 7 respectively, and their amino acid sequences are disclosed in SEQ ID NO: 10 and 8, respectively.

One full-length recombinant protein, Ct-089, was expressed in *E. coli*. The gene was identified using CtL2 expression screening but the serovar E homologue was expressed. The primers used to amplify this gene was based on serovar L2 sequence. The gene was amplified using serovar E genomic DNA as the template. Once amplified, the fragment was cloned in pET-17b with a N-terminal 6×-His Tag. After transforming the recombinant plasmid in XL-I blue cells, the DNA was prepared and the clone fully sequenced. The DNA was then transformed into the expression host BL21-pLysS cells (Novagen) for production of the recombinant proteins. The protein was induced with IPTG and purified on Ni-NTA agarose using standard methods.

One full-length recombinant protein, Ct-460, was expressed in *E. coli*. The gene was identified using CtL2 and CTE expression screening but the serovar L2 homologue was expressed. The primers used to amplify this gene was based on serovar L2 sequence. The genes were amplified using serovar L2 genomic DNA as the template. Once amplified, the fragment was cloned in pET-17b with a N-terminal 6×-His Tag. After transforming the recombinant plasmid in XL-I blue cells, the DNA was prepared and the clone fully sequenced. The DNA was then transformed into the expression host BL21-pLysE cells (Novagen) for production of the recombinant proteins. The protein was induced with IPTG and purified on Ni-NTA agarose using standard methods.

One full-length recombinant protein, Ct-858, was expressed in *E. coli*. The gene was identified using CtL2 and CTE expression screening but the serovar E homologue was expressed. The primers used to amplify this gene was based on serovar L2/E sequence. The genes were amplified using serovar E genomic DNA as the template. Once amplified, the fragment was cloned in pCRX2 with a N-terminal 6×-His Tag. After transforming the recombinant plasmid in XL-I blue cells, the DNA was prepared and the clone fully sequenced. The DNA was then transformed into the expression host Tuner DE3 cells (Novagen) for production of the recombinant proteins. The protein was induced with IPTG and purified on Ni-NTA agarose using standard methods.

One full-length recombinant protein, Ct-681, was expressed in *E. coli*. The gene was identified using CtL2 and CTE expression screening but the serovar F homologue was expressed. Clone/pET-15-construct was obtained from GSK (MompF). Once amplified, the fragment was cloned in pET-15b with a N-terminal 6×-His Tag. After transforming the recombinant plasmid in XL-I blue cells, the DNA was prepared and the clone fully sequenced. The DNA was then transformed into the expression host BL21-pLysS cells for production of the recombinant proteins. The protein was induced with IPTG and purified on Ni-NTA agarose using standard methods.

The passenger domain of two recombinant proteins, Ct-812 and Ct-871, were expressed in *E. coli*. Ct-812 was identified using CtL2 and CtE expression screening and Ct-871 was identified using CtE expression. For both genes the serovar L2 homologues were expressed. The primers used to amplify these genes were based on serovar L2 sequences. The genes were amplified using serovar L2 genomic DNA as the template. Once amplified, the fragments were cloned in pET-17b with a N-terminal 6×-His Tag. After transforming the recombinant plasmid in XL-I blue cells, the DNA was prepared and the clones fully sequenced. The DNA was then transformed into the expression host BL21-pLysS cells (Novagen) for production of the recombinant proteins. The proteins were induced with IPTG and purified on Ni-NTA agarose using standard methods.

Example 2

Formulation of Five Different Combinations of *Chlamydia trachomatis* Antigens with Adjuvant The antigen combinations in the table below were prepared as follows. 5 µg of each antigen was combined in 50 µl of PBS and then mixed with 50 l AS01B adjuvant which comprises 3D-MPL and QS21 formulated with cholesterol containing liposomes, to a total volume per dose of 100 µl.

After mixing with the antigen the final composition of the adjuvant is:

3D-MPL 100 ug/ml

QS21 100 ug/ml

DOPC 2 mg/ml

Cholesterol 0.5 mg/ml

| COMBO | Swib CT460 | Momp CT681 | Ct-858 | Ct-875 | Ct-622 | Ct-089 | PmpGpd CT871 | PmpDpd CT812 |
|---|---|---|---|---|---|---|---|---|
| 1 | X | X | X | | | X | | X |
| 1' | X | | X | | | X | | X |
| 2 | X | X | X | | X | X | | X |
| 3 | | X | X | | X | X | X | X |
| 4 | | X | X | X | X | X | | |
| 5 | | | X | X | | X | | |
| 5' | | | X | X | | X | | X |
| 6 | | X | X | | | X | X | X |

Example 3

Testing of Combinations of *Chlamydia trachomatis* Antigens in a Mouse Model—Immunization Against *Chlamydia* Genital Tract Infection This example demonstrates that vaccination with *Chlamydia* antigen combinations as described in Example 2 can significantly protect against *Chlamydia* infection in mice.

A murine model of genital tract infection with human serovar K strain of *Chlamydia trachomatis* (Ct) was developed that closely resembles the pathology of infection in humans. This model was used to evaluate the effectiveness of immunizing mice with a number of combinations of Ct-specific antigens from different serovars. Specifically, Balb/c mice and C57Bl/6 mice were vaccinated with formulations of adjuvant combinations as described in Example 2. This model was also attempted with a third mouse strain, DBA, but this model did not allow protection against Ct challenge to be demonstrated either in the positive control (UV irradiated chlamydial elementary bodies (UVEB) formulated in AS01B) or in mice vaccinated with the antigen combinations.

Figure 9:
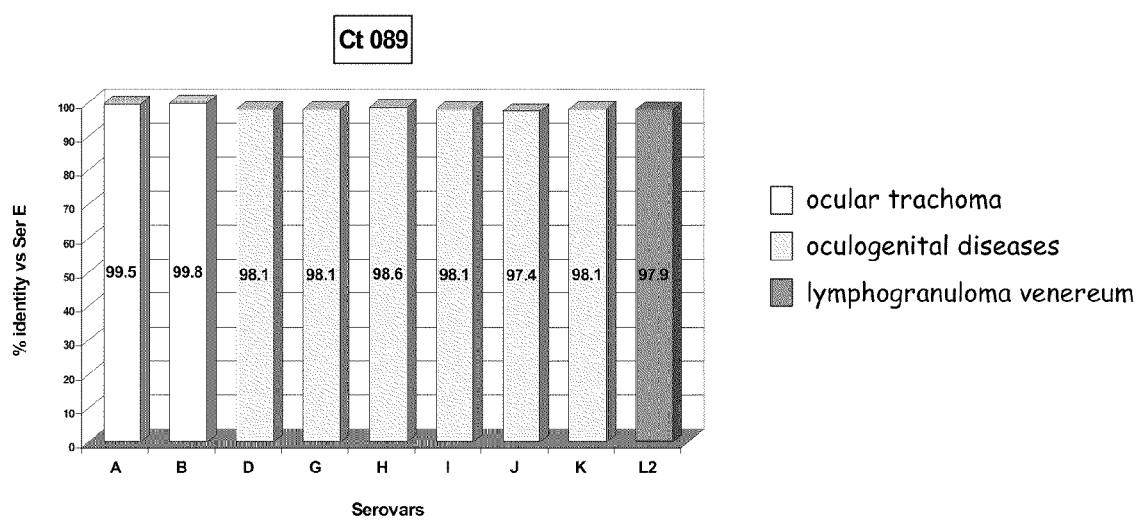
FIG. 9 shows the results of an amino acid sequence identity comparison of Ct-089 from *Chlamydia trachomatis* serovar E with Ct-089 from a range of other *Chlamydia trachomatis* serovars.
Figure 10:
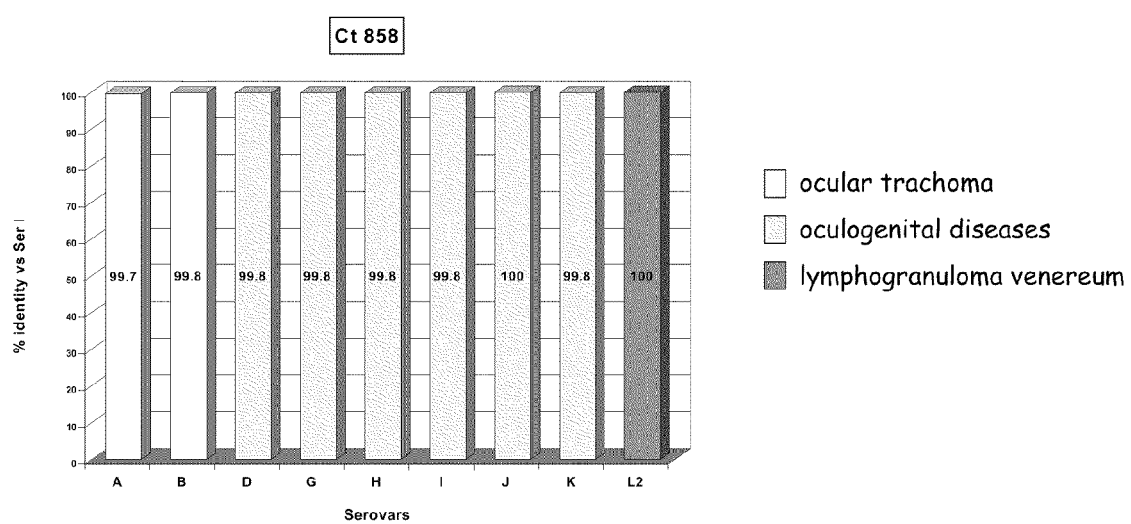
FIG. 10 shows the results of an amino acid sequence identity comparison of Ct-858 from *Chlamydia trachomatis* serovar E with Ct-858 from a range of other *Chlamydia trachomatis* serovars.
Figure 11:
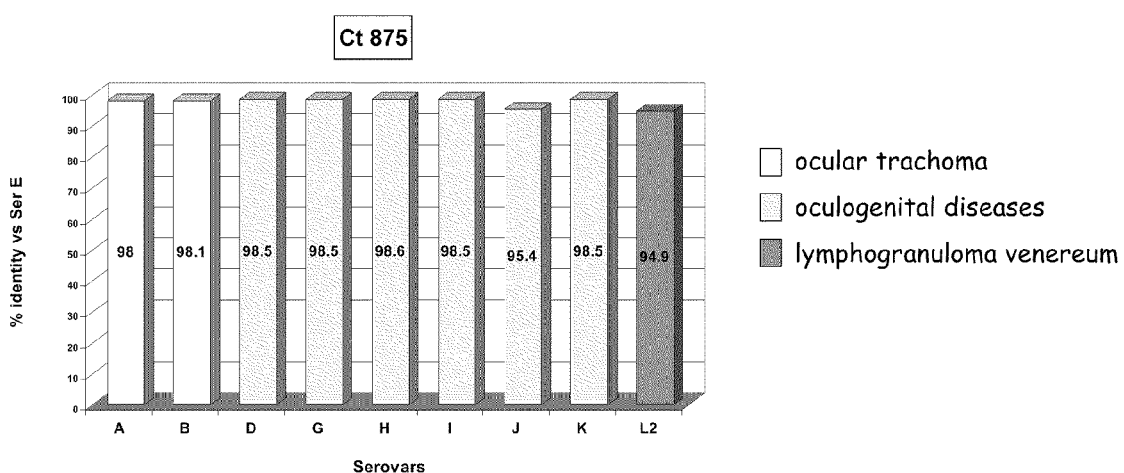
FIG. 11 shows the results of an amino acid sequence identity comparison of Ct-875 from *Chlamydia trachomatis* serovar E with Ct-875 from a range of other *Chlamydia trachomatis* serovars.

Two injections, separated by a three week time interval, were administered to the mice at the base of the tail. Four weeks following the final vaccination, the animals were treated with 1.25 mg of progesterone prior to being intra-vaginally infected with $5 \times 10^5$ Inclusion Forming Units (IFU) of purified *Chlamydia trachomatis*, serovar K. Mice were immunized with 10 g UVEB formulated in AS01B as a positive control and the Results FIG. 9 shows the results of comparison of Ct-089 sequences. FIG. 10 shows the results of comparison of Ct-858 sequences. FIG. 11 shows the results of comparison of Ct-875 sequences.

Ct-089 from *Chlamydia trachomatis* serovar E shows a high level of sequence identity to Ct-089 from *Chlamydia trachomatis* serovars A, B, D, G, H, I, J, K and L2. The minimum level of identity was 97.4%, with eight of the ten serovars having at least 98% identity. The ocular serovars A and B show particularly high identity to serovar E, with values of 99.5% and 99.8% respectively.

Ct-858 from *Chlamydia trachomatis* serovar E shows a very high level of sequence identity to Ct-858 from *Chlamydia trachomatis* serovars A, B, D, G, H, I, J, K and L2. The minimum level of identity was 99.7%, with ocular serovar J and LGV serovar L2 showing complete identity.

Ct-875 from *Chlamydia trachomatis* serovar E shows a high level of sequence identity to Ct-089 from *Chlamydia trachomatis* serovars A, B, D, G, H, I, J, K and L2. The minimum level of identity was 94.9%, with eight of the ten serovars having at least 98% identity.

For each of the three proteins Ct-089, Ct-858 and Ct-875, the percentage of HLA DRB1 predicted epitopes (for serovar E) which are fully conserved across all of the serovars tested is very high and estimated at 77%, 95% and 80%, respectively.

For comparative purposes, FIGS. 12, 13 and 14 show the sequence alignment for Ct-089, Ct-858 and Ct-875 from serovar E respectively with their equivalents from other *Chlamydia trachomatis* serovars and other *Chlamydia* species. Cpn indicates the corresponding sequence from *Chlamydia pneumoniae*, MoPn indicates the corresponding sequence from *Chlamydia muridarum*.

| Ct-089 (Serovar E) amino acid identity | |
|---|---|
| Ct-089 (Serovar D) | 99.8% |
| *C. pneumoniae* - CpN (SEQ ID No 78) | 47.4% |
| *C. muridarum* - MoPn (SEQ ID No 74) | 73.7% |
| Ct-858 (Serovar E) amino acid identity | |
| Ct-858 (Serovar D) | 99.8% |
| Ct-858 (Serovar L2) | 99.8% |
| *C. pneumoniae* - CpN (SEQ ID No 40) | 44.2% |
| *C. muridarum* - MoPn (SEQ ID No 36) | 82.2% |
| Ct-875 (Serovar E) amino acid identity | |
| Ct-875 (Serovar D) | 98.5% |
| *C. muridarum* - MoPn (SEQ ID No 24) | 52.3% |

Conclusion

In summary, each of the three proteins Ct-089, Ct-858 and Ct-875 have highly conserved sequences across all of the *Chlamydia trachomatis* serovars tested.

Furthermore, the data indicates that there is no link between the degree of sequence variation and disease state associated with a particular serovar. For example, in the case of Ct-089, the oculogenital serovar E shows the highest homology to the ocular serovars A and B, while in the case of Ct-858, serovar E shows the highest homology to the oculogenital serovar J and LGV serovar L2.

Sequence homology of Ct-089, Ct-858 and Ct-875 with the equivalent proteins in other *Chlamydia* species is relatively low.

The antigenic properties of Ct-089, Ct-858 and Ct-875 have already been described in the prior art. However, contrary to the expectation of one skilled in the art, as a result of the low sequence variation, vaccines containing Ct-089, Ct-858 and Ct-875, immunogenic fragments thereof or polynucleotides encoding them, and which are derived from a first *Chlamydia trachomatis* serovar may be expected to be of use in the treatment or prevention of Chlamydial infection by a second *Chlamydia trachomatis* serovar.

Example 5

Purification of *Chlamydia trachomatis* Elementary Bodies from Servers D, E, J and K Purified elementary bodies were required for challenge of vaccine test subjects and for the preparation of UV irradiated elementary bodies (UVEB) which are used as a positive control vaccine in later examples.

Method

EB from each of the *Chlamydia trachomatis* serovars were prepared. Briefly, all serovars were grown separately in confluent McCoy cell monolayers and cultured in RPMI medium (75 $cm^2$ culture flasks) that was supplemented with 1 μg/ml of cycloheximide immediately before inoculation. Flasks were inoculated with non-purified lysates from infected cells containing ~$10^6$ to $10^7$ Infectious Forming Units (IFU) in Sucrose Phosphate Glutamic Acid (SPG). Flasks were spun at 2000 rpm for 1 hour in a table-top cell culture centrifuge and then incubated for 48 or 72 hours at 37° C. in a $CO_2$ atmosphere. This process was repeated until there were at least 20 flasks of highly infected cell populations (>80% of cells were infected) ready for purification. *Chlamydia* elementary bodies were purified by ultracentrifugation over a series of Hypaque gradients (30%, 52%, 44% and 40%) with intervening washes in SPG.

Results

The titer of the purified EB for each *Chlamydia trachomatis* serovar was assessed using the *Chlamydia* titration infectivity assay and immunofluorescence microscopy (using FITC-conjugated anti-*C. trachomatis* antibody and Evan's Blue in PBS) to calculate the number of IFU per ml. Titers for the resulting purified EB were found to range from $1.2 \times 10^6$ to $2.6 \times 10^9$ IFU/ml Example 6

Expression and Purification of Ct-089, Ct-858 and Ct-875 Proteins

To prepare the test vaccines, stocks of purified *Chlamydia trachomatis* serovar E for use in later examples Ct-089, Ct-858 and Ct-875 proteins were prepared by expressing their genes in *E. coli*.

Method

Competent *E. coli* strains BL21 plys E, Tuner (DE3) and BL21 plys S were transformed with Ct-089, Ct-858 and Ct-875 expression plasmids respectively and grown on the appropriate antibiotic selection medium. The resulting expression clones were used in a mini-induction protocol, and protein yields analyzed by SDS-PAGE. If cells grew well during this process and proteins were induced by isopropyl-beta-D-thiogalactopyranoside (IPTG) in sufficient quantities to be detected on Coomassie blue-stained SDS gels, the clones were used in a large-scale induction experiment (IPTG, 1 mM).

Following lysis of cells in a CHAPS solution and centrifugation, aliquots of the soluble and pellet fractions were analyzed by SDS-PAGE to determine whether the majority of the protein of interest was in the pellet or soluble fraction. The fraction containing the majority of each antigen was subjected to Ni-NTA column purification (after appropriate solubilisation of proteins). Aliquots of the preparations, including material from before Ni-NTA binding, column flow-through, column washes, and column elution fractions, were analyzed by SDS-PAGE. Fractions containing the eluted protein were combined, dialyzed against 10 mM Tris pH 8 or pH 10, filtered sterilized, and concentrated. The BCA protein assay was used on the concentrated CT protein fractions, and purity was assessed by SDS-PAGE.

Example 7

Evaluation of the Protection Induced by a Vaccine Containing Ct-089, Ct-858 and Ct-875 from *Chlamydia trachomatis* Serovar E Against Challenge with *Chlamydia trachomatis* Serovars D, K and J The protection provided by a vaccine containing Ct-089, Ct-858 and Ct-875 *Chlamydia trachomatis* serovar E antigens was tested in vaginal challenge experiments with EB from heterologous (i.e. non-serovar E) *Chlamydia trachomatis* serovars.

Method

The study was conducted with 63 six-week old female C57Bl/6 mice. These mice were split into three groups of twenty-one mice, each group to be challenged by a different serovar (*Chlamydia trachomatis* serovar D, K, or J). The groups were then further separated into sub-groups of seven mice each. These three sub-groups were immunised intramuscularly with 50 ul of different vaccine preparations injected into each anterior tibialis (100 ul total), and repeated three weeks later. Mice were further treated with progesterone, 1.25 mg given in a volume of 100 ul by subcutaneous injection ten and three days before challenge to synchronise their cycles. The three test preparations were:

(i) Adjuvant Control (AS01B)
  The adjuvant utilised was based upon a liposomal formulation containing 3D-MPL, QS21 and cholesterol. The final composition of the adjuvant solution being:
  3D-MPL 100 ug/ml
  QS21 100 ug/ml
  DOPC 2 mg/ml
  Cholesterol 0.5 mg/ml
  Phosphate buffered saline was prepared from 9 mM $Na_2HPO_4$, 48 mM $KH_2PO_4$ and 100 mM NaCl at pH 6.1.
  A mixture of lipid, cholesterol and 3D-MPL was prepared in organic solvent, this was then dried under vacuum. PBS was then added and the vessel agitated until a suspension formed. This suspension was then microfluidised until a liposome size of around 100 nm was obtained (referred to as small unilamellar vesicles or SUV). Subsequently, the SUV were sterilized by passage through a 0.2 um filter.
  Sterile SUV were mixed with the appropriate quantity of aqueous QS21 (at a concentration of 2 mg./ml) with the addition of phosphate buffered saline to obtain the final desired concentrations. The pH was then adjusted to 6.1 (+/−0.1) as necessary using sodium hydroxide or hydrochloric acid.

(ii) UV Attenuated *Chlamydia trachomatis* Elementary Bodies with AS01B Adjuvant
  A preparation containing 10 ug of UV treated *Chlamydia trachomatis* elementary bodies (UVEB) from serovar E with adjuvant (as described above).

(iii) Ct-089, Ct-858 and Ct-875 with AS01B Adjuvant
  A preparation containing Ct-089 (5 ug), Ct-858 (5 ug) and Ct-875 (5 ug) from *Chlamydia trachomatis* serovar E with adjuvant (as described above).

Mice were challenged, under anaesthetic (1:1 Ketaject and Xylaject), four weeks after final boost with $1\times10^6$ IFU of serovar D, K or J suspended in 20 ul of sucrose phosphate glutamic acid (SPG).

The infection was allowed to proceed for 10 days, with genital swabs were taken under anaesthetic on Day 4 and Day 7. Mice were euthanized on Day 10 and the uterine horns harvested for histopathology and titration. For titration, one-half of the UGT was homogenized, and IFU was determined using McCoy cells.

Samples (vaginal swabs) collected from days 4, 7, and 10 post-challenge were thawed at 37° C. A small amount of glass beads (Sigma) was added to each sample and vortexed for five minutes in 1 ml of SPG. 100 µl of each sample was inoculated onto a monolayer of McCoy cells in medium containing 1 µg/ml cyclohexamide in a 24-well plate. Plates were spun at 2000 rpm for one hour before being transferred to a 37° C. incubator. Time of incubation is 48-72 hours before fixation.

After incubation, methanol that had been pre-chilled at −20° C. was used to fix the cells. Each well was filled with methanol and left at −20° C. for at least 10 minutes. Plates were then washed with PBS three times before staining with Goat anti-*chlamydia trachomatis* FITC conjugated polyclonal antibody (Chemicon). The stain solution consisted of Evan's Blue Stain (Sigma), FITC-conjugated anti-*C. trachomatis* antibody, and PBS. Evan's Blue stain was diluted 1:200 in PBS, and FITC-conjugated anti-*C. trachomatis* antibody was diluted at 1:100. 500 µl of the stain solution was added to each well. Plates were then incubated at 37° C. for 1.5-2 hours.

After the incubation period, the stain was aspirated and the plates were washed with PBS five times on a rocking platform, each time for at least 5 minutes. After the final wash, 1 ml of PBS was added to each well, and the plates were ready to be titered.

There were three methods used for calculating the number of IFU per swab. The primary way consisted of counting 10 random fields under a fluorescence microscope and then using the following formula (s):

$n \times 10 \times 190$ (using objective lens 10x)

$n \times 10 \times 283$ (using objective lens 20x)

$n \times 10 \times 1180$ (using objective lens 40x)

where n=mean of inclusion bodies counted in 10 random fields, 10 is the dilution factor, and 190, 283 and 1180 are the respective focal conversion factors.

The following method was used when low numbers of inclusion bodies were seen in an entire well:

$s \times 10$ where s=number of inclusion bodies counted in a well and 10 is the dilution factor.

Finally, when no inclusion bodies were seen, an arbitrary value of 7 was chosen to represent IFU/swab. This was based on the assumption that although no inclusion bodies were detected in a tenth of the swab, that did not necessarily mean that there were no inclusion bodies in the entire swab.
Results FIGS. 15 to 17 illustrate the results of Example 7.

Figure 15:
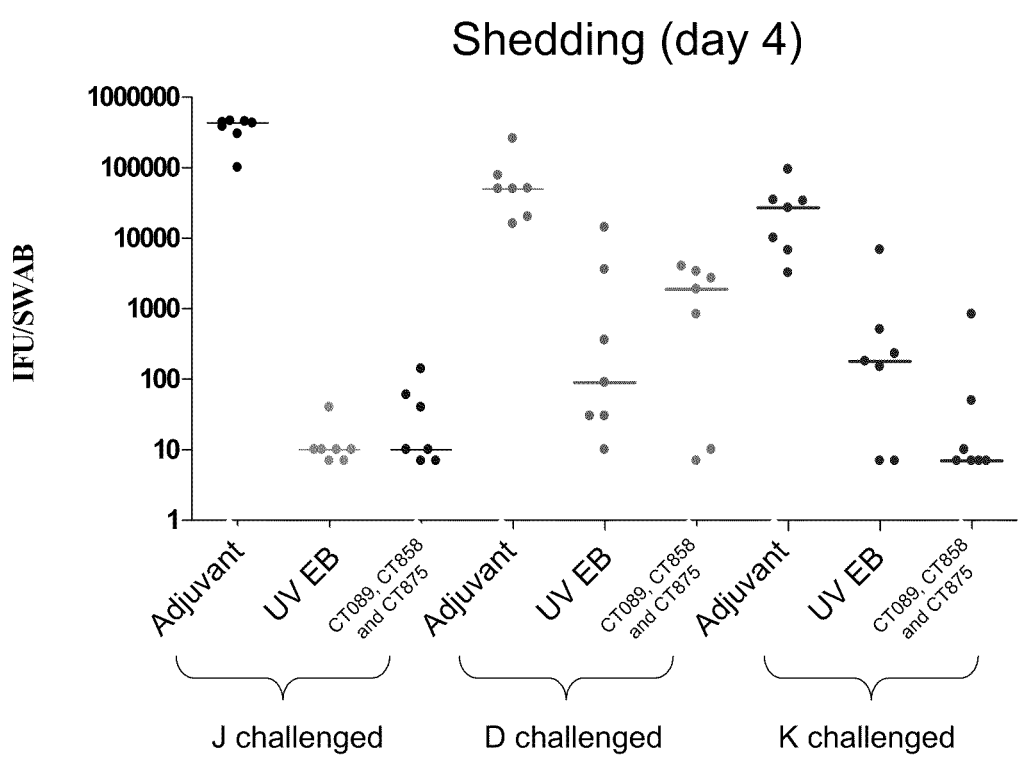
FIG. 15 shows swab results taken from *Chlamydia trachomatis* serovar E Ct-089, Ct-858 and Ct-875 immunised mice four days after challenge from *Chlamydia trachomatis* serovars D, K or J. UV EB in each case are 5b. Momp, Ct-858, Ct-875, Ct-089
5b'. Momp, Ct-858, Ct-875
6b. Momp, PmpD, Ct-858, PmpGpd, Ct-875, Ct-089
All of the above combinations comprise Ct-875 and Ct-858.

FIG. 15 indicates that four days after challenge, mice immunised with Ct-089, Ct-858 and Ct-875 according to the present invention show lower levels of shedding compared to the adjuvant control. Furthermore, levels of shedding are generally comparable to those achieved with immunisation by UVEB (lower levels are achieved in the case of serovar K challenge, and higher levels in the case of serovar D challenge).

Figure 16:
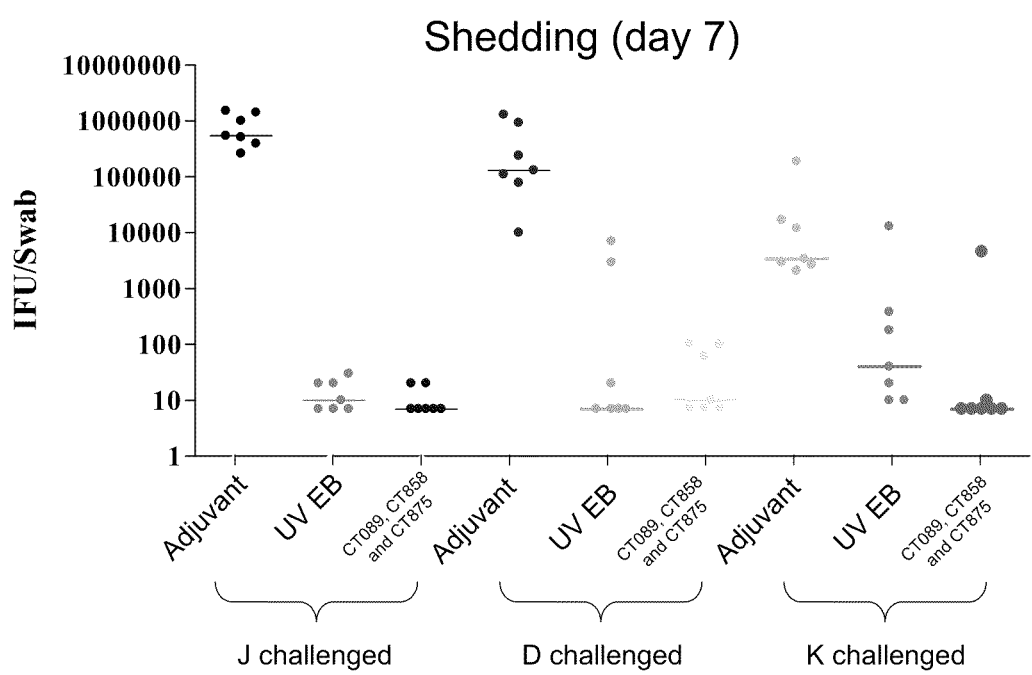

Seven days after challenge mice receiving the adjuvant control show higher levels of shedding than those immunised with UVEB or with Ct-089, Ct-858 and Ct-875 (see FIG. 16). Both UVEB and Ct-089, Ct-858 and Ct-875 immunised mice show very low levels of shedding.

Figure 17:
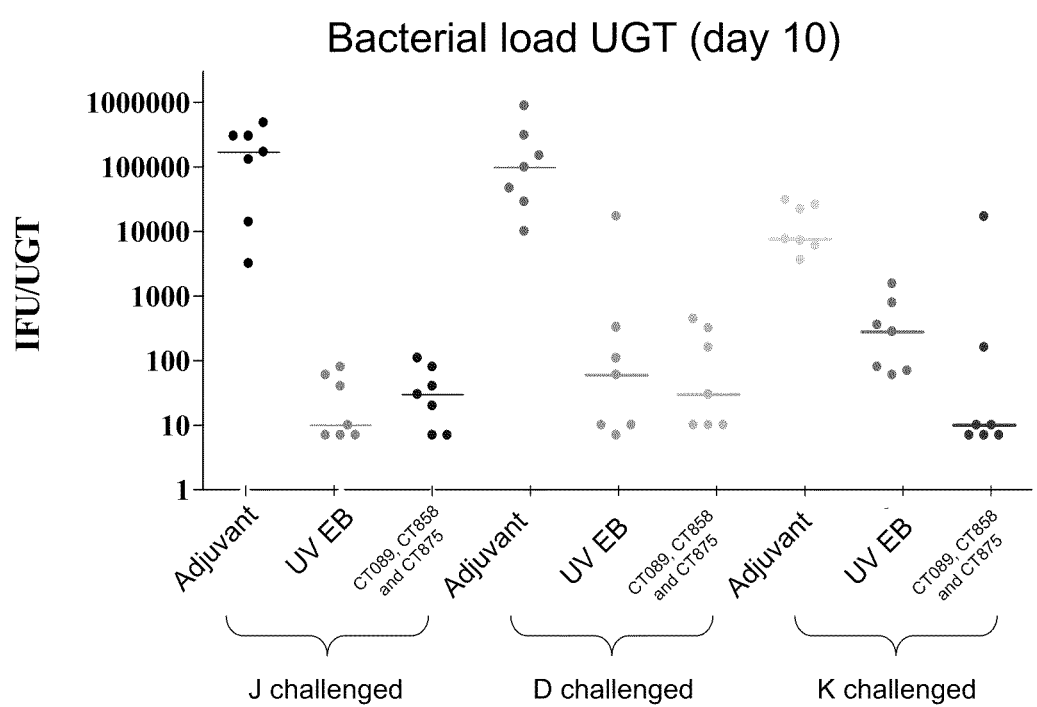
Figure 18:
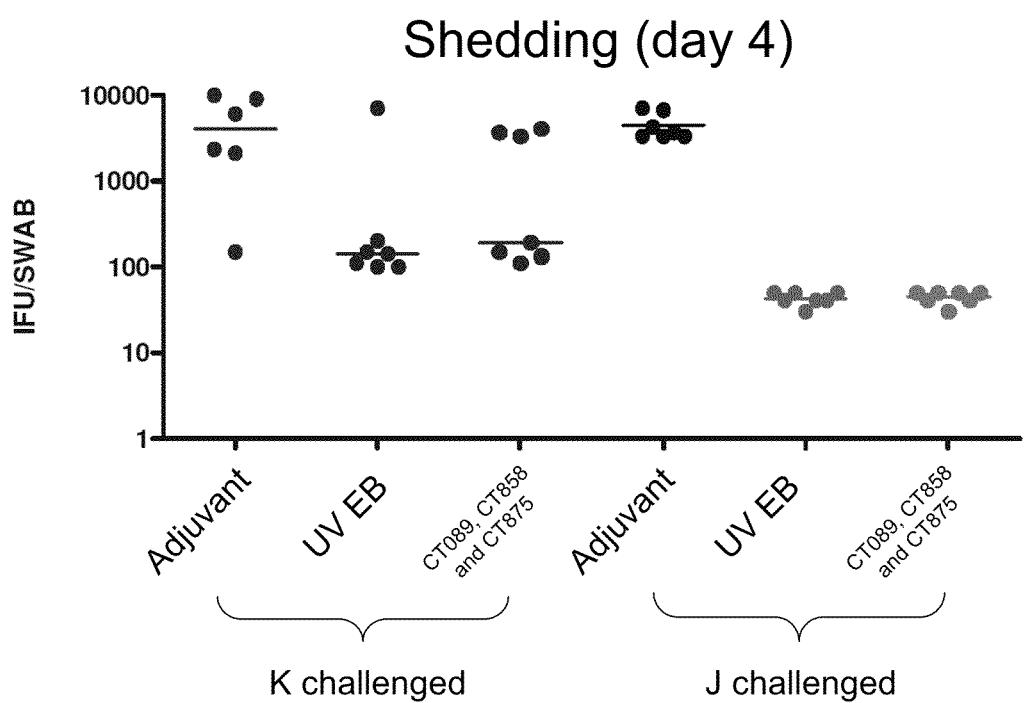

FIG. 17 shows that ten days after challenge the UGT of mice receiving the adjuvant control is highly colonised by bacteria. Both UVEB and Ct-089, Ct-0858 and Ct-875 immunised mice show low levels of UGT colonisation, with treatment according to the invention generally showing a slightly lower level than UVEB treatment.

Statistical analysis indicates that treatment using the Ct-089, Ct-0858 and Ct-875 antigens from *Chlamydia trachomatis* serovar E results in significant protection in mice challenged with *Chlamydia trachomatis* serovar J when compared to the negative control (adjuvant only) with $p<0.01$ by Dunnett's multiple comparison test. No significant difference is seen between antigen treatment and UVEB treatment ($p>0.05$).

Treatment using the Ct-089, Ct-858 and Ct-875 antigens from *Chlamydia trachomatis* serovar E results in significant protection in mice challenged with *Chlamydia trachomatis* serovar D on Day 4 and Day 7 when compared to the negative control (adjuvant only) with $p<0.05$. No significant difference is seen between antigen treatment and UVEB treatment ($p>0.05$).

Treatment using the Ct-089, Ct-858 and Ct-875 antigens from *Chlamydia trachomatis* serovar E results in significant protection in mice challenged with *Chlamydia trachomatis* serovar K on Day 4 and Day 10 when compared to the negative control (adjuvant only) with $p<0.05$ and $p<0.01$ respectively. No significant difference is seen between antigen treatment and UVEB treatment ($p>0.05$).

Conclusions

The experiments performed in Example 7 confirm that the combination of the three proteins, Ct-089, Ct-858 and Ct-875 from *Chlamydia trachomatis* serovar E is capable of eliciting a substantial protective response, which has been shown to be statistically significant. This protective response is one which can provide general protection against challenge by other serovars. In particular, it should be noted that serovars E and K are the most genetically diverse *Chlamydia trachomatis* serovars and the cross-protection observed between these two *Chlamydia trachomatis* serovars suggests that a combination of Ct-089, Ct-858 and Ct-875 antigens may be expected to have wide use in the treatment or prevention of Chlamydial infection.

The level of protection afforded by the vaccine formulation containing Ct-089, Ct-858 and Ct-875 was found to be comparable to the use of UVEB, although clearly the use of purified proteins is desirable in light of the risks involved with the use of the whole elementary bodies.

Example 8

Evaluation of the Protection Induced by a Vaccine Containing Ct-089, Ct-858 and Ct-875 from *Chlamydia trachomatis* Serovar E Against Challenge with Serovars K and J, in the Highly Susceptible Mouse Strain C3H/HeN The protection provided by a vaccine containing Ct-089, Ct-858 and Ct-875 serovar E antigens was tested in vaginal challenge experiments with EB from heterologous (i.e. non-serovar E) *Chlamydia trachomatis* serovars K and J.

Method

The study was conducted with 41 fifteen-week old female C3H/HeN mice, a strain known for their susceptibility to chlamydial infection. These mice were split into two groups, one of which was challenged by *Chlamydia trachomatis* serovar K and the other by serovar J. The groups were then further separated into three sub-groups, these sub-groups were immunised intramuscularly with 50 ul of different vaccine preparations injected into each anterior tibialis (100 ul total), and repeated four weeks later. Each sub-group contained seven mice, save for the group immunised with adjuvant control and challenged with serovar K which contained 6 mice. Mice were further treated with progesterone, 1.25 mg given in a volume of 100 ul by subcutaneous injection ten and three days before challenge to synchronise their cycles. The three test preparations were:

(i) Adjuvant control (AS01B)

The adjuvant utilised was based upon a liposomal formulation containing 3D-MPL, QS21 and cholesterol. The final composition of the adjuvant solution being:
3D-MPL 100 ug/ml
QS21 100 ug/ml
DOPC 2 mg/ml
Cholesterol 0.5 mg/ml Adjuvant was prepared as described above in Example 7.

(ii) UV attenuated *Chlamydia trachomatis* elementary bodies with AS01B adjuvant A preparation containing 10 ug of UV treated *Chlamydia trachomatis* elementary bodies (UVEB) from serovar E with adjuvant (as described above).

(iii) Ct-089, Ct-858 and Ct-875 with AS01B adjuvant

A preparation containing Ct-089 (5 ug), Ct-858 (5 ug) and Ct-875 (5 ug) from *Chlamydia trachomatis* serovar E with adjuvant (as described above).

Mice were challenged, under anaesthetic (1:1 Ketaject and Xylaject, 30 ul per mouse IP, 20 ul into each thigh), four weeks after final boost with $1\times10^6$ IFU of serovar K or J suspended in 20 ul of sucrose phosphate glutamic acid (SPG).

The infection was allowed to proceed for 10 days, with genital swabs were taken under anaesthetic on Day 4 and Day 7. Mice were euthanized on Day 10 and the uterine horns harvested for histopathology and titration. For titration, one-half of the UGT was homogenized, and IFU was then determined using McCoy cells as described in Example 7.

The detection limit for titering is 10 IFU, thus one inclusion per well is plotted as 10 IFU. An arbitrary number of 7 IFU was allocated where the number of inclusions observed was less than one.

Results

FIGS. 18 to 20 illustrate the results of Example 8.

FIG. 18 indicates that four days after challenge with either *Chlamydia trachomatis* serovar K or J, mice immunised with Ct-089, Ct-858 and Ct-875 from *Chlamydia trachomatis* serovar E show lower levels of shedding compared to the adjuvant control. Furthermore, levels of shedding are comparable to those achieved with immunisation by UVEB.

Figure 19:
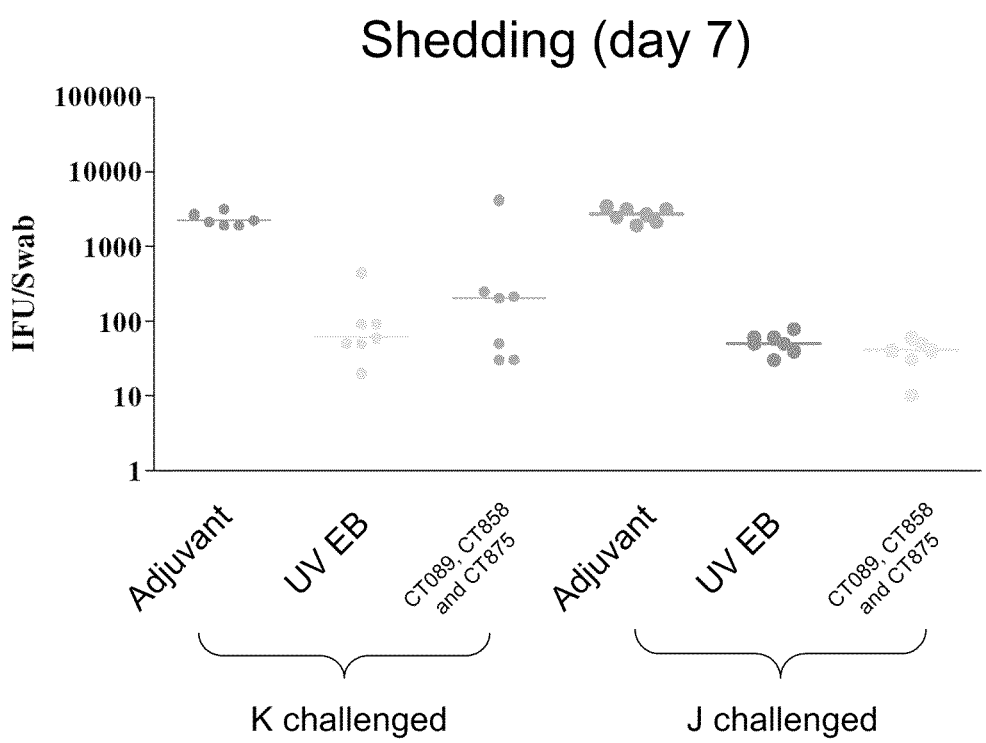

Seven days after challenge mice receiving the adjuvant control show higher levels of shedding than those immunised with UVEB or with Ct-089, Ct-858 and Ct-875 (see FIG. 19). Both UVEB and Ct-089, Ct-858 and Ct-875 immunised mice show very low levels of shedding.

Figure 20:
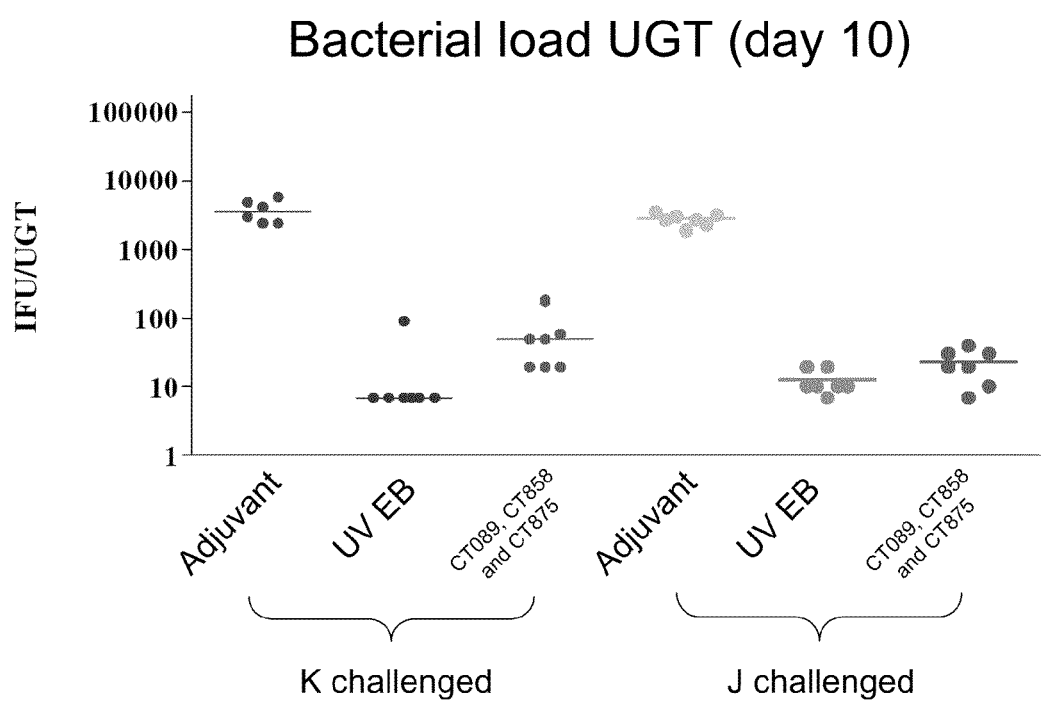
Figure 21:
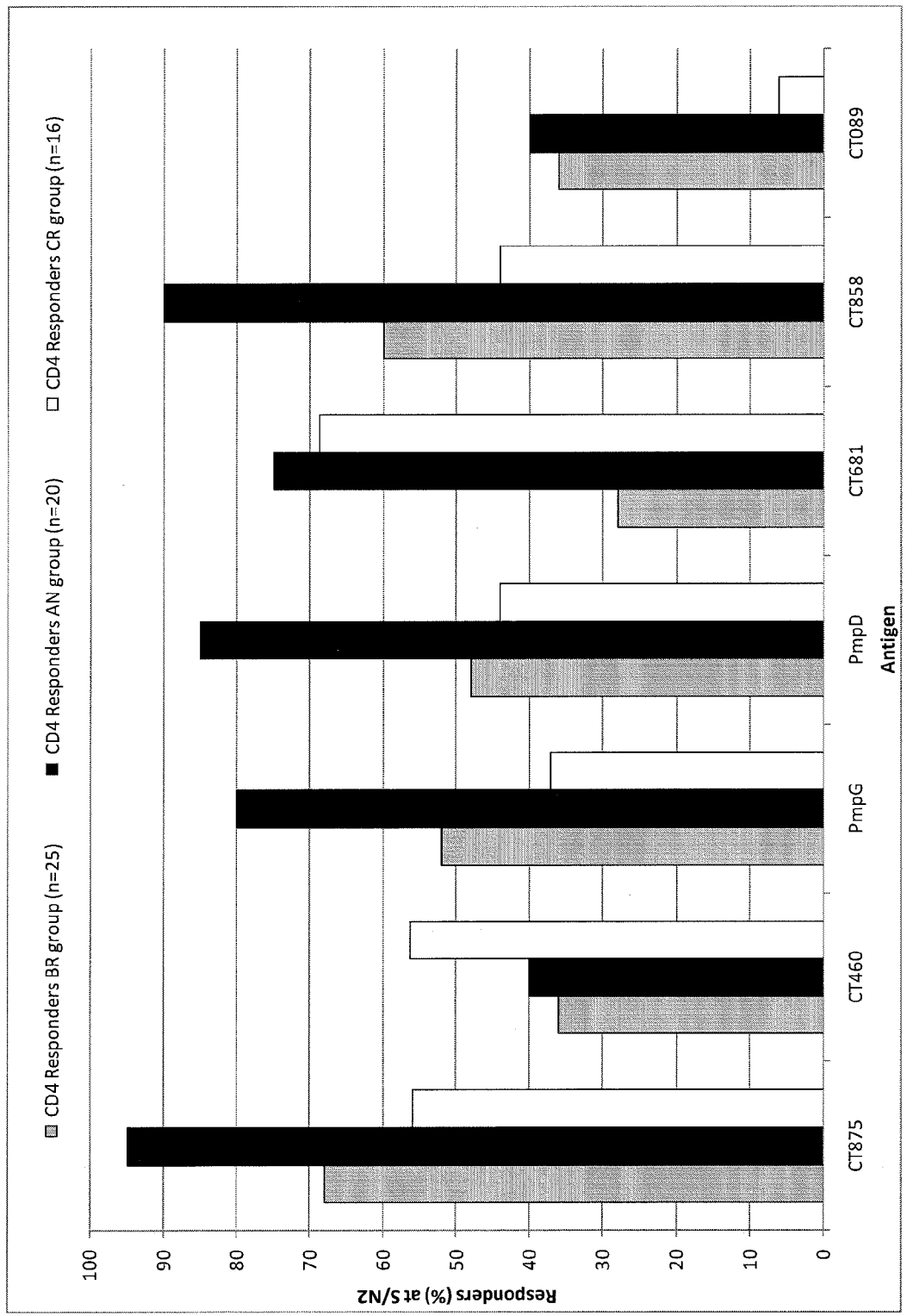
Figure 22:
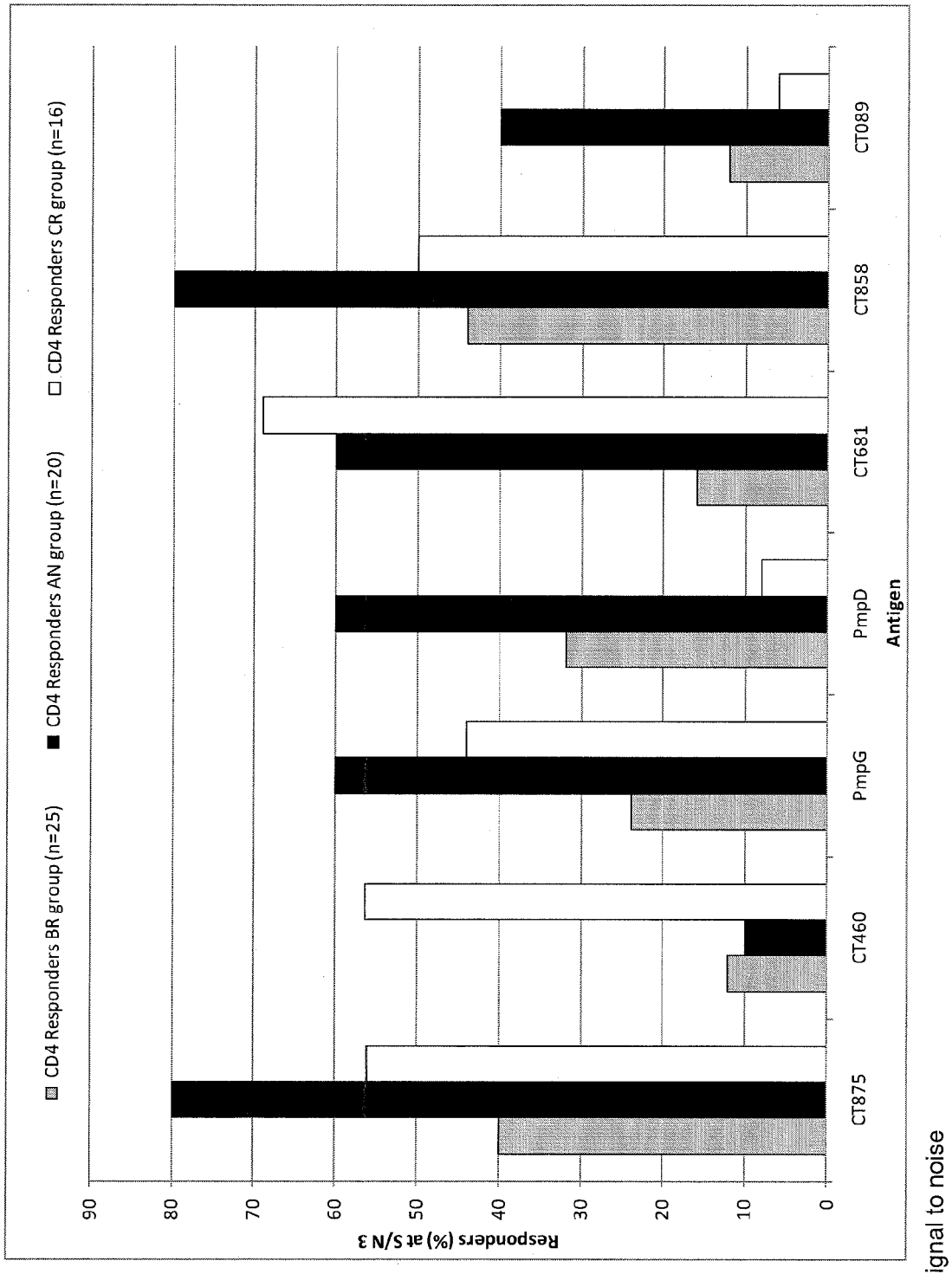
Figure 23:
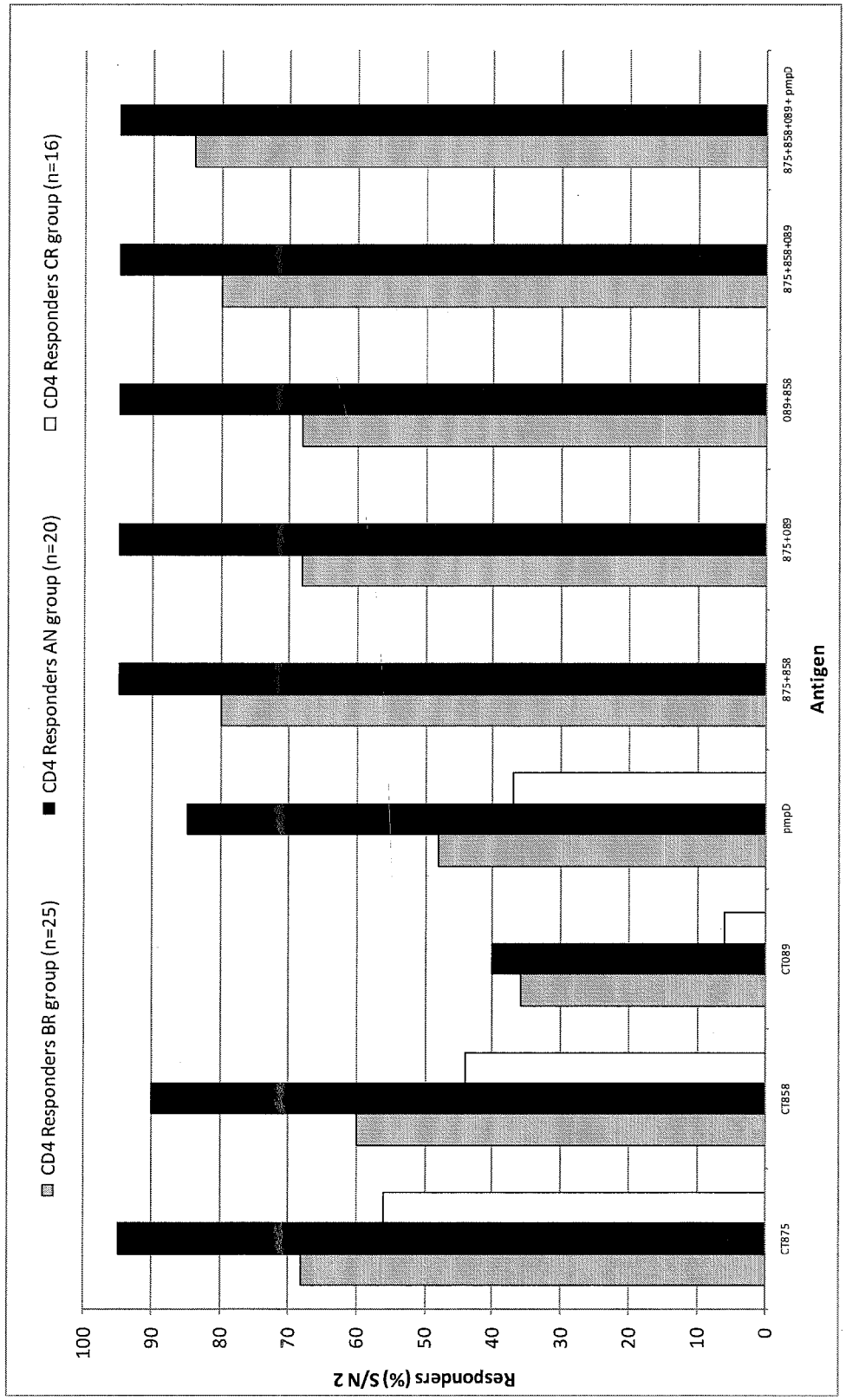

FIG. 20 shows that ten days after challenge with either *Chlamydia trachomatis* serovar K or J the UGT of mice receiving the adjuvant control is highly colonised by bacteria. Both UVEB and Ct-089, Ct-858 and Ct-875 immunised mice show low levels of UGT colonisation.

Statistical analysis indicates that treatment using the Ct-089, Ct-858 and Ct-875 antigens from *Chlamydia trachomatis* serovar E results in significant protection in mice challenged with serovar J when compared to the negative control (adjuvant only) with $p<0.01$. No significant difference is seen between antigen treatment and UVEB treatment ($p>0.05$).

Treatment using the Ct-089, Ct-858 and Ct-875 antigens from *Chlamydia trachomatis* serovar E results in significant protection in mice challenged with serovar K on Day 7 and Day 10 when compared to the negative control (adjuvant only) with $p<0.05$ and $p<0.01$ respectively. No significant difference is seen between antigen treatment and UVEB treatment ($p>0.05$).

Conclusions

The experiments performed in Example 8 confirm that the three proteins, Ct-089, Ct-858 and Ct-875 from *Chlamydia trachomatis* serovar E are capable of eliciting a substantial protective immune response, which has been shown to be statistically significant. The protection elicited is one which provides general protection against challenge by other serovars.

The level of protection afforded by the vaccine formulation containing Ct-089, Ct-858 and Ct-875 was found to be comparable to the use of UVEB, although clearly the use of purified proteins is desirable in light of the risks involved with the use of the whole elementary bodies.

Example 9

Response of Seropositive Individuals to Stimulation by Chlamydial Antigens

The response of seropositive subjects to a number of Chlamydial antigens was examined to investigate which *Chlamydia trachomatis* antigens may be of particular importance in the normal immune response of humans to *Chlamydia trachomatis* infection.

Method

Three subject groups from different locations were involved in the study:

(i) 25 pregnant women who were IgG positive for *Chlamydia trachomatis* (referred to as BR)

(ii) 20 women who were IgG or PCR positive for *Chlamydia trachomatis* (referred to as AN)

(iii) 16 individuals of mixed sex (referred to as CR)—

(a) seven patients who were treated for genital *Chlamydia trachomatis* infection, identified by Ligase chain reaction and serum titer (b) nine non-shedding donors with no history of chlamydial disease, identified by T-cell responses to chlamydial antigens and were not shedding at the time of recruitment to the study. *Chlamydia trachomatis* IFN-gamma and *Chlamydia pneumoniae* IFN-gamma response was determined by stimulating $0.3\times10^6$ PBMC with 1 ug/ml of the respective chlamydial elementary body. Supernatants were taken after 72 h and analysed by IFN-gamma specific ELISA.

Serology was performed using IgG and IgM complement binding tests supplied by Virion-Serion for subjects in the BR and group, and subjects referred as AN were screened using either the same test or using PCR-techniques (Cobas Amplicor®) on urine samples.

An in vitro assay was performed to evaluate the subjects' T-cell response to various *Chlamydia trachomatis* antigens and combinations thereof. Peripheral blood mononuclear cell (PBMC) samples were obtained from heparinised whole blood by Ficoll-Hypaque density gradient centrifugation following standard procedures. The cells are washed and cryopreserved in liquid nitrogen until testing (for further details see Lalvani A, Moris P et al. *J. Infect. Dis.* 1999 180:1656-1664).

For subjects in the CR group, the specific immune response to each *Chlamydia trachomatis* antigen was characterised by performing lymphocyte proliferation analysis using tritiated thymidine. This technique assessed the cellular expansion upon in vitro stimulation to an antigen. In practice, cell proliferation is determined by estimating incorporation of tritiated-thymidine into DNA, a process closely related to underlying changes in cell number.

For subjects in the AN and BR groups, the specific immune response to each *Chlamydia trachomatis* antigen was characterised by performing lymphocyte proliferation analysis using the succinimidyl ester of carboxyfluorsecein diacetate (CFSE). CFSE spontaneously and irreversibly couples to both intracellular and cell surface proteins by reaction with lysine side chains and other available amine groups. When lymphocyte cells divide, CFSE labeling is distributed equally between the daughter cells, which are therefore half as fluorescent as the parents. As a result, halving of cellular fluorescence intensity marks each successive generation in a population of proliferating cells and is readily followed by flow cytometry (for further details see Hodgkins, P D et al *J. Exp. Med.* 1996 184:277-281).

Practically, after thawing, PMBC were washed and stained with CFSE before being cultivated ($2\times10^5$ cells) for 72 hrs with 10 ug/ml of antigen in culture media (RPMI-1640 supplemented with glutamine, non essential amino acid, pyruvate and heat inactivated human AB serum). Cells were then harvested and their phenotype was characterized using surface staining to identify memory CD8 and CD4+ T-Cells. Subsequently, flow cytometry analysis indicated the extent of lymphocyte proliferation in response to each antigen (proportion of cells with decreased CFSE intensity upon in vitro stimulation).

Results

FIG. 21 shows the CD4 response of test subjects to specific antigens, responders in this case from BR and AN groups are defined has having a signal to noise ratio of at least 2:1. Responders in the CR group are defined as those demonstrating a proliferative S/N>10 and IFN-gamma response of 500 ug/ml from T-cells generated from the donor subjects. The proportion of responders can be seen to vary depending upon both the particular antigen being tested and subject group. The AN group generally shows the greatest number of responders (in six out of seven cases), with the CR group generally showing the fewest number of responders (in five out of seven cases) but the specific cellular response was evaluated in another technical setting. Subjects in the BR and AN groups both show their greatest response to the Ct-875 antigen. FIG. 22 shows the CD4 response plotted at a signal to noise ratio of at least 3:1 for BR and AN groups.

FIG. 23 shows the CD4 response of test subjects to certain antigens, and also to combinations of those antigens (response to the combinations was not examined for the CR subject group). Compared to the response observed for individual antigens, the combination of Ct-875+Ct-858 or Ct-858+Ct875+Ct-089 result in a higher proportion of responders in the BR subject group. The four antigen combination of Ct-875+Ct-858+Ct-089+PmpD results in the greatest number of responders in the BR subject group (85%). For the AN subject group, it may be noted that the combination of Ct-875+Ct-089 does not result in any improvement in the number of responders compared to Ct-875 alone, and neither does the combination of Ct-875+Ct-858+Ct-089 result in any improvement in the number of responders compared to the combination of Ct-875+Ct-858. However, the combination of Ct-858+Ct-089 result in a higher proportion of responders compared to Ct-858 or Ct-089 alone.

Conclusions

Although the frequency of responders was not consistent between the three subject groups, possibly as a result of the sample size or population differences, Ct-858 and Ct-875 were well recognized for all three groups.

In the human seropositive subjects tested, the optimal response for a two antigen combination is provided by Ct-875+Ct-858. Ct-089 only seems to result in improved response where Ct-875 is not already present, although Ct-089 may have benefit over and above Ct-875+Ct-858 in other population groups. The greatest response was observed for the four antigen combination of Ct-875+Ct-858+Ct-089+ PmpD.

In light of the results of Example 9, it can reasonably be expected that the antigen combinations of the present invention, whether in the form of whole proteins, immunogenic fragments thereof or polynucleotides encoding either of these, will be of particular value in human Chlamydial vaccines and in related diagnostic methods.

What is claimed is:

1. A composition comprising:
   (i) an isolated Ct-858 *Chlamydia* protein consisting of SEQ ID NO: 6;
   (ii) an isolated Ct-089 *Chlamydia* protein consisting of SEQ ID NO:16; and
   (iii) a pharmaceutically acceptable carrier.

2. A composition according to claim 1 which comprises a *Chlamydia* Ct-089 protein.

3. A composition according to claim 2 further comprising a *Chlamydia* Ct-875 protein or immunogenic fragment thereof.

4. A composition according to claim 3 further comprising a *Chlamydia* PmpDpd protein or an immunogenic fragment thereof.

5. A composition according to claim 1, wherein the composition is an immunogenic composition.

6. A composition according to claim 5 further comprising adjuvant.

7. A composition according to claim 6 wherein the adjuvant is a preferential stimulator of a Th1 response.

8. A composition according to claim 7 wherein the adjuvant comprises 3D-MPL, QS21 or a combination of 3D-MPL and QS21.

9. A composition according to claim 8 wherein the adjuvant further comprises an oil in water emulsion.

10. A composition according to claim 8 wherein the adjuvant further comprises liposomes.

11. A composition according to claim 1 wherein said isolated *Chlamydia* proteins are linked to form a fusion protein.

12. A composition comprising a polypeptide consisting of SEQ ID NO:6, a polypeptide consisting of SEQ ID NO:16, and an isolated *Chlamydia* polypeptide selected from:
   Ct-875, PmpD passenger domain, and PmpG passenger domain.

13. A composition according to claim 12, wherein:
   (a) Ct-875 is a polypeptide having at least 95% sequence identity to SEQ ID NO. 8;
   (b) PmpD passenger domain is a polypeptide having at least 95% sequence identity to SEQ ID NO. 14; and
   (e) PmpG passenger domain is a polypeptide having at least 95% sequence identity to SEQ ID NO 12.

14. A composition according to claim 12 wherein all of said *Chlamydia* polypeptides are from *Chlamydia trachomatis*.

* * * * *

SEQUENCE LISTING

```
<160> NUMBER OF SEQ ID NOS: 126

<210> SEQ ID NO 1
<211> LENGTH: 261
<212> TYPE: DNA
<213> ORGANISM: Chlamydia trachomatis

<400> SEQUENCE: 1
atgagtcaaa ataagaactc tgctttcatg cagcctgtga acgtatccgc tgatttagct      60
gccatcgttg gtgcaggacc tatgcctcgc acagagatca ttaagaaaat gtgggattac     120
attaaggaga atagtcttca agatcctaca aacaaacgta atatcaatcc cgatgataaa     180
ttggctaaag tttttggaac tgaaaaacct atcgatatgt tccaaatgac aaaaatggtt     240
tctcaacaca tcattaaata a                                               261

<210> SEQ ID NO 2
<211> LENGTH: 86
<212> TYPE: PRT
<213> ORGANISM: Chlamydia trachomatis

<400> SEQUENCE: 2

Met Ser Gln Asn Lys Asn Ser Ala Phe Met Gln Pro Val Asn Val Ser
1               5                   10                  15

Ala Asp Leu Ala Ala Ile Val Gly Ala Gly Pro Met Pro Arg Thr Glu
            20                  25                  30

Ile Ile Lys Lys Met Trp Asp Tyr Ile Lys Glu Asn Ser Leu Gln Asp
        35                  40                  45

Pro Thr Asn Lys Arg Asn Ile Asn Pro Asp Asp Lys Leu Ala Lys Val
    50                  55                  60

Phe Gly Thr Glu Lys Pro Ile Asp Met Phe Gln Met Thr Lys Met Val
65                  70                  75                  80

Ser Gln His Ile Ile Lys
                85

<210> SEQ ID NO 3
<211> LENGTH: 1122
<212> TYPE: DNA
<213> ORGANISM: Chlamydia trachomatis

<400> SEQUENCE: 3
```

```
ctgcctgtgg ggaatcctgc tgaaccaagc cttatgatcg acggaattct gtgggaaggt      60
ttcggcggag atccttgcga tccttgcacc acttggtgtg acgctatcag catgcgtatg     120
ggttactatg gtgactttgt tttcgaccgt gttttgaaaa cagatgtgaa taaagagttt     180
gaaatgggcg aggctttagc cggagcttct gggaatacga cctctactct ttcaaaattg     240
gtagaacgaa cgaaccctgc atatggcaag catatgcaag acgcagagat gtttaccaat     300
gccgcttgca tgacattgaa tatttgggat cgttttgatg tattctgtac attaggagcc     360
accagtggat atcttaaagg aaattcagca tctttcaact tagttgggtt attcggcgat     420
ggtgtaaacg ccacgaaacc tgctgcagat agtattccta acgtgcagtt aaatcagtct     480
gtggtggaac tgtatacaga tactactttt gcttggagtg ttggagctcg tgcagctttg     540
tgggaatgtg gatgtgcaac tttaggagct tctttccaat atgctcaatc taaacctaaa     600
atcgaagaat taaacgttct ctgtaacgca gcagagttta ctattaataa acctaaaggg     660
tatgtaggta aggagtttcc tcttgatctt acagcaggaa cagatgcagc gacgggcact     720
aaagatgcct ctattgatta ccatgagtgg caagcaagtt tatctctttc ttacagactc     780
aatatgttca ctccctacat tggagttaaa tggtctcgtg caagctttga ttctgataca     840
attcgtatag cccagccgag gttggtaaca cctgttgtag atattacaac ccttaaccca     900
actattgcag gatgcggcag tgtagctgga gctaacacgg aaggacagat atctgataca     960
atgcaaatcg tctccttgca attgaacaag atgaaatcta gaaaatcttg cggtattgca    1020
gtaggaacaa ctattgtgga tgcagacaaa tacgcagtta cagttgagac tcgcttgatc    1080
gatgagagag ctgctcacgt aaatgcacaa ttccgcttct ag                       1122
```

<210> SEQ ID NO 4
<211> LENGTH: 373
<212> TYPE: PRT
<213> ORGANISM: Chlamydia trachomatis

<400> SEQUENCE: 4

```
Leu Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Thr Thr Trp
            20                  25                  30

Cys Asp Ala Ile Ser Met Arg Met Gly Tyr Tyr Gly Asp Phe Val Phe
        35                  40                  45

Asp Arg Val Leu Lys Thr Asp Val Asn Lys Glu Phe Glu Met Gly Glu
    50                  55                  60

Ala Leu Ala Gly Ala Ser Gly Asn Thr Thr Ser Thr Leu Ser Lys Leu
65                  70                  75                  80

Val Glu Arg Thr Asn Pro Ala Tyr Gly Lys His Met Gln Asp Ala Glu
                85                  90                  95

Met Phe Thr Asn Ala Ala Cys Met Thr Leu Asn Ile Trp Asp Arg Phe
            100                 105                 110

Asp Val Phe Cys Thr Leu Gly Ala Thr Ser Gly Tyr Leu Lys Gly Asn
        115                 120                 125

Ser Ala Ser Phe Asn Leu Val Gly Leu Phe Gly Asp Gly Val Asn Ala
    130                 135                 140

Thr Lys Pro Ala Ala Asp Ser Ile Pro Asn Val Gln Leu Asn Gln Ser
145                 150                 155                 160

Val Val Glu Leu Tyr Thr Asp Thr Thr Phe Ala Trp Ser Val Gly Ala
                165                 170                 175

Arg Ala Ala Leu Trp Glu Cys Gly Cys Ala Thr Leu Gly Ala Ser Phe
```

```
                     180                 185                 190
Gln Tyr Ala Gln Ser Lys Pro Lys Ile Glu Glu Leu Asn Val Leu Cys
                195                 200                 205

Asn Ala Ala Glu Phe Thr Ile Asn Lys Pro Lys Gly Tyr Val Gly Lys
            210                 215                 220

Glu Phe Pro Leu Asp Leu Thr Ala Gly Thr Asp Ala Ala Thr Gly Thr
225                 230                 235                 240

Lys Asp Ala Ser Ile Asp Tyr His Glu Trp Gln Ala Ser Leu Ser Leu
                245                 250                 255

Ser Tyr Arg Leu Asn Met Phe Thr Pro Tyr Ile Gly Val Lys Trp Ser
            260                 265                 270

Arg Ala Ser Phe Asp Ser Asp Thr Ile Arg Ile Ala Gln Pro Arg Leu
                275                 280                 285

Val Thr Pro Val Val Asp Ile Thr Leu Asn Pro Thr Ile Ala Gly
            290                 295                 300

Cys Gly Ser Val Ala Gly Ala Asn Thr Glu Gly Gln Ile Ser Asp Thr
305                 310                 315                 320

Met Gln Ile Val Ser Leu Gln Leu Asn Lys Met Lys Ser Arg Lys Ser
                325                 330                 335

Cys Gly Ile Ala Val Gly Thr Thr Ile Val Asp Ala Asp Lys Tyr Ala
            340                 345                 350

Val Thr Val Glu Thr Arg Leu Ile Asp Glu Arg Ala Ala His Val Asn
                355                 360                 365

Ala Gln Phe Arg Phe
            370

<210> SEQ ID NO 5
<211> LENGTH: 1746
<212> TYPE: DNA
<213> ORGANISM: Chlamydia trachomatis

<400> SEQUENCE: 5
gtacgaggag aaagcttggt ttgcaagaat gctcttcaag atttgagttt tttagagcat      60
ttattacagg ttaaatatgc tcctaaaaca tggaaagagc aatacttagg atgggatctt     120
gttcaaagct ccgtttctgc acagcagaag cttcgtacac aagaaaatcc atcaacaagt     180
ttttgccagc aggtccttgc tgattttatc ggaggattaa atgactttca cgctggagta     240
actttctttg cgatagaaag tgcttacctt ccttataccg tacaaaaaag tagtgacggc     300
cgtttctact ttgtagatat catgactttt tcttcagaga tccgtgttgg agatgagttg     360
ctagaggtgg atggggcgcc tgtccaagat gtgctcgcta ctctatatgg aagcaatcac     420
aaagggactg cagctgaaga gtcggctgct taagaacac tattttctcg catggcctct     480
ttagggcaca agtaccttc tgggcgcact actttaaaga ttcgtcgtcc ttttggtact     540
acgagagaag ttcgtgtgaa atggcgttat gttcctgaag gtgtaggaga tttgctaccc     600
atagctcctt ctatcagggc tccacagtta cagaaatcga tgagaagctt tttccctaag     660
aaagatgatg cgtttcatcg gtctagttcg ctattctact ctccaatggt tccgcattt      720 tgggcagagc ttcgcaatca ttatgcaacg agtggtttga aaagcgggta caatattggg     780
agtaccgatg gtttctcccc tgtcattggg cctgttatat gggagtcgga gggtcttttc     840
cgcgcttata tttcttcggt gactgatggg gatggtaaga gccataaagt aggatttcta     900
agaattccta catatagttg gcaggacatg gaagattttg atccttcagg accgcctcct     960
tgggaagaat tgctaagat tattcaagta ttttcttcta atacagaagc tttgattatc    1020
```

-continued

```
gaccaaacga acaacccagg tggtagtgtc ctttatcttt atgcactgct ttccatgttg   1080
acagaccgtc ctttagaact tcctaaacat agaatgattc tgactcagga tgaagtggtt   1140
gatgctttag attggttaac cctgttggaa aacgtagaca caaacgtgga gtctcgcctt   1200
gctctgggag acaacatgga aggatatact gtggatctac aggttgccga gtatttaaaa   1260
agctttggac gtcaagtatt gaattgttgg agtaaagggg atatcgagtt atcaacacct   1320
attcctcttt ttggttttga gaagattcat ccacatcctc gagttcaata ctctaaaccg   1380
atttgtgttt tgatcaatga gcaagacttt tcttgtgctg acttcttccc tgtagttttg   1440
aaagacaatg atcgagctct tattgttggt actcgaacag ctggagctgg aggatttgtc   1500
tttaatgtgc agttcccaaa tagaactgga ataaaaactt gttctttaac aggatcatta   1560
gctgttagag agcatggtgc cttcattgag aacatcggag tcgaaccgca tatcgatctg   1620
ccttttacag cgaatgatat tcgctataaa ggctattccg agtatcttga taaggtcaaa   1680
aaattggttt gtcagctgat caataacgac ggtaccatta ttcttgcgga agatggtagt   1740
ttttaa                                                              1746
```

<210> SEQ ID NO 6
<211> LENGTH: 581
<212> TYPE: PRT
<213> ORGANISM: Chlamydia trachomatis

<400> SEQUENCE: 6

```
Val Arg Gly Glu Ser Leu Val Cys Lys Asn Ala Leu Gln Asp Leu Ser
1               5                   10                  15

Phe Leu Glu His Leu Leu Gln Val Lys Tyr Ala Pro Lys Thr Trp Lys
                20                  25                  30

Glu Gln Tyr Leu Gly Trp Asp Leu Val Gln Ser Val Ser Ala Gln
            35                  40                  45

Gln Lys Leu Arg Thr Gln Glu Asn Pro Ser Thr Ser Phe Cys Gln Gln
        50                  55                  60

Val Leu Ala Asp Phe Ile Gly Gly Leu Asn Asp Phe His Ala Gly Val
65                  70                  75                  80

Thr Phe Phe Ala Ile Glu Ser Ala Tyr Leu Pro Tyr Thr Val Gln Lys
                85                  90                  95

Ser Ser Asp Gly Arg Phe Tyr Phe Val Asp Ile Met Thr Phe Ser Ser
            100                 105                 110

Glu Ile Arg Val Gly Asp Glu Leu Leu Glu Val Asp Gly Ala Pro Val
        115                 120                 125

Gln Asp Val Leu Ala Thr Leu Tyr Gly Ser Asn His Lys Gly Thr Ala
    130                 135                 140

Ala Glu Glu Ser Ala Ala Leu Arg Thr Leu Phe Ser Arg Met Ala Ser
145                 150                 155                 160

Leu Gly His Lys Val Pro Ser Gly Arg Thr Thr Leu Lys Ile Arg Arg
                165                 170                 175

Pro Phe Gly Thr Thr Arg Glu Val Arg Val Lys Trp Arg Tyr Val Pro
            180                 185                 190

Glu Gly Val Gly Asp Leu Ala Thr Ile Ala Pro Ser Ile Arg Ala Pro
        195                 200                 205

Gln Leu Gln Lys Ser Met Arg Ser Phe Pro Lys Lys Asp Asp Ala
    210                 215                 220

Phe His Arg Ser Ser Ser Leu Phe Tyr Ser Pro Met Val Pro His Phe
225                 230                 235                 240

Trp Ala Glu Leu Arg Asn His Tyr Ala Thr Ser Gly Leu Lys Ser Gly
```

```
                    245                 250                 255
Tyr Asn Ile Gly Ser Thr Asp Gly Phe Leu Pro Val Ile Gly Pro Val
                260                 265                 270
Ile Trp Glu Ser Glu Gly Leu Phe Arg Ala Tyr Ile Ser Ser Val Thr
            275                 280                 285
Asp Gly Asp Gly Lys Ser His Lys Val Gly Phe Leu Arg Ile Pro Thr
        290                 295                 300
Tyr Ser Trp Gln Asp Met Glu Asp Phe Asp Pro Ser Gly Pro Pro Pro
305                 310                 315                 320
Trp Glu Glu Phe Ala Lys Ile Ile Gln Val Phe Ser Ser Asn Thr Glu
                325                 330                 335
Ala Leu Ile Ile Asp Gln Thr Asn Asn Pro Gly Gly Ser Val Leu Tyr
            340                 345                 350
Leu Tyr Ala Leu Leu Ser Met Leu Thr Asp Arg Pro Leu Glu Leu Pro
        355                 360                 365
Lys His Arg Met Ile Leu Thr Gln Asp Glu Val Val Asp Ala Leu Asp
    370                 375                 380
Trp Leu Thr Leu Leu Glu Asn Val Asp Thr Asn Val Glu Ser Arg Leu
385                 390                 395                 400
Ala Leu Gly Asp Asn Met Glu Gly Tyr Thr Val Asp Leu Gln Val Ala
                405                 410                 415
Glu Tyr Leu Lys Ser Phe Gly Arg Gln Val Leu Asn Cys Trp Ser Lys
            420                 425                 430
Gly Asp Ile Glu Leu Ser Thr Pro Ile Pro Leu Phe Gly Phe Glu Lys
        435                 440                 445
Ile His Pro His Pro Arg Val Gln Tyr Ser Lys Pro Ile Cys Val Leu
    450                 455                 460
Ile Asn Glu Gln Asp Phe Ser Cys Ala Asp Phe Pro Val Val Leu
465                 470                 475                 480
Lys Asp Asn Asp Arg Ala Leu Ile Val Gly Thr Arg Thr Ala Gly Ala
                485                 490                 495
Gly Gly Phe Val Phe Asn Val Gln Phe Pro Asn Arg Thr Gly Ile Lys
            500                 505                 510
Thr Cys Ser Leu Thr Gly Ser Leu Ala Val Arg Glu His Gly Ala Phe
        515                 520                 525
Ile Glu Asn Ile Gly Val Glu Pro His Ile Asp Leu Pro Phe Thr Ala
    530                 535                 540
Asn Asp Ile Arg Tyr Lys Gly Tyr Ser Glu Tyr Leu Asp Lys Val Lys
545                 550                 555                 560
Lys Leu Val Cys Gln Leu Ile Asn Asn Asp Gly Thr Ile Ile Leu Ala
                565                 570                 575
Glu Asp Gly Ser Phe
            580

<210> SEQ ID NO 7
<211> LENGTH: 1776
<212> TYPE: DNA
<213> ORGANISM: Chlamydia trachomatis

<400> SEQUENCE: 7
atgagcatca ggggagtagg aggcaacggg aatagtcgaa tcccttctca taatggggat    60
ggatcgaatc gcagaagtca aaatacgaag gtaataata aagttgaaga tcgagtttgt   120
tctctatatt catctcgtag taacgaaaat agagaatctc cttatgcagt agtagacgtc   180
agctctatga tcgagagcac cccaacgagt ggagagacga caagagcttc gcgtggagtg   240
```

```
ctcagtcgtt tccaaagagg tttagtacga atagctgaca aagtaagacg agctgttcag    300
tgtgcgtgga gttcagtctc tacaagcaga tcgtctgcaa caagagccgc agaatccgga    360
tcaagtagtc gtactgctcg tggtgcaagt tctgggtata gggagtattc tccttcagca    420
gctagagggc tgcgtcttat gttcacagat ttctggagaa ctcgggtttt acgccagacc    480
tctcctatgg ctggagtttt tgggaatctt gatgtgaacg aggctcgttt gatggctgcg    540
tacacaagtg agtgcgcgga tcatttagaa gcgaaggagt tggctggccc tgacgggta    600 gcggccgccc gggaaattgc taaaagatgg gagaaaagag ttagagatct acaagataaa    660
ggtgctgcac gaaaattatt aaatgatcct ttaggccgac gaacacctaa ttatcagagc    720
aaaaatccag gtgagtatac tgtagggaat ccatgttttt acgatggtcc tcaggtagcg    780
aatctccaga acgtcgacac tggttttggg ctggacatga gcaatctctc agacgttgta    840
ttatccagag agattcaaac aggacttcga gcacgagcta ctttggaaga atccatgccg    900
atgttagaga atttagaaga gcgttttaga cgtttgcaag aaacttgtga tgcggctcgt    960
actgagatag aagaatcggg atggactcga gagtccgcat caagaatgga aggcgatgag   1020
gcgcaaggac cttctagagt acaacaagct tttcagagct ttgtaaatga atgtaacagc   1080
atcgagttct catttgggag ctttggagag catgtgcgag ttctctgcgc tagagtatca   1140
cgaggattag ctgccgcagg agaggcgatt cgccgttgct tctcttgttg taaggatcg    1200 acgcatcgct acgctcctcg cgatgaccta tctcctgaag gtgcatcgtt agcagagact   1260
ttggctagat tcgcagatga tatgggaata gagcgaggtg ctgatggaac ctacgatatt   1320
cctttggtag atgattggag aagaggggtt cctagtattg aaggagaagg atctgactcg   1380
atctatgaaa tcatgatgcc tatctatgaa gttatgaata tggatctaga aacacgaaga   1440
tcttttgcgg tacagcaagg gcactatcag gacccaagag cttcagatta tgacctccca   1500
cgtgctagcg actatgattt gcctagaagc ccatatccta ctccacctt gcctcctaga    1560 tatcagctac agaatatgga tgtagaagca gggttccgtg aggcagttta tgcttctttt   1620
gtagcaggaa tgtacaatta tgtagtgaca cagccgcaag agcgtattcc caatagtcag   1680
caggtggaag ggattctgcg tgatatgctt accaacgggt cacagacatt tagagacctg   1740
atgaagcgtt ggaatagaga agtcgatagg gaataa                             1776
```

<210> SEQ ID NO 8
<211> LENGTH: 591
<212> TYPE: PRT
<213> ORGANISM: Chlamydia trachomatis

<400> SEQUENCE: 8

Met Ser Ile Arg Gly Val Gly Gly Asn Gly Asn Ser Arg Ile Pro Ser
1               5                   10                  15

His Asn Gly Asp Gly Ser Asn Arg Arg Ser Gln Asn Thr Lys Gly Asn
            20                  25                  30

Asn Lys Val Glu Asp Arg Val Cys Ser Leu Tyr Ser Ser Arg Ser Asn
        35                  40                  45

Glu Asn Arg Glu Ser Pro Tyr Ala Val Val Asp Val Ser Ser Met Ile
    50                  55                  60

Glu Ser Thr Pro Thr Ser Gly Glu Thr Thr Arg Ala Ser Arg Gly Val
65                  70                  75                  80

Leu Ser Arg Phe Gln Arg Gly Leu Val Arg Ile Ala Asp Lys Val Arg
                85                  90                  95

Arg Ala Val Gln Cys Ala Trp Ser Ser Val Ser Thr Ser Arg Ser Ser

```
                    100                 105                 110
Ala Thr Arg Ala Ala Glu Ser Gly Ser Ser Arg Thr Ala Arg Gly
            115                 120                 125

Ala Ser Ser Gly Tyr Arg Glu Tyr Ser Pro Ser Ala Ala Arg Gly Leu
        130                 135                 140

Arg Leu Met Phe Thr Asp Phe Trp Arg Thr Arg Val Leu Arg Gln Thr
145                 150                 155                 160

Ser Pro Met Ala Gly Val Phe Gly Asn Leu Asp Val Asn Glu Ala Arg
                165                 170                 175

Leu Met Ala Ala Tyr Thr Ser Glu Cys Ala Asp His Leu Glu Ala Lys
            180                 185                 190

Glu Leu Ala Gly Pro Asp Gly Val Ala Ala Arg Glu Ile Ala Lys
        195                 200                 205

Arg Trp Glu Lys Arg Val Arg Asp Leu Gln Asp Lys Gly Ala Ala Arg
    210                 215                 220

Lys Leu Leu Asn Asp Pro Leu Gly Arg Arg Thr Pro Asn Tyr Gln Ser
225                 230                 235                 240

Lys Asn Pro Gly Glu Tyr Thr Val Gly Asn Ser Met Phe Tyr Asp Gly
                245                 250                 255

Pro Gln Val Ala Asn Leu Gln Asn Val Asp Thr Gly Phe Trp Leu Asp
            260                 265                 270

Met Ser Asn Leu Ser Asp Val Val Leu Ser Arg Glu Ile Gln Thr Gly
        275                 280                 285

Leu Arg Ala Arg Ala Thr Leu Glu Glu Ser Met Pro Met Leu Glu Asn
    290                 295                 300

Leu Glu Glu Arg Phe Arg Arg Leu Gln Glu Thr Cys Asp Ala Ala Arg
305                 310                 315                 320

Thr Glu Ile Glu Glu Ser Gly Trp Thr Arg Glu Ser Ala Ser Arg Met
                325                 330                 335

Glu Gly Asp Glu Ala Gln Gly Pro Ser Arg Val Gln Gln Ala Phe Gln
            340                 345                 350

Ser Phe Val Asn Glu Cys Asn Ser Ile Glu Phe Ser Phe Gly Ser Phe
        355                 360                 365

Gly Glu His Val Arg Val Leu Cys Ala Arg Val Ser Arg Gly Leu Ala
    370                 375                 380

Ala Ala Gly Glu Ala Ile Arg Arg Cys Phe Ser Cys Cys Lys Gly Ser
385                 390                 395                 400

Thr His Arg Tyr Ala Pro Arg Asp Asp Leu Ser Pro Glu Gly Ala Ser
                405                 410                 415

Leu Ala Glu Thr Leu Ala Arg Phe Ala Asp Asp Met Gly Ile Glu Arg
            420                 425                 430

Gly Ala Asp Gly Thr Tyr Asp Ile Pro Leu Val Asp Trp Arg Arg
        435                 440                 445

Gly Val Pro Ser Ile Glu Gly Gly Ser Asp Ser Ile Tyr Glu Ile
    450                 455                 460

Met Met Pro Ile Tyr Glu Val Met Asn Met Asp Leu Glu Thr Arg Arg
465                 470                 475                 480

Ser Phe Ala Val Gln Gln Gly His Tyr Gln Asp Pro Arg Ala Ser Asp
                485                 490                 495

Tyr Asp Leu Pro Arg Ala Ser Asp Tyr Asp Leu Pro Arg Ser Pro Tyr
            500                 505                 510

Pro Thr Pro Pro Leu Pro Pro Arg Tyr Gln Leu Gln Asn Met Asp Val
        515                 520                 525
```

```
Glu Ala Gly Phe Arg Glu Ala Val Tyr Ala Ser Phe Val Ala Gly Met
            530                 535                 540

Tyr Asn Tyr Val Val Thr Gln Pro Gln Glu Arg Ile Pro Asn Ser Gln
545                 550                 555                 560

Gln Val Glu Gly Ile Leu Arg Asp Met Leu Thr Asn Gly Ser Gln Thr
                565                 570                 575

Phe Arg Asp Leu Met Lys Arg Trp Asn Arg Glu Val Asp Arg Glu
                580                 585                 590

<210> SEQ ID NO 9
<211> LENGTH: 1962
<212> TYPE: DNA
<213> ORGANISM: Chlamydia trachomatis

<400> SEQUENCE: 9
```

| | |
|---|---|
| atggaatcag gaccagaatc agtttcttct aatcagagct cgatgaatcc aattattaat | 60 |
| gggcaaatcg cttctaattc ggagaccaaa gagtccacga aggcgtccga agcgagtcct | 120 |
| tcagcatcgt cctctgtaag cagctggagt tttttatcct cagcaaagaa tgcattaatc | 180 |
| tctcttcgtg atgccatctt gaataaaaat tccagtccaa cagactctct ctctcaatta | 240 |
| gaggcctcta cttctaccct tacggttaca cgtgtagcgg caaaagatta tgatgaggct | 300 |
| aaatcgaatt ttgatacggc gaaaagtgga ttagagaacg ctaagacact tgctgaatac | 360 |
| gaaacgaaaa tggctgattt gatggcagct ctccaagata tggagcgttt agctaattca | 420 |
| gatcctagta acaatcatac cgaagaagta ataatatta agaaagcgct cgaagcacaa | 480 |
| aaagatacta ttgataagct gaataaactc gttacgctgc aaaatcagaa taaatcttta | 540 |
| acagaagtgt tgaaaacaac tgactctgca gatcagattc cagcgattaa tagtcagtta | 600 |
| gagatcaaca aaaattctgc agatcaaatt atcaaagatc tggaaagaca aaacataagt | 660 |
| tatgaagctg ttctcactaa cgcaggagag gttatcaaag cttcttctga gcgggaatt | 720 |
| aagttaggac aagctttgca gtctattgtg gatgctgggg accaaagtca ggctgcagtt | 780 |
| ctgcaagcac agcaaaataa tagcccagat aatattgcag ccacgaagga attaattgat | 840 |
| gctgctgaaa cgaaggtaaa cgagttaaaa caagagcata cagggctaac ggactcgcct | 900 |
| ttagtgaaaa agctgagga gcagattagt caagcacaaa aagatattca agagatcaaa | 960 |
| cctagtggtt cggatattcc tatcgttggt ccgagtgggt cagctgcttc cgcaggaagt | 1020 |
| gcggcaggag cgttgaaatc ctctaacaat tcaggaagaa tttccttgtt gcttgatgat | 1080 |
| gtagacaatg aaatggcagc gattgcactg caaggttttc gatctatgat cgaacaattt | 1140 |
| aatgtaaaca atcctgcaac agctaaagag ctacaagcta tggaggctca gctgactgcg | 1200 |
| atgtcagatc aactggttgg tgcggatggc gagctcccag ccgaaataca agcaatcaaa | 1260 |
| gatgctcttg cgcaagcttt gaaacaacca tcagcagatg gtttggctac agctatggga | 1320 |
| caagtggctt ttgcagctgc caaggttgga ggaggctccg caggaacagc tggcactgtc | 1380 |
| cagatgaatg taaaacagct ttacaagaca gcgttttctt cgacttcttc cagctcttat | 1440 |
| gcagcagcac tttccgatgg atattctgct tacaaaacac tgaactcttt atattccgaa | 1500 |
| agcagaagcg gcgtgcagtc agctattagt caaactgcaa atcccgcgct tccagaagc | 1560 |
| gtttctcgtt ctggcataga aagtcaagga cgcagtgcag atgctagcca agagcagca | 1620 |
| gaaactattg tcagagatag ccaaacgtta ggtgatgtat atagccgctt acaggttctg | 1680 |
| gattctttga tgtctacgat tgtgagcaat ccgcaagcaa atcaagaaga gattatgcag | 1740 |
| aagctcacgg catctattag caaagctcca caatttgggt atcctgctgt tcagaattct | 1800 |

-continued

```
gcggatagct tgcagaagtt tgctgcgcaa ttggaaagag agtttgttga tggggaacgt     1860
agtctcgcag aatctcaaga gaatgcgttt agaaaacagc ccgctttcat tcaacaggtg     1920
ttggtaaaca ttgcttctct attctctggt tatctttctt aa                        1962
```

<210> SEQ ID NO 10
<211> LENGTH: 653
<212> TYPE: PRT
<213> ORGANISM: Chlamydia trachomatis

<400> SEQUENCE: 10

```
Met Glu Ser Gly Pro Glu Ser Val Ser Ser Asn Gln Ser Ser Met Asn
1               5                   10                  15

Pro Ile Ile Asn Gly Gln Ile Ala Ser Asn Ser Glu Thr Lys Glu Ser
            20                  25                  30

Thr Lys Ala Ser Glu Ala Ser Pro Ser Ala Ser Ser Val Ser Ser
        35                  40                  45

Trp Ser Phe Leu Ser Ser Ala Lys Asn Ala Leu Ile Ser Leu Arg Asp
    50                  55                  60

Ala Ile Leu Asn Lys Asn Ser Ser Pro Thr Asp Ser Leu Ser Gln Leu
65                  70                  75                  80

Glu Ala Ser Thr Ser Thr Ser Thr Val Thr Arg Val Ala Ala Lys Asp
                85                  90                  95

Tyr Asp Glu Ala Lys Ser Asn Phe Asp Thr Ala Lys Ser Gly Leu Glu
            100                 105                 110

Asn Ala Lys Thr Leu Ala Glu Tyr Glu Thr Lys Met Ala Asp Leu Met
        115                 120                 125

Ala Ala Leu Gln Asp Met Glu Arg Leu Ala Asn Ser Asp Pro Ser Asn
130                 135                 140

Asn His Thr Glu Glu Val Asn Asn Ile Lys Lys Ala Leu Glu Ala Gln
145                 150                 155                 160

Lys Asp Thr Ile Asp Lys Leu Asn Lys Leu Val Thr Leu Gln Asn Gln
                165                 170                 175

Asn Lys Ser Leu Thr Glu Val Leu Lys Thr Thr Asp Ser Ala Asp Gln
            180                 185                 190

Ile Pro Ala Ile Asn Ser Gln Leu Glu Ile Asn Lys Asn Ser Ala Asp
        195                 200                 205

Gln Ile Ile Lys Asp Leu Glu Arg Gln Asn Ile Ser Tyr Glu Ala Val
210                 215                 220

Leu Thr Asn Ala Gly Glu Val Ile Lys Ala Ser Ser Glu Ala Gly Ile
225                 230                 235                 240

Lys Leu Gly Gln Ala Leu Gln Ser Ile Val Asp Ala Gly Asp Gln Ser
                245                 250                 255

Gln Ala Ala Val Leu Gln Ala Gln Asn Asn Ser Pro Asp Asn Ile
            260                 265                 270

Ala Ala Thr Lys Glu Leu Ile Asp Ala Ala Glu Thr Lys Val Asn Glu
        275                 280                 285

Leu Lys Gln Glu His Thr Gly Leu Thr Asp Ser Pro Leu Val Lys Lys
290                 295                 300

Ala Glu Glu Gln Ile Ser Gln Ala Gln Lys Asp Ile Gln Glu Ile Lys
305                 310                 315                 320

Pro Ser Gly Ser Asp Ile Pro Ile Val Gly Pro Gly Ser Ala Ala
                325                 330                 335

Ser Ala Gly Ser Ala Ala Gly Ala Leu Lys Ser Ser Asn Asn Ser Gly
            340                 345                 350
```

```
Arg Ile Ser Leu Leu Asp Asp Val Asp Asn Glu Met Ala Ala Ile
        355                 360                 365
Ala Leu Gln Gly Phe Arg Ser Met Ile Glu Gln Phe Asn Val Asn Asn
370                 375                 380
Pro Ala Thr Ala Lys Glu Leu Gln Ala Met Glu Ala Gln Leu Thr Ala
385                 390                 395                 400
Met Ser Asp Gln Leu Val Gly Ala Asp Gly Glu Leu Pro Ala Glu Ile
                405                 410                 415
Gln Ala Ile Lys Asp Ala Leu Ala Gln Ala Leu Lys Gln Pro Ser Ala
                420                 425                 430
Asp Gly Leu Ala Thr Ala Met Gly Gln Val Ala Phe Ala Ala Ala Lys
            435                 440                 445
Val Gly Gly Gly Ser Ala Gly Thr Ala Gly Thr Val Gln Met Asn Val
450                 455                 460
Lys Gln Leu Tyr Lys Thr Ala Phe Ser Ser Thr Ser Ser Ser Ser Tyr
465                 470                 475                 480
Ala Ala Ala Leu Ser Asp Gly Tyr Ser Ala Tyr Lys Thr Leu Asn Ser
                485                 490                 495
Leu Tyr Ser Glu Ser Arg Ser Gly Val Gln Ser Ala Ile Ser Gln Thr
                500                 505                 510
Ala Asn Pro Ala Leu Ser Arg Ser Val Ser Arg Ser Gly Ile Glu Ser
            515                 520                 525
Gln Gly Arg Ser Ala Asp Ala Ser Gln Arg Ala Glu Thr Ile Val
    530                 535                 540
Arg Asp Ser Gln Thr Leu Gly Asp Val Tyr Ser Arg Leu Gln Val Leu
545                 550                 555                 560
Asp Ser Leu Met Ser Thr Ile Val Ser Asn Pro Gln Ala Asn Gln Glu
                565                 570                 575
Glu Ile Met Gln Lys Leu Thr Ala Ser Ile Ser Lys Ala Pro Gln Phe
                580                 585                 590
Gly Tyr Pro Ala Val Gln Asn Ser Ala Asp Ser Leu Gln Lys Phe Ala
            595                 600                 605
Ala Gln Leu Glu Arg Glu Phe Val Asp Gly Glu Arg Ser Leu Ala Glu
    610                 615                 620
Ser Gln Glu Asn Ala Phe Arg Lys Gln Pro Ala Phe Ile Gln Val
625                 630                 635                 640
Leu Val Asn Ile Ala Ser Leu Phe Ser Gly Tyr Leu Ser
                645                 650

<210> SEQ ID NO 11
<211> LENGTH: 2010
<212> TYPE: DNA
<213> ORGANISM: Chlamydia trachomatis

<400> SEQUENCE: 11
gcagaaatca tgattcctca aggaatttac gatggggaga cgttaactgt atcatttccc      60
tatactgtta taggagatcc gagtgggact actgtttttt ctgcaggaga gttaacatta     120
aaaaatcttg acaattctat tgcagctttg cctttaagtt gttttgggaa cttattaggg     180
agttttactg ttttagggag aggacactcg ttgactttcg agaacatacg gacttctaca     240
aatggggcag ctctaagtaa tagcgctgct gatggactgt tactattga gggttttaaa      300 gaattatcct tttccaattg caattcatta cttgccgtac tgcctgctgc aacgactaat     360
aagggtagcc agactccgac gacaacatct acaccgtcta atggtactat ttattctaaa     420
acagatcttt tgttactcaa taatgagaag ttctcattct atagtaattt agtctctgga     480
```

```
gatggggag ctatagatgc taagagctta acggttcaag gaattagcaa gctttgtgtc      540
ttccaagaaa atactgctca agctgatggg ggagcttgtc aagtagtcac cagtttctct      600
gctatggcta acgaggctcc tattgccttt gtagcgaatg ttgcaggagt aagaggggga      660
gggattgctg ctgttcagga tgggcagcag ggagtgtcat catctacttc aacagaagat      720
ccagtagtaa gttttccag aaatactgcg gtagagtttg atgggaacgt agcccgagta       780
ggaggaggga tttactccta cgggaacgtt gctttcctga ataatggaaa aaccttgttt      840
ctcaacaatg ttgcttctcc tgtttacatt gctgctaagc aaccaacaag tggacaggct      900
tctaatacga gtaataatta cggagatgga ggagctatct tctgtaagaa tggtgcgcaa      960
gcaggatcca ataactctgg atcagtttcc tttgatggag agggagtagt tttctttagt     1020
agcaatgtag ctgctgggaa aggggagct atttatgcca aaaagctctc ggttgctaac      1080
tgtggccctg tacaatttt aaggaatatc gctaatgatg gtggagcgat ttatttagga      1140
gaatctggag agctcagttt atctgctgat tatggagata ttattttcga tgggaatctt     1200
aaaagaacag ccaaagagaa tgctgccgat gttaatggcg taactgtgtc ctcacaagcc     1260
atttcgatgg gatcgggagg gaaaataacg acattaagag ctaaagcagg gcatcagatt     1320
ctctttaatg atcccatcga gatggcaaac ggaaataacc agccagcgca gtcttccaaa     1380
cttctaaaaa ttaacgatgg tgaaggatac acaggggata ttgttttgc taatggaagc      1440 agtactttgt accaaaatgt tacgatagag caaggaagga ttgttcttcg tgaaaaggca     1500
aaattatcag tgaattctct aagtcagaca ggtgggagtc tgtatatgga agctgggagt     1560
acattggatt ttgtaactcc acaaccacca caacagcctc ctgccgctaa tcagttgatc     1620
acgctttcca atctgcattt gtctctttct tctttgttag caaacaatgc agttacgaat     1680
cctcctacca atcctccagc gcaagattct catcctgcag tcattggtag cacaactgct     1740
ggttctgtta caattagtgg gcctatcttt tttgaggatt tggatgatac agcttatgat     1800
aggtatgatt ggctaggttc taatcaaaaa atcaatgtcc tgaaattaca gttagggact     1860
aagcccccag ctaatgcccc atcagatttg actctaggga atgagatgcc taagtatggc     1920
tatcaaggaa gctggaagct tgcgtgggat cctaatacag caataatgg tccttatact      1980 ctgaaagcta catggactaa aactgggtaa                                       2010
```

<210> SEQ ID NO 12
<211> LENGTH: 669
<212> TYPE: PRT
<213> ORGANISM: Chlamydia trachomatis

<400> SEQUENCE: 12

```
Ala Glu Ile Met Ile Pro Gln Gly Ile Tyr Asp Gly Glu Thr Leu Thr
1               5                   10                  15

Val Ser Phe Pro Tyr Thr Val Ile Gly Asp Pro Ser Gly Thr Thr Val
            20                  25                  30

Phe Ser Ala Gly Glu Leu Thr Leu Lys Asn Leu Asp Asn Ser Ile Ala
        35                  40                  45

Ala Leu Pro Leu Ser Cys Phe Gly Asn Leu Leu Gly Ser Phe Thr Val
    50                  55                  60

Leu Gly Arg Gly His Ser Leu Thr Phe Glu Asn Ile Arg Thr Ser Thr
65                  70                  75                  80

Asn Gly Ala Ala Leu Ser Asn Ser Ala Ala Asp Gly Leu Phe Thr Ile
                85                  90                  95

Glu Gly Phe Lys Glu Leu Ser Phe Ser Asn Cys Asn Ser Leu Leu Ala
```

```
                100                 105                 110
Val Leu Pro Ala Ala Thr Thr Asn Lys Gly Ser Gln Thr Pro Thr Thr
            115                 120                 125
Thr Ser Thr Pro Ser Asn Gly Thr Ile Tyr Ser Lys Thr Asp Leu Leu
130                 135                 140
Leu Leu Asn Asn Glu Lys Phe Ser Phe Tyr Ser Asn Leu Val Ser Gly
145                 150                 155                 160
Asp Gly Gly Ala Ile Asp Ala Lys Ser Leu Thr Val Gln Gly Ile Ser
                165                 170                 175
Lys Leu Cys Val Phe Gln Glu Asn Thr Ala Gln Ala Asp Gly Gly Ala
            180                 185                 190
Cys Gln Val Val Thr Ser Phe Ser Ala Met Ala Asn Glu Ala Pro Ile
        195                 200                 205
Ala Phe Val Ala Asn Val Ala Gly Val Arg Gly Gly Ile Ala Ala
    210                 215                 220
Val Gln Asp Gly Gln Gln Gly Val Ser Ser Thr Ser Thr Glu Asp
225                 230                 235                 240
Pro Val Val Ser Phe Ser Arg Asn Thr Ala Val Glu Phe Asp Gly Asn
                245                 250                 255
Val Ala Arg Val Gly Gly Gly Ile Tyr Ser Tyr Gly Asn Val Ala Phe
            260                 265                 270
Leu Asn Asn Gly Lys Thr Leu Phe Leu Asn Asn Val Ala Ser Pro Val
        275                 280                 285
Tyr Ile Ala Ala Lys Gln Pro Thr Ser Gly Gln Ala Ser Asn Thr Ser
    290                 295                 300
Asn Asn Tyr Gly Asp Gly Gly Ala Ile Phe Cys Lys Asn Gly Ala Gln
305                 310                 315                 320
Ala Gly Ser Asn Asn Ser Gly Ser Val Ser Phe Asp Gly Glu Gly Val
                325                 330                 335
Val Phe Phe Ser Ser Asn Val Ala Ala Gly Lys Gly Gly Ala Ile Tyr
            340                 345                 350
Ala Lys Lys Leu Ser Val Ala Asn Cys Gly Pro Val Gln Phe Leu Arg
        355                 360                 365
Asn Ile Ala Asn Asp Gly Gly Ala Ile Tyr Leu Gly Glu Ser Gly Glu
    370                 375                 380
Leu Ser Leu Ser Ala Asp Tyr Gly Asp Ile Ile Phe Asp Gly Asn Leu
385                 390                 395                 400
Lys Arg Thr Ala Lys Glu Asn Ala Ala Asp Val Asn Gly Val Thr Val
                405                 410                 415
Ser Ser Gln Ala Ile Ser Met Gly Ser Gly Lys Ile Thr Thr Leu
            420                 425                 430
Arg Ala Lys Ala Gly His Gln Ile Leu Phe Asn Asp Pro Ile Glu Met
        435                 440                 445
Ala Asn Gly Asn Asn Gln Pro Ala Gln Ser Ser Lys Leu Leu Lys Ile
    450                 455                 460
Asn Asp Gly Glu Gly Tyr Thr Gly Asp Ile Val Phe Ala Asn Gly Ser
465                 470                 475                 480
Ser Thr Leu Tyr Gln Asn Val Thr Ile Glu Gln Gly Arg Ile Val Leu
                485                 490                 495
Arg Glu Lys Ala Lys Leu Ser Val Asn Ser Leu Ser Gln Thr Gly Gly
            500                 505                 510
Ser Leu Tyr Met Glu Ala Gly Ser Thr Leu Asp Phe Val Thr Pro Gln
        515                 520                 525
```

```
Pro Pro Gln Gln Pro Pro Ala Ala Asn Gln Leu Ile Thr Leu Ser Asn
        530                 535                 540

Leu His Leu Ser Leu Ser Ser Leu Leu Ala Asn Asn Ala Val Thr Asn
545                 550                 555                 560

Pro Pro Thr Asn Pro Pro Ala Gln Asp Ser His Pro Ala Val Ile Gly
                565                 570                 575

Ser Thr Thr Ala Gly Ser Val Thr Ile Ser Gly Pro Ile Phe Phe Glu
                580                 585                 590

Asp Leu Asp Asp Thr Ala Tyr Asp Arg Tyr Asp Trp Leu Gly Ser Asn
            595                 600                 605

Gln Lys Ile Asn Val Leu Lys Leu Gln Leu Gly Thr Lys Pro Pro Ala
        610                 615                 620

Asn Ala Pro Ser Asp Leu Thr Leu Gly Asn Glu Met Pro Lys Tyr Gly
625                 630                 635                 640

Tyr Gln Gly Ser Trp Lys Leu Ala Trp Asp Pro Asn Thr Ala Asn Asn
                645                 650                 655

Gly Pro Tyr Thr Leu Lys Ala Thr Trp Thr Lys Thr Gly
                660                 665

<210> SEQ ID NO 13
<211> LENGTH: 3519
<212> TYPE: DNA
<213> ORGANISM: Chlamydia trachomatis

<400> SEQUENCE: 13
agttgcgtag atcttcatgc tggaggacag tctgtaaatg agctggtata tgtaggccct     60
caagcggttt tattgttaga ccaaattcga gatctattcg ttgggtctaa agatagtcag    120
gctgaaggac agtataggtt aattgtagga gatccaagtt cttttccaag gaaagatgca    180
gatactcttc ccgggaaggt agagcaaagt actttgttct cagtaaccaa tcccgtggtt    240
ttccaaggtg tggaccaaca ggatcaagtc tcttcccaag ggttaaattg tagttttacg    300
agcagcaacc ttgattctcc ccgtgacgga gaatcttttt taggtattgc ttttgttggg    360
gatagtagta aggctggaat cacattaact gacgtgaaag cttctttgtc tggagcggct    420
ttatattcta cagaagatct tatctttgaa aagattaagg gtggattgga atttgcatca    480
tgttcttctc tagaacaggg gggagcttgt gcagctcaaa gtattttgat tcatgattgt    540
caaggattgc aggttaaaca ctgtactaca gccgtgaatg ctgagggggtc tagtgcgaat    600 gatcatcttg gatttggagg aggcgctttc tttgttacgg gttctctttc tggagagaaa    660
agtctctata tgcctgcagg agatatggta gttgcgaatt gtgatggggc tatatctttt    720
gaaggaaaca gcgcgaactt tgctaatgga ggagcgattg ctgcctctgg gaaagtgctt    780
tttgtcgcta atgataaaaa gacttctttt atagagaacc gagctttgtc tggaggagcg    840
attgcagcct cttctgatat tgccttttcaa aactgcgcag aactagtttt caaaggcaat    900
tgtgcaattg aacagagga taaaggttct ttaggtggag gggctatatc ttctctaggc    960
accgttcttt tgcaagggaa tcacgggata acttgtgata agaatgagtc tgcttcgcaa    1020
ggaggcgcca ttttttggcaa aaattgtcag atttctgaca cgaggggcc agtggttttc    1080 agagatagta cagcttgctt aggaggaggc gctattgcag ctcaagaaat tgtttctatt    1140
cagaacaatc aggctgggat tccttcgag ggaggtaagg ctagtttcgg aggaggtatt    1200
gcgtgtggat cttttttcttc cgcaggcggt gcttctgttt tagggactat tgatatttcg    1260
aagaatttag gcgcgatttc gttctctcgt actttatgta cgacctcaga tttaggacaa    1320
atggagtacc agggaggagg agctctattt ggtgaaaata tttctctttc tgagaatgct    1380
```

```
ggtgtgctca cctttaaaga caacattgtg aagacttttg cttcgaatgg gaaaattctg    1440
ggaggaggag cgatttttagc tactggtaag gtggaaatta ccaataattc cggaggaatt    1500
tcttttacag gaaatgcgag agctccacaa gctcttccaa ctcaagagga gtttcctttta   1560 ttcagcaaaa aagaagggcg accactctct tcaggatatt ctgggggagg agcgatttta    1620
ggaagagaag tagctattct ccacaacgct gcagtagtat ttgagcaaaa tcgtttgcag    1680
tgcagcgaag aagaagcgac attattaggt tgttgtggag gaggcgctgt tcatgggatg    1740
gatagcactt cgattgttgg caactcttca gtaagatttg gtaataatta cgcaatggga    1800
caaggagtct caggaggagc tcttttatct aaaacagtgc agttagctgg aaatggaagc    1860
gtcgattttt ctcgaaatat tgctagtttg ggaggaggag ctcttcaagc ttctgaagga    1920
aattgtgagc tagttgataa cggctatgtg ctattcagag ataatcgagg gagggtttat    1980
gggggtgcta tttcttgctt acgtggagat gtagtcattt ctggaaacaa gggtagagtt   2040
gaatttaaag acaacatagc aacacgtctt tatgtggaag aaactgtaga aaaggttgaa    2100
gaggtagagc cagctcctga gcaaaaagac aataatgagc tttctttctt agggagtgta    2160
gaacagagtt ttattactgc agctaatcaa gctcttttcg catctgaaga tggggattta    2220
tcacctgagt catccatttc ttctgaagaa cttgcgaaaa aagagagtg tgctggagga    2280 gctattttg caaaacgggt tcgtattgta gataaccaag aggccgttgt attctcgaat    2340
aacttctctg atatttatgg cggcgccatt tttacaggtt ctcttcgaga agaggataag    2400
ttagatgggc aaatccctga agtcttgatc tcaggcaatg caggggatgt tgttttttcc    2460
ggaaattcct cgaagcgtga tgagcatctt cctcatacag gtgggggagc catttgtact    2520
caaaatttga cgatttctca gaatacaggg aatgttctgt tttataacaa cgtggcctgt    2580
tcgggaggag ctgttcgtat agaggatcat ggtaatgttc ttttagaagc ttttggagga    2640
gatattgttt taaaggaaa ttcttctttc agagcacaag gatccgatgc tatctatttt    2700
gcaggtaaag aatcgcatat tacagccctg aatgctacgg aaggacatgc tattgttttc    2760
cacgacgcat tagtttttga aaatctaaaa gaaaggaaat ctgctgaagt attgttaatc    2820
aatagtcgag aaaatccagg ttacactgga tctattcgat ttttagaagc agaaagtaaa    2880
gttcctcaat gtattcatgt acaacaagga agccttgagt tgctaaatgg agctacatta    2940
tgtagttatg gttttaaaca agatgctgga gctaagttgg tattggctgc tggatctaaa    3000
ctgaagattt tagattcagg aactcctgta caagggcatg ctatcagtaa acctgaagca    3060
gaaatcgagt catcttctga accagagggt gcacattctc tttggattgc gaagaatgct    3120
caaacaacag ttcctatggt tgatatccat actatttctg tagatttagc ctccttctct    3180
tctagtcaac aggagggac agtagaagct cctcaggtta ttgttcctgg aggaagttat    3240
gttcgatctg gagagcttaa tttggagtta gttaacacaa caggtactgg ttatgaaaat    3300
catgctttgt tgaagaatga ggctaaagtt ccattgatgt cttttcgttgc ttctagtgat    3360 gaagcttcag ccgaaatcag taacttgtcg gtttctgatt tacagattca tgtagcaact    3420
ccagagattg aagaagacac atacggccat atgggagatt ggtctgaggc taaaattcaa    3480
gatggaactc ttgtcattag ttggaatcct actggataa                           3519
```

<210> SEQ ID NO 14
<211> LENGTH: 1172
<212> TYPE: PRT
<213> ORGANISM: Chlamydia trachomatis

<400> SEQUENCE: 14

```
Ser Cys Val Asp Leu His Ala Gly Gly Gln Ser Val Asn Glu Leu Val
  1               5                  10                  15

Tyr Val Gly Pro Gln Ala Val Leu Leu Asp Gln Ile Arg Asp Leu
             20                  25                  30

Phe Val Gly Ser Lys Asp Ser Gln Ala Glu Gly Gln Tyr Arg Leu Ile
             35                  40                  45

Val Gly Asp Pro Ser Ser Phe Gln Glu Lys Asp Ala Asp Thr Leu Pro
 50                  55                  60

Gly Lys Val Glu Gln Ser Thr Leu Phe Ser Val Thr Asn Pro Val Val
 65                  70                  75                  80

Phe Gln Gly Val Asp Gln Gln Asp Gln Val Ser Ser Gln Gly Leu Ile
                 85                  90                  95

Cys Ser Phe Thr Ser Ser Asn Leu Asp Ser Pro Arg Asp Gly Glu Ser
                100                 105                 110

Phe Leu Gly Ile Ala Phe Val Gly Asp Ser Ser Lys Ala Gly Ile Thr
             115                 120                 125

Leu Thr Asp Val Lys Ala Ser Leu Ser Gly Ala Ala Leu Tyr Ser Thr
     130                 135                 140

Glu Asp Leu Ile Phe Glu Lys Ile Lys Gly Leu Glu Phe Ala Ser
145                 150                 155                 160

Cys Ser Ser Leu Glu Gln Gly Gly Ala Cys Ala Ala Gln Ser Ile Leu
                 165                 170                 175

Ile His Asp Cys Gln Gly Leu Gln Val Lys His Cys Thr Thr Ala Val
             180                 185                 190

Asn Ala Glu Gly Ser Ser Ala Asn Asp His Leu Gly Phe Gly Gly Gly
         195                 200                 205

Ala Phe Phe Val Thr Gly Ser Leu Ser Gly Glu Lys Ser Leu Tyr Met
     210                 215                 220

Pro Ala Gly Asp Met Val Val Ala Asn Cys Asp Gly Ala Ile Ser Phe
225                 230                 235                 240

Glu Gly Asn Ser Ala Asn Phe Ala Asn Gly Gly Ala Ile Ala Ala Ser
                 245                 250                 255

Gly Lys Val Leu Phe Val Ala Asn Asp Lys Lys Thr Ser Phe Ile Glu
             260                 265                 270

Asn Arg Ala Leu Ser Gly Gly Ala Ile Ala Ser Ser Asp Ile Ala
         275                 280                 285

Phe Gln Asn Cys Ala Glu Leu Val Phe Lys Gly Asn Cys Ala Ile Gly
     290                 295                 300

Thr Glu Asp Lys Gly Ser Leu Gly Gly Gly Ala Ile Ser Ser Leu Gly
305                 310                 315                 320

Thr Val Leu Leu Gln Gly Asn His Gly Ile Thr Cys Asp Lys Asn Glu
                 325                 330                 335

Ser Ala Ser Gln Gly Gly Ala Ile Phe Gly Lys Asn Cys Gln Ile Ser
             340                 345                 350

Asp Asn Glu Gly Pro Val Val Phe Arg Asp Ser Thr Ala Cys Leu Gly
         355                 360                 365

Gly Gly Ala Ile Ala Ala Gln Glu Ile Val Ser Ile Gln Asn Asn Gln
     370                 375                 380

Ala Gly Ile Ser Phe Glu Gly Lys Ala Ser Phe Gly Gly Gly Ile
385                 390                 395                 400

Ala Cys Gly Ser Phe Ser Ser Ala Gly Gly Ala Ser Val Leu Gly Thr
                 405                 410                 415

Ile Asp Ile Ser Lys Asn Leu Gly Ala Ile Ser Phe Ser Arg Thr Leu
```

```
                    420                 425                 430
Cys Thr Thr Ser Asp Leu Gly Gln Met Glu Tyr Gln Gly Gly Ala
                435                 440                 445

Leu Phe Gly Glu Asn Ile Ser Leu Ser Glu Asn Ala Gly Val Leu Thr
450                 455                 460

Phe Lys Asp Asn Ile Val Lys Thr Phe Ala Ser Asn Gly Lys Ile Leu
465                 470                 475                 480

Gly Gly Gly Ala Ile Leu Ala Thr Gly Lys Val Glu Ile Thr Asn Asn
                485                 490                 495

Ser Gly Gly Ile Ser Phe Thr Gly Asn Ala Arg Ala Pro Gln Ala Leu
                500                 505                 510

Pro Thr Gln Glu Glu Phe Pro Leu Phe Ser Lys Lys Glu Gly Arg Pro
                515                 520                 525

Leu Ser Ser Gly Tyr Ser Gly Gly Ala Ile Leu Gly Arg Glu Val
                530                 535                 540

Ala Ile Leu His Asn Ala Ala Val Val Phe Glu Gln Asn Arg Leu Gln
545                 550                 555                 560

Cys Ser Glu Glu Glu Ala Thr Leu Leu Gly Cys Cys Gly Gly Gly Ala
                565                 570                 575

Val His Gly Met Asp Ser Thr Ser Ile Val Gly Asn Ser Ser Val Arg
                580                 585                 590

Phe Gly Asn Asn Tyr Ala Met Gly Gln Gly Val Ser Gly Gly Ala Leu
                595                 600                 605

Leu Ser Lys Thr Val Gln Leu Ala Gly Asn Gly Ser Val Asp Phe Ser
                610                 615                 620

Arg Asn Ile Ala Ser Leu Gly Gly Gly Ala Leu Gln Ala Ser Glu Gly
625                 630                 635                 640

Asn Cys Glu Leu Val Asp Asn Gly Tyr Val Leu Phe Arg Asp Asn Arg
                645                 650                 655

Gly Arg Val Tyr Gly Gly Ala Ile Ser Cys Leu Arg Gly Asp Val Val
                660                 665                 670

Ile Ser Gly Asn Lys Gly Arg Val Glu Phe Lys Asp Asn Ile Ala Thr
                675                 680                 685

Arg Leu Tyr Val Glu Glu Thr Val Glu Lys Val Glu Glu Val Glu Pro
                690                 695                 700

Ala Pro Glu Gln Lys Asp Asn Asn Glu Leu Ser Phe Leu Gly Ser Val
705                 710                 715                 720

Glu Gln Ser Phe Ile Thr Ala Ala Asn Gln Ala Leu Phe Ala Ser Glu
                725                 730                 735

Asp Gly Asp Leu Ser Pro Glu Ser Ser Ile Ser Ser Glu Glu Leu Ala
                740                 745                 750

Lys Arg Arg Glu Cys Ala Gly Gly Ala Ile Phe Ala Lys Arg Val Arg
                755                 760                 765

Ile Val Asp Asn Gln Glu Ala Val Val Phe Ser Asn Asn Phe Ser Asp
                770                 775                 780

Ile Tyr Gly Gly Ala Ile Phe Thr Gly Ser Leu Arg Glu Glu Asp Lys
785                 790                 795                 800

Leu Asp Gly Gln Ile Pro Glu Val Leu Ile Ser Gly Asn Ala Gly Asp
                805                 810                 815

Val Val Phe Ser Gly Asn Ser Ser Lys Arg Asp Glu His Leu Pro His
                820                 825                 830

Thr Gly Gly Gly Ala Ile Cys Thr Gln Asn Leu Thr Ile Ser Gln Asn
                835                 840                 845
```

```
Thr Gly Asn Val Leu Phe Tyr Asn Asn Val Ala Cys Ser Gly Gly Ala
            850                 855                 860

Val Arg Ile Glu Asp His Gly Asn Val Leu Leu Glu Ala Phe Gly Gly
865                 870                 875                 880

Asp Ile Val Phe Lys Gly Asn Ser Ser Phe Arg Ala Gln Gly Ser Asp
                885                 890                 895

Ala Ile Tyr Phe Ala Gly Lys Glu Ser His Ile Thr Ala Leu Asn Ala
                900                 905                 910

Thr Glu Gly His Ala Ile Val Phe His Asp Ala Leu Val Phe Glu Asn
                915                 920                 925

Leu Lys Glu Arg Lys Ser Ala Glu Val Leu Leu Ile Asn Ser Arg Glu
                930                 935                 940

Asn Pro Gly Tyr Thr Gly Ser Ile Arg Phe Leu Glu Ala Glu Ser Lys
945                 950                 955                 960

Val Pro Gln Cys Ile His Val Gln Gln Gly Ser Leu Glu Leu Leu Asn
                965                 970                 975

Gly Ala Thr Leu Cys Ser Tyr Gly Phe Lys Gln Asp Ala Gly Ala Lys
                980                 985                 990

Leu Val Leu Ala Ala Gly Ser Lys Leu Lys Ile Leu Asp Ser Gly Thr
                995                 1000                1005

Pro Val Gln Gly His Ala Ile Ser Lys Pro Glu Ala Glu Ile Glu Ser
        1010                1015                1020

Ser Ser Glu Pro Glu Gly Ala His Ser Leu Trp Ile Ala Lys Asn Ala
1025                1030                1035                1040

Gln Thr Thr Val Pro Met Val Asp Ile His Thr Ile Ser Val Asp Leu
                1045                1050                1055

Ala Ser Phe Ser Ser Gln Gln Glu Gly Thr Val Glu Ala Pro Gln
                1060                1065                1070

Val Ile Val Pro Gly Gly Ser Tyr Val Arg Ser Gly Glu Leu Asn Leu
                1075                1080                1085

Glu Leu Val Asn Thr Thr Gly Thr Gly Tyr Glu Asn His Ala Leu Leu
        1090                1095                1100

Lys Asn Glu Ala Lys Val Pro Leu Met Ser Phe Val Ala Ser Ser Asp
1105                1110                1115                1120

Glu Ala Ser Ala Glu Ile Ser Asn Leu Ser Val Ser Asp Leu Gln Ile
                1125                1130                1135

His Val Ala Thr Pro Glu Ile Glu Asp Thr Tyr Gly His Met Gly
                1140                1145                1150

Asp Trp Ser Glu Ala Lys Ile Gln Asp Gly Thr Leu Val Ile Ser Trp
        1155                1160                1165

Asn Pro Thr Gly
    1170

<210> SEQ ID NO 15
<211> LENGTH: 1266
<212> TYPE: DNA
<213> ORGANISM: Chlamydia trachomatis

<400> SEQUENCE: 15
atgactgcat caggaggagc tggagggcta ggcagcaccc aaacagtaga cgttgcgcga      60
gcacaagctg ctgcagctac tcaagatgca caagaggtta tcggctctca ggaagcttct     120
gaggcaagta tgctcaaagg atgtgaggat ctcataaatc ctgcagctgc aacccgaatc     180
aaaaaaaaag aagagaagtt tgaatcatta gaagctcgtc gcaaaccaac agcggataaa     240
gcagaaaaga aatccgagag cacagaggaa aaaggcgata ctcctcttga agatcgtttc     300
```

```
acagaagatc tttccgaagt ctccggagaa gattttcgag gattgaaaaa ttcgttcgat    360
gatgattctt ctcctgaaga aattctcgat gcgctcacaa gtaaattttc tgatcccaca    420
ataaaggatc tagctcttga ttatctaatt caaacagctc cctctgatag gaaacttaag    480
tccgctctca ttcaggcaaa gcatcaactg atgagccaga atcctcaggc gattgttgga    540
ggacgcaatg ttctgttagc ttcagaaacc tttgcttcca gagcaaatac atctccttca    600
tcgcttcgct ccttatatct ccaagtaacc tcatccccct ctaattgtga taatttacgt    660
caaatgcttg cttcttactt gccatcagag aaaaccgctg ttatggagtt tctagtaaat    720
ggcatggtag cagatttaaa atcggagggc ccttccattc ctcctgcaaa attgcaagta    780
tatatgacgg aactaagcaa tctccaagcc ttacactctg tagatagctt ttttgataga    840
aatattggga acttggaaaa tagcttaaag catgaaggac atgcccctat tccatcctta    900
acgacaggaa atttaactaa aaccttctta caattagtag aagataaatt cccttcctct    960
tccaaagctc aaaaggcatt aaatgaactg gtaggcccag atactggtcc tcaaactgaa   1020
gttttaaact tattcttccg cgctcttaat ggctgttcgc ctagaatatt ctctggagct   1080
gaaaaaaaac agcagctggc atcggttatc acaaatacgc tagatgcgat aaatgcggat   1140
aatgaggatt atcctaaacc aggtgacttc ccacgatctt ccttctctag tacgcctcct   1200
catgctccag tacctcaatc tgagattcca acgtcaccta cctcaacaca gcctccatca   1260
ccctaa                                                              1266
```

<210> SEQ ID NO 16
<211> LENGTH: 421
<212> TYPE: PRT
<213> ORGANISM: Chlamydia trachomatis

<400> SEQUENCE: 16

```
Met Thr Ala Ser Gly Gly Ala Gly Gly Leu Gly Ser Thr Gln Thr Val
1               5                   10                  15

Asp Val Ala Arg Ala Gln Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Ser Ser Pro Glu Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Arg Lys Leu Lys
145                 150                 155                 160

Ser Ala Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Leu Gln
```

```
                195                 200                 205
Val Thr Ser Ser Pro Ser Asn Cys Asp Asn Leu Arg Gln Met Leu Ala
210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
                260                 265                 270

Ser Val Asp Ser Phe Phe Asp Arg Asn Ile Gly Asn Leu Glu Asn Ser
                275                 280                 285

Leu Lys His Glu Gly His Ala Pro Ile Pro Ser Leu Thr Thr Gly Asn
                290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
                340                 345                 350

Ser Pro Arg Ile Phe Ser Gly Ala Glu Lys Lys Gln Gln Leu Ala Ser
                355                 360                 365

Val Ile Thr Asn Thr Leu Asp Ala Ile Asn Ala Asp Asn Glu Asp Tyr
                370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
                420

<210> SEQ ID NO 17
<211> LENGTH: 1170
<212> TYPE: DNA
<213> ORGANISM: Chlamydia psitacci

<400> SEQUENCE: 17
atgaaaaaac tcttgaaatc ggcattattg tttgccacta cgggttccgc tctctcctta      60
caagccttgc ctgtagggaa tccagctgaa ccaagtttat taattgatgg cactatgtgg     120
gaaggcgctt caggcgatcc ttgtgatcct tgctctactt ggtgtgatgc tatcagcatc     180
cgcgcagggt actacggaga ttatgttttc gatcgcatct aaaagttga tgttaataaa      240 actatcagca tggggacagc tccaactggt aatgcagctg ctgactttaa aaccgttgca     300
gacaggaata acatagccta cggcaaacat atgcaagatg cagaatggtc cacaaacgcg     360
gctttcttag cattaaacat ttgggatcgt tttgatgtct tctgcacatt agggcatct      420 aacggctatc tcaaagcaaa tgctgcagct ttcaatctag tcggcttact tggggtaaca     480
ggaacagatc ttcaaggcca atatccaaac gtagccatct ctcaaggcct tgtagagctt     540
tatactgaca caaccttctc ttggagcgtt ggtgcgcgtg agctttatg ggaatgtggt      600 tgcgcaactt taggagcaga gttccaatat gcgcagtcta atcctaagat cgaaatgctt     660
aatgtaattt ctagcccaac acaatttgtg attcataagc ctagaggata taagggaca     720 gcggccaact tccctctgcc tttaaccgct ggaacagaga gcgctactga tactaaatca     780
gctacaatta gtatcatga atggcaaatt ggtttagctc tttcttatag attgaacatg     840
```

```
cttgttccat atattggagt aaactggtcc agagctacat ttgatgctga ctctatccgc    900
attgctcagc ctaaattacc tacggccatt ttaaacctaa ctacatggaa ccctacttta    960
ttaggggagg ctactactat aaacactgga gcaaaatatg ctgaccagtt acaaattgct   1020
tcgcttcaaa tcaacaaaat gaagtctaga aaagcttgtg gtattgctgt tggtgcaacc   1080
ttaattgatg ctgacaaatg gtcgatcact ggtgaagctc gcttaatcaa cgaaagagct   1140
gctcacgtaa acgctcaatt cagattctaa                                    1170

<210> SEQ ID NO 18
<211> LENGTH: 389
<212> TYPE: PRT
<213> ORGANISM: Chlamydia psitacci

<400> SEQUENCE: 18

Met Lys Lys Leu Leu Lys Ser Ala Leu Leu Phe Ala Thr Thr Gly Ser
1               5                   10                  15

Ala Leu Ser Leu Gln Ala Leu Pro Val Gly Asn Pro Ala Glu Pro Ser
            20                  25                  30

Leu Leu Ile Asp Gly Thr Met Trp Glu Gly Ala Ser Gly Asp Pro Cys
        35                  40                  45

Asp Pro Cys Ser Thr Trp Cys Asp Ala Ile Ser Ile Arg Ala Gly Tyr
    50                  55                  60

Tyr Gly Asp Tyr Val Phe Asp Arg Ile Leu Lys Val Asp Val Asn Lys
65                  70                  75                  80

Thr Ile Ser Met Gly Thr Ala Pro Thr Gly Asn Ala Ala Ala Asp Phe
                85                  90                  95

Lys Thr Val Ala Asp Arg Asn Asn Ile Ala Tyr Gly Lys His Met Gln
            100                 105                 110

Asp Ala Glu Trp Ser Thr Asn Ala Ala Phe Leu Ala Leu Asn Ile Trp
        115                 120                 125

Asp Arg Phe Asp Val Phe Cys Thr Leu Gly Ala Ser Asn Gly Tyr Leu
    130                 135                 140

Lys Ala Asn Ala Ala Ala Phe Asn Leu Val Gly Leu Leu Gly Val Thr
145                 150                 155                 160

Gly Thr Asp Leu Gln Gly Gln Tyr Pro Asn Val Ala Ile Ser Gln Gly
                165                 170                 175

Leu Val Glu Leu Tyr Thr Asp Thr Thr Phe Ser Trp Ser Val Gly Ala
            180                 185                 190

Arg Gly Ala Leu Trp Glu Cys Gly Cys Ala Thr Leu Gly Ala Glu Phe
        195                 200                 205

Gln Tyr Ala Gln Ser Asn Pro Lys Ile Glu Met Leu Asn Val Ile Ser
    210                 215                 220

Ser Pro Thr Gln Phe Val Ile His Lys Pro Arg Gly Tyr Lys Gly Thr
225                 230                 235                 240

Ala Ala Asn Phe Pro Leu Pro Leu Thr Ala Gly Thr Glu Ser Ala Thr
                245                 250                 255

Asp Thr Lys Ser Ala Thr Ile Lys Tyr His Glu Trp Gln Ile Gly Leu
            260                 265                 270

Ala Leu Ser Tyr Arg Leu Asn Met Leu Val Pro Tyr Ile Gly Val Asn
        275                 280                 285

Trp Ser Arg Ala Thr Phe Asp Ala Asp Ser Ile Arg Ile Ala Gln Pro
    290                 295                 300

Lys Leu Pro Thr Ala Ile Leu Asn Leu Thr Thr Trp Asn Pro Thr Leu
305                 310                 315                 320
```

```
Leu Gly Glu Ala Thr Thr Ile Asn Thr Gly Ala Lys Tyr Ala Asp Gln
            325                 330                 335

Leu Gln Ile Ala Ser Leu Gln Ile Asn Lys Met Lys Ser Arg Lys Ala
            340                 345                 350

Cys Gly Ile Ala Val Gly Ala Thr Leu Ile Asp Ala Asp Lys Trp Ser
            355                 360                 365

Ile Thr Gly Glu Ala Arg Leu Ile Asn Glu Arg Ala Ala His Val Asn
            370                 375                 380

Ala Gln Phe Arg Phe
385

<210> SEQ ID NO 19
<211> LENGTH: 1170
<212> TYPE: DNA
<213> ORGANISM: Chlamydia pneumoniae

<400> SEQUENCE: 19
atgaaaaaac tcttaaagtc ggcgttatta tccgccgcat ttgctggttc tgttggctcc      60
ttacaagcct tgcctgtagg gaacccttct gatccaagct tattaattga tggtacaata     120
tgggaaggtg ctgcaggaga tccttgcgat ccttgcgcta cttggtgcga cgctattagc     180
ttacgtgctg gattttacgg agactatgtt tcgaccgta tcttaaaagt agatgcacct      240
aaaacatttt ctatgggagc caagcctact ggatccgctg ctgcaaacta ctactgcc      300 gtagatagac ctaacccggc ctacaataag catttacacg atgcagagtg gttcactaat     360
gcaggcttca ttgccttaaa catttgggat cgctttgatg ttttctgtac tttaggagct     420
tctaatggtt acattagagg aaactctaca gcgttcaatc tcgttggttt attcggagtt     480
aaaggtacta ctgtaaatgc aaatgaacta ccaaacgttt ctttaagtaa cggagttgtt     540
gaactttaca cagacaccctc tttctcttgg agcgtaggcg ctcgtggagc cttatgggaa     600
tgcggttgtg caactttggg agctgaattc caatatgcac agtccaaacc taaagttgaa     660
gaacttaatg tgatctgtaa cgtatcgcaa ttctctgtaa acaaacccaa gggctataaa     720
ggcgttgctt tccccttgcc aacagacgct ggcgtagcaa cagctactgg aacaaagtct     780
gcgaccatca attatcatga atggcaagta ggagcctctc tatcttacag actaaactct     840
ttagtgccat acattggagt acaatggtct cgagcaactt ttgatgctga aacatccgc     900 attgctcagc caaaactacc tacagctgtt ttaaacttaa ctgcatggaa ccctctttta     960
ctaggaaatg ccacagcatt gtctactact gattcgttct cagacttcat gcaaattgtt    1020
tcctgtcaga tcaacaagtt taaatctaga aaagcttgtg gagttactgt aggagctact    1080
ttagttgatg ctgataaatg gtcacttact gcagaagctc gtttaattaa cgagagagct    1140
gctcacgtat ctggtcagtt cagattctaa                                     1170

<210> SEQ ID NO 20
<211> LENGTH: 389
<212> TYPE: PRT
<213> ORGANISM: Chlamydia pneumoniae

<400> SEQUENCE: 20

Met Lys Lys Leu Leu Lys Ser Ala Leu Leu Ser Ala Ala Phe Ala Gly
1               5                   10                  15

Ser Val Gly Ser Leu Gln Ala Leu Pro Val Gly Asn Pro Ser Asp Pro
            20                  25                  30

Ser Leu Leu Ile Asp Gly Thr Ile Trp Glu Gly Ala Ala Gly Asp Pro
        35                  40                  45
```

```
Cys Asp Pro Cys Ala Thr Trp Cys Asp Ala Ile Ser Leu Arg Ala Gly
 50                  55                  60

Phe Tyr Gly Asp Tyr Val Phe Asp Arg Ile Leu Lys Val Asp Ala Pro
 65                  70                  75                  80

Lys Thr Phe Ser Met Gly Ala Lys Pro Thr Gly Ser Ala Ala Ala Asn
                 85                  90                  95

Tyr Thr Thr Ala Val Asp Arg Pro Asn Pro Ala Tyr Asn Lys His Leu
            100                 105                 110

His Asp Ala Glu Trp Phe Thr Asn Ala Gly Phe Ile Ala Leu Asn Ile
            115                 120                 125

Trp Asp Arg Phe Asp Val Phe Cys Thr Leu Gly Ala Ser Asn Gly Tyr
    130                 135                 140

Ile Arg Gly Asn Ser Thr Ala Phe Asn Leu Val Gly Leu Phe Gly Val
145                 150                 155                 160

Lys Gly Thr Thr Val Asn Ala Asn Glu Leu Pro Asn Val Ser Leu Ser
                165                 170                 175

Asn Gly Val Val Glu Leu Tyr Thr Asp Thr Ser Phe Ser Trp Ser Val
            180                 185                 190

Gly Ala Arg Gly Ala Leu Trp Glu Cys Gly Cys Ala Thr Leu Gly Ala
            195                 200                 205

Glu Phe Gln Tyr Ala Gln Ser Lys Pro Lys Val Glu Glu Leu Asn Val
    210                 215                 220

Ile Cys Asn Val Ser Gln Phe Ser Val Asn Lys Pro Lys Gly Tyr Lys
225                 230                 235                 240

Gly Val Ala Phe Pro Leu Pro Thr Asp Ala Gly Val Ala Thr Ala Thr
                245                 250                 255

Gly Thr Lys Ser Ala Thr Ile Asn Tyr His Glu Trp Gln Val Gly Ala
            260                 265                 270

Ser Leu Ser Tyr Arg Leu Asn Ser Leu Val Pro Tyr Ile Gly Val Gln
            275                 280                 285

Trp Ser Arg Ala Thr Phe Asp Ala Asp Asn Ile Arg Ile Ala Gln Pro
    290                 295                 300

Lys Leu Pro Thr Ala Val Leu Asn Leu Thr Ala Trp Asn Pro Ser Leu
305                 310                 315                 320

Leu Gly Asn Ala Thr Ala Leu Ser Thr Thr Asp Ser Phe Ser Asp Phe
                325                 330                 335

Met Gln Ile Val Ser Cys Gln Ile Asn Lys Phe Lys Ser Arg Lys Ala
            340                 345                 350

Cys Gly Val Thr Val Gly Ala Thr Leu Val Asp Ala Asp Lys Trp Ser
            355                 360                 365

Leu Thr Ala Glu Ala Arg Leu Ile Asn Glu Arg Ala Ala His Val Ser
    370                 375                 380

Gly Gln Phe Arg Phe
385

<210> SEQ ID NO 21
<211> LENGTH: 1776
<212> TYPE: DNA
<213> ORGANISM: Chlamydia trachomatis

<400> SEQUENCE: 21
atgagcatca gggagtagg aggcaacggg aatagtcgaa tcccttctca taatggggat      60
ggatcgaatc gcagaagtca aaatacgaag ggtaataata aagttgaaga tcgagtttgt    120
tctctatatt catctcgtag taacgaaaat agagaatctc cttatgcagt agtagacgtc    180
```

```
agctctatga tcgagagcac cccaacgagt ggagagacga caagagcttc gcgtggagtg     240
ttcagtcgtt tccaaagagg tttagtacga gtagctgaca aagtaagacg agctgttcag     300
tgtgcgtgga gttcagtctc tacaagaaga tcgtctgcaa caagagccgc agaatccgga     360
tcaagtagtc gtactgctcg tggtgcaagt tctgggtata gggagtattc tccttcagca     420
gctagagggc tgcgtcttat gttcacagat ttctggagaa ctcgggtttt acgccagacc     480
tctcctatgg ctggagtttt tgggaatctt gatgtgaacg aggctcgttt gatggctgcg     540
tacacaagtg agtgcgcgga tcatttagaa gcgaacaagt tggctggccc tgacggggta     600
gcggccgccc gggaaattgc taaagatgg gagcaaagag ttagagatct acaagataaa     660
ggtgctgcac gaaaattatt aaatgatcct ttaggccgac gaacacctaa ttatcagagc     720
aaaaatccag gtgagtatac tgtagggaat tccatgtttt acgatggtcc tcaggtagcg     780
aatctccaga acgtcgacac tggttttggg ctggacatga gcaatctctc agacgttgta     840
ttatccagag agattcaaac aggacttcga gcacgagcta ctttggaaga atccatgccg     900
atgttagaga atttagaaga gcgttttaga cgtttgcaag aaacttgtga tgcggctcgt     960
actgagatag aagaatcggg atggactcga gagtccgcat caagaatgga aggcgatgag    1020
gcgcaaggac cttctagagc acaacaagct tttcagagct ttgtaaatga atgtaacagc    1080
atcgagttct catttgggag ctttggagag catgtgcgag ttctctgcgc tagagtatca    1140
cgaggattag ctgccgcagg agaggcgatt cgccgttgct tctcttgttg taaaggatcg    1200
acgcatcgct acgctcctcg cgatgaccta tctcctgaag gtgcatcgtt agcagagact    1260
ttggctagat tcgcagatga tatgggaata gagcgaggtg ctgatggaac ctacgatatt    1320
cctttggtag atgattggag aagagggggtt cctagtattg aaggagaagg atctgactcg    1380
atctatgaaa tcatgatgcc tatctatgaa gttatggata tggatctaga aacacgaaga    1440
tcttttgcgg tacagcaagg gcactatcag gacccaagag cttcagatta tgacctccca    1500
cgtgctagcg actatgattt gcctagaagc ccatatccta ctccacctttt gcctcctaga    1560
tatcagctac agaatatgga tgtagaagca gggttccgtg aggcagttta tgcttctttt    1620
gtagcaggaa tgtacaatta tgtagtgaca cagccgcaag agcgtattcc caatagtcag    1680
caggtggaag ggattctgcg tgatatgctt accaacgggt cacagacatt tagagacctg    1740
atgaggcgtt ggaatagaga agtcgatagg gaataa                              1776
```

<210> SEQ ID NO 22  
<211> LENGTH: 591  
<212> TYPE: PRT  
<213> ORGANISM: Chlamydia trachomatis

<400> SEQUENCE: 22

```
Met Ser Ile Arg Gly Val Gly Gly Asn Gly Asn Ser Arg Ile Pro Ser
1               5                   10                  15

His Asn Gly Asp Gly Ser Asn Arg Arg Ser Gln Asn Thr Lys Gly Asn
            20                  25                  30

Asn Lys Val Glu Asp Arg Val Cys Ser Leu Tyr Ser Ser Arg Ser Asn
        35                  40                  45

Glu Asn Arg Glu Ser Pro Tyr Ala Val Val Asp Val Ser Ser Met Ile
    50                  55                  60

Glu Ser Thr Pro Thr Ser Gly Glu Thr Thr Arg Ala Ser Arg Gly Val
65                  70                  75                  80

Phe Ser Arg Phe Gln Arg Gly Leu Val Arg Val Ala Asp Lys Val Arg
                85                  90                  95
```

```
Arg Ala Val Gln Cys Ala Trp Ser Ser Val Ser Thr Arg Arg Ser Ser
            100                 105                 110

Ala Thr Arg Ala Ala Glu Ser Gly Ser Ser Ser Arg Thr Ala Arg Gly
        115                 120                 125

Ala Ser Ser Gly Tyr Arg Glu Tyr Ser Pro Ser Ala Ala Arg Gly Leu
    130                 135                 140

Arg Leu Met Phe Thr Asp Phe Trp Arg Thr Arg Val Leu Arg Gln Thr
145                 150                 155                 160

Ser Pro Met Ala Gly Val Phe Gly Asn Leu Asp Val Asn Glu Ala Arg
                165                 170                 175

Leu Met Ala Ala Tyr Thr Ser Glu Cys Ala Asp His Leu Glu Ala Asn
            180                 185                 190

Lys Leu Ala Gly Pro Asp Gly Val Ala Ala Arg Glu Ile Ala Lys
        195                 200                 205

Arg Trp Glu Gln Arg Val Arg Asp Leu Gln Asp Lys Gly Ala Ala Arg
    210                 215                 220

Lys Leu Leu Asn Asp Pro Leu Gly Arg Arg Thr Pro Asn Tyr Gln Ser
225                 230                 235                 240

Lys Asn Pro Gly Glu Tyr Thr Val Gly Asn Ser Met Phe Tyr Asp Gly
                245                 250                 255

Pro Gln Val Ala Asn Leu Gln Asn Val Asp Thr Gly Phe Trp Leu Asp
            260                 265                 270

Met Ser Asn Leu Ser Asp Val Val Leu Ser Arg Glu Ile Gln Thr Gly
        275                 280                 285

Leu Arg Ala Arg Ala Thr Leu Glu Glu Ser Met Pro Met Leu Glu Asn
    290                 295                 300

Leu Glu Glu Arg Phe Arg Arg Leu Gln Glu Thr Cys Asp Ala Ala Arg
305                 310                 315                 320

Thr Glu Ile Glu Glu Ser Gly Trp Thr Arg Glu Ser Ala Ser Arg Met
                325                 330                 335

Glu Gly Asp Glu Ala Gln Gly Pro Ser Arg Ala Gln Gln Ala Phe Gln
            340                 345                 350

Ser Phe Val Asn Glu Cys Asn Ser Ile Glu Phe Ser Phe Gly Ser Phe
        355                 360                 365

Gly Glu His Val Arg Val Leu Cys Ala Arg Val Ser Arg Gly Leu Ala
    370                 375                 380

Ala Ala Gly Glu Ala Ile Arg Arg Cys Phe Ser Cys Cys Lys Gly Ser
385                 390                 395                 400

Thr His Arg Tyr Ala Pro Arg Asp Asp Leu Ser Pro Glu Gly Ala Ser
                405                 410                 415

Leu Ala Glu Thr Leu Ala Arg Phe Ala Asp Asp Met Gly Ile Glu Arg
            420                 425                 430

Gly Ala Asp Gly Thr Tyr Asp Ile Pro Leu Val Asp Asp Trp Arg Arg
        435                 440                 445

Gly Val Pro Ser Ile Glu Gly Glu Gly Ser Asp Ser Ile Tyr Glu Ile
    450                 455                 460

Met Met Pro Ile Tyr Glu Val Met Asp Met Leu Glu Thr Arg Arg
465                 470                 475                 480

Ser Phe Ala Val Gln Gln Gly His Tyr Gln Asp Pro Arg Ala Ser Asp
                485                 490                 495

Tyr Asp Leu Pro Arg Ala Ser Asp Tyr Asp Leu Pro Arg Ser Pro Tyr
            500                 505                 510

Pro Thr Pro Pro Leu Pro Pro Arg Tyr Gln Leu Gln Asn Met Asp Val
        515                 520                 525
```

```
Glu Ala Gly Phe Arg Glu Ala Val Tyr Ala Ser Phe Val Ala Gly Met
    530                 535                 540

Tyr Asn Tyr Val Val Thr Gln Pro Gln Glu Arg Ile Pro Asn Ser Gln
545                 550                 555                 560

Gln Val Glu Gly Ile Leu Arg Asp Met Leu Thr Asn Gly Ser Gln Thr
                565                 570                 575

Phe Arg Asp Leu Met Arg Arg Trp Asn Arg Glu Val Asp Arg Glu
            580                 585                 590

<210> SEQ ID NO 23
<211> LENGTH: 1845
<212> TYPE: DNA
<213> ORGANISM: Chlamydia muridarum
<400> SEQUENCE: 23
atgttttatt ttttaggttg gtttgttatg ggcatcaagg gagtaggcgg tagcggtcat      60
agcgattatc caatcccttc tcataatgga gatggggaga gtgaaaaaaa cagctcagat     120
tcaacaagta gtaaggttaa tgcaaaagtt acttcttcct tacagggggc tccgtcaacg     180
aatgatgaaa attcagtttc cccttattct gtggtggatg tcactgattt aatagagagc     240
ggagagtctt ctaggcatgt aataaagaaa tctatagaaa cagaagaagc tgctcatcga     300
gaatctagtg tagagggggc tgggcattct tctcgcggaa tatttggacg gttgcaagca     360
ggattaggac gtctggctag aagagtgggg gaagctgtca gaaatactgt aggctctatc     420
tttccacaaa gagctggtgc tgagcaaaga acaggcaaag ctcggacaaa atattcccct     480
tcagcatcaa gaggattacg cctcatgttc acagacttct ggcgatatcg agttttgcat     540
cggaatcctc ctatggatgg actttttgca aagcttgatg ccgatgaggc tgaagatatg     600
gcagcttaca cgaaagagta tgttagcaat ctagaaaaac gaggagcagc tgatcgagaa     660
actatagaac actgtcaaat ggtagctaaa aattgggaaa aaagagctag agatttgcga     720
gacatggggg ccgcaaaaaa atttttacgc gaccctttttg gtaagagtga tcctaagtat     780
aaggggacac tgcctggaga atacactgtc ggaaatacca tgttttacga tggaccaggt     840
gtgagcaaac tatcagaggt tgatacaggt ttttggttgg acatggagaa gctctcggat     900
gctgtcttgt ctgcaaatat tcaaaaaggg cttcgagctc gatttgtttt aaatcagtct     960
attccacagt tagagagtct agaagagcgt tttagaaaac tggagagtgc ttgcgatgag    1020
gctcgtgctt cgttaaagga agcaggttgg ataaaagaag gcaaggaacc taacaaagcg    1080
caacgagctt ttcggcgatt tgtagaagaa agccggaatc tagagctttc ttttggtagt    1140
tttggagaaa gtgctcgtcg tctttccgct cgtgtttccc aaggtttagc tgctgcaggg    1200
gaggcaattc gccgctgctt tgattgtcgc aaaggcaaat attcccttaa aaaggacttg    1260
tcttctgaag aattaaattt ggcagaagag ttaattaggt ttactgatga gatggggata    1320
gagagagacc cagatggaaa ttacaatatt ccttgggtag aaaactggag aacaggagtt    1380
cctgttattg aaggagaagg ggcagaacat atttatgaaa cgatgatgcc tgtccaggaa    1440
tcttttgagc aggtttatga agttatggat atgggattgg aagagcgtag ggattttgct    1500
gtgagtcaac aacactatca agttcctcct agatcttcgt tgaattacga gactccgcga    1560
ttcagagaat atgacgttcc acgtaattcc gctcgttctt attacgatgt tccaagagta    1620
cctccccaaa atgaggtaga agagatgcat gtgactaaag gaatgaggag ttctgtgtat    1680
gcttgttttg tagcaggaat gcgcaactac attgtttcac agccacaaga acagattcca    1740
aattctgaac aggtggagca gcttttccaa gagcttatta acgatgggga tcagataatt    1800
```
caagagctta tgaagatatg gaatgaggaa ctagataatc aataa 1845

<210> SEQ ID NO 24
<211> LENGTH: 614
<212> TYPE: PRT
<213> ORGANISM: Chlamydia muridarum

<400> SEQUENCE: 24

Met Phe Tyr Phe Leu Gly Trp Phe Val Met Gly Ile Lys Gly Val Gly
1 5 10 15

Gly Ser Gly His Ser Asp Tyr Pro Ile Pro Ser His Asn Gly Asp Gly
20 25 30

Glu Ser Glu Lys Asn Ser Ser Asp Ser Thr Ser Ser Lys Val Asn Ala
35 40 45

Lys Val Thr Ser Ser Leu Gln Gly Ala Pro Ser Thr Asn Asp Glu Asn
50 55 60

Ser Val Ser Pro Tyr Ser Val Val Asp Val Thr Asp Leu Ile Glu Ser
65 70 75 80

Gly Glu Ser Ser Arg His Val Ile Lys Lys Ser Ile Glu Thr Glu Glu
85 90 95

Ala Ala His Arg Glu Ser Ser Val Glu Gly Ala Gly His Ser Ser Arg
100 105 110

Gly Ile Phe Gly Arg Leu Gln Ala Gly Leu Gly Arg Leu Ala Arg Arg
115 120 125

Val Gly Glu Ala Val Arg Asn Thr Val Gly Ser Ile Phe Pro Gln Arg
130 135 140

Ala Gly Ala Glu Gln Arg Thr Gly Lys Ala Arg Thr Lys Tyr Ser Pro
145 150 155 160

Ser Ala Ser Arg Gly Leu Arg Leu Met Phe Thr Asp Phe Trp Arg Tyr
165 170 175

Arg Val Leu His Arg Asn Pro Pro Met Asp Gly Leu Phe Ala Lys Leu
180 185 190

Asp Ala Asp Glu Ala Glu Asp Met Ala Ala Tyr Thr Lys Glu Tyr Val
195 200 205

Ser Asn Leu Glu Lys Arg Gly Ala Ala Asp Arg Glu Thr Ile Glu His
210 215 220

Cys Gln Met Val Ala Lys Asn Trp Glu Lys Arg Ala Arg Asp Leu Arg
225 230 235 240

Asp Met Gly Ala Ala Lys Lys Phe Leu Arg Asp Pro Phe Gly Lys Ser
245 250 255

Asp Pro Lys Tyr Lys Gly Thr Leu Pro Gly Glu Tyr Thr Val Gly Asn
260 265 270

Thr Met Phe Tyr Asp Gly Pro Gly Val Ser Lys Leu Ser Glu Val Asp
275 280 285

Thr Gly Phe Trp Leu Asp Met Glu Lys Leu Ser Asp Ala Val Leu Ser
290 295 300

Ala Asn Ile Gln Lys Gly Leu Arg Ala Arg Phe Val Leu Asn Gln Ser
305 310 315 320

Ile Pro Gln Leu Glu Ser Leu Glu Glu Arg Phe Arg Lys Leu Glu Ser
325 330 335

Ala Cys Asp Glu Ala Arg Ala Ser Leu Lys Glu Ala Gly Trp Ile Lys
340 345 350

Glu Gly Lys Glu Pro Asn Lys Ala Gln Arg Ala Phe Arg Arg Phe Val
355 360 365

```
Glu Glu Ser Arg Asn Leu Glu Leu Ser Phe Gly Ser Phe Gly Glu Ser
    370                 375                 380

Ala Arg Arg Leu Ser Ala Arg Val Ser Gln Gly Leu Ala Ala Ala Gly
385                 390                 395                 400

Glu Ala Ile Arg Arg Cys Phe Asp Cys Arg Lys Gly Lys Tyr Ser Leu
                405                 410                 415

Lys Lys Asp Leu Ser Ser Glu Glu Leu Asn Leu Ala Glu Glu Leu Ile
            420                 425                 430

Arg Phe Thr Asp Glu Met Gly Ile Glu Arg Asp Pro Asp Gly Asn Tyr
        435                 440                 445

Asn Ile Pro Trp Val Glu Asn Trp Arg Thr Gly Val Pro Val Ile Glu
    450                 455                 460

Gly Glu Gly Ala Glu His Ile Tyr Glu Thr Met Met Pro Val Gln Glu
465                 470                 475                 480

Ser Phe Glu Gln Val Tyr Glu Val Met Asp Met Gly Leu Glu Glu Arg
                485                 490                 495

Arg Asp Phe Ala Val Ser Gln Gln His Tyr Gln Val Pro Pro Arg Ser
            500                 505                 510

Ser Leu Asn Tyr Glu Thr Pro Arg Phe Arg Glu Tyr Asp Val Pro Arg
        515                 520                 525

Asn Ser Ala Arg Ser Tyr Tyr Asp Val Pro Arg Val Pro Pro Gln Asn
    530                 535                 540

Glu Val Glu Glu Met His Val Thr Lys Gly Met Arg Ser Ser Val Tyr
545                 550                 555                 560

Ala Cys Phe Val Ala Gly Met Arg Asn Tyr Ile Val Ser Gln Pro Gln
                565                 570                 575

Glu Gln Ile Pro Asn Ser Glu Gln Val Glu Gln Leu Phe Gln Glu Leu
            580                 585                 590

Ile Asn Asp Gly Asp Gln Ile Ile Gln Glu Leu Met Lys Ile Trp Asn
        595                 600                 605

Glu Glu Leu Asp Asn Gln
    610
```

```
<210> SEQ ID NO 25
<211> LENGTH: 2346
<212> TYPE: DNA
<213> ORGANISM: Chlamydia psitacci

<400> SEQUENCE: 25
atggctgggg taagcggaat tgaggtggc ggtgggccag ggaaactccc tcctcatgga      60
aatgatgatg ataaacaatc taaatcagcc agtttcggag ccatgatat agttttggaa     120 gatgggagc gctctagatc cggtagtgtg agtagtgaac actcaataga ggagagaacc    180
cggacgttaa tggaggaggg ttttcaagta cgcactcctg aagaggtaga ggaaactcga    240
agagcgtcta tttccccaga ggaagcatct aacccaggat tcttttctcg tatatggtca    300
tctgttaagg gaatattcac aggtgggaaa aagagtgata gagctcaagg accagaaatt    360
tcctctccta tcattgcggg atataaacgt catggcgtgc gtcttcctga tgcgcgcgct    420
atgcaggcac atttgcaaag tcaaagtctc caagagattt ctgcatcaga cgtttcagaa    480
ataggagatt tagattctgg ggatacagat atcacggata tttctgatga agttcgcta    540 cagtcgatag atttggatac agacgataga gccgaagctt ctacatcttc agggagaggt    600
gttggtggat tggcggctcg tgttcgtggt ttgtgggatt ttgctactag gcagcaagaa    660
actcctgttg atggatttac ggggatgact tttttctgagt tggtcgatac ggtccaattg    720
```

| | |
|---|---|
| tatgatcaga tgattttaga tgcggacaat gagactgagc ggcaggaact cttaaagtat | 780 |
| cgcgatatgt atcaaagcta tgttaatacg atgttaggtg agggcaatac ctcacctaca | 840 |
| gatcagttcg atgtgagtgc ttctgctggt atcccagggg cttcttctag aagatatagc | 900 |
| gatggcgttg gagaagcgag attttttagac atagatgacg atttatccag tgtgtcggaa | 960 |
| agtgagcttt tagatgctat agaaagtgga gagtatgccg atcatgtctt agaagagatc | 1020 |
| agccctgaag taagaagagt tttagatgaa gctaataact tgcgtttaca gtttgatatg | 1080 |
| gaagtttctg caagtgtaac accttcatta agagagcgta ttcaatttgc tcttgtgagg | 1140 |
| ttggaaagag ggattatccg tatacttact ttgattagac gtaacctagt cgctctagca | 1200 |
| cgtttagtaa gaagaggtct tcgatccctt ggggagcttg taagacgttg ttgcgtgcgt | 1260 |
| gagagaggtg tttacagatt tcttggtaga gatcgggctt atgctaggga ggccgaaaga | 1320 |
| tttattcaaa ggcataccaa ctcagagaat ttttacagtc caggaactct tacggttccc | 1380 |
| tatgaggtta taaacgcttg ggtaaatgga agacctgatg ttgtctatgt ttctgatgtt | 1440 |
| agaggtatgt ttggtcatga agttgtgaga cttcacgttg atgatcgtga gggtacatat | 1500 |
| gagataattg gctctagctg gattccttat gaaagtgatg gtggggatac acccccacct | 1560 |
| ttaccgggaa atcatcctag tttagattac gcagatatta acgatgactc tgaagatctt | 1620 |
| cccacaacag gggatagga tgctgagccg ctatatgctc agatgagacc ccgccctcgt | 1680 |
| ggaagagatg agggaccgat ttacgatgtc ccaagtcctc aaagtagaag gcccagagca | 1740 |
| ggtgatgata gggatacacc tccgccttta ccgggaaatc atcccggttt agattctaca | 1800 |
| gatcttccca caacagggggg tagagatcct gagctactat atgctcagat gagacgtcgc | 1860 |
| cctcgtggaa gagatgaggg aacgatttac gatgttccaa gttctcaaaa tagaaggccc | 1920 |
| ggaacaggtg atgctaggga ttctatttac gacacgccaa gacctgtctc tgatggtatt | 1980 |
| tacgacgtcc ccagatctcc ttccgaagat atttataatg tgccaagatc tggccctcaa | 2040 |
| ctatttactg tgcttcctga ggatgggtat aggcttccaa atctatcagg atctgctctt | 2100 |
| ggagtgactc caggatttgg aaatggtgtt ggggcagctt ctatggcaga agaaattgat | 2160 |
| aggtttattg aagaaaccca tgaaagaaga gagtcggcag cggcagcgcg tcgtcccttta | 2220 |
| cccctcttc ctccgttgca aactcctccg gaaagtcctt atggaagtaa tcggatgatg | 2280 |
| cggttgttga gactcatgaa cgatagggta caggagtaca aagagcgtcg taaggataag | 2340 |
| caataa | 2346 |

<210> SEQ ID NO 26
<211> LENGTH: 781
<212> TYPE: PRT
<213> ORGANISM: Chlamydia psitacci

<400> SEQUENCE: 26

Met Ala Gly Val Ser Gly Ile Gly Gly Gly Gly Pro Gly Lys Leu
1               5                   10                  15

Pro Pro His Gly Asn Asp Asp Lys Gln Ser Lys Ser Ala Ser Phe
                20                  25                  30

Gly Gly His Asp Ile Val Phe Gly Asp Gly Glu Arg Ser Arg Ser Gly
            35                  40                  45

Ser Val Ser Ser Glu His Ser Ile Glu Glu Arg Thr Arg Thr Leu Met
        50                  55                  60

Glu Glu Gly Phe Gln Val Arg Thr Pro Glu Glu Val Glu Glu Thr Arg
65                  70                  75                  80

Arg Ala Ser Ile Ser Pro Glu Glu Ala Ser Asn Pro Gly Phe Phe Ser

-continued

```
                85                  90                  95
Arg Ile Trp Ser Ser Val Lys Gly Ile Phe Thr Gly Gly Lys Lys Ser
            100                 105                 110

Asp Arg Ala Gln Gly Pro Glu Ile Ser Ser Pro Ile Ile Ala Gly Tyr
            115                 120                 125

Lys Arg His Gly Val Arg Leu Pro Asp Ala Arg Ala Met Gln Ala His
            130                 135                 140

Leu Gln Ser Gln Ser Leu Gln Glu Ile Ser Ala Ser Asp Val Ser Glu
145                 150                 155                 160

Ile Gly Asp Leu Asp Ser Gly Asp Thr Asp Ile Thr Asp Ile Ser Asp
                165                 170                 175

Glu Ser Ser Leu Gln Ser Ile Asp Leu Asp Thr Asp Arg Ala Glu
            180                 185                 190

Ala Ser Thr Ser Ser Gly Arg Gly Val Gly Gly Leu Ala Ala Arg Val
            195                 200                 205

Arg Gly Leu Trp Asp Phe Ala Thr Arg Gln Gln Glu Thr Pro Val Asp
            210                 215                 220

Gly Phe Thr Gly Met Thr Phe Ser Glu Leu Val Asp Thr Val Gln Leu
225                 230                 235                 240

Tyr Asp Gln Met Ile Leu Asp Ala Asp Asn Glu Thr Glu Arg Gln Glu
                245                 250                 255

Leu Leu Lys Tyr Arg Asp Met Tyr Gln Ser Tyr Val Asn Thr Met Leu
            260                 265                 270

Gly Glu Gly Asn Thr Ser Pro Thr Asp Gln Phe Asp Val Ser Ala Ser
            275                 280                 285

Ala Gly Ile Pro Gly Ala Ser Ser Arg Arg Tyr Ser Asp Gly Val Gly
            290                 295                 300

Glu Ala Arg Phe Leu Asp Ile Asp Asp Leu Ser Ser Val Ser Glu
305                 310                 315                 320

Ser Glu Leu Leu Asp Ala Ile Glu Ser Gly Tyr Ala Asp His Val
                325                 330                 335

Leu Glu Glu Ile Ser Pro Glu Val Arg Arg Val Leu Asp Glu Ala Asn
            340                 345                 350

Asn Leu Arg Leu Gln Phe Asp Met Glu Val Ser Ala Ser Val Thr Pro
            355                 360                 365

Ser Leu Arg Glu Arg Ile Gln Phe Ala Leu Val Arg Leu Glu Arg Gly
            370                 375                 380

Ile Ile Arg Ile Leu Thr Leu Ile Arg Arg Asn Leu Val Ala Leu Ala
385                 390                 395                 400

Arg Leu Val Arg Arg Gly Leu Arg Ser Leu Gly Glu Leu Val Arg Arg
            405                 410                 415

Cys Cys Val Arg Glu Arg Gly Val Tyr Arg Phe Leu Gly Arg Asp Arg
            420                 425                 430

Ala Tyr Ala Arg Glu Ala Glu Arg Phe Ile Gln Arg His Thr Asn Ser
            435                 440                 445

Glu Asn Phe Tyr Ser Pro Gly Thr Leu Thr Val Pro Tyr Glu Val Val
            450                 455                 460

Asn Ala Trp Val Asn Gly Arg Pro Asp Val Val Tyr Val Ser Asp Val
465                 470                 475                 480

Arg Gly Met Phe Gly His Glu Val Val Arg Leu His Val Asp Asp Arg
                485                 490                 495

Glu Gly Thr Tyr Glu Ile Ile Gly Ser Ser Trp Ile Pro Tyr Glu Ser
            500                 505                 510
```

```
                                  -continued

Asp Gly Gly Asp Thr Pro Pro Leu Pro Gly Asn His Pro Ser Leu
            515                 520                 525

Asp Tyr Ala Asp Ile Asn Asp Ser Glu Asp Leu Pro Thr Thr Gly
        530                 535                 540

Asp Arg Asp Ala Glu Pro Leu Tyr Ala Gln Met Arg Pro Arg Pro Arg
545                 550                 555                 560

Gly Arg Asp Glu Gly Pro Ile Tyr Asp Val Pro Ser Pro Gln Ser Arg
                565                 570                 575

Arg Pro Arg Ala Gly Asp Asp Arg Asp Thr Pro Pro Leu Pro Gly
            580                 585                 590

Asn His Pro Gly Leu Asp Ser Thr Asp Leu Pro Thr Thr Gly Gly Arg
        595                 600                 605

Asp Pro Glu Leu Leu Tyr Ala Gln Met Arg Arg Pro Arg Gly Arg
    610                 615                 620

Asp Glu Gly Thr Ile Tyr Asp Val Pro Ser Ser Gln Asn Arg Arg Pro
625                 630                 635                 640

Gly Thr Gly Asp Ala Arg Asp Ser Ile Tyr Asp Thr Pro Arg Pro Val
                645                 650                 655

Ser Asp Gly Ile Tyr Asp Val Pro Arg Ser Pro Ser Glu Asp Ile Tyr
            660                 665                 670

Asn Val Pro Arg Ser Gly Pro Gln Leu Phe Thr Val Leu Pro Glu Asp
        675                 680                 685

Gly Tyr Arg Leu Pro Asn Leu Ser Gly Ser Ala Leu Gly Val Thr Pro
    690                 695                 700

Gly Phe Gly Asn Gly Val Gly Ala Ala Ser Met Ala Glu Glu Ile Asp
705                 710                 715                 720

Arg Phe Ile Glu Glu Thr His Glu Arg Arg Glu Ser Ala Ala Ala Ala
                725                 730                 735

Arg Arg Pro Leu Pro Pro Leu Pro Pro Leu Gln Thr Pro Pro Glu Ser
            740                 745                 750

Pro Tyr Gly Ser Asn Arg Met Met Arg Leu Leu Arg Leu Met Asn Asp
        755                 760                 765

Arg Val Gln Glu Tyr Lys Glu Arg Arg Lys Asp Lys Gln
    770                 775                 780

<210> SEQ ID NO 27
<211> LENGTH: 3042
<212> TYPE: DNA
<213> ORGANISM: Chlamydia trachomatis

<400> SEQUENCE: 27
atgcaaacgt ctttccataa gttctttctt tcaatgattc tagcttattc ttgctgctct    60
ttaagtgggg gggggtatgc agcagaaatc atgattcctc aaggaattta cgatggggag   120
acgttaactg tatcatttcc ctatactgtt ataggagatc cgagtgggac tactgttttt   180
tctgcaggag agttaacgtt aaaaaatctt gacaattcta ttgcagcttt gccttaagt   240 tgttttggga acttattagg gagttttact gttttaggga aggacactc gttgactttc   300 gagaacatac ggacttctac aaatggagct gcactaagtg acagcgctaa tagcgggtta   360
tttactattg agggtttaa agaattatct ttttccaatt gcaactcatt acttgccgta   420
ctgcctgctg caacgactaa taatggtagc cagactccga cgacaacatc tacaccgtct   480
aatggtacta tttattctaa aacgatcttt tgttactca ataatgagaa gttctcattc   540
tatagtaatt tagtctctgg agatggggga gctatagatg ctaagagctt aacggttcaa   600
ggaattagca agctttgtgt cttccaagaa aatactgctc aagctgatgg gggagcttgt   660
```

```
caagtagtca ccagtttctc tgctatggct aacgaggctc ctattgcctt tatagcgaat    720
gttgcaggag taagagggg agggattgct gctgttcagg atgggcagca gggagtgtca    780
tcatctactt caacagaaga tccagtagta agttttttcca gaaatactgc ggtagagttt    840
gatgggaacg tagcccgagt aggaggaggg atttactcct acgggaacgt tgctttcctg    900
aataatggaa aaaccttgtt tctcaacaat gttgcttctc ctgtttacat tgctgctgag    960
caaccaacaa atggacaggc ttctaatacg agtgataatt acggagatgg aggagctatc   1020
ttctgtaaga atggtgcgca agcagcagga tccaataact ctggatcagt ttcctttgat   1080
ggagagggag tagttttctt tagtagcaat gtagctgctg ggaaagggg agctatttat    1140
gccaaaaagc tctcggttgc taactgtggc cctgtacaat tcttaggaa tatcgctaat    1200
gatggtggag cgatttattt aggagaatct ggagagctca gtttatctgc tgattatgga   1260
gatattattt tcgatgggaa tcttaaaaga acagccaaag agaatgctgc cgatgttaat   1320
ggcgtaactg tgtcctcaca agccatttcg atgggatcgg gagggaaaat aacgacatta   1380
agagctaaag cagggcatca gattctcttt aatgatccca tcgagatggc aaacggaaat   1440
aaccagccag cgcagtcttc cgaacctcta aaaattaacg atggtgaagg atacacaggg   1500
gatattgttt ttgctaatgg aaacagtact ttgtaccaaa atgttacgat agagcaagga   1560
aggattgttc ttcgtgaaaa ggcaaaatta tcagtgaatt ctctaagtca gacaggtggg   1620
agtctgtata tggaagctgg gagtacattg gattttgtaa ctccacaacc accacaacag   1680
cctcctgccg ctaatcagtt gatcacgctt tccaatctgc atttgtctct ttcttcttg    1740
ttagcaaaca atgcagttac gaatcctcct accaatcctc cagcgcaaga ttctcatcct   1800
gcaatcattg gtagcacaac tgctggttct gttacaatta gtgggcctat ctttttgag    1860
gatttggatg atacagctta tgataggat gattggctag gttctaatca aaaaatcgat   1920
gtcctgaaat tacagttagg gactcagccc tcagctaatg ccccatcaga tttgactcta   1980
gggaatgaga tgcctaagta tggctatcaa ggaagctgga agcttgcgtg ggatcctaat   2040
acagcaaata atggtcctta tactctgaaa gctacatgga ctaaaactgg gtataatcct   2100
gggcctgagc gagtagcttc ttttggttcca aatagtttat ggggatccat tttagatata   2160
cgatctgcgc attcagcaat tcaagcaagt gtggatgggc gctcttattg tcgaggatta   2220
tgggtttctg gagtttcgaa tttcttctat catgaccgcg atgctttagg tcagggatat   2280
cggtatatta gtgggggtta ttccttagga gcaaactcct actttggatc atcgatgttt   2340
ggtctagcat ttaccgaagt atttggtaga tctaaagatt atgtagtgtg tcgttccaat   2400
catcatgctt gcataggatc cgtttatcta tctaccaaac aagctttatg tggatcctat   2460
ttgttcggag atgcgtttat ccgtgctagc tacgggtttg ggaaccagca tatgaaaacc   2520
tcatacacat ttgcagagga gagcgatgtt cgttgggata taactgtct ggttggagag    2580
attggagtgg gattaccgat tgtgattact ccatctaagc tctatttgaa tgagttgcgt   2640
cctttcgtgc aagctgagtt ttcttatgcc gatcatgaat cttttacaga ggaaggcgat   2700
caagctcggg cattcaggag tggacatctc atgaatctat cagttcctgt tggagtaaaa   2760
tttgatcgat gttctagtac acaccctaat aaatatagct ttatggggc ttatatctgt    2820
gatgcttatc gcaccatctc tgggactcag acaacactcc tatcccatca agagacatgg   2880
acaacagatg cctttcattt ggcaagacat ggagtcatag ttagagggtc tatgtatgct   2940
tctctaacaa gcaatataga agtatatggc catggaagat atgagtatcg agatacttct   3000
cgaggttatg gtttgagtgc aggaagtaaa gtccggttct aa                       3042
```

<210> SEQ ID NO 28
<211> LENGTH: 1013
<212> TYPE: PRT
<213> ORGANISM: Chlamydia trachomatis

<400> SEQUENCE: 28

```
Met Gln Thr Ser Phe His Lys Phe Phe Leu Ser Met Ile Leu Ala Tyr
1               5                   10                  15

Ser Cys Cys Ser Leu Ser Gly Gly Tyr Ala Ala Glu Ile Met Ile
            20                  25                  30

Pro Gln Gly Ile Tyr Asp Gly Glu Thr Leu Thr Val Ser Phe Pro Tyr
            35                  40                  45

Thr Val Ile Gly Asp Pro Ser Gly Thr Thr Val Phe Ser Ala Gly Glu
        50                  55                  60

Leu Thr Leu Lys Asn Leu Asp Asn Ser Ile Ala Ala Leu Pro Leu Ser
65                  70                  75                  80

Cys Phe Gly Asn Leu Leu Gly Ser Phe Thr Val Leu Gly Arg Gly His
                85                  90                  95

Ser Leu Thr Phe Glu Asn Ile Arg Thr Ser Thr Asn Gly Ala Ala Leu
            100                 105                 110

Ser Asp Ser Ala Asn Ser Gly Leu Phe Thr Ile Glu Gly Phe Lys Glu
        115                 120                 125

Leu Ser Phe Ser Asn Cys Asn Ser Leu Leu Ala Val Leu Pro Ala Ala
130                 135                 140

Thr Thr Asn Asn Gly Ser Gln Thr Pro Thr Thr Thr Ser Thr Pro Ser
145                 150                 155                 160

Asn Gly Thr Ile Tyr Ser Lys Thr Asp Leu Leu Leu Asn Asn Glu
                165                 170                 175

Lys Phe Ser Phe Tyr Ser Asn Leu Val Ser Gly Asp Gly Ala Ile
            180                 185                 190

Asp Ala Lys Ser Leu Thr Val Gln Gly Ile Ser Lys Leu Cys Val Phe
        195                 200                 205

Gln Glu Asn Thr Ala Gln Ala Asp Gly Gly Ala Cys Gln Val Val Thr
    210                 215                 220

Ser Phe Ser Ala Met Ala Asn Glu Ala Pro Ile Ala Phe Ile Ala Asn
225                 230                 235                 240

Val Ala Gly Val Arg Gly Gly Ile Ala Ala Val Gln Asp Gly Gln
                245                 250                 255

Gln Gly Val Ser Ser Thr Ser Thr Glu Asp Pro Val Val Ser Phe
            260                 265                 270

Ser Arg Asn Thr Ala Val Glu Phe Asp Gly Asn Val Ala Arg Val Gly
        275                 280                 285

Gly Gly Ile Tyr Ser Tyr Gly Asn Val Ala Phe Leu Asn Asn Gly Lys
    290                 295                 300

Thr Leu Phe Leu Asn Asn Val Ala Ser Pro Val Tyr Ile Ala Ala Glu
305                 310                 315                 320

Gln Pro Thr Asn Gly Gln Ala Ser Asn Thr Ser Asp Asn Tyr Gly Asp
                325                 330                 335

Gly Gly Ala Ile Phe Cys Lys Asn Gly Ala Gln Ala Gly Ser Asn
            340                 345                 350

Asn Ser Gly Ser Val Ser Phe Asp Gly Glu Gly Val Val Phe Phe Ser
        355                 360                 365

Ser Asn Val Ala Ala Gly Lys Gly Gly Ala Ile Tyr Ala Lys Lys Leu
    370                 375                 380
```

```
Ser Val Ala Asn Cys Gly Pro Val Gln Phe Leu Gly Asn Ile Ala Asn
385                 390                 395                 400

Asp Gly Gly Ala Ile Tyr Leu Gly Glu Ser Gly Glu Leu Ser Leu Ser
                405                 410                 415

Ala Asp Tyr Gly Asp Ile Ile Phe Asp Gly Asn Leu Lys Arg Thr Ala
            420                 425                 430

Lys Glu Asn Ala Ala Asp Val Asn Gly Val Thr Val Ser Ser Gln Ala
        435                 440                 445

Ile Ser Met Gly Ser Gly Gly Lys Ile Thr Thr Leu Arg Ala Lys Ala
    450                 455                 460

Gly His Gln Ile Leu Phe Asn Asp Pro Ile Glu Met Ala Asn Gly Asn
465                 470                 475                 480

Asn Gln Pro Ala Gln Ser Ser Glu Pro Leu Lys Ile Asn Asp Gly Glu
                485                 490                 495

Gly Tyr Thr Gly Asp Ile Val Phe Ala Asn Gly Asn Ser Thr Leu Tyr
            500                 505                 510

Gln Asn Val Thr Ile Glu Gln Gly Arg Ile Val Leu Arg Glu Lys Ala
        515                 520                 525

Lys Leu Ser Val Asn Ser Ser Leu Ser Gln Thr Gly Gly Ser Leu Tyr Met
    530                 535                 540

Glu Ala Gly Ser Thr Leu Asp Phe Val Thr Pro Gln Pro Pro Gln Gln
545                 550                 555                 560

Pro Pro Ala Ala Asn Gln Leu Ile Thr Leu Ser Asn Leu His Leu Ser
                565                 570                 575

Leu Ser Ser Leu Leu Ala Asn Asn Ala Val Thr Asn Pro Pro Thr Asn
            580                 585                 590

Pro Pro Ala Gln Asp Ser His Pro Ala Ile Ile Gly Ser Thr Thr Ala
        595                 600                 605

Gly Ser Val Thr Ile Ser Gly Pro Ile Phe Phe Glu Asp Leu Asp Asp
    610                 615                 620

Thr Ala Tyr Asp Arg Tyr Asp Trp Leu Gly Ser Asn Gln Lys Ile Asp
625                 630                 635                 640

Val Leu Lys Leu Gln Leu Gly Thr Gln Pro Ser Ala Asn Ala Pro Ser
                645                 650                 655

Asp Leu Thr Leu Gly Asn Glu Met Pro Lys Tyr Gly Tyr Gln Gly Ser
            660                 665                 670

Trp Lys Leu Ala Trp Asp Pro Asn Thr Ala Asn Asn Gly Pro Tyr Thr
        675                 680                 685

Leu Lys Ala Thr Trp Thr Lys Thr Gly Tyr Asn Pro Gly Pro Glu Arg
    690                 695                 700

Val Ala Ser Leu Val Pro Asn Ser Leu Trp Gly Ser Ile Leu Asp Ile
705                 710                 715                 720

Arg Ser Ala His Ser Ala Ile Gln Ala Ser Val Asp Gly Arg Ser Tyr
                725                 730                 735

Cys Arg Gly Leu Trp Val Ser Gly Val Ser Asn Phe Tyr His Asp
            740                 745                 750

Arg Asp Ala Leu Gly Gln Gly Tyr Arg Tyr Ile Ser Gly Gly Tyr Ser
        755                 760                 765

Leu Gly Ala Asn Ser Tyr Phe Gly Ser Ser Met Phe Gly Leu Ala Phe
    770                 775                 780

Thr Glu Val Phe Gly Arg Ser Lys Asp Tyr Val Val Cys Arg Ser Asn
785                 790                 795                 800

His His Ala Cys Ile Gly Ser Val Tyr Leu Ser Thr Lys Gln Ala Leu
```

```
                     805                 810                 815
Cys Gly Ser Tyr Leu Phe Gly Asp Ala Phe Ile Arg Ala Ser Tyr Gly
            820                 825                 830

Phe Gly Asn Gln His Met Lys Thr Ser Tyr Thr Phe Ala Glu Glu Ser
            835                 840                 845

Asp Val Arg Trp Asp Asn Asn Cys Leu Val Gly Glu Ile Gly Val Gly
            850                 855                 860

Leu Pro Ile Val Ile Thr Pro Ser Lys Leu Tyr Leu Asn Glu Leu Arg
865                 870                 875                 880

Pro Phe Val Gln Ala Glu Phe Ser Tyr Ala Asp His Glu Ser Phe Thr
                885                 890                 895

Glu Glu Gly Asp Gln Ala Arg Ala Phe Arg Ser Gly His Leu Met Asn
            900                 905                 910

Leu Ser Val Pro Val Gly Val Lys Phe Asp Arg Cys Ser Ser Thr His
            915                 920                 925

Pro Asn Lys Tyr Ser Phe Met Gly Ala Tyr Ile Cys Asp Ala Tyr Arg
            930                 935                 940

Thr Ile Ser Gly Thr Gln Thr Thr Leu Leu Ser His Gln Glu Thr Trp
945                 950                 955                 960

Thr Thr Asp Ala Phe His Leu Ala Arg His Gly Val Ile Val Arg Gly
                965                 970                 975

Ser Met Tyr Ala Ser Leu Thr Ser Asn Ile Glu Val Tyr Gly His Gly
            980                 985                 990

Arg Tyr Glu Tyr Arg Asp Thr Ser Arg Gly Tyr Gly Leu Ser Ala Gly
            995                 1000                1005

Ser Lys Val Arg Phe
    1010

<210> SEQ ID NO 29
<211> LENGTH: 2964
<212> TYPE: DNA
<213> ORGANISM: Chlamydia muridarum

<400> SEQUENCE: 29
gtgatgcaaa cgccttttca taagttcttt cttctagcaa tgctatctta ctctttattg      60
caaggagggc atgcggcaga tatttccatg cctccgggaa tttatgatgg acaacattg     120 acggcgccat ttccctacac tgtgatcgga gatcccagag ggacaaaggt tacttcatcg     180
ggatcgctag agttgaaaaa cctggacaat tccattgcga ctttacctct aagttgtttt     240
ggtaatttgt tggggaattt cactattgca ggaagagggc attcgttagt atttgagaat     300
atacgaacat ctacaaatgg ggcggcattg agtaatcatg ctccttctgg actgtttgta     360
attgaagctt ttgatgaact ctctctttg aattgtaatt cattggtatc tgtagttcct     420
caaacagggg gtacgactac ttctgttcct tctaatggga cgatctattc tagaacagat     480
cttgttctaa gagatatcaa gaaggtttct ttctatagta acttagtttc tggagatggg     540
ggagctatag atgcacaaag tttaatggtt aacggaattg aaaaactttg taccttccaa     600
gaaaatgtag cgcagtccga tggggagcg tgtcaggtaa caaagacctt ctctgctgtg     660
ggcaataagg ttccttttgtc ttttttaggc aatgttgctg gtaataaggg gggaggagtt     720
gctgctgtca aagatggtca gggggcagga ggggcgactg atctatcggt taattttgcc     780
aataatactg ctgtagaatt tgagggaaat agtgctcgaa taggtggagg gatctactcg     840 gacgaaata tttccttttt agggaatgca aagcacagttt tcctaagtaa cgtagcttcg     900
cctatttatg ttgacccctgc tgctgcagga ggacagcccc ctgcagataa agataactat     960
```

```
ggagatggag gagccatctt ctgcaaaaat gatactaaca taggtgaagt ctctttcaaa    1020
gacgagggtg ttgttttctt tagtaaaaat attgccgcag gaaagggggg cgctatttat    1080
gctaagaaac tgacaatttc tgactgtggt ccggtccagt ttcttggtaa tgtcgcgaat    1140 gacggggggcg ctatttatct agtagatcag ggggaactta gtctatctgc tgatcgcgga    1200
gatattattt tgatggaaa tttaaagaga atggctacgc aaggcgctgc caccgtccat    1260
gatgtaatgg ttgcatcgaa tgctatctct atggctacag ggggcaaat cacaacatta    1320 agggctaagg aaggtcgccg aattctttt aatgacccta ttgaaatggc gaatggacaa    1380
cctgtaatac aaactcttac agtaaacgag gcgaaggat atacgggga cattgttttt    1440 gctaaaggtg ataatgtttt gtactcaagt attgagctga gtcagggaag aattattctc    1500
cgagagcaaa caaattatt ggttaactcc ctgactcaga ctggaagggag tgtacatatg    1560 gaaggggga gtacactaga ctttgcagta acaacgccac cagctgctaa ttcgatggct    1620
cttactaatg tacacttctc cttagcttct ttactaaaaa ataatggggt tacaaatcct    1680
ccaacgaatc ctccagtaca ggtttctagt ccagctgtaa ttggtaatac agctgctggt    1740
actgttacga tttctggtcc gatctttttt gaagatttag atgaaactgc ttacgataat    1800
aatcagtggt taggtgcgga tcaaactatt gatgtgctgc agttgcattt aggagcgaat    1860
cctccggcta acgctccaac tgatttgact ttagggaacg aaagttctaa atatgggtat    1920
caaggaagtt ggacacttca atgggaacca gatcctgcga atcctccaca gaacaatagc    1980
tacatgttga aggcaagctg gactaaaaca ggttataatc ctggtccgga gcgcgtagct    2040
tctctggtct ctaatagtct ttggggatcc atttttagatg tgcgttccgc gcattctgcg    2100
attcaagcaa gtatagatgg acgagcttat tgtcggggta tttggatttc tgggatttcg    2160 aacttttct atcatgatca ggatgcttta ggacaggggt atcgtcatat tagtggggga    2220
tattcgatag gagcaaactc ttatttcggg tcttctatgt ttggacttgc ttttactgaa    2280
acttttggta ggtccaaaga ttatgtggtc tgtcgatcta acgatcacac ttgtgtaggc    2340
tctgtttact tatccactag acaagcgtta tgcggatcct gtttatttgg agatgctttt    2400
gttcgggcga gttacggatt tggaaatcag catatgaaga cctcttatac atttgctgaa    2460
gagagtaatg tgcgttggga taataactgt gtagtgggag aagttggagc tgggctccct    2520
atcatgctcg ctgcatctaa gctttatcta aatgagttgc gtcccttcgt gcaagcagag    2580
tttgcttatg cagagcatga atcttttaca gagagagggg atcaggctag ggagtttaag    2640
agtgggcatc ttatgaatct atctattcca gttggggtga agtttgatcg atgctctagt    2700
aaacatccta acaagtatag tttatggga gcttatatct gtgatgctta ccggtccatt    2760
tctggaacgg agacaacact cctgtctcat aaagagactt ggacaacaga tgcttttccat    2820 ttagcaaggc atggagttat ggtcagagga tctatgtatg cttctttaac aggtaatata    2880
gaagtctatg gccatggaaa atatgaatac agggatgcct ctcgagggta tggtttaagt    2940
attggaagta aaatccgatt ctaa                                           2964
```

<210> SEQ ID NO 30
<211> LENGTH: 987
<212> TYPE: PRT
<213> ORGANISM: Chlamydia muridarum

<400> SEQUENCE: 30

```
Met Met Gln Thr Pro Phe His Lys Phe Phe Leu Leu Ala Met Leu Ser
1               5                   10                  15
```

```
Tyr Ser Leu Leu Gln Gly Gly His Ala Ala Asp Ile Ser Met Pro Pro
             20                  25                  30

Gly Ile Tyr Asp Gly Thr Thr Leu Thr Ala Pro Phe Pro Tyr Thr Val
             35                  40                  45

Ile Gly Asp Pro Arg Gly Thr Lys Val Thr Ser Ser Gly Ser Leu Glu
 50                  55                  60

Leu Lys Asn Leu Asp Asn Ser Ile Ala Thr Leu Pro Leu Ser Cys Phe
 65                  70                  75                  80

Gly Asn Leu Leu Gly Asn Phe Thr Ile Ala Gly Arg Gly His Ser Leu
             85                  90                  95

Val Phe Glu Asn Ile Arg Thr Ser Thr Asn Gly Ala Ala Leu Ser Asn
            100                 105                 110

His Ala Pro Ser Gly Leu Phe Val Ile Glu Ala Phe Asp Glu Leu Ser
            115                 120                 125

Leu Leu Asn Cys Asn Ser Leu Val Ser Val Pro Gln Thr Gly Gly
            130                 135                 140

Thr Thr Thr Ser Val Pro Ser Asn Gly Thr Ile Tyr Ser Arg Thr Asp
145                 150                 155                 160

Leu Val Leu Arg Asp Ile Lys Lys Val Ser Phe Tyr Ser Asn Leu Val
                165                 170                 175

Ser Gly Asp Gly Gly Ala Ile Asp Ala Gln Ser Leu Met Val Asn Gly
            180                 185                 190

Ile Glu Lys Leu Cys Thr Phe Gln Glu Asn Val Ala Gln Ser Asp Gly
            195                 200                 205

Gly Ala Cys Gln Val Thr Lys Thr Phe Ser Ala Val Gly Asn Lys Val
210                 215                 220

Pro Leu Ser Phe Leu Gly Asn Val Ala Gly Asn Lys Gly Gly Val
225                 230                 235                 240

Ala Ala Val Lys Asp Gly Gln Gly Ala Gly Ala Thr Asp Leu Ser
                245                 250                 255

Val Asn Phe Ala Asn Asn Thr Ala Val Glu Phe Gly Asn Ser Ala
                260                 265                 270

Arg Ile Gly Gly Gly Ile Tyr Ser Asp Gly Asn Ile Ser Phe Leu Gly
            275                 280                 285

Asn Ala Lys Thr Val Phe Leu Ser Asn Val Ala Ser Pro Ile Tyr Val
            290                 295                 300

Asp Pro Ala Ala Ala Gly Gly Gln Pro Pro Ala Asp Lys Asp Asn Tyr
305                 310                 315                 320

Gly Asp Gly Gly Ala Ile Phe Cys Lys Asn Asp Thr Asn Ile Gly Glu
                325                 330                 335

Val Ser Phe Lys Asp Glu Gly Val Phe Phe Ser Lys Asn Ile Ala
                340                 345                 350

Ala Gly Lys Gly Gly Ala Ile Tyr Ala Lys Lys Leu Thr Ile Ser Asp
            355                 360                 365

Cys Gly Pro Val Gln Phe Leu Gly Asn Val Ala Asn Asp Gly Gly Ala
            370                 375                 380

Ile Tyr Leu Val Asp Gln Gly Glu Leu Ser Leu Ser Ala Asp Arg Gly
385                 390                 395                 400

Asp Ile Ile Phe Asp Gly Asn Leu Lys Arg Met Ala Thr Gln Gly Ala
                405                 410                 415

Ala Thr Val His Asp Val Met Val Ala Ser Asn Ala Ile Ser Met Ala
                420                 425                 430

Thr Gly Gly Gln Ile Thr Thr Leu Arg Ala Lys Glu Gly Arg Arg Ile
            435                 440                 445
```

```
Leu Phe Asn Asp Pro Ile Glu Met Ala Asn Gly Gln Pro Val Ile Gln
    450                 455                 460
Thr Leu Thr Val Asn Glu Gly Glu Gly Tyr Thr Gly Asp Ile Val Phe
465                 470                 475                 480
Ala Lys Gly Asp Asn Val Leu Tyr Ser Ser Ile Glu Leu Ser Gln Gly
                485                 490                 495
Arg Ile Ile Leu Arg Glu Gln Thr Lys Leu Leu Val Asn Ser Leu Thr
                500                 505                 510
Gln Thr Gly Gly Ser Val His Met Glu Gly Gly Ser Thr Leu Asp Phe
            515                 520                 525
Ala Val Thr Thr Pro Ala Ala Asn Ser Met Ala Leu Thr Asn Val
        530                 535                 540
His Phe Ser Leu Ala Ser Leu Leu Lys Asn Asn Gly Val Thr Asn Pro
545                 550                 555                 560
Pro Thr Asn Pro Pro Val Gln Val Ser Ser Pro Ala Val Ile Gly Asn
                565                 570                 575
Thr Ala Ala Gly Thr Val Thr Ile Ser Gly Pro Ile Phe Phe Glu Asp
                580                 585                 590
Leu Asp Glu Thr Ala Tyr Asp Asn Asn Gln Trp Leu Gly Ala Asp Gln
            595                 600                 605
Thr Ile Asp Val Leu Gln Leu His Leu Gly Ala Asn Pro Pro Ala Asn
        610                 615                 620
Ala Pro Thr Asp Leu Thr Leu Gly Asn Glu Ser Ser Lys Tyr Gly Tyr
625                 630                 635                 640
Gln Gly Ser Trp Thr Leu Gln Trp Glu Pro Asp Pro Ala Asn Pro Pro
                645                 650                 655
Gln Asn Asn Ser Tyr Met Leu Lys Ala Ser Trp Thr Lys Thr Gly Tyr
                660                 665                 670
Asn Pro Gly Pro Glu Arg Val Ala Ser Leu Val Ser Asn Ser Leu Trp
            675                 680                 685
Gly Ser Ile Leu Asp Val Arg Ser Ala His Ser Ala Ile Gln Ala Ser
    690                 695                 700
Ile Asp Gly Arg Ala Tyr Cys Arg Gly Ile Trp Ile Ser Gly Ile Ser
705                 710                 715                 720
Asn Phe Phe Tyr His Asp Gln Asp Ala Leu Gly Gln Gly Tyr Arg His
                725                 730                 735
Ile Ser Gly Gly Tyr Ser Ile Gly Ala Asn Ser Tyr Phe Gly Ser Ser
                740                 745                 750
Met Phe Gly Leu Ala Phe Thr Glu Thr Phe Gly Arg Ser Lys Asp Tyr
            755                 760                 765
Val Val Cys Arg Ser Asn Asp His Thr Cys Val Gly Ser Val Tyr Leu
    770                 775                 780
Ser Thr Arg Gln Ala Leu Cys Gly Ser Cys Leu Phe Gly Asp Ala Phe
785                 790                 795                 800
Val Arg Ala Ser Tyr Gly Phe Gly Asn Gln His Met Lys Thr Ser Tyr
                805                 810                 815
Thr Phe Ala Glu Glu Ser Asn Val Arg Trp Asp Asn Cys Val Val
                820                 825                 830
Gly Glu Val Gly Ala Gly Leu Pro Ile Met Leu Ala Ala Ser Lys Leu
            835                 840                 845
Tyr Leu Asn Glu Leu Arg Pro Phe Val Gln Ala Glu Phe Ala Tyr Ala
    850                 855                 860
Glu His Glu Ser Phe Thr Glu Arg Gly Asp Gln Ala Arg Glu Phe Lys
```

```
865                 870                 875                 880

Ser Gly His Leu Met Asn Leu Ser Ile Pro Val Gly Val Lys Phe Asp
                885                 890                 895

Arg Cys Ser Ser Lys His Pro Asn Lys Tyr Ser Phe Met Gly Ala Tyr
            900                 905                 910

Ile Cys Asp Ala Tyr Arg Ser Ile Ser Gly Thr Glu Thr Thr Leu Leu
        915                 920                 925

Ser His Lys Glu Thr Trp Thr Thr Asp Ala Phe His Leu Ala Arg His
    930                 935                 940

Gly Val Met Val Arg Gly Ser Met Tyr Ala Ser Leu Thr Gly Asn Ile
945                 950                 955                 960
Glu Val Tyr Gly His Gly Lys Tyr Glu Tyr Arg Asp Ala Ser Arg Gly
                965                 970                 975

Tyr Gly Leu Ser Ile Gly Ser Lys Ile Arg Phe
            980                 985
```

<210> SEQ ID NO 31
<211> LENGTH: 3036
<212> TYPE: DNA
<213> ORGANISM: Chlamydia psitacci

<400> SEQUENCE: 31

```
atgaaagcgt ctcttcgtaa gtttctaatt tcaacaacgc taacacttcc atactcattc     60
caagcctttt ctttggaagt cgtagtccct aatggaactt atgatgggaa ccttagagaa    120
acgttcccct atacgattac atccaatcct gaaggaacaa cggcaatact gtcaggaaat    180
ttaaatcttt taaatcttga taactccatg gtagcaacgc cttcaagttg ctttttcaac    240
tctgcaggat ccatgacaat tgtggggaga aaccacaatc taacctttac aaaccttcgc    300
acgtcggcaa acggtgctgc cctaagctct attcctacaa caactcctga atcgttccct    360
tatacgatta aaggagtgaa caccctctcc ttttctaact gcctagccct aatggcccgc    420
acaacaacgg cgccaaatac gacaactcct gtaaatccaa acggaggggc gttctactcc    480
aaagctcctg tatttctaga gaatattcag aatgtgctat ttaaaaataa cagggctgct    540
gatagcggcg gtggcctatg ggtagaaaca gctgggatta gcaatatcaa aaaatccatg    600
cagttcctta gcaacgtcgg agccaacggt ggcgctatca acgcgtctaa aagcctagat    660
gttacgcaat gtccttcgat tctcttcaga tctaactctg ctgagaaact cggaggagct    720
atccaagctg ttgatcctgc aacaacaaat caagtaaata ctgccgtcag attctccgaa    780
aatggctcag tacaatttga tgccaataat gcgaaatctg gcggagcgat ttattcgaaa    840
gggaacgtcg atttctcaaa taatgcgcaa ttgctgatac agaataactc cgcatctcct    900
gaagtcgcta atactaatga agtattagga caaggtgggg cgattttctg tgtacaacag    960
actcctactc aaccgccgcc gccaccacca cctacaacga atcctgtctt ctcaggatta   1020
actataacca atcaaaaaga tatcctcttt gcaaataact ttgccgcaac tgcaggcgga   1080
gcgatttatg gagaaaaggt cagcattacc tcctcaggga aaacgatgtt tacaaacaac   1140
atcgctaaag atggcggagc tatctacatt cctgaaaatg gagagctcac cttatctgct   1200
gactacggcg atatgatttt ctatgaaaat ctaaaaaaag atgacgctac tgtcacaaga   1260
aacgctgtta ccttagcaaa aggagcaacg attaagttac tagcagcttc tggggatcat   1320
aaactctgtt tctacgatcc tattgtgact acacttccag aaacagctcc tactaatgac   1380
aagactctaa cgatcaacca agataaaaca tcctccaccc cttttactaa ctatattgga   1440
accctcctat tttcaggagc ttatgtagat agccaaagcg ctagcactac agcgaatttt   1500
```

```
gaatccacta tctatcaaaa agtcatctta ggtggcggga agcttgttct agcagataaa    1560
gccagcctat ctgtagcttc ctttactcag gaaacagatt ctattctttt aatggataat    1620
ggaactactc tagcaattac agagcattcc catcaaacac cagcagctgg tgggggtggc    1680
ggaggcggag gaaccccccac tcaggaagcc aatactgatg gagttatttc cttaacaaat    1740
cttcatgtca atatcagctc gcttacggaa caaggtgagg gggcgaaact tgaaacaaaa    1800
aatacagatg ggacgataac tttaactggg catgtatcct tagacgatgt ttcaggaact    1860
gcttacgaga atcacgatct tttcaataaa gataccgtca cgataaatct gctttctctt    1920
tctacagcag gagatagtaa aacgacgatc aatggtttgg acctcactct tagaggagac    1980
gcagaacctc aatacggtta ccaaggatca tggcaactgg cttgggaaaa tggagctgat    2040
gccaataaac agaaaatcct aaaagctaca tggacaaaaa caggattcac tcctaatcct    2100
gagcgtcaag catctttagt tcctaatagc ttatggggag cattcatcga cctacgttct    2160
atgaatgcct tagcgacagc aagctgtgac ggcttcggtt atggtaaggg attgtgggta    2220
gctgggattt ccaatatctt ccaccatgat cgcaatagcg tatcccatgg tttccgtcgt    2280
attagcggtg gttatgttat tggagccaat tcacaaacag taacggattc tgtatttgga    2340
gtggccttct cccagatatt tgctaagtct aaagactatg ttgtctcctc agcaaaatca    2400
caagctatag caggtagcgc ttacctatcg gtaaaacgtc agttaagcaa cacgatattc    2460
tcatccttcg ctgcaagaat taactacagc catactaacg aggatatgaa aacacgctat    2520
accttcattc ctgaaaaaga tggcaattgg gataataact gctggttagg agaaataggc    2580
ggaagcttac ctattgtttt acaaattact aaattacatc taaatcaaat cattccttt    2640 atgaatgttc agcttggcta tgctgagcat ggatcgttta agaaaaaact tgcagaagca    2700
cgctccttct gttcttctcg tttgattaac ttagcggttc ctgttggatt taaaattgat    2760
aggcgttccc actcccatcc ggattttac agcctagcta tatcctacat tcccgatgta    2820
tggcgaagga atccaggatg taacacttta ttgctcgcaa atggagtccg ttggaaaacg    2880
ccagcaacta atctaaatag acatggttta ttgatgcaag gatccacaca tacagctgtg    2940
ctcagtaata ttgagatctt tagccatggt agttgcgaat tacgtagctc ctcacgcaac    3000
tacaatataa atgtaggaag taaaattcga ttctaa    3036
```

<210> SEQ ID NO 32
<211> LENGTH: 1011
<212> TYPE: PRT
<213> ORGANISM: Chlamydia psitacci

<400> SEQUENCE: 32

```
Met Lys Ala Ser Leu Arg Lys Phe Leu Ile Ser Thr Thr Leu Thr Leu
1               5                   10                  15

Pro Tyr Ser Phe Gln Ala Phe Ser Leu Glu Val Val Val Pro Asn Gly
            20                  25                  30

Thr Tyr Asp Gly Asn Leu Arg Glu Thr Phe Pro Tyr Thr Ile Thr Ser
        35                  40                  45

Asn Pro Glu Gly Thr Thr Ala Ile Leu Ser Gly Asn Leu Asn Leu Leu
    50                  55                  60

Asn Leu Asp Asn Ser Met Val Ala Thr Pro Ser Ser Cys Phe Phe Asn
65                  70                  75                  80

Ser Ala Gly Ser Met Thr Ile Val Gly Arg Asn His Asn Leu Thr Phe
                85                  90                  95

Thr Asn Leu Arg Thr Ser Ala Asn Gly Ala Ala Leu Ser Ser Ile Pro
```

```
                    100                 105                 110
Thr Thr Thr Pro Glu Ser Phe Pro Tyr Thr Ile Lys Gly Val Asn Thr
            115                 120                 125

Leu Ser Phe Ser Asn Cys Leu Ala Leu Met Ala Arg Thr Thr Thr Ala
        130                 135                 140

Pro Asn Thr Thr Thr Pro Val Asn Pro Asn Gly Gly Ala Phe Tyr Ser
145                 150                 155                 160

Lys Ala Pro Val Phe Leu Glu Asn Ile Gln Asn Val Leu Phe Lys Asn
                165                 170                 175

Asn Arg Ala Ala Asp Ser Gly Gly Leu Trp Val Glu Thr Ala Gly
            180                 185                 190

Ile Ser Asn Ile Lys Lys Ser Met Gln Phe Leu Ser Asn Val Gly Ala
        195                 200                 205

Asn Gly Gly Ala Ile Asn Ala Ser Lys Ser Leu Asp Val Thr Gln Cys
    210                 215                 220

Pro Ser Ile Leu Phe Arg Ser Asn Ser Ala Glu Lys Leu Gly Gly Ala
225                 230                 235                 240

Ile Gln Ala Val Asp Pro Ala Thr Thr Asn Gln Val Asn Thr Ala Val
                245                 250                 255

Arg Phe Ser Glu Asn Gly Ser Val Gln Phe Asp Ala Asn Asn Ala Lys
            260                 265                 270

Ser Gly Gly Ala Ile Tyr Ser Lys Gly Asn Val Asp Phe Ser Asn Asn
        275                 280                 285

Ala Gln Leu Leu Ile Gln Asn Asn Ser Ala Ser Pro Glu Val Ala Asn
    290                 295                 300

Thr Asn Glu Val Leu Gly Gln Gly Gly Ala Ile Phe Cys Val Gln Gln
305                 310                 315                 320

Thr Pro Thr Gln Pro Pro Pro Pro Pro Thr Thr Asn Pro Val
                325                 330                 335

Phe Ser Gly Leu Thr Ile Thr Asn Gln Lys Asp Ile Leu Phe Ala Asn
            340                 345                 350

Asn Phe Ala Ala Thr Ala Gly Gly Ala Ile Tyr Gly Glu Lys Val Ser
        355                 360                 365

Ile Thr Ser Ser Gly Lys Thr Met Phe Thr Asn Asn Ile Ala Lys Asp
    370                 375                 380

Gly Gly Ala Ile Tyr Ile Pro Glu Asn Gly Glu Leu Thr Leu Ser Ala
385                 390                 395                 400

Asp Tyr Gly Asp Met Ile Phe Tyr Glu Asn Leu Lys Lys Asp Asp Ala
                405                 410                 415

Thr Val Thr Arg Asn Ala Val Thr Leu Ala Lys Gly Ala Thr Ile Lys
            420                 425                 430

Leu Leu Ala Ala Ser Gly Asp His Lys Leu Cys Phe Tyr Asp Pro Ile
        435                 440                 445

Val Thr Thr Leu Pro Glu Thr Ala Pro Thr Asn Asp Lys Thr Leu Thr
    450                 455                 460

Ile Asn Gln Asp Lys Thr Ser Ser Thr Pro Phe Thr Asn Tyr Ile Gly
465                 470                 475                 480

Thr Leu Leu Phe Ser Gly Ala Tyr Val Asp Ser Gln Ser Ala Ser Thr
                485                 490                 495

Thr Ala Asn Phe Glu Ser Thr Ile Tyr Gln Lys Val Ile Leu Gly Gly
            500                 505                 510

Gly Lys Leu Val Leu Ala Asp Lys Ala Ser Leu Ser Val Ala Ser Phe
        515                 520                 525
```

```
Thr Gln Glu Thr Asp Ser Ile Leu Leu Met Asp Asn Gly Thr Thr Leu
    530                 535                 540
Ala Ile Thr Glu His Ser His Gln Thr Pro Ala Gly Gly Gly Gly
545                 550                 555                 560
Gly Gly Gly Gly Thr Pro Thr Gln Glu Ala Asn Thr Asp Gly Val Ile
                565                 570                 575
Ser Leu Thr Asn Leu His Val Asn Ile Ser Ser Leu Thr Glu Gln Gly
                580                 585                 590
Glu Gly Ala Lys Leu Glu Thr Lys Asn Thr Asp Gly Thr Ile Thr Leu
                595                 600                 605
Thr Gly His Val Ser Leu Asp Asp Val Ser Gly Thr Ala Tyr Glu Asn
    610                 615                 620
His Asp Leu Phe Asn Lys Asp Thr Val Thr Ile Asn Leu Leu Ser Leu
625                 630                 635                 640
Ser Thr Ala Gly Asp Ser Lys Thr Thr Ile Asn Gly Leu Asp Leu Thr
                645                 650                 655
Leu Arg Gly Asp Ala Glu Pro Gln Tyr Gly Tyr Gln Gly Ser Trp Gln
                660                 665                 670
Leu Ala Trp Glu Asn Gly Ala Asp Ala Asn Lys Gln Lys Ile Leu Lys
                675                 680                 685
Ala Thr Trp Thr Lys Thr Gly Phe Thr Pro Asn Pro Glu Arg Gln Ala
    690                 695                 700
Ser Leu Val Pro Asn Ser Leu Trp Gly Ala Phe Ile Asp Leu Arg Ser
705                 710                 715                 720
Met Asn Ala Leu Ala Thr Ala Ser Cys Asp Gly Phe Tyr Gly Lys
                725                 730                 735
Gly Leu Trp Val Ala Gly Ile Ser Asn Ile Phe His His Asp Arg Asn
                740                 745                 750
Ser Val Ser His Gly Phe Arg Arg Ile Ser Gly Gly Tyr Val Ile Gly
                755                 760                 765
Ala Asn Ser Gln Thr Val Thr Asp Ser Val Phe Gly Val Ala Phe Ser
    770                 775                 780
Gln Ile Phe Ala Lys Ser Lys Asp Tyr Val Val Ser Ser Ala Lys Ser
785                 790                 795                 800
Gln Ala Ile Ala Gly Ser Ala Tyr Leu Ser Val Lys Arg Gln Leu Ser
                805                 810                 815
Asn Thr Ile Phe Ser Ser Phe Ala Ala Arg Ile Asn Tyr Ser His Thr
                820                 825                 830
Asn Glu Asp Met Lys Thr Arg Tyr Thr Phe Ile Pro Glu Lys Asp Gly
                835                 840                 845
Asn Trp Asp Asn Asn Cys Trp Leu Gly Glu Ile Gly Gly Ser Leu Pro
    850                 855                 860
Ile Val Leu Gln Ile Thr Lys Leu His Leu Asn Gln Ile Ile Pro Phe
865                 870                 875                 880
Met Asn Val Gln Leu Gly Tyr Ala Glu His Gly Ser Phe Lys Glu Lys
                885                 890                 895
Leu Ala Glu Ala Arg Ser Phe Cys Ser Ser Arg Leu Ile Asn Leu Ala
                900                 905                 910
Val Pro Val Gly Phe Lys Ile Asp Arg Arg Ser His Ser His Pro Asp
                915                 920                 925
Phe Tyr Ser Leu Ala Ile Ser Tyr Ile Pro Asp Val Trp Arg Arg Asn
    930                 935                 940
Pro Gly Cys Asn Thr Leu Leu Leu Ala Asn Gly Val Arg Trp Lys Thr
945                 950                 955                 960
```

```
Pro Ala Thr Asn Leu Asn Arg His Gly Leu Leu Met Gln Gly Ser Thr
            965                 970                 975

His Thr Ala Val Leu Ser Asn Ile Glu Ile Phe Ser His Gly Ser Cys
        980                 985                 990

Glu Leu Arg Ser Ser Ser Arg Asn Tyr Asn Ile Asn Val Gly Ser Lys
        995                 1000                1005

Ile Arg Phe
    1010

<210> SEQ ID NO 33
<211> LENGTH: 1806
<212> TYPE: DNA
<213> ORGANISM: Chlamydia trachomatis

<400> SEQUENCE: 33
```

| | | | | | |
|---|---|---|---|---|---|
| atgaaaatga | ataggatttg | gctattactg | cttacctttt | cttctgccat | acattctcct | 60 |
| gtacaaggag | aaagcttggt | ttgcaagaat | gctcttcaag | atttgagttt | tttagagcat | 120 |
| ttattacagg | ttaaatatgc | tcctaaaaca | tggaagagc | aatacttagg | atgggatctt | 180 |
| gttcaaagct | ccgtttctgc | acagcagaag | cttcgtacac | aagaaaatcc | atcaacaagt | 240 |
| ttttgccagc | aggtccttgc | tgattttatc | ggaggattaa | atgactttca | cgctggagta | 300 |
| actttctttg | cgatagaaag | tgcttacctt | ccttataccg | tacaaaaaag | tagtgacggc | 360 |
| cgtttctact | ttgtagatat | catgactttt | tcttcagaga | tccgtgttgg | agatgagttg | 420 |
| ctagaggtgg | atggggcgcc | tgtccaagat | gtactcgcta | ctctatatgg | aagcaatcac | 480 |
| aaagggactg | cagctgaaga | gtcggctgct | ttaagaacac | tattttctcg | catggcctct | 540 |
| ttagggcaca | aagtaccttc | tgggcgcact | actttaaaga | ttcgtcgtcc | ttttggtact | 600 |
| acgagagaag | ttcgtgtgaa | atggcgttat | gttcctgaag | gtgtaggaga | tttggctacc | 660 |
| atagctcctt | ctatcagggc | tccacagtta | cagaaatcga | tgagaagctt | tttccctaag | 720 |
| aaagatgatg | cgtttcatcg | gtctagttcg | ctattctact | ctccaatggt | tccgcatttt | 780 |
| tgggcagagc | ttcgcaatca | ttatgcaacg | agtggtttga | aaagcgggta | caatattggg | 840 |
| agtaccgatg | ggtttctccc | tgtcattggg | cctgttatat | gggagtcgga | gggtcttttc | 900 |
| cgcgcttata | tttcttcggt | gactgatggg | gatggtaaga | gccataaagt | aggatttcta | 960 |
| agaattccta | catatagttg | gcaggacatg | gaagattttg | atccttcagg | accgcctcct | 1020 |
| tgggaagaat | ttgctaagat | tattcaagta | ttttcttcta | atacagaagc | tttgattatc | 1080 |
| gaccaaacga | caacccagg | tggtagtgtc | ctttatcttt | atgcactgct | ttccatgttg | 1140 |
| acagaccgtc | ctttagaact | tcctaaacat | agaatgattc | tgactcagga | tgaagtggtt | 1200 |
| gatgctttag | attggttaac | cctgttggaa | aacgtagaca | caaacgtgga | gtctcgcctt | 1260 |
| gctctgggag | acaacatgga | aggatatact | gtggatctac | aggttgccga | gtatttaaaa | 1320 |
| agctttggac | gtcaagtatt | gaattgttgg | agtaaagggg | atatcgagtt | atcaacgcct | 1380 |
| attcctcttt | ttggttttga | aagattcat | ccacatcctc | gagttcaata | ctctaaaccg | 1440 |
| atttgtgttt | tgatcaatga | gcaagacttt | tcttgtgctg | acttcttccc | tgtagttttg | 1500 |
| aaagacaatg | atcgagctct | tattgttggt | actcgaacag | ctggagctgg | aggatttgtc | 1560 |
| tttaatgtgc | agttcccaaa | tagaactgga | ataaaaactt | gttctttaac | aggatcatta | 1620 |
| gctgttagag | agcatggtgc | cttcattgag | aacatcggag | tcgaaccgca | tatcgatctg | 1680 |
| ccttttacag | cgaatgatat | tcgctataaa | ggctattccg | agtatcttga | taaggtcaaa | 1740 |
| aaattggttt | gtcagctgat | caataacgac | ggtaccatta | ttcttgcgga | agatggtagt | 1800 |

```
tttaa                                                              1806
```

\<210\> SEQ ID NO 34
\<211\> LENGTH: 601
\<212\> TYPE: PRT
\<213\> ORGANISM: Chlamydia trachomatis

\<400\> SEQUENCE: 34

| | | | | | | | | | | | | | | | |
|---|---|---|---|---|---|---|---|---|---|---|---|---|---|---|---|
| Met | Lys | Met | Asn | Arg | Ile | Trp | Leu | Leu | Leu | Thr | Phe | Ser | Ser | Ala | |
| 1 | | | | 5 | | | | | 10 | | | | | 15 | |
| Ile | His | Ser | Pro | Val | Gln | Gly | Glu | Ser | Leu | Val | Cys | Lys | Asn | Ala | Leu |
| | | | 20 | | | | | 25 | | | | | 30 | | |
| Gln | Asp | Leu | Ser | Phe | Leu | Glu | His | Leu | Leu | Gln | Val | Lys | Tyr | Ala | Pro |
| | | | 35 | | | | | 40 | | | | | 45 | | |
| Lys | Thr | Trp | Lys | Glu | Gln | Tyr | Leu | Gly | Trp | Asp | Leu | Val | Gln | Ser | Ser |
| | | | 50 | | | | | 55 | | | | | 60 | | |
| Val | Ser | Ala | Gln | Gln | Lys | Leu | Arg | Thr | Gln | Glu | Asn | Pro | Ser | Thr | Ser |
| 65 | | | | | 70 | | | | | 75 | | | | | 80 |
| Phe | Cys | Gln | Gln | Val | Leu | Ala | Asp | Phe | Ile | Gly | Gly | Leu | Asn | Asp | Phe |
| | | | | 85 | | | | | 90 | | | | | 95 | |
| His | Ala | Gly | Val | Thr | Phe | Phe | Ala | Ile | Glu | Ser | Ala | Tyr | Leu | Pro | Tyr |
| | | | 100 | | | | | 105 | | | | | 110 | | |
| Thr | Val | Gln | Lys | Ser | Ser | Asp | Gly | Arg | Phe | Tyr | Phe | Val | Asp | Ile | Met |
| | | | 115 | | | | | 120 | | | | | 125 | | |
| Thr | Phe | Ser | Ser | Glu | Ile | Arg | Val | Gly | Asp | Glu | Leu | Leu | Glu | Val | Asp |
| | | | 130 | | | | | 135 | | | | | 140 | | |
| Gly | Ala | Pro | Val | Gln | Asp | Val | Leu | Ala | Thr | Leu | Tyr | Gly | Ser | Asn | His |
| 145 | | | | | 150 | | | | | 155 | | | | | 160 |
| Lys | Gly | Thr | Ala | Ala | Glu | Glu | Ser | Ala | Ala | Leu | Arg | Thr | Leu | Phe | Ser |
| | | | | 165 | | | | | 170 | | | | | 175 | |
| Arg | Met | Ala | Ser | Leu | Gly | His | Lys | Val | Pro | Ser | Gly | Arg | Thr | Thr | Leu |
| | | | 180 | | | | | 185 | | | | | 190 | | |
| Lys | Ile | Arg | Arg | Pro | Phe | Gly | Thr | Thr | Arg | Glu | Val | Arg | Val | Lys | Trp |
| | | | 195 | | | | | 200 | | | | | 205 | | |
| Arg | Tyr | Val | Pro | Glu | Gly | Val | Gly | Asp | Leu | Ala | Thr | Ile | Ala | Pro | Ser |
| | | | 210 | | | | | 215 | | | | | 220 | | |
| Ile | Arg | Ala | Pro | Gln | Leu | Gln | Lys | Ser | Met | Arg | Ser | Phe | Phe | Pro | Lys |
| 225 | | | | | 230 | | | | | 235 | | | | | 240 |
| Lys | Asp | Asp | Ala | Phe | His | Arg | Ser | Ser | Ser | Leu | Phe | Tyr | Ser | Pro | Met |
| | | | | 245 | | | | | 250 | | | | | 255 | |
| Val | Pro | His | Phe | Trp | Ala | Glu | Leu | Arg | Asn | His | Tyr | Ala | Thr | Ser | Gly |
| | | | 260 | | | | | 265 | | | | | 270 | | |
| Leu | Lys | Ser | Gly | Tyr | Asn | Ile | Gly | Ser | Thr | Asp | Gly | Phe | Leu | Pro | Val |
| | | | 275 | | | | | 280 | | | | | 285 | | |
| Ile | Gly | Pro | Val | Ile | Trp | Glu | Ser | Glu | Gly | Leu | Phe | Arg | Ala | Tyr | Ile |
| | | | 290 | | | | | 295 | | | | | 300 | | |
| Ser | Ser | Val | Thr | Asp | Gly | Asp | Gly | Lys | Ser | His | Lys | Val | Gly | Phe | Leu |
| 305 | | | | | 310 | | | | | 315 | | | | | 320 |
| Arg | Ile | Pro | Thr | Tyr | Ser | Trp | Gln | Asp | Met | Glu | Asp | Phe | Asp | Pro | Ser |
| | | | | 325 | | | | | 330 | | | | | 335 | |
| Gly | Pro | Pro | Pro | Trp | Glu | Glu | Phe | Ala | Lys | Ile | Ile | Gln | Val | Phe | Ser |
| | | | 340 | | | | | 345 | | | | | 350 | | |
| Ser | Asn | Thr | Glu | Ala | Leu | Ile | Ile | Asp | Gln | Thr | Asn | Asn | Pro | Gly | Gly |
| | | | 355 | | | | | 360 | | | | | 365 | | |

```
Ser Val Leu Tyr Leu Tyr Ala Leu Leu Ser Met Leu Thr Asp Arg Pro
    370                 375                 380

Leu Glu Leu Pro Lys His Arg Met Ile Leu Thr Gln Asp Glu Val Val
385                 390                 395                 400

Asp Ala Leu Asp Trp Leu Thr Leu Leu Glu Asn Val Asp Thr Asn Val
                405                 410                 415

Glu Ser Arg Leu Ala Leu Gly Asp Asn Met Glu Gly Tyr Thr Val Asp
            420                 425                 430

Leu Gln Val Ala Glu Tyr Leu Lys Ser Phe Gly Arg Gln Val Leu Asn
        435                 440                 445

Cys Trp Ser Lys Gly Asp Ile Glu Leu Ser Thr Pro Ile Pro Leu Phe
    450                 455                 460

Gly Phe Glu Lys Ile His Pro His Pro Arg Val Gln Tyr Ser Lys Pro
465                 470                 475                 480

Ile Cys Val Leu Ile Asn Glu Gln Asp Phe Ser Cys Ala Asp Phe Phe
                485                 490                 495

Pro Val Val Leu Lys Asp Asn Asp Arg Ala Leu Ile Val Gly Thr Arg
            500                 505                 510

Thr Ala Gly Ala Gly Gly Phe Val Phe Asn Val Gln Phe Pro Asn Arg
        515                 520                 525

Thr Gly Ile Lys Thr Cys Ser Leu Thr Gly Ser Leu Ala Val Arg Glu
    530                 535                 540

His Gly Ala Phe Ile Glu Asn Ile Gly Val Glu Pro His Ile Asp Leu
545                 550                 555                 560

Pro Phe Thr Ala Asn Asp Ile Arg Tyr Lys Gly Tyr Ser Glu Tyr Leu
                565                 570                 575

Asp Lys Val Lys Lys Leu Val Cys Gln Leu Ile Asn Asn Asp Gly Thr
            580                 585                 590

Ile Ile Leu Ala Glu Asp Gly Ser Phe
        595                 600
```

<210> SEQ ID NO 35
<211> LENGTH: 1806
<212> TYPE: DNA
<213> ORGANISM: Chlamydia muridarum

<400> SEQUENCE: 35

```
atgaaaatga ataggatttt gctactgctg ctaacctttt cttccgctat acattctcct      60
ttgcatgggg aaagtttagt ctgtcagaat gctctgaaag atttgagttt tttggagcat     120
ttgctgcaag tcaagtatgc ccctaaaact tggaaagaac agtatttagg ttgggatctt     180
tctaaaagct ctgtttttgc agagcagaaa ttgcgttccg aggacaaccc ttcaacaagc     240
ttttgtcagc aagtaattgc ggactttatt ggagcgttga gtgattttca tgccggggtc     300
tctttctttg ctgtagagag tgcctacctt ccctactctg tacaaaaaag tagcgatgga     360
cgcttctatt tcgttgatgt aatgaccttt tcttctgata ttcgcgtcgg ggatgagtta     420
cttgaggtag acgggcagcc tgttgcagaa gcacttgcta ccctatatgg aaccaatcac     480
aaggggactc tcgctgaaga atctgctgct ttaagaacgt tattttctcg tatggcttct     540
ttaggacata aagtcccttc cgggagaatc accctcaaag ttcgtcgttc ttctggttct     600
gtgaaagatg tgcgagcaaa atggcgttat actccagaaa gtgtagggga tttagctacg     660
atagctcctt ccataaaagc tccacagctg cagaagtcta tgagaggggc ctttcctaaa     720
aaagaaagtg tatttcatca gtcgagcact ctgttttatt ctccaatggt tcctcatttt     780
tggtcggagt ttcgtaatca ctacgcaacg agtggtttaa aaagtgggta caatattggg     840
```

```
gataccgatg gatttttccc agtcatggga cccgttattt gggagtcgga cggaattttt    900
catgcttata ttttcccctt ggttgatgaa aatggtagaa gccataacgt aggatttatc    960
agaattccta cgtatggttg gcaagagatg gaagatttag attctatagg gacacctcct   1020
tgggaagagt ttggtaagat cattacgcta ttttctgaaa aaacagaggc tttgatcatt   1080
gaccaaacga ataatcctgg ggggagcgtt atgtatttat acggattgct ctctatgttg   1140
acggataaac ctttagatct tcctaaacat agaatgattc taactcagga cgaagtagtt   1200
gatgctttag attggttgaa tttattggaa aatgtggata caaacgcaga ggctcggatt   1260
gctttgggag ataatatgga aggatatccc attgacttgc aggctgctga atatctgaaa   1320
agctttgctc atcaggtatt ggcatgttgg aagaatggag atatcgaatt atctacaccg   1380
attcctcttt ttgggtttga gaaaattcat ccacatcctc gagtccaata tactaagcct   1440
atttgtgttt tgattaatga acaggatttt tcttgtgcgg atttcttccc tgctattctg   1500
aaagacaatg acagagccct tgtcgttgga actcgaacag cgggagctgg gggatttgtc   1560
ttcaatgtac aattccctaa cagaacggga attaaaagtt gctctttaac aggatcttta   1620
gcagttagag agcatgggga tttgattgaa aatgttgggg ttgaacctca tattgaaatt   1680
cctttcacag ctaatgatat tcgttataga gggtattctg aatatattca gaaagtacaa   1740
aaattggttg ctcagctaat caataatgac agtgtaatta ttctctcaga ggatggaagt   1800
ttttaa                                                              1806
```

<210> SEQ ID NO 36
<211> LENGTH: 601
<212> TYPE: PRT
<213> ORGANISM: Chlamydia muridarum

<400> SEQUENCE: 36

```
Met Lys Met Asn Arg Ile Leu Leu Leu Leu Leu Thr Phe Ser Ser Ala
1               5                   10                  15

Ile His Ser Pro Leu His Gly Glu Ser Leu Val Cys Gln Asn Ala Leu
            20                  25                  30

Lys Asp Leu Ser Phe Leu Glu His Leu Leu Gln Val Lys Tyr Ala Pro
        35                  40                  45

Lys Thr Trp Lys Glu Gln Tyr Leu Gly Trp Asp Leu Ser Lys Ser Ser
    50                  55                  60

Val Phe Ala Glu Gln Lys Leu Arg Ser Glu Asp Asn Pro Ser Thr Ser
65                  70                  75                  80

Phe Cys Gln Gln Val Ile Ala Asp Phe Ile Gly Ala Leu Ser Asp Phe
                85                  90                  95

His Ala Gly Val Ser Phe Phe Ala Val Glu Ser Ala Tyr Leu Pro Tyr
            100                 105                 110

Ser Val Gln Lys Ser Ser Asp Gly Arg Phe Tyr Phe Val Asp Val Met
        115                 120                 125

Thr Phe Ser Ser Asp Ile Arg Val Gly Asp Glu Leu Leu Glu Val Asp
    130                 135                 140

Gly Gln Pro Val Ala Glu Ala Leu Ala Thr Leu Tyr Gly Thr Asn His
145                 150                 155                 160

Lys Gly Thr Leu Ala Glu Glu Ser Ala Ala Leu Arg Thr Leu Phe Ser
                165                 170                 175

Arg Met Ala Ser Leu Gly His Lys Val Pro Ser Gly Arg Ile Thr Leu
            180                 185                 190

Lys Val Arg Arg Ser Ser Gly Ser Val Lys Asp Val Arg Ala Lys Trp
```

```
                195                 200                 205
Arg Tyr Thr Pro Glu Ser Val Gly Asp Leu Ala Thr Ile Ala Pro Ser
210                 215                 220

Ile Lys Ala Pro Gln Leu Gln Lys Ser Met Arg Gly Ala Phe Pro Lys
225                 230                 235                 240

Lys Glu Ser Val Phe His Gln Ser Ser Thr Leu Phe Tyr Ser Pro Met
                245                 250                 255

Val Pro His Phe Trp Ser Glu Phe Arg Asn His Tyr Ala Thr Ser Gly
                260                 265                 270

Leu Lys Ser Gly Tyr Asn Ile Gly Asp Thr Asp Gly Phe Phe Pro Val
                275                 280                 285

Met Gly Pro Val Ile Trp Glu Ser Asp Gly Ile Phe His Ala Tyr Ile
290                 295                 300

Phe Pro Leu Val Asp Glu Asn Gly Arg Ser His Asn Val Gly Phe Ile
305                 310                 315                 320

Arg Ile Pro Thr Tyr Gly Trp Gln Glu Met Glu Asp Leu Asp Ser Ile
                325                 330                 335

Gly Thr Pro Pro Trp Glu Glu Phe Gly Lys Ile Ile Thr Leu Phe Ser
                340                 345                 350

Glu Lys Thr Glu Ala Leu Ile Ile Asp Gln Thr Asn Asn Pro Gly Gly
                355                 360                 365

Ser Val Met Tyr Leu Tyr Gly Leu Leu Ser Met Leu Thr Asp Lys Pro
370                 375                 380

Leu Asp Leu Pro Lys His Arg Met Ile Leu Thr Gln Asp Glu Val Val
385                 390                 395                 400

Asp Ala Leu Asp Trp Leu Asn Leu Leu Glu Asn Val Asp Thr Asn Ala
                405                 410                 415

Glu Ala Arg Ile Ala Leu Gly Asp Asn Met Glu Gly Tyr Pro Ile Asp
                420                 425                 430

Leu Gln Ala Ala Glu Tyr Leu Lys Ser Phe Ala His Gln Val Leu Ala
                435                 440                 445

Cys Trp Lys Asn Gly Asp Ile Glu Leu Ser Thr Pro Ile Pro Leu Phe
450                 455                 460

Gly Phe Glu Lys Ile His Pro His Pro Arg Val Gln Tyr Thr Lys Pro
465                 470                 475                 480

Ile Cys Val Leu Ile Asn Glu Gln Asp Phe Ser Cys Ala Asp Phe Phe
                485                 490                 495

Pro Ala Ile Leu Lys Asp Asn Asp Arg Ala Leu Val Val Gly Thr Arg
                500                 505                 510

Thr Ala Gly Ala Gly Gly Phe Val Phe Asn Val Gln Phe Pro Asn Arg
                515                 520                 525

Thr Gly Ile Lys Ser Cys Ser Leu Thr Gly Ser Leu Ala Val Arg Glu
530                 535                 540

His Gly Asp Leu Ile Glu Asn Val Gly Val Glu Pro His Ile Glu Ile
545                 550                 555                 560

Pro Phe Thr Ala Asn Asp Ile Arg Tyr Arg Gly Tyr Ser Glu Tyr Ile
                565                 570                 575

Gln Lys Val Gln Lys Leu Val Ala Gln Leu Ile Asn Asn Asp Ser Val
                580                 585                 590

Ile Ile Leu Ser Glu Asp Gly Ser Phe
595                 600

<210> SEQ ID NO 37
<211> LENGTH: 1782
```

<212> TYPE: DNA
<213> ORGANISM: Chlamydia psitacci

<400> SEQUENCE: 37

```
atgaaagtga aacaaattac agccttgatt tgctccttag tattaggttt tcaaatttca     60
ggttccgcta agactttagt tcaaaaaaat gcatgttctg acttggattt tttggaacac    120
ttacttgatg ttaaatatgc tcctaaagag tggaaacata agctttttca ttgggatttg    180
aaagatgcaa cggatcaagc acgtttaaaa ttgtgtattg aggaaaatcc ttcaacaagc    240
tactgccaag gagttcttgc agaatatatc tctgatttaa aagattttca tgccgggatt    300
actttcttcc gcacagagaa ttctcatcta ccttatacgg ttaagttaag caattctcgc    360
agatgcttta ttgttgatgt gcatacgtat aactctgaaa tttctgtagg tgatgaaatt    420
ttagagatgg acggtatgcc gattatggag gtaatcgaga gtatacgtac tggtagagga    480
gctctttctg attacgctgc agctgcacga acactctttt ctcgttctgc tgccttaggc    540
catcaaattc ctatgggagt ggcaacatta aaaattcgtc gtcctagcgg tttaacgcgt    600
acggtaaaag ctaaatggcg ccatacgcct gaatatattc aagatctatc tttaatatct    660
cctttagtaa aagatcctat catccagatg agatctagcc gtgcttgccc tttattatct    720
agtgcttctg aaaattgttt attcacaaac gaaatggttc cttatttctg gaaggaatta    780
cgtcagcaat ataaacgtgg tttaagtagt gattacaata tcggaagtaa aagaggtttc    840
ttacctgatt ttggacatgt gacatggaaa gctaaaagtg gtccttacca tgcttatgtg    900
ttcacctgca ccgataatca tggacagtct cacagtattg gattccttag gatttctaca    960
tattcttgga cagatatgga agatcgtact gctatgaata tggaatcccc atgggatgac   1020
ttcagcgaga tcattagtgt tttacaagag aaaaccgaag ctttgattat cgatcagaca   1080
aacaatcctg gtggtagtgt cttctatctt tatgcattga tttctagatt aacagacaga   1140
cctttagaaa cacctaaaca tagaatgatt ctcactcaaa gtgaagtaca atctgcagta   1200
caatggttga accttcttga aggagttgaa accgatgagc aagcaagaaa tgctctcggt   1260
gaggatatgg aaggttatcc tatcgatatg aatgcggcag gatatctaca gacattttct   1320
aatactgttt taaaatgttg ggcaaatggg gatattaatc tctctacacc tatgcctttg   1380
ttaggatttg ctaaagtaca tccacatcct gaacatcgtt atacacgtcc tatctgcgtc   1440
ttaatcaatc aggaagattt ctcctgcgga gatttattcc ctgcgattat gaaggatagc   1500
ggtcgagctc ttattgtagg aacggccaca gcaggagccg gaggttttgt ctttaacgta   1560
gagttcccta atagaacagg cattaaaagt tgttctttaa caggatctct agcagtaaga   1620
cctgacggtt cttacataga gaatttaggg gtctctcctc atatattctt agattttaca   1680
gatacggatg tacaaacagg aaaatattct gattacatta gcactgtgaa aagtttagtt   1740
cttgatctta ttgaaagaga agctgataac aaagcttctt aa                      1782
```

<210> SEQ ID NO 38
<211> LENGTH: 593
<212> TYPE: PRT
<213> ORGANISM: Chlamydia psitacci

<400> SEQUENCE: 38

```
Met Lys Val Lys Gln Ile Thr Ala Leu Ile Cys Ser Leu Val Leu Gly
1               5                   10                  15

Phe Gln Ile Ser Gly Ser Ala Lys Thr Leu Val Gln Lys Asn Ala Cys
            20                  25                  30

Ser Asp Leu Asp Phe Leu Glu His Leu Leu Asp Val Lys Tyr Ala Pro
```

```
                35                  40                  45
Lys Glu Trp Lys His Lys Leu Phe His Trp Asp Leu Lys Asp Ala Thr
                50                  55                  60
Asp Gln Ala Arg Leu Lys Leu Cys Ile Glu Glu Asn Pro Ser Thr Ser
 65                  70                  75                  80
Tyr Cys Gln Gly Val Leu Ala Glu Tyr Ile Ser Asp Leu Lys Asp Phe
                 85                  90                  95
His Ala Gly Ile Thr Phe Phe Arg Thr Glu Asn Ser His Leu Pro Tyr
            100                 105                 110
Thr Val Lys Leu Ser Asn Ser Arg Arg Cys Phe Ile Val Asp Val His
            115                 120                 125
Thr Tyr Asn Ser Glu Ile Ser Val Gly Asp Glu Ile Leu Glu Met Asp
            130                 135                 140
Gly Met Pro Ile Met Glu Val Ile Glu Ser Ile Arg Thr Gly Arg Gly
145                 150                 155                 160
Ala Leu Ser Asp Tyr Ala Ala Ala Arg Thr Leu Phe Ser Arg Ser
            165                 170                 175
Ala Ala Leu Gly His Gln Ile Pro Met Gly Val Ala Thr Leu Lys Ile
            180                 185                 190
Arg Arg Pro Ser Gly Leu Thr Arg Thr Val Lys Ala Lys Trp Arg His
            195                 200                 205
Thr Pro Glu Tyr Ile Gln Asp Leu Ser Leu Ile Ser Pro Leu Val Lys
            210                 215                 220
Asp Pro Ile Ile Gln Met Arg Ser Ser Arg Ala Cys Pro Leu Leu Ser
225                 230                 235                 240
Ser Ala Ser Glu Asn Cys Leu Phe Thr Asn Glu Met Val Pro Tyr Phe
            245                 250                 255
Trp Lys Glu Leu Arg Gln Gln Tyr Lys Arg Gly Leu Ser Ser Asp Tyr
            260                 265                 270
Asn Ile Gly Ser Lys Arg Gly Phe Leu Pro Asp Phe Gly His Val Thr
            275                 280                 285
Trp Lys Ala Lys Ser Gly Pro Tyr His Ala Tyr Val Phe Thr Cys Thr
            290                 295                 300
Asp Asn His Gly Gln Ser His Ser Ile Gly Phe Leu Arg Ile Ser Thr
305                 310                 315                 320
Tyr Ser Trp Thr Asp Met Glu Asp Arg Thr Ala Met Asn Met Glu Ser
            325                 330                 335
Pro Trp Asp Asp Phe Ser Glu Ile Ile Ser Val Leu Gln Glu Lys Thr
            340                 345                 350
Glu Ala Leu Ile Ile Asp Gln Thr Asn Asn Pro Gly Gly Ser Val Phe
            355                 360                 365
Tyr Leu Tyr Ala Leu Ile Ser Arg Leu Thr Asp Arg Pro Leu Glu Thr
            370                 375                 380
Pro Lys His Arg Met Ile Leu Thr Gln Ser Glu Val Gln Ser Ala Val
385                 390                 395                 400
Gln Trp Leu Asn Leu Leu Glu Gly Val Glu Thr Asp Glu Gln Ala Arg
            405                 410                 415
Asn Ala Leu Gly Glu Asp Met Glu Gly Tyr Pro Ile Asp Met Asn Ala
            420                 425                 430
Ala Gly Tyr Leu Gln Thr Phe Ser Asn Thr Val Leu Lys Cys Trp Ala
            435                 440                 445
Asn Gly Asp Ile Asn Leu Ser Thr Pro Met Pro Leu Leu Gly Phe Ala
        450                 455                 460
```

```
Lys Val His Pro His Pro Glu His Arg Tyr Thr Arg Pro Ile Cys Val
465                 470                 475                 480

Leu Ile Asn Gln Glu Asp Phe Ser Cys Gly Asp Leu Phe Pro Ala Ile
                485                 490                 495

Met Lys Asp Ser Gly Arg Ala Leu Ile Val Gly Thr Ala Thr Ala Gly
            500                 505                 510

Ala Gly Gly Phe Val Phe Asn Val Glu Phe Pro Asn Arg Thr Gly Ile
        515                 520                 525

Lys Ser Cys Ser Leu Thr Gly Ser Leu Ala Val Arg Pro Asp Gly Ser
    530                 535                 540

Tyr Ile Glu Asn Leu Gly Val Ser Pro His Ile Phe Leu Asp Phe Thr
545                 550                 555                 560

Asp Thr Asp Val Gln Thr Gly Lys Tyr Ser Asp Tyr Ile Ser Thr Val
                565                 570                 575

Lys Ser Leu Val Leu Asp Leu Ile Glu Arg Glu Ala Asp Asn Lys Ala
                580                 585                 590

Ser
```

<210> SEQ ID NO 39
<211> LENGTH: 1860
<212> TYPE: DNA
<213> ORGANISM: Chlamydia pneumoniae

<400> SEQUENCE: 39

```
atgaaaaaag ggaaattagg agccatagtt tttggccttc tatttacaag tagtgttgct      60
ggttttccta aggatttgac taaagacaac gcttatcaag atttaaatgt catagagcat     120
ttaatatcgt taaatatagc tcctttacca tggaaggaac tattatttgg ttgggattta     180
tctcagcaaa cacagcaagc tcgcttgcaa ctggtcttag aagaaaaacc aacaaccaac     240
tactgccaga aggtactctc taactacgtg agatcattaa acgattatca tgcagggatt     300
acgttttatc gtactgaaag tgcgtatatc ccttacgtat tgaagttaag tgaagatggt     360
catgtctttg tagtcgacgt acagactagc caaggggata tttacttagg ggatgaaatc     420
cttgaagtag atggaatggg gattcgtgag ctatcgaaaa gccttcgctt tggacgaggg     480
agtgccacag actattctgc tgcagttcgt tccttgacat cgcgttccgc cgcttttgga     540
gatgcggttc cttcaggaat tgccatgttg aaacttcgcc gacccagtgg tttgatccgt     600
tcgacaccgg tccgttggcg ttatactcca gagcatatcg agattttttc tttagttgct     660
cctttgattc ctgaacataa acctcaatta cctacacaaa gttgtgtgct attccgttcc     720
ggggtaaatt cacagtcttc tagtagctct ttattcagtt cctacatggt gccttatttc     780
tggaagaat  tgcgggttca aaataagcag cgttttgaca gtaatcacca tagggagc      840
cgtaatggat ttttacctac gtttggtcct attctttggg aacaagacaa ggggccctat     900
cgttcctata tctttaaagc aaaagattct caggcaatc cccatcgcat aggattttta      960
agaatttctt cttatgtttg gactgattta gaaggacttg aagaggatca taaggatagt    1020
ccttgggagc tctttggaga gatcatcgat catttggaaa aagagactga tgctttgatt    1080
attgatcaga cccataatcc tggaggcagt gttttctatc tctattcgtt actatctatg    1140
ttaacagatc atcctttaga tactcctaaa catagaatga ttttcactca ggatgaagtc    1200
agctcggctt tgcactggca agatctacta gaagatgtct tcacagatga gcaggcagtt    1260
gccgtgctag gggaaactat ggaaggatat gcatggata  tgcatgctgt agcctctctt    1320
caaaacttct ctcagagtgt cctttcttcc tgggtttcag gtgatattaa cctttcaaaa    1380
```

```
cctatgcctt tgctaggatt tgcacaggtt cgacctcatc ctaaacatca atatactaaa   1440
cctttgttta tgttgataga cgaggatgac ttctcttgtg agatttagc gcctgcaatt    1500 ttgaaggata atggccgcgc tactctcatt ggaaagccaa cagcaggagc tggaggtttt   1560
gtattccaag tcactttccc taaccgttct ggaattaaag gtctttcttt aacaggatct   1620
ttagctgtta ggaaagatgg tgagtttatt gaaaacttag gagtggctcc tcatattgat   1680
ttaggattta cctccaggga tttgcaaact tccaggttta ctgattacgt tgaggcagtg   1740
aaaactatag ttttaacttc tttgtctgag aacgctaaga agagtgaaga gcagacttct   1800
ccgcaagaga cgcctgaagt tattcgagtc tcttatccca caacgacttc tgcttcgtaa   1860
```

<210> SEQ ID NO 40
<211> LENGTH: 619
<212> TYPE: PRT
<213> ORGANISM: Chlamydia pneumoniae

<400> SEQUENCE: 40

```
Met Lys Lys Gly Lys Leu Gly Ala Ile Val Phe Gly Leu Leu Phe Thr
1               5                   10                  15

Ser Ser Val Ala Gly Phe Ser Lys Asp Leu Thr Lys Asp Asn Ala Tyr
            20                  25                  30

Gln Asp Leu Asn Val Ile Glu His Leu Ile Ser Leu Lys Tyr Ala Pro
        35                  40                  45

Leu Pro Trp Lys Glu Leu Leu Phe Gly Trp Asp Leu Ser Gln Gln Thr
    50                  55                  60

Gln Gln Ala Arg Leu Gln Leu Val Leu Glu Glu Lys Pro Thr Thr Asn
65                  70                  75                  80

Tyr Cys Gln Lys Val Leu Ser Asn Tyr Val Arg Ser Leu Asn Asp Tyr
                85                  90                  95

His Ala Gly Ile Thr Phe Tyr Arg Thr Glu Ser Ala Tyr Ile Pro Tyr
            100                 105                 110

Val Leu Lys Leu Ser Glu Asp Gly His Val Phe Val Asp Val Gln
        115                 120                 125

Thr Ser Gln Gly Asp Ile Tyr Leu Gly Asp Glu Ile Leu Glu Val Asp
    130                 135                 140

Gly Met Gly Ile Arg Glu Ala Ile Glu Ser Leu Arg Phe Gly Arg Gly
145                 150                 155                 160

Ser Ala Thr Asp Tyr Ser Ala Ala Val Arg Ser Leu Thr Ser Arg Ser
                165                 170                 175

Ala Ala Phe Gly Asp Ala Val Pro Ser Gly Ile Ala Met Leu Lys Leu
            180                 185                 190

Arg Arg Pro Ser Gly Leu Ile Arg Ser Thr Pro Val Arg Trp Arg Tyr
        195                 200                 205

Thr Pro Glu His Ile Gly Asp Phe Ser Leu Val Ala Pro Leu Ile Pro
    210                 215                 220

Glu His Lys Pro Gln Leu Pro Thr Gln Ser Cys Val Leu Phe Arg Ser
225                 230                 235                 240

Gly Val Asn Ser Gln Ser Ser Ser Ser Leu Phe Ser Ser Tyr Met
                245                 250                 255

Val Pro Tyr Phe Trp Glu Glu Leu Arg Val Gln Asn Lys Gln Arg Phe
            260                 265                 270

Asp Ser Asn His His Ile Gly Ser Arg Asn Gly Phe Leu Pro Thr Phe
        275                 280                 285

Gly Pro Ile Leu Trp Glu Gln Asp Lys Gly Pro Tyr Arg Ser Tyr Ile
    290                 295                 300
```

Phe Lys Ala Lys Asp Ser Gln Gly Asn Pro His Arg Ile Gly Phe Leu
305                 310                 315                 320

Arg Ile Ser Ser Tyr Val Trp Thr Asp Leu Glu Gly Leu Glu Glu Asp
            325                 330                 335

His Lys Asp Ser Pro Trp Glu Leu Phe Gly Glu Ile Ile Asp His Leu
            340                 345                 350

Glu Lys Glu Thr Asp Ala Leu Ile Ile Asp Gln Thr His Asn Pro Gly
            355                 360                 365

Gly Ser Val Phe Tyr Leu Tyr Ser Leu Leu Ser Met Leu Thr Asp His
    370                 375                 380

Pro Leu Asp Thr Pro Lys His Arg Met Ile Phe Thr Gln Asp Glu Val
385                 390                 395                 400

Ser Ser Ala Leu His Trp Gln Asp Leu Leu Glu Asp Val Phe Thr Asp
                405                 410                 415

Glu Gln Ala Val Ala Val Leu Gly Glu Thr Met Glu Gly Tyr Cys Met
            420                 425                 430

Asp Met His Ala Val Ala Ser Leu Gln Asn Phe Ser Gln Ser Val Leu
            435                 440                 445

Ser Ser Trp Val Ser Gly Asp Ile Asn Leu Ser Lys Pro Met Pro Leu
    450                 455                 460

Leu Gly Phe Ala Gln Val Arg Pro His Pro Lys His Gln Tyr Thr Lys
465                 470                 475                 480

Pro Leu Phe Met Leu Ile Asp Glu Asp Phe Ser Cys Gly Asp Leu
                485                 490                 495

Ala Pro Ala Ile Leu Lys Asp Asn Gly Arg Ala Thr Leu Ile Gly Lys
            500                 505                 510

Pro Thr Ala Gly Ala Gly Gly Phe Val Phe Gln Val Thr Phe Pro Asn
            515                 520                 525

Arg Ser Gly Ile Lys Gly Leu Ser Leu Thr Gly Ser Leu Ala Val Arg
    530                 535                 540

Lys Asp Gly Glu Phe Ile Glu Asn Leu Gly Val Ala Pro His Ile Asp
545                 550                 555                 560

Leu Gly Phe Thr Ser Arg Asp Leu Gln Thr Ser Arg Phe Thr Asp Tyr
                565                 570                 575

Val Glu Ala Val Lys Thr Ile Val Leu Thr Ser Leu Ser Glu Asn Ala
            580                 585                 590

Lys Lys Ser Glu Glu Gln Thr Ser Pro Gln Glu Thr Pro Glu Val Ile
            595                 600                 605

Arg Val Ser Tyr Pro Thr Thr Thr Ser Ala Ser
    610                 615

<210> SEQ ID NO 41
<211> LENGTH: 4596
<212> TYPE: DNA
<213> ORGANISM: Chlamydia trachomatis

<400> SEQUENCE: 41
atgagttccg agaaagatat aaaaagcacc tgttctaagt tttctttgtc tgtagtagca    60
gctatccttg cctctgttag cgggttagct agttgcgtag atcttcatgc tggaggacag    120
tctgtaaatg agctggtata tgtaggccct caagcggttt tattgttaga ccaaattcga    180
gatctattcg ttgggtctaa agatagtcag gctgaaggac agtataggtt aattgtagga    240
gatccaagtt ctttccaaga gaaagatgcg atactcttc ccgggaaggt agagcaaagt    300
actttgttct cagtaaccaa tcccgtggtt ttccaaggtg tggaccaaca ggatcaagtc    360

```
tcttcccaag ggttaatttg tagttttacg agcagcaacc ttgattctcc tcgtgacgga      420
gaatcttttt taggtattgc ttttgttggg gatagtagta aggctggaat cacattaact      480
gacgtgaaag cttctttgtc tggagcggct ttatattcta cagaagatct tatctttgaa      540
aagattaagg gtggattgga atttgcatca tgttcttctc tagaacaggg gggagcttgt      600
gcagctcaaa gtattttgat tcatgattgt caaggattgc aggttaaaca ctgtactaca      660
gccgtgaatg ctgaggggtc tagtgcgaat gatcatcttg gatttggagg aggcgctttc      720
tttgttacgg gttctctttc tggagagaaa agtctctata tgcctgcagg agatatggta      780
gttgcgaatt gtgatgggc tatatctttt gaaggaaaca gcgcgaactt tgctaatgga       840
ggagcgattg ctgcctctgg gaaagtgctt tttgtcgcta atgataaaaa gacttctttt      900
atagagaacc gagctttgtc tggaggagcg attgcagcct cttctgatat tgcctttcaa      960
aactgcgcag aactagttt caaaggcaat tgtgcaattg aacagagga taaaggttct      1020 ttaggtggag gggctatatc ttctctaggc accgttcttt tgcaagggaa tcacgggata      1080
acttgtgata agaatgagtc tgcttcgcaa ggaggcgcca tttttggcaa aaattgtcag      1140
atttctgaca acgaggggcc agtggttttc agagatagta cagcttgctt aggaggaggc      1200
gctattgcag ctcaagaaat tgtttctatt cagaacaatc aggctgggat ttccttcgag      1260
ggaggtaagc ctagtttcgg aggaggtatt gcgtgtggat cttttcttc cgcaggtggt      1320 gcttctgttt tagggaccat tgatatttcg aagaatttag gcgcgatttc gttctctcgt      1380
actttatgta cgacctcaga tttaggacaa atggagtacc agggaggagg agctctattt      1440
ggtgaaaata tttctctttc tgagaatgct ggtgtgctca cctttaaaga caacattgtg      1500 aagactttg cttcgaatgg gaaaattctg ggaggaggag cgattttagc tactggtaag      1560
gtggaaatta ctaataattc cgaaggaatt tcttttacag gaaatgcgag agctccacaa      1620
gctcttccaa ctcaagagga gtttccttta ttcagcaaaa aagaagggcg accactctct      1680
tcaggatatt ctgggggagg agcgatttta ggaagagaag tagctattct ccacaacgct      1740
gcagtagtat ttgagcaaaa tcgtttgcag tgcagcgaag aagaagcgac attattaggt      1800
tgttgtggag gaggcgctgt tcatgggatg gatagcactt cgattgttgg caactcttca      1860
gtaagatttg gtaataatta cgcaatggga caaggagtct caggaggagc tcttttatct      1920
aaaacagtgc agttagctgg gaatggaagc gtcgattttt ctcgaaatat tgctagtttg      1980
ggaggaggag ctcttcaagc ttctgaagga aattgtgagc tagttgataa cggctatgtg      2040
ctattcagag ataatcgagg gagggtttat ggggtgcta tttcttgctt acgtggagat       2100
gtagtcattt ctggaaacaa gggtagagtt gaatttaaag acaacatagc aacacgtctt      2160
tatgtggaag aaactgtaga aaggttgaa gaggtagagc cagctcctga gcaaaaagac       2220
aataatgagc tttcttttctt agggagagca gaacagagtt ttattactgc agctaatcaa      2280
gctcttttcg catctgaaga tggggattta tcacctgagt catccatttc ttctgaagaa      2340
cttgcgaaaa gaagagagtg tgctggagga gctattttg caaaacgggt tcgtattgta       2400
gataaccaag aggccgttgt attctcgaat aacttctctg atatttatgg cggcgccatt      2460
tttacaggtt ctcttcgaga agaggataag ttagatgggc aaatccctga agtcttgatc      2520
tcaggcaatg caggggatgt tgttttttcc ggaaattcct cgaagcgtga tgagcatctt      2580
cctcatacag gtgggggagc catttgtact caaaatttga cgatttctca gaatacaggg      2640
aatgttctgt tttataacaa cgtggcctgt tcgggaggag ctgttcgtat agaggatcat      2700
ggtaatgttc ttttagaagc ttttggagga gatattgttt ttaaaggaaa ttcttctttc      2760
```

```
agagcacaag gatccgatgc tatctatttt gcaggtaaag aatcgcatat tacagccctg    2820
aatgctacgg aaggacatgc tattgttttc cacgacgcat tagttttga aaatctagaa    2880 gaaaggaaat ctgctgaagt attgttaatc aatagtcgag aaaatccagg ttacactgga    2940
tctattcgat ttttagaagc agaaagtaaa gttcctcaat gtattcatgt acaacaagga    3000
agccttgagt tgctaaatgg agccacatta tgtagttatg gttttaaaca agatgctgga    3060
gctaagttgg tattggctgc tggagctaaa ctgaagattt tagattcagg aactcctgta    3120
caacaagggc atgctatcag taaacctgaa gcagaaatcg agtcatcttc tgaaccagag    3180
ggtgcacatt ctctttggat gcgaagaat gctcaaacaa cagttcctat ggttgatatc    3240
catactattt ctgtagattt agcctccttc tcttctagtc aacaggaggg gacagtagaa    3300
gctcctcagg ttattgttcc tggaggaagt tatgttcgat ctggagagct taatttggag    3360
ttagttaaca caacaggtac tggttatgaa aatcatgctt tattgaagaa tgaggctaaa    3420
gttccattga tgtctttcgt tgcttctggt gatgaagctt cagccgaaat cagtaacttg    3480
tcggtttctg atttacagat tcatgtagta actccagaga ttgaagaaga cacatacggc    3540
catatgggag attggtctga ggctaaaatt caagatggaa ctcttgtcat tagttggaat    3600
cctactggat atcgattaga tcctcaaaaa gcagggctt tagtatttaa tgcattatgg    3660
gaagaagggg ctgtcttgtc tgctctgaaa aatgcacgct ttgctcataa tctcactgct    3720
cagcgtatgg aattcgatta ttctacaaat gtgtgggat cgcctttgg tggtttccga    3780 actctatctg cagagaatct ggttgctatt gatggataca aaggagctta tggtggtgct    3840
tctgctggag tcgatattca attgatggaa gattttgttc taggagttag tggagctgct    3900
ttcctaggta aaatggatag tcagaagttt gatgcggagg tttctcggaa gggagttgtt    3960
ggttctgtat atacaggatt tttagctgga tcctggttct tcaaaggaca atatagcctt    4020
ggagaaacac agaacgatat gaaaacgcgt tatgagtac taggagagtc gagtgcttct    4080
tggacatctc gaggagtact ggcagatgct ttagttgaat accgaagttt agttggtcct    4140
gtgagaccta cttttatgc tttgcatttc aatccttatg tcgaagtatc ttatgcttct    4200
atgaaattcc ctggctttac agaacaagga agagaagcgc gttcttttga agacgcttcc    4260
cttaccaata tcaccattcc tttagggatg aagtttgaat tggcgttcat aaaaggacag    4320
ttttcagagg tgaactcttt gggaataagt tatgcatggg aagcttatcg aaaagtagaa    4380
ggaggcgcgg tgcagctttt agaagctggg tttgattggg agggagctcc aatggatctt    4440
cctagacagg agctgcgtgt cgctctggaa aataatacgg aatggagttc ttacttcagc    4500
acagtcttag gattaacagc ttttttgtgga ggatttactt ctacagatag taaactagga    4560
tatgaggcga atactggatt gcgattgatc tttaa                              4596
```

<210> SEQ ID NO 42
<211> LENGTH: 1531
<212> TYPE: PRT
<213> ORGANISM: Chlamydia trachomatis

<400> SEQUENCE: 42

```
Met Ser Ser Glu Lys Asp Ile Lys Ser Thr Cys Ser Lys Phe Ser Leu
 1               5                  10                  15

Ser Val Val Ala Ala Ile Leu Ala Ser Val Ser Gly Leu Ala Ser Cys
            20                  25                  30

Val Asp Leu His Ala Gly Gly Gln Ser Val Asn Glu Leu Val Tyr Val
        35                  40                  45
```

```
Gly Pro Gln Ala Val Leu Leu Leu Asp Gln Ile Arg Asp Leu Phe Val
 50                  55                  60
Gly Ser Lys Asp Ser Gln Ala Glu Gly Gln Tyr Arg Leu Ile Val Gly
 65                  70                  75                  80
Asp Pro Ser Ser Phe Gln Glu Lys Asp Ala Asp Thr Leu Pro Gly Lys
                 85                  90                  95
Val Glu Gln Ser Thr Leu Phe Ser Val Thr Asn Pro Val Val Phe Gln
            100                 105                 110
Gly Val Asp Gln Gln Asp Gln Val Ser Ser Gln Gly Leu Ile Cys Ser
            115                 120                 125
Phe Thr Ser Ser Asn Leu Asp Ser Pro Arg Asp Gly Glu Ser Phe Leu
130                 135                 140
Gly Ile Ala Phe Val Gly Asp Ser Ser Lys Ala Gly Ile Thr Leu Thr
145                 150                 155                 160
Asp Val Lys Ala Ser Leu Ser Gly Ala Ala Leu Tyr Ser Thr Glu Asp
                165                 170                 175
Leu Ile Phe Glu Lys Ile Lys Gly Gly Leu Glu Phe Ala Ser Cys Ser
            180                 185                 190
Ser Leu Glu Gln Gly Gly Ala Cys Ala Ala Gln Ser Ile Leu Ile His
            195                 200                 205
Asp Cys Gln Gly Leu Gln Val Lys His Cys Thr Thr Ala Val Asn Ala
210                 215                 220
Glu Gly Ser Ser Ala Asn Asp His Leu Gly Phe Gly Gly Ala Phe
225                 230                 235                 240
Phe Val Thr Gly Ser Leu Ser Gly Glu Lys Ser Leu Tyr Met Pro Ala
                245                 250                 255
Gly Asp Met Val Val Ala Asn Cys Asp Gly Ala Ile Ser Phe Glu Gly
            260                 265                 270
Asn Ser Ala Asn Phe Ala Asn Gly Gly Ala Ile Ala Ala Ser Gly Lys
            275                 280                 285
Val Leu Phe Val Ala Asn Asp Lys Lys Thr Ser Phe Ile Glu Asn Arg
290                 295                 300
Ala Leu Ser Gly Gly Ala Ile Ala Ala Ser Ser Asp Ile Ala Phe Gln
305                 310                 315                 320
Asn Cys Ala Glu Leu Val Phe Lys Gly Asn Cys Ala Ile Gly Thr Glu
                325                 330                 335
Asp Lys Gly Ser Leu Gly Gly Ala Ile Ser Ser Leu Gly Thr Val
            340                 345                 350
Leu Leu Gln Gly Asn His Gly Ile Thr Cys Asp Lys Asn Glu Ser Ala
            355                 360                 365
Ser Gln Gly Gly Ala Ile Phe Gly Lys Asn Cys Gln Ile Ser Asp Asn
370                 375                 380
Glu Gly Pro Val Val Phe Arg Asp Ser Thr Ala Cys Leu Gly Gly
385                 390                 395                 400
Ala Ile Ala Ala Gln Glu Ile Val Ser Ile Gln Asn Asn Gln Ala Gly
                405                 410                 415
Ile Ser Phe Glu Gly Gly Lys Ala Ser Phe Gly Gly Ile Ala Cys
            420                 425                 430
Gly Ser Phe Ser Ser Ala Gly Gly Ala Ser Val Leu Gly Thr Ile Asp
            435                 440                 445
Ile Ser Lys Asn Leu Gly Ala Ile Ser Phe Ser Arg Thr Leu Cys Thr
450                 455                 460
Thr Ser Asp Leu Gly Gln Met Glu Tyr Gln Gly Gly Gly Ala Leu Phe
465                 470                 475                 480
```

```
Gly Glu Asn Ile Ser Leu Ser Glu Asn Ala Gly Val Leu Thr Phe Lys
                485                 490                 495
Asp Asn Ile Val Lys Thr Phe Ala Ser Asn Gly Lys Ile Leu Gly Gly
                500                 505                 510
Gly Ala Ile Leu Ala Thr Gly Lys Val Glu Ile Thr Asn Asn Ser Glu
                515                 520                 525
Gly Ile Ser Phe Thr Gly Asn Ala Arg Ala Pro Gln Ala Leu Pro Thr
                530                 535                 540
Gln Glu Glu Phe Pro Leu Phe Ser Lys Lys Glu Gly Arg Pro Leu Ser
545                 550                 555                 560
Ser Gly Tyr Ser Gly Gly Ala Ile Leu Gly Arg Glu Val Ala Ile
                565                 570                 575
Leu His Asn Ala Ala Val Val Phe Glu Gln Asn Arg Leu Gln Cys Ser
                580                 585                 590
Glu Glu Glu Ala Thr Leu Leu Gly Cys Cys Gly Gly Ala Val His
                595                 600                 605
Gly Met Asp Ser Thr Ser Ile Val Gly Asn Ser Ser Val Arg Phe Gly
                610                 615                 620
Asn Asn Tyr Ala Met Gly Gln Gly Val Ser Gly Gly Ala Leu Leu Ser
625                 630                 635                 640
Lys Thr Val Gln Leu Ala Gly Asn Gly Ser Val Asp Phe Ser Arg Asn
                645                 650                 655
Ile Ala Ser Leu Gly Gly Gly Ala Leu Gln Ala Ser Glu Gly Asn Cys
                660                 665                 670
Glu Leu Val Asp Asn Gly Tyr Val Leu Phe Arg Asp Asn Arg Gly Arg
                675                 680                 685
Val Tyr Gly Gly Ala Ile Ser Cys Leu Arg Gly Asp Val Val Ile Ser
                690                 695                 700
Gly Asn Lys Gly Arg Val Glu Phe Lys Asp Asn Ile Ala Thr Arg Leu
705                 710                 715                 720
Tyr Val Glu Glu Thr Val Glu Lys Val Glu Glu Val Glu Pro Ala Pro
                725                 730                 735
Glu Gln Lys Asp Asn Asn Glu Leu Ser Phe Leu Gly Arg Ala Glu Gln
                740                 745                 750
Ser Phe Ile Thr Ala Ala Asn Gln Ala Leu Phe Ala Ser Glu Asp Gly
                755                 760                 765
Asp Leu Ser Pro Glu Ser Ser Ile Ser Ser Glu Glu Leu Ala Lys Arg
                770                 775                 780
Arg Glu Cys Ala Gly Gly Ala Ile Phe Ala Lys Arg Val Arg Ile Val
785                 790                 795                 800
Asp Asn Gln Glu Ala Val Val Phe Ser Asn Asn Phe Ser Asp Ile Tyr
                805                 810                 815
Gly Gly Ala Ile Phe Thr Gly Ser Leu Arg Glu Glu Asp Lys Leu Asp
                820                 825                 830
Gly Gln Ile Pro Glu Val Leu Ile Ser Gly Asn Ala Gly Asp Val Val
                835                 840                 845
Phe Ser Gly Asn Ser Ser Lys Arg Asp Glu His Leu Pro His Thr Gly
                850                 855                 860
Gly Gly Ala Ile Cys Thr Gln Asn Leu Thr Ile Ser Gln Asn Thr Gly
865                 870                 875                 880
Asn Val Leu Phe Tyr Asn Asn Val Ala Cys Ser Gly Gly Ala Val Arg
                885                 890                 895
Ile Glu Asp His Gly Asn Val Leu Leu Glu Ala Phe Gly Gly Asp Ile
```

```
                    900             905             910
Val Phe Lys Gly Asn Ser Ser Phe Arg Ala Gln Gly Ser Asp Ala Ile
        915                     920                 925

Tyr Phe Ala Gly Lys Glu Ser His Ile Thr Ala Leu Asn Ala Thr Glu
        930                     935             940

Gly His Ala Ile Val Phe His Asp Ala Leu Val Phe Glu Asn Leu Glu
945                     950                 955                 960

Glu Arg Lys Ser Ala Glu Val Leu Leu Ile Asn Ser Arg Glu Asn Pro
            965                     970                 975

Gly Tyr Thr Gly Ser Ile Arg Phe Leu Glu Ala Glu Ser Lys Val Pro
                980                     985             990

Gln Cys Ile His Val Gln Gln Gly Ser Leu Glu Leu Leu Asn Gly Ala
        995                     1000                1005

Thr Leu Cys Ser Tyr Gly Phe Lys Gln Asp Ala Gly Ala Lys Leu Val
        1010                    1015                1020

Leu Ala Ala Gly Ala Lys Leu Lys Ile Leu Asp Ser Gly Thr Pro Val
1025                    1030                    1035                1040

Gln Gln Gly His Ala Ile Ser Lys Pro Glu Ala Glu Ile Glu Ser Ser
            1045                    1050                1055

Ser Glu Pro Glu Gly Ala His Ser Leu Trp Ile Ala Lys Asn Ala Gln
            1060                    1065                1070

Thr Thr Val Pro Met Val Asp Ile His Thr Ile Ser Val Asp Leu Ala
            1075                    1080                1085

Ser Phe Ser Ser Gln Gln Glu Gly Thr Val Glu Ala Pro Gln Val
        1090                    1095                    1100

Ile Val Pro Gly Gly Ser Tyr Val Arg Ser Gly Glu Leu Asn Leu Glu
1105                    1110                    1115                1120

Leu Val Asn Thr Thr Gly Thr Gly Tyr Glu Asn His Ala Leu Leu Lys
                1125                    1130                1135

Asn Glu Ala Lys Val Pro Leu Met Ser Phe Val Ala Ser Gly Asp Glu
            1140                    1145                1150

Ala Ser Ala Glu Ile Ser Asn Leu Ser Val Ser Asp Leu Gln Ile His
        1155                    1160                    1165

Val Val Thr Pro Glu Ile Glu Glu Asp Thr Tyr Gly His Met Gly Asp
        1170                    1175                1180

Trp Ser Glu Ala Lys Ile Gln Asp Gly Thr Leu Val Ile Ser Trp Asn
1185                    1190                    1195                1200

Pro Thr Gly Tyr Arg Leu Asp Pro Gln Lys Ala Gly Ala Leu Val Phe
            1205                    1210                1215

Asn Ala Leu Trp Glu Glu Gly Ala Val Leu Ser Ala Leu Lys Asn Ala
            1220                    1225                1230

Arg Phe Ala His Asn Leu Thr Ala Gln Arg Met Glu Phe Asp Tyr Ser
        1235                    1240                    1245

Thr Asn Val Trp Gly Phe Ala Phe Gly Gly Phe Arg Thr Leu Ser Ala
        1250                    1255                1260

Glu Asn Leu Val Ala Ile Asp Gly Tyr Lys Gly Ala Tyr Gly Gly Ala
1265                    1270                    1275                1280

Ser Ala Gly Val Asp Ile Gln Leu Met Glu Asp Phe Val Leu Gly Val
                1285                    1290                1295

Ser Gly Ala Ala Phe Leu Gly Lys Met Asp Ser Gln Lys Phe Asp Ala
        1300                    1305                    1310

Glu Val Ser Arg Lys Gly Val Val Gly Ser Val Tyr Thr Gly Phe Leu
        1315                    1320                    1325
```

```
Ala Gly Ser Trp Phe Phe Lys Gly Gln Tyr Ser Leu Gly Glu Thr Gln
    1330                1335                1340

Asn Asp Met Lys Thr Arg Tyr Gly Val Leu Gly Glu Ser Ser Ala Ser
1345                1350                1355                1360

Trp Thr Ser Arg Gly Val Leu Ala Asp Ala Leu Val Glu Tyr Arg Ser
                1365                1370                1375

Leu Val Gly Pro Val Arg Pro Thr Phe Tyr Ala Leu His Phe Asn Pro
            1380                1385                1390

Tyr Val Glu Val Ser Tyr Ala Ser Met Lys Phe Pro Gly Phe Thr Glu
        1395                1400                1405

Gln Gly Arg Glu Ala Arg Ser Phe Glu Asp Ala Ser Leu Thr Asn Ile
    1410                1415                1420

Thr Ile Pro Leu Gly Met Lys Phe Glu Leu Ala Phe Ile Lys Gly Gln
1425                1430                1435                1440

Phe Ser Glu Val Asn Ser Leu Gly Ile Ser Tyr Ala Trp Glu Ala Tyr
                1445                1450                1455

Arg Lys Val Glu Gly Gly Ala Val Gln Leu Leu Glu Ala Gly Phe Asp
            1460                1465                1470

Trp Glu Gly Ala Pro Met Asp Leu Pro Arg Gln Glu Leu Arg Val Ala
        1475                1480                1485

Leu Glu Asn Asn Thr Glu Trp Ser Ser Tyr Phe Ser Thr Val Leu Gly
    1490                1495                1500

Leu Thr Ala Phe Cys Gly Gly Phe Thr Ser Thr Asp Ser Lys Leu Gly
1505                1510                1515                1520

Tyr Glu Ala Asn Thr Gly Leu Arg Leu Ile Phe
                1525                1530
```

<210> SEQ ID NO 43
<211> LENGTH: 4563
<212> TYPE: DNA
<213> ORGANISM: Chlamydia muridarum

<400> SEQUENCE: 43

```
atgagttccg agaaagataa aaaaaactcc tgttctaagt tttccttatc ggtagtagca      60
gctattctcg cttctatgag tggtttatcg aattgttccg atctttatgc cgtaggaagt     120
tctgcagacc atcctgccta cttgattcct caagcggggt tattattgga tcatattaag     180
gatatattca ttggccctaa agatagtcag gataaggggc agtataagtt gattattggt     240
gaggctggct ctttccaaga tagtaatgca gagactcttc ctcaaaaggt agagcacagc     300
actttgtttt cagttacaac acctataatt gtgcaaggaa tagatcaaca agatcaggtc     360
tcttcgcagg gattggtctg taatttttca ggagatcatt cagaggagat tttgagagaa     420
gaatcctttt tagggatcgc tttcctaggg aatggtagca aggatggaat cacgttaaca     480
gatataaaat cttcgttatc tggtgctgcc ttgtattctt cagatgatct tatttttgaa     540
agaattaagg gagatataga gctttcttct tgttcatctt tagaaagagg aggagcttgt     600
tcagctcaaa gtattttaat tcatgattgt caaggattaa cggtaaaaca ttgtgccgca     660
ggggtgaatg ttgaaggagt tagtgctagc gaccatctcg gatttggggg cggggccttc     720
tctactacaa gttctctttc tggagagaag agtttgtata tgcctgcagg cgatattgtg     780
gtggctacct gcgatggtcc tgtgtgtttc gaaggaaata gtgctcagtt agcaaatggt     840
ggcgctattg ccgcttctgg taaagttctt tttgtagcta acgaaaaaaa gatttccttt     900
acagacaacc aagctttgtc tggaggagct atttctgcat cttctagtat ttctttccaa     960
aattgtgctg agcttgtgtt caagagtaat cttgcaaaag gagttaaaga taaatgttct    1020
```

```
ttgggaggag gtgctttagc ctctttagaa tccgtagttt tgaaagataa tctcggtatt   1080
acttatgaaa aaaatcagtc ctattcggaa ggaggggcta ttttttgggaa ggattgtgag   1140 atttttgaaa acaggggggcc tgttgtattc agagataata cagctgcttt aggaggcgga   1200
gctattttgg cgcaacaaac tgtggcgatt tgtggtaata agtctggaat atcttttgaa   1260
ggaagtaagt ctagttttgg aggggccatt gcttgtggaa atttctcttc tgagaataat   1320
tcttcagctt tgggatcaat tgatatctct aacaatctag gagatatctc ttttcttcgg   1380
actctgtgta ctacttcgga tttagggcaa acggattacc aaggggggagg ggccttattc   1440 gctgaaaata tttctctttc tgagaatgct ggtgcaatta ctttcaaaga caatattgtg   1500
aagacatttg cctcaaatgg aaaaatgttg ggtggagggg caattttagc ttcaggaaat   1560
gttttgatta gcaaaaactc tggagagatt tcttttgtag ggaatgctcg agctcctcag   1620
gctattccga ctcgttcatc tgacgaattg tcttttggcg cacaattaac tcaaactact   1680
tcaggatgtt ctgaggaggg agctctttt ggtaaagagg ttgccattgt tcaaaatgcc   1740
actgttgtat tcgagcaaaa tcgcttacag tgtggcgagc aggaaacaca tggtggaggc   1800
ggtgctgttt atggtatgga gagtgcctct attattggaa actcttttgt gagattcgga   1860
aataattacg ctgtagggaa tcagatttct ggaggagctc ttttatccaa gaaggtccgt   1920
ttagctgaaa atacaagggt agattttct cgaaatatcg ctactttctg cggcggggct   1980
gttcaagttt ctgatggaag ttgcgaattg atcaacaatg ggtatgtgct attcagagat   2040
aaccgagggc agacatttgg tgggctatt tcttgcttga aaggagatgt gatcatttcc   2100
ggaaataaag atagggttga gtttagagat aacattgtga cgcggcctta ttttgaagaa   2160
aatgaagaaa aagttgagac agcagatatt aattcagata gcaagaagc agaagagcgc   2220 tctttattag agaacattga gcagagcttt attactgcaa ctaatcagac ctttttctta   2280
gaggaagaga aactcccatc agaagctttt atctctgctg aagaactttc aaagagaaga   2340
gaatgtgctg gtggggcgat ttttgcaaaa cgggtctaca ttacggataa taaagaaccct   2400 atcttgtttt cgcataattt ttctgatgtt tatggggggag ctattttac gggttctcta   2460 caggaaactg ataaacaaga tgttgtaact cctgaagttg tgatatcagg caacgatggg   2520
gatgtcattt tttctggaaa tgcagctaaa catgataagc atttacctga tacaggtggt   2580
ggagccattt gtacacagaa tttgacgatt tcccaaaaca atgggaatgt cttgttcttg   2640 aacaatttttg cttgttctgg tggagcagtt cgcatagagg atcatggaga agttcttta   2700 gaggcttttg ggggagatat tattttcaat ggaaactctt ctttcagagc tcaaggatcg   2760
gatgcgatct attttgctgg taaggactct agaattaaag ctttaaatgc tactgaagga   2820
catgcgattg tgttccaaga tgcattggtg tttgaaaata tagaagaaag aaagtcttcg   2880
ggactattgg tgattaactc tcaggaaaat gagggttata cgggatccgt ccgatttta   2940 ggatctgaaa gtaaggttcc tcaatggatt catgtgcaac agggaggtct tgagttgcta   3000
catggagcta ttttatgtag ttatgggggtt aaacaagatc ctagagctaa aatagtatta   3060
tctgctggat ctaaattgaa gattctgat tcagagcaag aaaataacgc agaaattgga   3120
gatcttgaag attctgttaa ttcagaaaaa acaccatctc tttggattgg gaagaacgct   3180
caagcaaaag tccctctggt tgatatccat actatttcta ttgatttagc atcatttct   3240 tctaaagctc aggaaacccc tgaggaagct ccacaagtca tcgtcccctaa gggaagttgt   3300 gtccactcgg gagagttaag tttggagttg gttaatacaa caggaaaagg ttatgagaat   3360
catgcgttgt taaaaaatga tactcaggtt tctctcatgt ctttcaaaga ggaaaatgat   3420
```

```
ggatctttag aagatttgag taagttgtct gtttcggatt tacgcattaa agtttctact    3480
ccagatattg tagaagaaac ttatggccat atgggggatt ggtctgaagc tacaattcaa    3540 gatgggctc ttgtcattaa ttggcatcct actggatata aattagatcc gcaaaaagct    3600
ggttctttgg tattcaatgc attatgggag gaagaggctg tattgtctac tctaaaaaat    3660
gctcggattg cccataacct taccattcag agaatggaat ttgattattc tacaaatgct    3720
tggggattag cttttagtag ctttagagag ctatcttcag agaagcttgt ttctgttgat    3780
ggatatagag gctcttatat aggggcttct gcaggcattg atactcagtt gatggaagat    3840
tttgttttgg gaatcagcac ggcttccttc ttcgggaaaa tgcatagtca gaattttgat    3900
gcagagattt ctcgacatgg ttttgttggt tcggtctata caggcttcct agctggggcc    3960
tggttcttca agggcagta cagtcttggc gaaacacata cgatatgac aactcgttac    4020 ggggttttgg gagaatctaa tgctacttgg aagtctcgag gagtactagc agatgcttta    4080
gttgaatatc gtagtttagt cggtccagca cgacctaaat tttatgcttt gcattttaat    4140
ccttatgtcg aggtatctta tgcatctgcg aagttcccta gttttgtaga caaggagga    4200 gaagctcgtg cttttgaaga aacctcttta acaaacatta ccgttccctt tggtatgaaa    4260
tttgaactat cttttacaaa aggacagttt tcagagacta attctcttgg aataggttgt    4320
gcatgggaaa tgtatcggaa agtcgaagga agatctgtag agctactaga agctggtttt    4380
gattgggaag atctcctat agatctccct aaacaagagc tgagagtggc tttagaaaac    4440
aatacggaat ggagttcgta ttttagtaca gctctaggag taacagcatt ttgtggagga    4500
ttttcttcta tggataataa actaggatac gaagcgaatg ctggaatgcg tttgattttc    4560
tag                                                                  4563

<210> SEQ ID NO 44
<211> LENGTH: 1520
<212> TYPE: PRT
<213> ORGANISM: Chlamydia muridarum

<400> SEQUENCE: 44

Met Ser Ser Glu Lys Asp Lys Lys Asn Ser Cys Ser Lys Phe Ser Leu
1               5                   10                  15

Ser Val Ala Ala Ile Leu Ala Ser Met Ser Gly Leu Ser Asn Cys
            20                  25                  30

Ser Asp Leu Tyr Ala Val Gly Ser Ser Asp His Pro Ala Tyr Leu
        35                  40                  45

Ile Pro Gln Ala Gly Leu Leu Leu Asp His Ile Lys Asp Ile Phe Ile
    50                  55                  60

Gly Pro Lys Asp Ser Gln Asp Lys Gly Gln Tyr Lys Leu Ile Ile Gly
65                  70                  75                  80

Glu Ala Gly Ser Phe Gln Asp Ser Asn Ala Glu Thr Leu Pro Gln Lys
                85                  90                  95

Val Glu His Ser Thr Leu Phe Ser Val Thr Thr Pro Ile Ile Val Gln
            100                 105                 110

Gly Ile Asp Gln Gln Asp Gln Val Ser Ser Gln Gly Leu Val Cys Asn
        115                 120                 125

Phe Ser Gly Asp His Ser Glu Glu Ile Phe Glu Arg Glu Ser Phe Leu
    130                 135                 140

Gly Ile Ala Phe Leu Gly Asn Gly Ser Lys Asp Gly Ile Thr Leu Thr
145                 150                 155                 160

Asp Ile Lys Ser Ser Leu Ser Gly Ala Ala Leu Tyr Ser Ser Asp Asp
```

```
                        165                 170                 175
Leu Ile Phe Glu Arg Ile Lys Gly Asp Ile Glu Leu Ser Ser Cys Ser
                180                 185                 190

Ser Leu Glu Arg Gly Gly Ala Cys Ser Ala Gln Ser Ile Leu Ile His
            195                 200                 205

Asp Cys Gln Gly Leu Thr Val Lys His Cys Ala Ala Gly Val Asn Val
        210                 215                 220

Glu Gly Val Ser Ala Ser Asp His Leu Gly Phe Gly Gly Ala Phe
225                 230                 235                 240

Ser Thr Thr Ser Ser Leu Ser Gly Glu Lys Ser Leu Tyr Met Pro Ala
                245                 250                 255

Gly Asp Ile Val Val Ala Thr Cys Asp Gly Pro Val Cys Phe Glu Gly
                260                 265                 270

Asn Ser Ala Gln Leu Ala Asn Gly Gly Ala Ile Ala Ala Ser Gly Lys
            275                 280                 285

Val Leu Phe Val Ala Asn Glu Lys Lys Ile Ser Phe Thr Asp Asn Gln
        290                 295                 300

Ala Leu Ser Gly Gly Ala Ile Ser Ala Ser Ser Ile Ser Phe Gln
305                 310                 315                 320

Asn Cys Ala Glu Leu Val Phe Lys Ser Asn Leu Ala Lys Gly Val Lys
                325                 330                 335

Asp Lys Cys Ser Leu Gly Gly Ala Leu Ala Ser Leu Glu Ser Val
            340                 345                 350

Val Leu Lys Asp Asn Leu Gly Ile Thr Tyr Glu Lys Asn Gln Ser Tyr
        355                 360                 365

Ser Glu Gly Gly Ala Ile Phe Gly Lys Asp Cys Glu Ile Phe Glu Asn
    370                 375                 380

Arg Gly Pro Val Val Phe Arg Asp Asn Thr Ala Ala Leu Gly Gly Gly
385                 390                 395                 400

Ala Ile Leu Ala Gln Gln Thr Val Ala Ile Cys Gly Asn Lys Ser Gly
                405                 410                 415

Ile Ser Phe Glu Gly Ser Lys Ser Ser Phe Gly Gly Ala Ile Ala Cys
            420                 425                 430

Gly Asn Phe Ser Ser Glu Asn Asn Ser Ser Ala Leu Gly Ser Ile Asp
        435                 440                 445

Ile Ser Asn Asn Leu Gly Asp Ile Ser Phe Leu Arg Thr Leu Cys Thr
    450                 455                 460

Thr Ser Asp Leu Gly Gln Thr Asp Tyr Gln Gly Gly Ala Leu Phe
465                 470                 475                 480

Ala Glu Asn Ile Ser Leu Ser Glu Asn Ala Gly Ala Ile Thr Phe Lys
                485                 490                 495

Asp Asn Ile Val Lys Thr Phe Ala Ser Asn Gly Lys Met Leu Gly Gly
            500                 505                 510

Gly Ala Ile Leu Ala Ser Gly Asn Val Leu Ile Ser Lys Asn Ser Gly
        515                 520                 525

Glu Ile Ser Phe Val Gly Asn Ala Arg Ala Pro Gln Ala Ile Pro Thr
    530                 535                 540

Arg Ser Ser Asp Glu Leu Ser Phe Gly Ala Gln Leu Thr Gln Thr Thr
545                 550                 555                 560

Ser Gly Cys Ser Gly Gly Ala Leu Phe Gly Lys Glu Val Ala Ile
                565                 570                 575

Val Gln Asn Ala Thr Val Val Phe Glu Gln Asn Arg Leu Gln Cys Gly
            580                 585                 590
```

-continued

```
Glu Gln Glu Thr His Gly Gly Gly Ala Val Tyr Gly Met Glu Ser
        595                 600                 605
Ala Ser Ile Ile Gly Asn Ser Phe Val Arg Phe Gly Asn Asn Tyr Ala
610                 615                 620
Val Gly Asn Gln Ile Ser Gly Gly Ala Leu Leu Ser Lys Lys Val Arg
625                 630                 635                 640
Leu Ala Glu Asn Thr Arg Val Asp Phe Ser Arg Asn Ile Ala Thr Phe
                645                 650                 655
Cys Gly Gly Ala Val Gln Val Ser Asp Gly Ser Cys Glu Leu Ile Asn
                660                 665                 670
Asn Gly Tyr Val Leu Phe Arg Asp Asn Arg Gly Gln Thr Phe Gly Gly
            675                 680                 685
Ala Ile Ser Cys Leu Lys Gly Asp Val Ile Ile Ser Gly Asn Lys Asp
        690                 695                 700
Arg Val Glu Phe Arg Asp Asn Ile Val Thr Arg Pro Tyr Phe Glu Glu
705                 710                 715                 720
Asn Glu Glu Lys Val Glu Thr Ala Asp Ile Asn Ser Asp Lys Gln Glu
                725                 730                 735
Ala Glu Glu Arg Ser Leu Leu Glu Asn Ile Glu Gln Ser Phe Ile Thr
            740                 745                 750
Ala Thr Asn Gln Thr Phe Phe Leu Glu Glu Lys Leu Pro Ser Glu
        755                 760                 765
Ala Phe Ile Ser Ala Glu Glu Leu Ser Lys Arg Arg Glu Cys Ala Gly
770                 775                 780
Gly Ala Ile Phe Ala Lys Arg Val Tyr Ile Thr Asp Asn Lys Glu Pro
785                 790                 795                 800
Ile Leu Phe Ser His Asn Phe Ser Asp Val Tyr Gly Gly Ala Ile Phe
                805                 810                 815
Thr Gly Ser Leu Gln Glu Thr Asp Lys Gln Asp Val Val Thr Pro Glu
            820                 825                 830
Val Val Ile Ser Gly Asn Asp Gly Asp Val Ile Phe Ser Gly Asn Ala
        835                 840                 845
Ala Lys His Asp Lys His Leu Pro Asp Thr Gly Gly Gly Ala Ile Cys
850                 855                 860
Thr Gln Asn Leu Thr Ile Ser Gln Asn Asn Gly Asn Val Leu Phe Leu
865                 870                 875                 880
Asn Asn Phe Ala Cys Ser Gly Gly Ala Val Arg Ile Glu Asp His Gly
                885                 890                 895
Glu Val Leu Leu Glu Ala Phe Gly Asp Ile Ile Phe Asn Gly Asn
            900                 905                 910
Ser Ser Phe Arg Ala Gln Gly Ser Asp Ala Ile Tyr Phe Ala Gly Lys
        915                 920                 925
Asp Ser Arg Ile Lys Ala Leu Asn Ala Thr Glu Gly His Ala Ile Val
930                 935                 940
Phe Gln Asp Ala Leu Val Phe Glu Asn Ile Glu Glu Arg Lys Ser Ser
945                 950                 955                 960
Gly Leu Leu Val Ile Asn Ser Gln Glu Asn Glu Gly Tyr Thr Gly Ser
                965                 970                 975
Val Arg Phe Leu Gly Ser Glu Ser Lys Val Pro Gln Trp Ile His Val
            980                 985                 990
Gln Gln Gly Gly Leu Glu Leu Leu His Gly Ala Ile Leu Cys Ser Tyr
        995                 1000                1005
Gly Val Lys Gln Asp Pro Arg Ala Lys Ile Val Leu Ser Ala Gly Ser
        1010                1015                1020
```

```
Lys Leu Lys Ile Leu Asp Ser Glu Gln Glu Asn Asn Ala Glu Ile Gly
1025                1030                1035                1040

Asp Leu Glu Asp Ser Val Asn Ser Glu Lys Thr Pro Ser Leu Trp Ile
            1045                1050                1055

Gly Lys Asn Ala Gln Ala Lys Val Pro Leu Val Asp Ile His Thr Ile
        1060                1065                1070

Ser Ile Asp Leu Ala Ser Phe Ser Ser Lys Ala Gln Glu Thr Pro Glu
    1075                1080                1085

Glu Ala Pro Gln Val Ile Val Pro Lys Gly Ser Cys Val His Ser Gly
1090                1095                1100

Glu Leu Ser Leu Glu Leu Val Asn Thr Thr Gly Lys Gly Tyr Glu Asn
1105                1110                1115                1120

His Ala Leu Leu Lys Asn Asp Thr Gln Val Ser Leu Met Ser Phe Lys
            1125                1130                1135

Glu Glu Asn Asp Gly Ser Leu Glu Asp Leu Ser Lys Leu Ser Val Ser
            1140                1145                1150

Asp Leu Arg Ile Lys Val Ser Thr Pro Asp Ile Val Glu Glu Thr Tyr
        1155                1160                1165

Gly His Met Gly Asp Trp Ser Glu Ala Thr Ile Gln Asp Gly Ala Leu
    1170                1175                1180

Val Ile Asn Trp His Pro Thr Gly Tyr Lys Leu Asp Pro Gln Lys Ala
1185                1190                1195                1200

Gly Ser Leu Val Phe Asn Ala Leu Trp Glu Glu Ala Val Leu Ser
            1205                1210                1215

Thr Leu Lys Asn Ala Arg Ile Ala His Asn Leu Thr Ile Gln Arg Met
            1220                1225                1230

Glu Phe Asp Tyr Ser Thr Asn Ala Trp Gly Leu Ala Phe Ser Ser Phe
        1235                1240                1245

Arg Glu Leu Ser Ser Glu Lys Leu Val Ser Val Asp Gly Tyr Arg Gly
            1250                1255                1260

Ser Tyr Ile Gly Ala Ser Ala Gly Ile Asp Thr Gln Leu Met Glu Asp
1265                1270                1275                1280

Phe Val Leu Gly Ile Ser Thr Ala Ser Phe Phe Gly Lys Met His Ser
            1285                1290                1295

Gln Asn Phe Asp Ala Glu Ile Ser Arg His Gly Phe Val Gly Ser Val
        1300                1305                1310

Tyr Thr Gly Phe Leu Ala Gly Ala Trp Phe Phe Lys Gly Gln Tyr Ser
        1315                1320                1325

Leu Gly Glu Thr His Asn Asp Met Thr Thr Arg Tyr Gly Val Leu Gly
        1330                1335                1340

Glu Ser Asn Ala Thr Trp Lys Ser Arg Gly Val Leu Ala Asp Ala Leu
1345                1350                1355                1360

Val Glu Tyr Arg Ser Leu Val Gly Pro Ala Arg Pro Lys Phe Tyr Ala
            1365                1370                1375

Leu His Phe Asn Pro Tyr Val Glu Val Ser Tyr Ala Ser Ala Lys Phe
        1380                1385                1390

Pro Ser Phe Val Glu Gln Gly Gly Glu Ala Arg Ala Phe Glu Glu Thr
        1395                1400                1405

Ser Leu Thr Asn Ile Thr Val Pro Phe Gly Met Lys Phe Glu Leu Ser
        1410                1415                1420

Phe Thr Lys Gly Gln Phe Ser Glu Thr Asn Ser Leu Gly Ile Gly Cys
1425                1430                1435                1440

Ala Trp Glu Met Tyr Arg Lys Val Glu Gly Arg Ser Val Glu Leu Leu
```

```
                    1445                1450                1455
Glu Ala Gly Phe Asp Trp Glu Gly Ser Pro Ile Asp Leu Pro Lys Gln
            1460                1465                1470

Glu Leu Arg Val Ala Leu Glu Asn Asn Thr Glu Trp Ser Ser Tyr Phe
        1475                1480                1485

Ser Thr Ala Leu Gly Val Thr Ala Phe Cys Gly Phe Ser Ser Met
    1490                1495                1500

Asp Asn Lys Leu Gly Tyr Glu Ala Asn Ala Gly Met Arg Leu Ile Phe
1505                1510                1515                1520

<210> SEQ ID NO 45
<211> LENGTH: 4614
<212> TYPE: DNA
<213> ORGANISM: Chlamydia psitacci

<400> SEQUENCE: 45
atggtcgcaa aaaaggtatc aagatttcca aaatctacat tttcccattc cgtagtttta      60
gcaatattag tttctactgg gatgactgct aataatcata gattatatgg ttatgagaca     120
gtttcagagg cgttttttgag tgattcttct ttgaaaaccc aattagaaac gacttctgcg     180
ggtgttttta gaaaagtaaa atctactgat acacaagagg ttcagaaaga aaataaagaa     240
gaaaatacgc ctgtagagac ttcttttata gagaatgctt cttcatgttc tgttgctatt     300
ttaggctcag aatgcggtca agacagcat ttagtcaatg ccagtacttt gtttgagata     360
tcggattctt tatcatggaa gagtatagat ggcgagttgt ctaaaagctc caagaagtct     420
gctacagccg aagatgcaga gagaaaatat cttgtggatg attccagtca aggtttagct     480
ttttgttata aaaacccatc agattgtgtt gtggatgaaa ctacgcctgg attcttaggt     540
gttgctcttg taggagtggg atctacatca ggactatctt tttctaattt aaagtcgctc     600
tcagcaggat ctgcggtcta ttctgatgaa gatgttgttt ttgaacacct taaagaaaaa     660
ctgttttttg aaggttgtga gtctcaagca ggtggtggag ctgtttcagg acgtagtatt     720
gctataaatg gttgccatga cgtttctgca gtgtcttgta agaccgattt agatcttgca     780
tcttctgaag tcgtagattt ttccaaaggt ggaggtgctt taacgcgca taaggtgcat     840 ggtgaagcac ataaatccag attttttact ggagaaatca tctttacagc caattctggg     900
aatgttttgc tagatggtaa tcatgcagac aaggcgaacg tggagttgt agcctgtgga     960 gcatttgttt gttctgtaaa tcgtggagat atccgctaca caagtaaccg cgctctatct    1020
ggaggcgctg tatctgcttt taagtctatt gattttgttg gaaacgtagg attgatagag    1080
tttgtagata accaggcttt aatttctcct gaaagttctt tattttttag tggtggggcc    1140
ttagcttctg gagagagaat tagttttctt aacaatggag gcatccattg ttgcaaaaac    1200
acctctaaat cctctggagg agctctttta tctagggatg taagaattgt agagaacatc    1260
ggaaattctt tgtttaagga aaactctgct caagtcgtag gtggagccat tagttctcaa    1320
aatcaagtag aggttggtca gaattttgga aatatcactt tgaaggtaa tacttccaag    1380 atgggtggtg gagctattca ctgtttatct gctcagcaac cttatacgag ttctgaagaa    1440
gctctggaag gatctgggga tatcaagatt gttgataatt cggggggctgt aaattttgca    1500 tctaatgaga accttattga atctcaagag acacatagtc atattggtgg tggtgctcta    1560
tacggatcaa atgttttagt ttcaggcaat attggagagg ttacttttttc taagaatacc    1620 gctggtcaat gtgaatccga cagtacctgt ataggtggtg gagcggtttt tgctaatgag    1680
gctgttagaa tagtagataa ctcaggagcg attacttttct cttataataa agggacaatt    1740
```

```
cttccatttc ctaaagttgc tgcaagttct gaaggggaaa gtgctccaga agctcctaaa    1800
gagtcatctc ctgtagattt aggggttcgc ggcggtggag caattttgc caagcgtata      1860 gagatagcag ataactctgg tgtactatct ttctcagata atttcatgaa aattagagat    1920
aataaggcac aaaaagagaa tcctctaggc ggtggtgctt tatttgggat agatgaagtc    1980
ggtttgaaaa ataataaga acttgcattc actaataacc atgtctctgg tgagaatagt    2040
agcggtggtg ctgtcctatc taaagttgtc actattgctg ataatggaaa agtacaattt    2100
ttccgcaatt attcgaattt ccttggtggt gccgtttgtt ctctaggaga tgctctaaac    2160
attaaaaata tgaatcttc agtatctttt attggcaaca gaactgtgac tgctggtgga    2220
gcgcttgcta gtgctgcagg tgatgtttct atttctaaaa accttgggaa agtagaattt    2280
aaggataatt tagttttgg cgattctcgt gtagataatc ttgaagaagg tcaactcaac    2340
actacaggac atcatagtgg cggcggtgcc attttgcta aagcttcagt ggttattcgt    2400
gaaaataaag atcaggtgct tttctcaggg aattcttcag gatgtttcgg tggtgcgatt    2460
ttaacaggtt ctttaacccc agaagatcaa gagcgttttg cttctaaggt agtgaatgat    2520
aatactaaag tcgttattac agagaacatt ggagacgtag tattttcagg aaatagcact    2580
acggcttcaa acatcctga gcataatttg ttcggtggtg gtgctatcta tacccaagac    2640
ttaattatca ataaaaatgc aggttctgta gcttttttata ataactacgc tcctacaggt    2700
ggtgctgtcc gtattagtga aagggaact gtgatttag aggctctagg aggagatatt    2760
gttttccaag gaaatagaaa ttctgaagat atctctaatg gattatattt tgccggaaaa    2820
gagtcgaaat tagttgaggt atctgcttct ggggaaaaaa cggttaattt ttcagatgcc    2880
attatctttg aagatttaac cttaagacaa ggcctagaag gtcgtgagga tattttaaat    2940
gatcctacat tagtattgaa ttctaaggct aaagatgatt ctgaagtttc tcattctgga    3000
aacattcgct ttgcctatgc gacatctaag attcctcaag tcgctgtatt agaatcagga    3060
actcttattt tatctgataa tgctgagttg tggttgtgtg gcttaaaaca agagaaaggt    3120
agtgagatct tgctctcagc aggaactgta ttacgtattt tcgatcctaa tgctaagcct    3180
gaagaaaagc ctgaaagtcc ttctgcaaga tcttactata gtgcttatga ttctgctaga    3240
aatcctgaag agaagacttt ggcagacatc agtgttattg gtgtagatct agcttctttt    3300
gttgctagtg aggatgaagc tgctccttta cctccacaga ttatcgttcc taagggcaca    3360
acaatcggtt cgggatcttt agacttgaat cttgtggatt ctgcaggtgt tggttatgaa    3420
aaccatgcct tattaaataa agagactgat atcacattgc tttcatttag gagtgcctca    3480
gcagtctcgg atgttcctga tttagaccat gctttggaag agttacgtat taacgtttct    3540
gttcctaaaa ttacggacga cacttatggg catatgggaa aatggtcaga tcctcaggtt    3600
gttaacggta aattaacgat caactggaag cctaccagct ataagttaaa tcctgaaaaa    3660
ggaggctcta tcgtattgaa cactttatgg ggacaatgcg gagatttgcg cgccttaaaa    3720
caacagcatt tatctcataa tattactgca caaagaatgg aattagattt ctcaacaaac    3780
atttggggat ctggaatggg aacattctcc aattgtgcaa cgattgctgg agtggacggc    3840
tttactcatc gtgctggcgg ctatgcttta ggtttagata cacagttgat agaagatttc    3900
ttgataggag gaagctttgc gcagttcttt ggttacactg atagtcagtc attttcatca    3960
cgtagtgacc aaagtggtta cttaggtacg ggatatgtcg gtatctttgc gggttcttgg    4020
ttattcaagg ggatgtttat ctatagtgat attcaaaacg acttgaatac aacatatcct    4080
acaccaaaca ttggtagatc taaaggatcg tggaatagcc gcggtatctt agcagatgct    4140
```

-continued

```
catgtggatt atcgctatat tgtgaattca cgtaggttta tctcatcgat tgtttcggct    4200
gtggtacctt tcgtagaagc tgaatatgtt tacattgatc ttcctacatt tgcggaagta    4260
ggtagtgaag tgagaacatt tgctgaaggg catttacaaa atatagcgat tccttttggg    4320
attactttgg agcataacta ttctcgaggg cagcgttcag aagtgaatag cttaagtttc    4380
tcctatgctt tagatgtcta tcgtaaagca cctacagtgc ttatcaattt gcctgcagct    4440
tcttattctt gggaggggt aggttctgat ctttctagaa agtttatgaa agcacagttt     4500
agtaatgata cggagtggag ttcctacttc tctactttct tagggtttac ctatgaatgg    4560
agagaacaca cggtatctta tgatgtgaat ggaggtatac gtttgatatt ctag          4614
```

<210> SEQ ID NO 46
<211> LENGTH: 1537
<212> TYPE: PRT
<213> ORGANISM: Chlamydia psitacci

<400> SEQUENCE: 46

```
Met Val Ala Lys Lys Val Ser Arg Phe Pro Lys Ser Thr Phe Ser His
  1               5                  10                  15

Ser Val Val Leu Ala Ile Leu Val Ser Thr Gly Met Thr Ala Asn Asn
                 20                  25                  30

His Arg Leu Tyr Gly Tyr Glu Thr Val Ser Glu Ala Phe Leu Ser Asp
             35                  40                  45

Ser Ser Leu Lys Thr Gln Leu Glu Thr Thr Ser Ala Gly Val Phe Arg
         50                  55                  60

Lys Val Lys Ser Thr Asp Thr Gln Glu Val Gln Lys Glu Asn Lys Glu
 65                  70                  75                  80

Glu Asn Thr Pro Val Glu Thr Ser Phe Ile Glu Asn Ala Ser Ser Cys
                 85                  90                  95

Ser Val Ala Ile Leu Gly Ser Glu Cys Gly Gln Arg Gln His Leu Val
            100                 105                 110

Asn Ala Ser Thr Leu Phe Glu Ile Ser Asp Ser Leu Ser Trp Lys Ser
            115                 120                 125

Ile Asp Gly Glu Leu Ser Lys Ser Ser Lys Ser Ala Thr Ala Glu
            130                 135                 140

Asp Ala Glu Arg Lys Tyr Leu Val Asp Ser Ser Gln Gly Leu Ala
145                 150                 155                 160

Phe Cys Tyr Lys Asn Pro Ser Asp Cys Val Val Asp Glu Thr Thr Pro
                165                 170                 175

Gly Phe Leu Gly Val Ala Leu Val Gly Val Ser Thr Ser Gly Leu
            180                 185                 190

Ser Phe Ser Asn Leu Lys Ser Leu Ser Ala Gly Ser Ala Val Tyr Ser
            195                 200                 205

Asp Glu Asp Val Val Phe Glu His Leu Lys Glu Lys Leu Phe Phe Glu
        210                 215                 220

Gly Cys Glu Ser Gln Ala Gly Gly Ala Val Ser Gly Arg Ser Ile
225                 230                 235                 240

Ala Ile Asn Gly Cys His Asp Val Ser Ala Val Ser Cys Lys Thr Asp
                245                 250                 255

Leu Asp Leu Ala Ser Ser Glu Val Val Asp Phe Ser Lys Gly Gly Gly
            260                 265                 270

Ala Phe Asn Ala His Lys Val His Gly Glu Ala His Lys Ser Arg Phe
            275                 280                 285

Phe Thr Gly Glu Ile Ile Phe Thr Ala Asn Ser Gly Asn Val Leu Leu
            290                 295                 300
```

```
Asp Gly Asn His Ala Asp Lys Ala Asn Gly Val Ala Cys Gly
305                 310                 315                 320

Ala Phe Val Cys Ser Val Asn Arg Gly Asp Ile Arg Tyr Thr Ser Asn
                325                 330                 335

Arg Ala Leu Ser Gly Gly Ala Val Ser Ala Phe Lys Ser Ile Asp Phe
                340                 345                 350

Val Gly Asn Val Gly Leu Ile Glu Phe Val Asp Asn Gln Ala Leu Ile
                355                 360                 365

Ser Pro Glu Ser Ser Leu Phe Leu Gly Gly Ala Leu Ala Ser Gly
370                 375                 380

Glu Arg Ile Ser Phe Leu Asn Asn Gly Gly Ile His Cys Cys Lys Asn
385                 390                 395                 400

Thr Ser Lys Ser Ser Gly Gly Ala Leu Leu Ser Arg Asp Val Arg Ile
                405                 410                 415

Val Glu Asn Ile Gly Asn Ser Leu Phe Lys Glu Asn Ser Ala Gln Val
                420                 425                 430

Val Gly Gly Ala Ile Ser Ser Gln Asn Gln Val Glu Val Gly Gln Asn
                435                 440                 445

Phe Gly Asn Ile Thr Phe Glu Gly Asn Thr Ser Lys Met Gly Gly Gly
                450                 455                 460

Ala Ile His Cys Leu Ser Ala Gln Gln Pro Tyr Thr Ser Ser Glu Glu
465                 470                 475                 480

Ala Leu Glu Gly Ser Gly Asp Ile Lys Ile Val Asp Asn Ser Gly Ala
                485                 490                 495

Val Asn Phe Ala Ser Asn Glu Asn Leu Leu Glu Ser Gln Glu Thr His
                500                 505                 510

Ser His Ile Gly Gly Ala Leu Tyr Gly Ser Asn Val Leu Val Ser
                515                 520                 525

Gly Asn Ile Gly Glu Val Thr Phe Ser Lys Asn Thr Ala Gly Gln Cys
530                 535                 540

Glu Ser Asp Ser Thr Cys Ile Gly Gly Gly Ala Val Phe Ala Asn Glu
545                 550                 555                 560

Ala Val Arg Ile Val Asp Asn Ser Gly Ala Ile Thr Phe Ser Tyr Asn
                565                 570                 575

Lys Gly Thr Ile Leu Pro Phe Pro Lys Val Ala Ser Ser Glu Gly
                580                 585                 590

Glu Ser Ala Pro Glu Ala Pro Lys Glu Ser Ser Pro Val Asp Leu Gly
                595                 600                 605

Val Arg Gly Gly Gly Ala Ile Phe Ala Lys Arg Ile Glu Ile Ala Asp
                610                 615                 620

Asn Ser Gly Val Leu Ser Phe Ser Asp Asn Phe Met Lys Ile Arg Asp
625                 630                 635                 640

Asn Lys Ala Gln Lys Glu Asn Pro Leu Gly Gly Ala Leu Phe Gly
                645                 650                 655

Ile Asp Glu Val Gly Leu Lys Asn Asn Lys Glu Leu Ala Phe Thr Asn
                660                 665                 670

Asn His Val Ser Gly Glu Asn Ser Gly Gly Ala Val Leu Ser Lys
                675                 680                 685

Val Val Thr Ile Ala Asp Asn Gly Lys Val Gln Phe Phe Arg Asn Tyr
                690                 695                 700

Ser Asn Phe Leu Gly Gly Ala Val Cys Ser Leu Gly Asp Ala Leu Asn
705                 710                 715                 720

Ile Lys Asn Asn Glu Ser Ser Val Ser Phe Ile Gly Asn Arg Thr Val
```

```
                     725                 730                 735
Thr Ala Gly Gly Ala Leu Ala Ser Ala Ala Gly Asp Val Ser Ile Ser
        740                 745                 750

Lys Asn Leu Gly Lys Val Glu Phe Lys Asp Asn Leu Val Phe Gly Asp
        755                 760                 765

Ser Arg Val Asp Asn Leu Glu Glu Gly Gln Leu Asn Thr Thr Gly His
        770                 775                 780

His Ser Gly Gly Gly Ala Ile Phe Ala Lys Ala Ser Val Val Ile Arg
785                 790                 795                 800

Glu Asn Lys Asp Gln Val Leu Phe Ser Gly Asn Ser Ser Gly Cys Phe
                805                 810                 815

Gly Gly Ala Ile Leu Thr Gly Ser Leu Thr Pro Glu Asp Gln Glu Arg
            820                 825                 830

Phe Ala Ser Lys Val Val Asn Asp Asn Thr Lys Val Val Ile Thr Glu
                835                 840                 845

Asn Ile Gly Asp Val Val Phe Ser Gly Asn Ser Thr Thr Ala Ser Lys
            850                 855                 860

His Pro Glu His Asn Leu Phe Gly Gly Ala Ile Tyr Thr Gln Asp
865                 870                 875                 880

Leu Ile Ile Asn Lys Asn Ala Gly Ser Val Ala Phe Tyr Asn Asn Tyr
                885                 890                 895

Ala Pro Thr Gly Gly Ala Val Arg Ile Ser Lys Gly Thr Val Ile
            900                 905                 910

Leu Glu Ala Leu Gly Gly Asp Ile Val Phe Gln Gly Asn Arg Asn Ser
                915                 920                 925

Glu Asp Ile Ser Asn Gly Leu Tyr Phe Ala Gly Lys Glu Ser Lys Leu
        930                 935                 940

Val Glu Val Ser Ala Ser Gly Glu Lys Thr Val Asn Phe Ser Asp Ala
945                 950                 955                 960

Ile Ile Phe Glu Asp Leu Thr Leu Arg Gln Gly Leu Glu Gly Arg Glu
                965                 970                 975

Asp Ile Leu Asn Asp Pro Thr Leu Val Leu Asn Ser Lys Ala Lys Asp
            980                 985                 990

Asp Ser Glu Val Ser His Ser Gly Asn Ile Arg Phe Ala Tyr Ala Thr
        995                 1000                1005

Ser Lys Ile Pro Gln Val Ala Val Leu Glu Ser Gly Thr Leu Ile Leu
        1010                1015                1020

Ser Asp Asn Ala Glu Leu Trp Leu Cys Gly Leu Lys Gln Glu Lys Gly
1025                1030                1035                1040

Ser Glu Ile Leu Leu Ser Ala Gly Thr Val Leu Arg Ile Phe Asp Pro
                1045                1050                1055

Asn Ala Lys Pro Glu Glu Lys Pro Glu Ser Pro Ser Ala Arg Ser Tyr
        1060                1065                1070

Tyr Ser Ala Tyr Asp Ser Ala Arg Asn Pro Glu Lys Thr Leu Ala
            1075                1080                1085

Asp Ile Ser Val Ile Gly Val Asp Leu Ala Ser Phe Val Ala Ser Glu
        1090                1095                1100

Asp Glu Ala Ala Pro Leu Pro Pro Gln Ile Ile Val Pro Lys Gly Thr
1105                1110                1115                1120

Thr Ile Gly Ser Gly Ser Leu Asp Leu Asn Leu Val Asp Ser Ala Gly
                1125                1130                1135

Val Gly Tyr Glu Asn His Ala Leu Leu Asn Lys Glu Thr Asp Ile Thr
        1140                1145                1150
```

-continued

```
Leu Leu Ser Phe Arg Ser Ala Ser Ala Val Ser Asp Val Pro Asp Leu
        1155                1160                1165

Asp His Ala Leu Glu Glu Leu Arg Ile Asn Val Ser Val Pro Lys Ile
        1170                1175                1180

Thr Asp Asp Thr Tyr Gly His Met Gly Lys Trp Ser Asp Pro Gln Val
1185                1190                1195                1200

Val Asn Gly Lys Leu Thr Ile Asn Trp Lys Pro Thr Ser Tyr Lys Leu
                1205                1210                1215

Asn Pro Glu Lys Gly Gly Ser Ile Val Leu Asn Thr Leu Trp Gly Gln
                1220                1225                1230

Cys Gly Asp Leu Arg Ala Leu Lys Gln Gln His Leu Ser His Asn Ile
                1235                1240                1245

Thr Ala Gln Arg Met Glu Leu Asp Phe Ser Thr Asn Ile Trp Gly Ser
                1250                1255                1260

Gly Met Gly Thr Phe Ser Asn Cys Ala Thr Ile Ala Gly Val Asp Gly
1265                1270                1275                1280

Phe Thr His Arg Ala Gly Gly Tyr Ala Leu Gly Leu Asp Thr Gln Leu
                1285                1290                1295

Ile Glu Asp Phe Leu Ile Gly Gly Ser Phe Ala Gln Phe Phe Gly Tyr
                1300                1305                1310

Thr Asp Ser Gln Ser Phe Ser Ser Arg Ser Asp Gln Ser Gly Tyr Leu
                1315                1320                1325

Gly Thr Gly Tyr Val Gly Ile Phe Ala Gly Ser Trp Leu Phe Lys Gly
                1330                1335                1340

Met Phe Ile Tyr Ser Asp Ile Gln Asn Asp Leu Asn Thr Thr Tyr Pro
1345                1350                1355                1360

Thr Pro Asn Ile Gly Arg Ser Lys Gly Ser Trp Asn Ser Arg Gly Ile
                1365                1370                1375

Leu Ala Asp Ala His Val Asp Tyr Arg Tyr Ile Val Asn Ser Arg Arg
                1380                1385                1390

Phe Ile Ser Ser Ile Val Ser Ala Val Val Pro Phe Val Glu Ala Glu
                1395                1400                1405

Tyr Val Tyr Ile Asp Leu Pro Thr Phe Ala Glu Val Gly Ser Glu Val
                1410                1415                1420

Arg Thr Phe Ala Glu Gly His Leu Gln Asn Ile Ala Ile Pro Phe Gly
1425                1430                1435                1440

Ile Thr Leu Glu His Asn Tyr Ser Arg Gly Gln Arg Ser Glu Val Asn
                1445                1450                1455

Ser Leu Ser Phe Ser Tyr Ala Leu Asp Val Tyr Arg Lys Ala Pro Thr
                1460                1465                1470

Val Leu Ile Asn Leu Pro Ala Ala Ser Tyr Ser Trp Glu Gly Val Gly
                1475                1480                1485

Ser Asp Leu Ser Arg Lys Phe Met Lys Ala Gln Phe Ser Asn Asp Thr
                1490                1495                1500

Glu Trp Ser Ser Tyr Phe Ser Thr Phe Leu Gly Phe Thr Tyr Glu Trp
1505                1510                1515                1520

Arg Glu His Thr Val Ser Tyr Asp Val Asn Gly Gly Ile Arg Leu Ile
                1525                1530                1535

Phe

<210> SEQ ID NO 47
<211> LENGTH: 1185
<212> TYPE: DNA
<213> ORGANISM: Chlamydia trachomatis
```

<400> SEQUENCE: 47

```
atgaaaaaac tcttgaaatc ggtattagtg tttgccgctt tgagttctgc ttcctccttg      60
caagctctgc ctgtggggaa tcctgctgaa ccaagcctta tgatcgacgg aattctatgg     120
gaaggtttcg gcggagatcc ttgcgatcct tgcaccactt ggtgtgacgc tatcagcatg     180
cgtatgggtt actatggtga ctttgttttc gaccgtgttt tgcaaacaga tgtgaataaa     240
gaattccaaa tgggtgccaa gcctacaact gctacaggca atgctgcagc tccatcccact    300
tgtacagcaa gagagaatcc tgcttacggc cgacatatgc aggatgctga tgtttaca      360
aatgctgctt acatggcatt gaatatttgg gatcgttttg atgtattctg tacattagga    420
gccaccagtg gatatcttaa aggaaattca gcatctttca acttagttgg cttattcgga    480
gataatgaga accatgctac agtttcagat agtaagcttg taccaaatat gagcttagat    540
caatctgttg ttgagttgta tacagatact acttttgctt ggagtgctgg agctcgtgca    600
gctttgtggg aatgtggatg cgcgacttta ggcgcttctt tccaatacgc tcaatccaag    660
cctaaagtcg aagaattaaa cgttctctgt aacgcagctg agtttactat caataagcct    720
aaaggatatg tagggcaaga attccctctt gatcttaaag caggaacaga tggtgtgaca    780
ggaactaagg atgcctctat tgattaccat gaatggcaag caagtttagc tctctcttac    840
agactgaata tgttcactcc ctacattgga gttaaatggt ctcgagcaag ttttgatgca    900
gacacgattc gtattgctca gccgaagtca gctacaactg tctttgatgt taccactctg    960
aacccaacta ttgctggagc tggcgatgtg aaagctagcg cagagggtca gctcggagat   1020
accatgcaaa tcgtttcctt gcaattgaac aagatgaaat ctagaaaatc ttgcggtatt   1080
gcagtaggaa caactattgt ggatgcagac aaatacgcag ttacagttga gactcgcttg   1140
atcgatgaga gagctgctca cgtaaatgca caattccgct ctaa                    1185
```

<210> SEQ ID NO 48
<211> LENGTH: 394
<212> TYPE: PRT
<213> ORGANISM: Chlamydia trachomatis

<400> SEQUENCE: 48

```
Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Gln Thr Asp Val Asn Lys
65                  70                  75                  80

Glu Phe Gln Met Gly Ala Lys Pro Thr Thr Ala Thr Gly Asn Ala Ala
                85                  90                  95

Ala Pro Ser Thr Cys Thr Ala Arg Glu Asn Pro Ala Tyr Gly Arg His
            100                 105                 110

Met Gln Asp Ala Glu Met Phe Thr Asn Ala Ala Tyr Met Ala Leu Asn
        115                 120                 125

Ile Trp Asp Arg Phe Asp Val Phe Cys Thr Leu Gly Ala Thr Ser Gly
    130                 135                 140

Tyr Leu Lys Gly Asn Ser Ala Ser Phe Asn Leu Val Gly Leu Phe Gly
145                 150                 155                 160
```

Asp Asn Glu Asn His Ala Thr Val Ser Asp Ser Lys Leu Val Pro Asn
            165                 170                 175

Met Ser Leu Asp Gln Ser Val Val Glu Leu Tyr Thr Asp Thr Thr Phe
        180                 185                 190

Ala Trp Ser Ala Gly Ala Arg Ala Ala Leu Trp Glu Cys Gly Cys Ala
        195                 200                 205

Thr Leu Gly Ala Ser Phe Gln Tyr Ala Gln Ser Lys Pro Lys Val Glu
        210                 215                 220

Glu Leu Asn Val Leu Cys Asn Ala Ala Glu Phe Thr Ile Asn Lys Pro
225                 230                 235                 240

Lys Gly Tyr Val Gly Gln Glu Phe Pro Leu Asp Leu Lys Ala Gly Thr
                245                 250                 255

Asp Gly Val Thr Gly Thr Lys Asp Ala Ser Ile Asp Tyr His Glu Trp
        260                 265                 270

Gln Ala Ser Leu Ala Leu Ser Tyr Arg Leu Asn Met Phe Thr Pro Tyr
        275                 280                 285

Ile Gly Val Lys Trp Ser Arg Ala Ser Phe Asp Ala Asp Thr Ile Arg
        290                 295                 300

Ile Ala Gln Pro Lys Ser Ala Thr Thr Val Phe Asp Val Thr Thr Leu
305                 310                 315                 320

Asn Pro Thr Ile Ala Gly Ala Gly Asp Val Lys Ala Ser Ala Glu Gly
                325                 330                 335

Gln Leu Gly Asp Thr Met Gln Ile Val Ser Leu Gln Leu Asn Lys Met
        340                 345                 350

Lys Ser Arg Lys Ser Cys Gly Ile Ala Val Gly Thr Thr Ile Val Asp
        355                 360                 365

Ala Asp Lys Tyr Ala Val Thr Val Glu Thr Arg Leu Ile Asp Glu Arg
370                 375                 380

Ala Ala His Val Asn Ala Gln Phe Arg Phe
385                 390

<210> SEQ ID NO 49
<211> LENGTH: 1194
<212> TYPE: DNA
<213> ORGANISM: Chlamydia trachomatis

<400> SEQUENCE: 49

```
atgaaaaaac tcttgaaatc ggtattagta tttgccgctt tgagttctgc ttcctccttg      60
caagctctgc ctgtggggaa tcctgctgaa ccaagcctta tgatcgacgg aattctgtgg     120
gaaggtttcg gtggagatcc ttgcgatcct tgcaccactt ggtgtgacgc tatcagcatg     180
cgtatgggtt actatggtga ctttgttttc gaccgtgttt tgaaaacaga tgtgaataaa     240
gaatttcaga tgggagcggc gcctactacc agcgatgtag caggcttaca aaacgatcca     300
acaacaaatg ttgctcgtcc aaatcccgct tatggcaaac acatgcaaga tgctgaaatg     360
tttacgaacg ctgcttacat ggcattaaat atctgggatc gttttgatgt attttgtaca     420
ttgggagcaa ctaccggtta tttaaaagga aactccgctt ccttcaactt agttggatta     480
ttcggaacaa aaacacaagc ttctagcttt aatacagcga atcttttttcc taacactgct     540 ttgaatcaag ctgtggttga gctttataca gacactacct tgcttggag cgtaggtgct     600 cgtgcagctc tctgggaatg tgggtgtgca acgttaggag cttctttcca atatgctcaa     660
tctaaaccta agtagaaga gttaaatgtt ctttgtaatg catccgaatt tactattaat     720
aagccgaaag gatatgttgg ggcggaattt ccacttgata ttaccgcagg aacagaagct     780
gcgacaggga ctaaggatgc ctctattgac taccatgagt ggcaagcaag tttagcccct     840
```

```
tcttacagat taaatatgtt cactccttac attggagtta aatggtctag agtaagtttt      900
gatgccgaca cgatccgtat cgctcagcct aaattggctg aagcaatctt ggatgtcact      960
actctaaacc cgaccatcgc tggtaaagga actgtggtcg cttccggaag cgaaaacgac     1020
ctggctgata caatgcaaat cgtttccttg cagttgaaca agatgaaatc tagaaaatct     1080
tgcggtattg cagtaggaac gactattgta gatgcagaca aatacgcagt tacagttgag     1140
actcgcttga tcgatgagag agcagctcac gtaaatgcac aattccgctt ctaa           1194
```

<210> SEQ ID NO 50
<211> LENGTH: 397
<212> TYPE: PRT
<213> ORGANISM: Chlamydia trachomatis

<400> SEQUENCE: 50

```
Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Ser Asp Val Ala Gly Leu
                85                  90                  95

Gln Asn Asp Pro Thr Thr Asn Val Ala Arg Pro Asn Pro Ala Tyr Gly
            100                 105                 110

Lys His Met Gln Asp Ala Glu Met Phe Thr Asn Ala Ala Tyr Met Ala
        115                 120                 125

Leu Asn Ile Trp Asp Arg Phe Asp Val Phe Cys Thr Leu Gly Ala Thr
    130                 135                 140

Thr Gly Tyr Leu Lys Gly Asn Ser Ala Ser Phe Asn Leu Val Gly Leu
145                 150                 155                 160

Phe Gly Thr Lys Thr Gln Ala Ser Ser Phe Asn Thr Ala Asn Leu Phe
                165                 170                 175

Pro Asn Thr Ala Leu Asn Gln Ala Val Val Glu Leu Tyr Thr Asp Thr
            180                 185                 190

Thr Phe Ala Trp Ser Val Gly Ala Arg Ala Ala Leu Trp Glu Cys Gly
        195                 200                 205

Cys Ala Thr Leu Gly Ala Ser Phe Gln Tyr Ala Gln Ser Lys Pro Lys
    210                 215                 220

Val Glu Glu Leu Asn Val Leu Cys Asn Ala Ser Glu Phe Thr Ile Asn
225                 230                 235                 240

Lys Pro Lys Gly Tyr Val Gly Ala Glu Phe Pro Leu Asp Ile Thr Ala
                245                 250                 255

Gly Thr Glu Ala Ala Thr Gly Thr Lys Asp Ala Ser Ile Asp Tyr His
            260                 265                 270

Glu Trp Gln Ala Ser Leu Ala Leu Ser Tyr Arg Leu Asn Met Phe Thr
        275                 280                 285

Pro Tyr Ile Gly Val Lys Trp Ser Arg Val Ser Phe Asp Ala Asp Thr
    290                 295                 300

Ile Arg Ile Ala Gln Pro Lys Leu Ala Glu Ala Ile Leu Asp Val Thr
305                 310                 315                 320
```

```
Thr Leu Asn Pro Thr Ile Ala Gly Lys Gly Thr Val Ala Ser Gly
                325                 330                 335

Ser Glu Asn Asp Leu Ala Asp Thr Met Gln Ile Val Ser Leu Gln Leu
            340                 345                 350

Asn Lys Met Lys Ser Arg Lys Ser Cys Gly Ile Ala Val Gly Thr Thr
            355                 360                 365

Ile Val Asp Ala Asp Lys Tyr Ala Val Thr Val Glu Thr Arg Leu Ile
        370                 375                 380

Asp Glu Arg Ala Ala His Val Asn Ala Gln Phe Arg Phe
385                 390                 395
```

<210> SEQ ID NO 51
<211> LENGTH: 1194
<212> TYPE: DNA
<213> ORGANISM: Chlamydia trachomatis

<400> SEQUENCE: 51

```
atgaaaaaac tcttgaaatc ggtattagta tttgccgctt tgagttctgc ttcctccttg      60
caagctctgc ctgtggggaa tcctgctgaa ccaagcctta tgatcgacgg aattctgtgg     120
gaaggttttg gcggagatcc ttgcgatcct tgcgccactt ggtgtgacgc tatcagcatg     180
cgtgttggtt actacggaga ctttgttttc gaccgtgttt tgaaaactga tgtgaataaa     240
gaatttcaga tgggagcggc gcctactacc aacgatgcag cagacttaca aaacgatcca     300
aaaacaaatg ttgctcgtcc aaatcccgct tatggcaaac acatgcaaga tgctgaaatg     360
tttacgaacg ctgcttacat ggcattaaat atctgggatc gttttgatgt attttgtaca     420
ttgggagcaa ctaccggtta tttaaaagga actccgcttc cttcaacttt agttggatta     480
ttcggaacaa aaacaaaatc ttctgatttt aatacagcga agcttgttcc taacattgct     540
ttgaatcgag ctgtggttga gctttataca gacactacct ttgcttggag cgtaggtgct     600
cgtgcagctc tctgggaatg tgggtgtgca acgttaggag cttcttttcca atatgctcaa     660
tctaaaccta agtagaaga gttaaatgtt ctttgtaatg catccgaatt tactattaat     720
aagccgaaag gatatgttgg ggcggaattt ccacttgata ttaccgcagg aacagaagct     780
gcgacaggga ctaaggatgc ctctattgac taccatgagt ggcaagcaag tttagccctt     840
tcttacagac taaatatgtt cactccttac attggagtta atggtctag agtaagttttt    900
gatgccgaca cgatccgtat cgctcagcct aaattggctg aagcaatctt ggatgtcact     960
actctaaacc cgaccatcgc tggtaaagga actgtggtcg cttccggaag cgataacgac    1020
ctggctgata caatgcaaat cgtttccttg cagttgaaca agatgaaatc tagaaaatct    1080
tgcggtattg cagtaggaac gactattgta gatgcagaca atacgcagt tacagttgag    1140
actcgcttga tcgatgagag agcagctcac gtaaatgcac aattccgctt ctaa          1194
```

<210> SEQ ID NO 52
<211> LENGTH: 397
<212> TYPE: PRT
<213> ORGANISM: Chlamydia trachomatis

<400> SEQUENCE: 52

```
Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45
```

Asp Pro Cys Ala Thr Trp Cys Asp Ala Ile Ser Met Arg Val Gly Tyr
 50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Asn Asp Ala Ala Asp Leu
                 85                  90                  95

Gln Asn Asp Pro Lys Thr Asn Val Ala Arg Pro Asn Pro Ala Tyr Gly
                100                 105                 110

Lys His Met Gln Asp Ala Glu Met Phe Thr Asn Ala Ala Tyr Met Ala
            115                 120                 125

Leu Asn Ile Trp Asp Arg Phe Asp Val Phe Cys Thr Leu Gly Ala Thr
        130                 135                 140

Thr Gly Tyr Leu Lys Gly Asn Ser Ala Ser Phe Asn Leu Val Gly Leu
145                 150                 155                 160

Phe Gly Thr Lys Thr Lys Ser Ser Asp Phe Asn Thr Ala Lys Leu Val
                165                 170                 175

Pro Asn Ile Ala Leu Asn Arg Ala Val Val Glu Leu Tyr Thr Asp Thr
            180                 185                 190

Thr Phe Ala Trp Ser Val Gly Ala Arg Ala Leu Trp Glu Cys Gly
        195                 200                 205

Cys Ala Thr Leu Gly Ala Ser Phe Gln Tyr Ala Gln Ser Lys Pro Lys
210                 215                 220

Val Glu Glu Leu Asn Val Leu Cys Asn Ala Ser Glu Phe Thr Ile Asn
225                 230                 235                 240

Lys Pro Lys Gly Tyr Val Gly Ala Glu Phe Pro Leu Asp Ile Thr Ala
                245                 250                 255

Gly Thr Glu Ala Ala Thr Gly Thr Lys Asp Ala Ser Ile Asp Tyr His
            260                 265                 270

Glu Trp Gln Ala Ser Leu Ala Leu Ser Tyr Arg Leu Asn Met Phe Thr
        275                 280                 285

Pro Tyr Ile Gly Val Lys Trp Ser Arg Val Ser Phe Asp Ala Asp Thr
290                 295                 300

Ile Arg Ile Ala Gln Pro Lys Leu Ala Glu Ala Ile Leu Asp Val Thr
305                 310                 315                 320

Thr Leu Asn Pro Thr Ile Ala Gly Lys Gly Thr Val Val Ala Ser Gly
                325                 330                 335

Ser Asp Asn Asp Leu Ala Asp Thr Met Gln Ile Val Ser Leu Gln Leu
            340                 345                 350

Asn Lys Met Lys Ser Arg Lys Ser Cys Gly Ile Ala Val Gly Thr Thr
        355                 360                 365

Ile Val Asp Ala Asp Lys Tyr Ala Val Thr Val Glu Thr Arg Leu Ile
370                 375                 380

Asp Glu Arg Ala Ala His Val Asn Ala Gln Phe Arg Phe
385                 390                 395

<210> SEQ ID NO 53
<211> LENGTH: 1182
<212> TYPE: DNA
<213> ORGANISM: Chlamydia trachomatis

<400> SEQUENCE: 53
atgaaaaaac tcttgaaatc ggtattagta tttgccgctt tgagttctgc ttcctccttg      60
caagctctgc ctgtggggaa tcctgctgaa ccaagcctta tgatcgacgg aattctgtgg     120
gaaggtttcg gcggagatcc ttgcgatcct tgcaccactt ggtgtgacgc tatcagcatg     180

```
cgtatgggtt actatggtga ctttgttttc gaccgtgttt tgaaaacaga tgtgaataaa    240
gaattccaaa tgggtgacaa gcctacaagt actacaggca atgctacagc tccaaccact    300
cttacagcaa gagagaatcc tgcttacggc cgacatatgc aggatgctga gatgtttaca    360
aatgccgctt gcatggcatt gaatatttgg gatcgctttg atgtattctg tacactagga    420
gcctctagcg gataccttaa aggaaactct gcttctttca atttagttgg attgtttgga    480
gataatgaaa atcaaagcac ggtcaaaacg aattctgtac aaatatgag cttagatcaa     540
tctgttgttg aactttacac agatactgcc ttctcttgga gcgtgggcgc tcgagcagct    600
ttgtgggagt gcggatgtgc gactttaggg gcttctttcc aatacgctca atctaaacct    660
aaagtcgaag aattaaacgt tctctgtaac gcagctgagt ttactatcaa taagcctaaa    720
ggatatgtag ggcaagaatt ccctcttgca ctcatagcag gaactgatgc agcgacgggc    780
actaaagatg cctctattga ttaccatgag tggcaagcaa gtttagctct ctcttacaga    840
ttgaatatgt tcactcccta cattggagtt aaatggtctc gagcaagttt tgatgccgat    900
acgattcgta tagcccagcc aaaatcagct acagctatct ttgatactac cacgcttaac    960
ccaactattg ctggagctgg cgatgtgaaa gctagcgcag agggtcagct cggagatacc    1020
atgcaaatcg tctccttgca attgaacaag atgaaatcta gaaatcttg cggtattgca    1080
gtaggaacga ctattgtaga tgcagacaaa tacgcagtta cagttgagac tcgcttgatc    1140
gatgagagag ctgctcacgt aaatgcacaa ttccgcttct aa                       1182
```

<210> SEQ ID NO 54  
<211> LENGTH: 393  
<212> TYPE: PRT  
<213> ORGANISM: Chlamydia trachomatis

<400> SEQUENCE: 54

```
Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Arg Met Gly Tyr
        50                  55                  60

Tyr Gly Asp Phe Val Phe Asp Arg Val Leu Lys Thr Asp Val Asn Lys
65                  70                  75                  80

Glu Phe Gln Met Gly Asp Lys Pro Thr Ser Thr Gly Asn Ala Thr
                85                  90                  95

Ala Pro Thr Thr Leu Thr Ala Arg Glu Asn Pro Ala Tyr Gly Arg His
                100                 105                 110

Met Gln Asp Ala Glu Met Phe Thr Asn Ala Ala Cys Met Ala Leu Asn
            115                 120                 125

Ile Trp Asp Arg Phe Asp Val Phe Cys Thr Leu Gly Ala Ser Ser Gly
        130                 135                 140

Tyr Leu Lys Gly Asn Ser Ala Ser Phe Asn Leu Val Gly Leu Phe Gly
145                 150                 155                 160

Asp Asn Glu Asn Gln Ser Thr Val Lys Thr Asn Ser Val Pro Asn Met
                165                 170                 175

Ser Leu Asp Gln Ser Val Val Glu Leu Tyr Thr Asp Thr Ala Phe Ser
            180                 185                 190

Trp Ser Val Gly Ala Arg Ala Ala Leu Trp Glu Cys Gly Cys Ala Thr
```

```
                195                 200                 205
Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Gln Glu Phe Pro Leu Ala Leu Ile Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
    290                 295                 300

Ala Gln Pro Lys Ser Ala Thr Ala Ile Phe Asp Thr Thr Thr Leu Asn
305                 310                 315                 320

Pro Thr Ile Ala Gly Ala Gly Asp Val Lys Ala Ser Ala Glu Gly Gln
                325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
        355                 360                 365

Asp Lys Tyr Ala Val Thr Val Glu Thr Arg Leu Ile Asp Glu Arg Ala
    370                 375                 380

Ala His Val Asn Ala Gln Phe Arg Phe
385                 390

<210> SEQ ID NO 55
<211> LENGTH: 1179
<212> TYPE: DNA
<213> ORGANISM: Chlamydia trachomatis

<400> SEQUENCE: 55
atgaaaaaac tcttgaaatc ggtattagta tttgccgctt tgagttctgc ttcctccttg      60
caagctctgc ctgtggggaa tcctgctgaa ccaagcctta tgatcgacgg aattctgtgg     120
gaaggtttcg gcggagatcc ttgcgatcct tgcgccactt ggtgtgacgc tatcagcatg     180
cgtgttggtt actacggaga ctttgttttc gaccgtgttt tgaaaactga tgtgaataaa     240
gaatttcaga tgggtgccaa gcctacaact gatacaggca atagtgcagc tccatccact     300
cttacagcaa gagagaatcc tgcttacggc cgacatatgc aggatgctga gatgtttaca     360
aatgccgctt gcatggcatt gaatatttgg gatcgttttg atgtattctg tacattagga     420
gccaccagtg gatatcttaa aggaaactct gcttctttca tttagttgg attgtttgga      480 gataatgaaa tcaaaaaac ggtcaaagcg gagtctgtac caaatatgag ctttgatcaa      540
tctgttgttg agttgtatac agatactact tttgcgtgga gcgtcggcgc tcgcgcagct     600
ttgtgggaat gtggatgtgc aacttagga gcttcattcc aatatgctca atctaaacct      660
aaagtagaag aattaaacgt tctctgcaat gcagcagagt ttactattaa taaacctaaa     720
gggtatgtag gtaaggagtt tcctcttgat cttacagcag aacagatgc tgcgacagga      780 actaaggatg cctctattga ttaccatgaa tggcaagcaa gtttagctct ctcttacaga     840
ctgaatatgt tcactcccta cattggagtt aaatggtctc gagcaagctt tgatgccgat     900
acgattcgta tagcccagcc aaaatcagct cagctatttt ttgatactac cacgcttaac     960
ccaactattg ctggagctgg cgatgtgaaa actggcgcag agggtcagct cggagacaca    1020
```

-continued

```
atgcaaatcg tttccttgca attgaacaag atgaaatcta gaaaatcttg cggtattgca   1080
gtaggaacaa ctattgtgga tgcagacaaa tacgcagtta cagttgagac tcgcttgatc   1140
gatgagagag cagctcacgt aaatgcacaa ttccgcttc                          1179
```

<210> SEQ ID NO 56
<211> LENGTH: 393
<212> TYPE: PRT
<213> ORGANISM: Chlamydia trachomatis

<400> SEQUENCE: 56

```
Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Asp Pro Cys
        35                  40                  45

Asp Pro Cys Ala Thr Trp Cys Asp Ala Ile Ser Met Arg Val Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Lys Pro Thr Thr Asp Thr Gly Asn Ser Ala
                85                  90                  95

Ala Pro Ser Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Thr Ser Gly
    130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
                165                 170                 175

Ser Phe Asp Gln Ser Val Val Glu Leu Tyr Thr Asp Thr Thr Phe Ala
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
    290                 295                 300

Ala Gln Pro Lys Ser Ala Thr Ala Ile Phe Asp Thr Thr Leu Asn
305                 310                 315                 320

Pro Thr Ile Ala Gly Ala Gly Asp Val Lys Thr Gly Ala Glu Gly Gln
                325                 330                 335

Leu Gly Asp Thr Met Gln Ile Val Ser Leu Gln Leu Asn Lys Met Lys
            340                 345                 350
```

```
Ser Arg Lys Ser Cys Gly Ile Ala Val Gly Thr Thr Ile Val Asp Ala
        355                 360                 365

Asp Lys Tyr Ala Val Thr Val Glu Thr Arg Leu Ile Asp Glu Arg Ala
    370                 375                 380

Ala His Val Asn Ala Gln Phe Arg Phe
385                 390

<210> SEQ ID NO 57
<211> LENGTH: 1944
<212> TYPE: DNA
<213> ORGANISM: Chlamydia trachomatis

<400> SEQUENCE: 57
atggaatcag gaccagaatc agtttcttct aatcagagct cgatgaatcc aattattaat      60
gggcaaatcg cttctaattc ggagaccaaa gagtccacga aggagtcaga agcgagtcct     120
tcagcatcgt cctctgtaag cagctggagt tttttatcct cagcaaagca tgcattaatc     180
tctcttcgtg atgccatctt gaataaaaat tctagtccaa cagactctct ctctcaatta     240
gaggcctcta cttctacctc tacggttaca cgtgtagctg cgcgagatta taatgaggct     300
aaatcgaatt ttgatacggc gaaaagtgga ttagagaacg ctacgacact tgctgaatac     360
gagacgaaaa tggctgattt aatggcagct ctccaagata tggagcgttt ggctaaacag     420
aaggctgaag ttacaagaat taagaagct cttcaagaga acaagaggt tattgataag     480
ctcaatcagt tagttaaact tgaaaaacag aatcagactt taaggaaac tttaacaacc     540
acagactctg cagatcagat tccagcgatt aatagtcagt tagagatcaa caaaaattct     600
gcagatcaaa ttatcaaaga tctggaagga caaaacataa gttatgaagc tgttctcact     660
aacgcaggag aggttatcaa agcttcttct gaagcgggaa ttaagttagg acaagctttg     720
cagtctattg tggatgctgg ggatcaaagc caggctgcag ttcttcaagc acagcaaaat     780
aatagcccag ataatatcgc agccacgaag aaattaattg atgctgctga acgaaggta     840
aacgagttaa acaagagca tacagggcta acggactcgc ctttagtgaa aaaagctgag     900
gagcagatta gtcaagcaca aaaagatatt caagagatca aacctagtgg ttcggatatt     960
cctatcgttg gtccgagtgg gtcagctgct tccgcaggaa gtgcggtagg agcgttgaaa    1020
tcctctaaca attcaggaag aatttccttg ttgcttgatg atgtagacaa tgaaatggca    1080
gcgattgcaa tgcaaggttt tcgatctatg atcgaacaat ttaatgtaaa caatcctgca    1140
acagctaaag agctacaagc tatggaggct cagctgactg cgatgtcaga tcaactggtt    1200
ggtgcggatg gcgagctccc agccgaaata caagcaatca agatgctctc tgcgcaagct    1260
ttgaaacaac catcaacaga tggtttagct acagctatgg gacaagtggc ttttgcagct    1320
gccaaggttg gaggaggctc cgcaggaaca gctggcactg tccagatgaa tgtaaaacag    1380
ctttacaaga cagcgttttc ttcgacttct tccagctctt atgcagcagc actttccgat    1440
ggatattctg cttacaaaac actgaactct ttatattccg aaagcagaag cggcgtgcag    1500
tcagctatta gtcaaactgc aaatcccgcg cttccagaa gcgtttctcg ttctggcata    1560
gaaagtcaag gacgcagtgc agatgctagc caaagagcag cagaaactat tgtcagagat    1620
agccaaacgt taggtgatgt atatagccgc ttacaggttc tggattcttt gatgtctacg    1680
attgtgagca atccgcaagt aaatcaagaa gagattatgc agaagctcac ggcatctatt    1740
agcaaagctc cacaatttgg gtatcctgct gttcagaatt ctgcggatag cttgcagaag    1800
tttgctgcgc aattggaaag agagtttgtt gatggggaac gtagtctcgc agaatctcga    1860
gagaatgcgt ttagaaaaca gcccgctttc attcaacagg tgttggtaaa cattgcttct    1920
```

```
ctattctctg gttatctttc ttaa                                              1944
```

<210> SEQ ID NO 58
<211> LENGTH: 647
<212> TYPE: PRT
<213> ORGANISM: Chlamydia trachomatis

<400> SEQUENCE: 58

```
Met Glu Ser Gly Pro Glu Ser Val Ser Ser Asn Gln Ser Ser Met Asn
1               5                   10                  15

Pro Ile Ile Asn Gly Gln Ile Ala Ser Asn Ser Glu Thr Lys Glu Ser
            20                  25                  30

Thr Lys Glu Ser Glu Ala Ser Pro Ser Ala Ser Ser Val Ser Ser
        35                  40                  45

Trp Ser Phe Leu Ser Ser Ala Lys His Ala Leu Ile Ser Leu Arg Asp
        50                  55                  60

Ala Ile Leu Asn Lys Asn Ser Ser Pro Thr Asp Ser Leu Ser Gln Leu
65                  70                  75                  80

Glu Ala Ser Thr Ser Thr Ser Thr Val Thr Arg Val Ala Ala Arg Asp
                85                  90                  95

Tyr Asn Glu Ala Lys Ser Asn Phe Asp Thr Ala Lys Ser Gly Leu Glu
            100                 105                 110

Asn Ala Thr Thr Leu Ala Glu Tyr Glu Thr Lys Met Ala Asp Leu Met
        115                 120                 125

Ala Ala Leu Gln Asp Met Glu Arg Leu Ala Lys Gln Lys Ala Glu Val
    130                 135                 140

Thr Arg Ile Lys Glu Ala Leu Gln Glu Lys Gln Glu Val Ile Asp Lys
145                 150                 155                 160

Leu Asn Gln Leu Val Lys Leu Glu Lys Gln Asn Gln Thr Leu Lys Glu
                165                 170                 175

Thr Leu Thr Thr Thr Asp Ser Ala Asp Gln Ile Pro Ala Ile Asn Ser
            180                 185                 190

Gln Leu Glu Ile Asn Lys Asn Ser Ala Asp Gln Ile Ile Lys Asp Leu
        195                 200                 205

Glu Gly Gln Asn Ile Ser Tyr Glu Ala Val Leu Thr Asn Ala Gly Glu
    210                 215                 220

Val Ile Lys Ala Ser Ser Glu Ala Gly Ile Lys Leu Gly Gln Ala Leu
225                 230                 235                 240

Gln Ser Ile Val Asp Ala Gly Asp Gln Ser Gln Ala Ala Val Leu Gln
                245                 250                 255

Ala Gln Gln Asn Asn Ser Pro Asp Asn Ile Ala Ala Thr Lys Lys Leu
            260                 265                 270

Ile Asp Ala Ala Glu Thr Lys Val Asn Glu Leu Lys Gln Glu His Thr
        275                 280                 285

Gly Leu Thr Asp Ser Pro Leu Val Lys Lys Ala Glu Gly Gln Ile Ser
    290                 295                 300

Gln Ala Gln Lys Asp Ile Gln Glu Ile Lys Pro Ser Gly Ser Asp Ile
305                 310                 315                 320

Pro Ile Val Gly Pro Ser Gly Ser Ala Ala Ser Ala Gly Ser Ala Val
                325                 330                 335

Gly Ala Leu Lys Ser Ser Asn Asn Ser Gly Arg Ile Ser Leu Leu Leu
            340                 345                 350

Asp Asp Val Asp Asn Glu Met Ala Ala Ile Ala Met Gln Gly Phe Arg
        355                 360                 365
```

```
Ser Met Ile Glu Gln Phe Asn Val Asn Asn Pro Ala Thr Ala Lys Glu
    370                 375                 380

Leu Gln Ala Met Glu Ala Gln Leu Thr Ala Met Ser Asp Gln Leu Val
385                 390                 395                 400

Gly Ala Asp Gly Glu Leu Pro Ala Glu Ile Gln Ala Ile Lys Asp Ala
                405                 410                 415

Leu Ala Gln Ala Leu Lys Gln Pro Ser Thr Asp Gly Leu Ala Thr Ala
            420                 425                 430

Met Gly Gln Val Ala Phe Ala Ala Ala Lys Val Gly Gly Gly Ser Ala
        435                 440                 445

Gly Thr Ala Gly Thr Val Gln Met Asn Val Lys Gln Leu Tyr Lys Thr
    450                 455                 460

Ala Phe Ser Ser Thr Ser Ser Ser Ser Tyr Ala Ala Ala Leu Ser Asp
465                 470                 475                 480

Gly Tyr Ser Ala Tyr Lys Thr Leu Asn Ser Leu Tyr Ser Glu Ser Arg
                485                 490                 495

Ser Gly Val Gln Ser Ala Ile Ser Gln Thr Ala Asn Pro Ala Leu Ser
            500                 505                 510

Arg Ser Val Ser Arg Ser Gly Ile Glu Ser Gln Gly Arg Ser Ala Asp
        515                 520                 525

Ala Ser Gln Arg Ala Ala Glu Thr Ile Val Arg Asp Ser Gln Thr Leu
    530                 535                 540

Gly Asp Val Tyr Ser Arg Leu Gln Val Leu Asp Ser Leu Met Ser Thr
545                 550                 555                 560

Ile Val Ser Asn Pro Gln Val Asn Gln Glu Glu Ile Met Gln Lys Leu
                565                 570                 575

Thr Ala Ser Ile Ser Lys Ala Pro Gln Phe Gly Tyr Pro Ala Val Gln
            580                 585                 590

Asn Ser Ala Asp Ser Leu Gln Lys Phe Ala Ala Gln Leu Glu Arg Glu
        595                 600                 605

Phe Val Asp Gly Glu Arg Ser Leu Ala Glu Ser Arg Glu Asn Ala Phe
    610                 615                 620

Arg Lys Gln Pro Ala Phe Ile Gln Gln Val Leu Val Asn Ile Ala Ser
625                 630                 635                 640

Leu Phe Ser Gly Tyr Leu Ser
                645
```

<210> SEQ ID NO 59
<211> LENGTH: 1911
<212> TYPE: DNA
<213> ORGANISM: Chlamydia psitacci

<400> SEQUENCE: 59

```
atggttaatc ctgtcggccc tatagatgaa tcaaaaaaca ttgctcctgc agacttatct      60
actttaggta tgcaggcgag cgcagcaaat cgtagctcag aagctcaatc gataaccgga     120
attgcaggca agtccgggtc atcgcagcct tctgtggaaa ctgtaggacg attgagcttt     180
ttgagctctg ctcggaaaag tttagcaagt cttttcgata agatttcctc gttcttttca     240
gggaaaacga ctcctcaaac ttttgatgaa gctaagacgc aagcagagag tgcgaaaact     300
gcgctgcaga gtgcgactac ttatgatcag ttcaagaccg ctttacagca gctgcaagat     360
gctgtgaaac agatggagca attagctact actgatgcag aaaaagctac agttgctaca     420
tggaaaacgg ctcttgaggc gcagaagagt acgctggata cacttaacca gttgggtgct     480
attcttacag agaaccagaa gcttcttgag gcaataaaga cgacctcgtc tatggatcag     540
```

-continued

```
attatgggag ctgccggaca agtagaaacc aataaaacaa ctgctgagga gttaattaaa    600
cagttgaagg aagctggggt tagctatcct gtgatagatg accttgagaa gcaaattaca    660
acctcaggaa ctcaggttac tgaattagca gatgctatat cggaagctta tgctgcgggg    720
aaaaacagta ccgcggctgt ggggcaagca caggcaaata cagccccgc aaatatagaa     780 gcttccaaac aaactattgc aaatgcacaa aaagtcatag aagacgctct taaacttgct    840
ccagattctc cgatactcaa agctgctttg aaagaacaac aacaggcagc aaaagatatc    900
ctcaatgtga aacctagtgg tggtagtgat gtgcctatcg gtggtcctgg agctcctggt    960
agtgtgggga cttctcaaaa tcgcggtgct accttagggg aagttcgcgt atcgatgtta   1020
ttgactgatg ttgataatga aaccgcagcg atcattatgc aaggtttcag aaatatgatc   1080
gataacttcc atgatcaaaa ctctgatttt acagcgcctt tagaagagat tatgaatcaa   1140
gtaaccgact tatcaacgca gatcaatcct gcagatgcgg aagctacagc acaactacaa   1200
gaaatacaac aaaccataca agatgcccct caagggactg ccggtcaaga cggcatgatc   1260
aatgctttag gagctataac aacagcagct tcaatttcta caggagctcc tatcgcttct   1320
gcaaatcaag gtggatcagc tgtaaagcag ctttacaaaa caggatctac tgctgcgagt   1380
tctaaatctt acgcggattc cttatctgca gggtatgggg catatcaatc tttaaatgat   1440
gtgtactcac gtagtagtgc atctaaccgt gaggttttag atcgtacatc gactccagca   1500
ttaacgcaga cagtttctag aacagaaact cggcctcgtg ataatgataa cgcagctcag   1560
cgttttgcaa gaactatagc tgctaatagt aatactcttg gggatgttta tgcatccgta   1620
ggtgtattgc aaacattgct aggtgtatta caaaataatc cccaagcgaa tgaagaagaa   1680
atcaaacaga agctcacttc tgaggttacg aaagctccgc agtcaggtta tcctcatgta   1740
cagctttcta acgactctac gaagaagttc attgctcaac tcgagaatga atttgttcag   1800
ggatcgaaaa gacttgccga agcaaaagaa gctgcgtttg agaaacagcc tttgttcatc   1860
cagcaggtat tagtgaacgt agcatctctg ttctcgggat acctacagta a            1911
```

<210> SEQ ID NO 60
<211> LENGTH: 636
<212> TYPE: PRT
<213> ORGANISM: Chlamydia psitacci

<400> SEQUENCE: 60

```
Met Val Asn Pro Val Gly Pro Ile Asp Glu Ser Lys Asn Ile Ala Pro
1               5                   10                  15

Ala Asp Leu Ser Thr Leu Gly Met Gln Ala Ser Ala Ala Asn Arg Ser
            20                  25                  30

Ser Glu Ala Gln Ser Ile Thr Gly Ile Ala Gly Lys Ser Gly Ser Ser
        35                  40                  45

Gln Pro Ser Val Glu Thr Val Gly Arg Leu Ser Phe Leu Ser Ser Ala
    50                  55                  60

Arg Lys Ser Leu Ala Ser Leu Phe Asp Lys Ile Ser Ser Phe Phe Ser
65                  70                  75                  80

Gly Lys Thr Thr Pro Gln Thr Phe Asp Glu Ala Lys Thr Gln Ala Glu
                85                  90                  95

Ser Ala Lys Thr Ala Leu Gln Ser Ala Thr Thr Tyr Asp Gln Phe Lys
            100                 105                 110

Thr Ala Leu Gln Gln Leu Gln Asp Ala Val Lys Gln Met Glu Gln Leu
        115                 120                 125

Ala Thr Thr Asp Ala Glu Lys Ala Thr Val Ala Thr Trp Lys Thr Ala
    130                 135                 140
```

```
Leu Glu Ala Gln Lys Ser Thr Leu Asp Thr Leu Asn Gln Leu Gly Ala
145                 150                 155                 160

Ile Leu Thr Glu Asn Gln Lys Leu Leu Glu Ala Ile Lys Thr Thr Ser
                165                 170                 175

Ser Met Asp Gln Ile Met Gly Ala Ala Gly Gln Val Glu Thr Asn Lys
            180                 185                 190

Thr Thr Ala Glu Glu Leu Ile Lys Gln Leu Lys Glu Ala Gly Val Ser
                195                 200                 205

Tyr Pro Val Ile Asp Asp Leu Glu Lys Gln Ile Thr Thr Ser Gly Thr
210                 215                 220

Gln Val Thr Glu Leu Ala Asp Ala Ile Ser Glu Ala Tyr Ala Ala Gly
225                 230                 235                 240

Lys Asn Ser Thr Ala Ala Val Gly Gln Ala Gln Ala Asn Asn Ser Pro
                245                 250                 255

Ala Asn Ile Glu Ala Ser Lys Gln Thr Ile Ala Asn Ala Gln Lys Val
            260                 265                 270

Ile Glu Asp Ala Leu Lys Leu Ala Pro Asp Ser Pro Ile Leu Lys Ala
        275                 280                 285

Ala Leu Lys Glu Gln Gln Gln Ala Ala Lys Asp Ile Leu Asn Val Lys
    290                 295                 300

Pro Ser Gly Gly Ser Asp Val Pro Ile Gly Gly Pro Gly Ala Pro Gly
305                 310                 315                 320

Ser Val Gly Thr Ser Gln Asn Arg Gly Ala Thr Leu Gly Glu Val Arg
                325                 330                 335

Val Ser Met Leu Leu Thr Asp Val Asp Asn Glu Thr Ala Ala Ile Ile
                340                 345                 350

Met Gln Gly Phe Arg Asn Met Ile Asp Asn Phe His Asp Gln Asn Ser
            355                 360                 365

Asp Phe Thr Ala Pro Leu Glu Glu Ile Met Asn Gln Val Thr Asp Leu
370                 375                 380

Ser Thr Gln Ile Asn Pro Ala Asp Ala Glu Ala Thr Ala Gln Leu Gln
385                 390                 395                 400

Glu Ile Gln Gln Thr Ile Gln Asp Ala Leu Gln Gly Thr Ala Gly Gln
                405                 410                 415

Asp Gly Met Ile Asn Ala Leu Gly Ala Ile Thr Thr Ala Ala Ser Ile
            420                 425                 430

Ser Thr Gly Ala Pro Ile Ala Ser Ala Asn Gln Gly Gly Ser Ala Val
        435                 440                 445

Lys Gln Leu Tyr Lys Thr Gly Ser Thr Ala Ala Ser Ser Lys Ser Tyr
    450                 455                 460

Ala Asp Ser Leu Ser Ala Gly Tyr Gly Ala Tyr Gln Ser Leu Asn Asp
465                 470                 475                 480

Val Tyr Ser Arg Ser Ser Ala Ser Asn Arg Glu Val Leu Asp Arg Thr
                485                 490                 495

Ser Thr Pro Ala Leu Thr Gln Thr Val Ser Arg Thr Glu Thr Arg Pro
            500                 505                 510

Arg Asp Asn Asp Asn Ala Ala Gln Arg Phe Ala Arg Thr Ile Ala Ala
        515                 520                 525

Asn Ser Asn Thr Leu Gly Asp Val Tyr Ala Ser Val Gly Val Leu Gln
    530                 535                 540

Thr Leu Leu Gly Val Leu Gln Asn Asn Pro Gln Ala Asn Glu Glu Glu
545                 550                 555                 560

Ile Lys Gln Lys Leu Thr Ser Glu Val Thr Lys Ala Pro Gln Ser Gly
```

```
                565                570                575
Tyr Pro His Val Gln Leu Ser Asn Asp Ser Thr Lys Lys Phe Ile Ala
            580                585                590

Gln Leu Glu Asn Glu Phe Val Gln Gly Ser Lys Arg Leu Ala Glu Ala
        595                600                605

Lys Glu Ala Ala Phe Glu Lys Gln Pro Leu Phe Ile Gln Gln Val Leu
610                615                620

Val Asn Val Ala Ser Leu Phe Ser Gly Tyr Leu Gln
625                630                635

<210> SEQ ID NO 61
<211> LENGTH: 1956
<212> TYPE: DNA
<213> ORGANISM: Chlamydia pneumoniae

<400> SEQUENCE: 61
atggttaatc ctattggtcc aggtcctata gacgaaacag aacgcacacc tcccgcagat      60 cttttctgctc aaggattgga ggcgagtgca gcaaataaga gtgcggaagc tcaaagaata     120
gcaggtgcgg aagctaagcc taaagaatct aagaccgatt ctgtagagcg atggagcatc     180
ttgcgttctg cagtgaatgc tctcatgagt ctggcagata agctgggtat tgcttctagt     240
aacagctcgt cttctactag cagatctgca gacgtggact caacgacagc gaccgcacct     300
acgcctcctc cacccacgtt tgatgattat aagactcaag cgcaaacagc ttacgatact     360
atctttacct caacatcact agctgacata caggctgctt tggtgagcct ccaggatgct     420
gtcactaata taaggatac agcggctact gatgaggaaa ccgcaatcgc tgcggagtgg      480
gaaactaaga tgccgatgc agttaaagtt ggcgcgcaaa ttacagaatt agcgaaatat      540
gcttcggata ccaagcgat tcttgactct ttaggtaaac tgacttcctt cgacctctta     600
caggctgctc ttctccaatc tgtagcaaac aataacaaag cagctgagct tcttaaagag     660
atgcaagata acccagtagt cccagggaaa acgcctgcaa ttgctcaatc tttagttgat     720
cagacagatg ctacagcgac acagatagag aaagatggaa atgcgattag ggatgcatat    780
tttgcaggac agaacgctag tggagctgta gaaaatgcta atctaataa cagtataagc     840 aacatagatt cagctaaagc agcaatcgct actgctaaga cacaaatagc tgaagctcag     900
aaaaagttcc ccgactctcc aattcttcaa gaagcggaac aaatggtaat acaggctgag    960
aaagatctta aaatatcaa acctgcagat ggttctgatg ttccaaatcc aggaactaca    1020
gttggaggct ccaagcaaca aggaagtagt attggtagta ttcgtgtttc catgctgtta   1080
gatgatgctg aaaatgagac cgcttccatt ttgatgtctg ggtttcgtca gatgattcac   1140
atgttcaata cggaaaatcc tgattctcaa gctgcccaac aggagctcgc agcacaagct   1200
agagcagcga agccgctgg agatgacagt gctgctgcag cgctggcaga tgctcagaaa   1260
gctttagaag cggctctagg taaagctggg caacaacagg gcatactcaa tgctttagga   1320
cagatcgctt ctgctgctgt tgtgagcgca ggagttcctc ccgctgcagc aagttctata   1380
gggtcatctg taaacagct ttacaagacc tcaaaatcta caggtctga ttataaaaca    1440 cagatatcag caggttatga tgcttacaaa tccatcaatg atgcctatgg tagggcacga   1500
aatgatgcga ctcgtgatgt gataaacaat gtaagtaccc ccgctctcac acgatccgtt   1560
cctagagcac gaacagaagc tcgaggacca gaaaaaacag atcaagccct cgctagggtg   1620
atttctggca atagcagaac tcttggagat gtctatagtc aagtttcggc actacaatct   1680
gtaatgcaga tcatccagtc gaatcctcaa gcgaataatg aggagatcag acaaaagctt   1740
```

-continued

```
acatcggcag tgacaaagcc tccacagttt ggctatcctt atgtgcaact ttctaatgac    1800
tctacacaga agttcatagc taaattagaa agtttgtttg ctgaaggatc taggacagca    1860
gctgaaataa aagcactttc ctttgaaacg aactccttgt ttattcagca ggtgctggtc    1920
aatatcggct ctctatattc tggttatctc caataa                              1956
```

<210> SEQ ID NO 62
<211> LENGTH: 651
<212> TYPE: PRT
<213> ORGANISM: Chlamydia peneumoniae

<400> SEQUENCE: 62

```
Met Val Asn Pro Ile Gly Pro Gly Pro Ile Asp Glu Thr Glu Arg Thr
1               5                   10                  15

Pro Pro Ala Asp Leu Ser Ala Gln Gly Leu Glu Ala Ser Ala Ala Asn
            20                  25                  30

Lys Ser Ala Glu Ala Gln Arg Ile Ala Gly Ala Glu Ala Lys Pro Lys
        35                  40                  45

Glu Ser Lys Thr Asp Ser Val Glu Arg Trp Ser Ile Leu Arg Ser Ala
    50                  55                  60

Val Asn Ala Leu Met Ser Leu Ala Asp Lys Leu Gly Ile Ala Ser Ser
65                  70                  75                  80

Asn Ser Ser Ser Thr Ser Arg Ser Ala Asp Val Asp Ser Thr Thr
                85                  90                  95

Ala Thr Ala Pro Thr Pro Pro Pro Thr Phe Asp Asp Tyr Lys Thr
            100                 105                 110

Gln Ala Gln Thr Ala Tyr Asp Thr Ile Phe Thr Ser Ser Leu Ala
        115                 120                 125

Asp Ile Gln Ala Ala Leu Val Ser Leu Gln Asp Ala Val Thr Asn Ile
    130                 135                 140

Lys Asp Thr Ala Ala Thr Asp Glu Gly Thr Ala Ile Ala Ala Glu Trp
145                 150                 155                 160

Glu Thr Lys Asn Ala Asp Ala Val Lys Val Gly Ala Gln Ile Thr Glu
                165                 170                 175

Leu Ala Lys Tyr Ala Ser Asp Asn Gln Ala Ile Leu Asp Ser Leu Gly
            180                 185                 190

Lys Leu Thr Ser Phe Asp Leu Leu Gln Ala Ala Leu Leu Gln Ser Val
        195                 200                 205

Ala Asn Asn Asn Lys Ala Ala Glu Leu Leu Lys Glu Met Gln Asp Asn
    210                 215                 220

Pro Val Val Pro Gly Lys Thr Pro Ala Ile Ala Gln Ser Leu Val Asp
225                 230                 235                 240

Gln Thr Asp Ala Thr Ala Thr Gln Ile Glu Lys Asp Gly Asn Ala Ile
                245                 250                 255

Arg Asp Ala Tyr Phe Ala Gly Gln Asn Ala Ser Gly Ala Val Glu Asn
            260                 265                 270

Ala Lys Ser Asn Asn Ser Ile Ser Asn Ile Asp Ser Ala Lys Ala Ala
        275                 280                 285

Ile Ala Thr Ala Lys Thr Gln Ile Ala Glu Ala Gln Lys Lys Phe Pro
    290                 295                 300

Asp Ser Pro Ile Leu Gln Glu Ala Glu Gln Met Val Ile Gln Ala Glu
305                 310                 315                 320

Lys Asp Leu Lys Asn Ile Lys Pro Ala Asp Gly Ser Asp Val Pro Asn
                325                 330                 335

Pro Gly Thr Thr Val Gly Gly Ser Lys Gln Gln Gly Ser Ser Ile Gly
```

|  |  |  | 340 |  |  |  | 345 |  |  |  | 350 |  |
|---|---|---|---|---|---|---|---|---|---|---|---|---|
| Ser | Ile | Arg | Val | Ser | Met | Leu | Leu | Asp | Asp | Ala | Glu | Asn | Glu | Thr | Ala |
|  |  |  | 355 |  |  |  | 360 |  |  |  | 365 |  |

Ser Ile Leu Met Ser Gly Phe Arg Gln Met Ile His Met Phe Asn Thr
370               375               380

Glu Asn Pro Asp Ser Gln Ala Ala Gln Gln Glu Leu Ala Ala Gln Ala
385               390               395               400

Arg Ala Ala Lys Ala Ala Gly Asp Asp Ser Ala Ala Ala Leu Ala
                  405               410               415

Asp Ala Gln Lys Ala Leu Glu Ala Ala Leu Gly Lys Ala Gly Gln Gln
                  420               425               430

Gln Gly Ile Leu Asn Ala Leu Gly Gln Ile Ala Ser Ala Ala Val Val
                  435               440               445

Ser Ala Gly Val Pro Pro Ala Ala Ser Ser Ile Gly Ser Ser Val
    450               455               460

Lys Gln Leu Tyr Lys Thr Ser Lys Ser Thr Gly Ser Asp Tyr Lys Thr
465               470               475               480

Gln Ile Ser Ala Gly Tyr Asp Ala Tyr Lys Ser Ile Asn Asp Ala Tyr
                  485               490               495

Gly Arg Ala Arg Asn Asp Ala Thr Arg Asp Val Ile Asn Asn Val Ser
                  500               505               510

Thr Pro Ala Leu Thr Arg Ser Val Pro Arg Ala Arg Thr Glu Ala Arg
                  515               520               525

Gly Pro Glu Lys Thr Asp Gln Ala Leu Ala Arg Val Ile Ser Gly Asn
                  530               535               540

Ser Arg Thr Leu Gly Asp Val Tyr Ser Gln Val Ser Ala Leu Gln Ser
545               550               555               560

Val Met Gln Ile Ile Gln Ser Asn Pro Gln Ala Asn Asn Glu Glu Ile
                  565               570               575

Arg Gln Lys Leu Thr Ser Ala Val Thr Lys Pro Pro Gln Phe Gly Tyr
                  580               585               590

Pro Tyr Val Gln Leu Ser Asn Asp Ser Thr Gln Lys Phe Ile Ala Lys
                  595               600               605

Leu Glu Ser Leu Phe Ala Glu Gly Ser Arg Thr Ala Ala Glu Ile Lys
    610               615               620

Ala Leu Ser Phe Glu Thr Asn Ser Leu Phe Ile Gln Gln Val Leu Val
625               630               635               640

Asn Ile Gly Ser Leu Tyr Ser Gly Tyr Leu Gln
                  645               650

<210> SEQ ID NO 63
<211> LENGTH: 261
<212> TYPE: DNA
<213> ORGANISM: Chlamydia trachomatis

<400> SEQUENCE: 63
atgagtcaaa ataagaactc tgctttcatg cagcctgtga acgtatccgc tgatttagct    60
gccatcgttg gtgcaggacc tatgcctcgc acagagatca ttaagaaaat gtgggattac   120
attaagaaga atggccttca agatcctaca aacaaacgta atatcaatcc cgatgataaa   180
ttggctaaag tttttggaac tgaaaaacct atcgatatgt ccaaatgac aaaaatggtt   240 tctcaacaca tcattaaata a                                              261

<210> SEQ ID NO 64
<211> LENGTH: 86

```
<212> TYPE: PRT
<213> ORGANISM: Chlamydia trachomatis

<400> SEQUENCE: 64

Met Ser Gln Asn Lys Asn Ser Ala Phe Met Gln Pro Val Asn Val Ser
1               5                   10                  15

Ala Asp Leu Ala Ala Ile Val Gly Ala Gly Pro Met Pro Arg Thr Glu
            20                  25                  30

Ile Ile Lys Lys Met Trp Asp Tyr Ile Lys Lys Asn Gly Leu Gln Asp
        35                  40                  45

Pro Thr Asn Lys Arg Asn Ile Asn Pro Asp Asp Lys Leu Ala Lys Val
    50                  55                  60

Phe Gly Thr Glu Lys Pro Ile Asp Met Phe Gln Met Thr Lys Met Val
65                  70                  75                  80

Ser Gln His Ile Ile Lys
                85

<210> SEQ ID NO 65
<211> LENGTH: 261
<212> TYPE: DNA
<213> ORGANISM: Chlamydia muridarum

<400> SEQUENCE: 65
atgagtcaaa ataagaactc tgctttcatg cagcctgtga acgtatcttc tgatttagct        60
gccattgttg gtacagggcc tatgcctcgc acagaaatca ttaagaaaat tgggattat       120 attaagcaga ataacttca agatcctact aacaaacgca acatcaatcc tgatgataaa       180
ttagccaagg tttttggttc aaagaccct gtagatatgt tccaaatgac aaaaatagtc       240
tctaaacaca ttgttaaata a                                                 261

<210> SEQ ID NO 66
<211> LENGTH: 86
<212> TYPE: PRT
<213> ORGANISM: Chlamydia muridarum

<400> SEQUENCE: 66

Met Ser Gln Asn Lys Asn Ser Ala Phe Met Gln Pro Val Asn Val Ser
1               5                   10                  15

Ser Asp Leu Ala Ala Ile Val Gly Thr Gly Pro Met Pro Arg Thr Glu
            20                  25                  30

Ile Ile Lys Lys Ile Trp Asp Tyr Ile Lys Gln Asn Lys Leu Gln Asp
        35                  40                  45

Pro Thr Asn Lys Arg Asn Ile Asn Pro Asp Asp Lys Leu Ala Lys Val
    50                  55                  60

Phe Gly Ser Lys Asp Pro Val Asp Met Phe Gln Met Thr Lys Ile Val
65                  70                  75                  80

Ser Lys His Ile Val Lys
                85

<210> SEQ ID NO 67
<211> LENGTH: 264
<212> TYPE: DNA
<213> ORGANISM: Chlamydia psitacci

<400> SEQUENCE: 67
atgagtcaaa aaacaaaaa ctctgctttt atgaaccccg tcaatattac ccccgattta        60
gcagctatcg ttggcgaggg accaatgccc cgcactgaaa ttgtcaaaaa agtatgggag      120
cacattaaaa aaaataacct tcaagaccct aagaataaaa gaaatatcct tcccgatgac      180
```
gccctagcta aagtctttgg ttctaaaaat ccaatcgata tgtttcaaat gacgaaagcc 240
ctttccgctc atatcgtaaa ataa 264

<210> SEQ ID NO 68
<211> LENGTH: 87
<212> TYPE: PRT
<213> ORGANISM: Chlamydia psitacci

<400> SEQUENCE: 68

Met Ser Gln Lys Asn Lys Asn Ser Ala Phe Met Asn Pro Val Asn Ile
1 5 10 15

Thr Pro Asp Leu Ala Ala Ile Val Gly Glu Gly Pro Met Pro Arg Thr
20 25 30

Glu Ile Val Lys Lys Val Trp Glu His Ile Lys Lys Asn Asn Leu Gln
35 40 45

Asp Pro Lys Asn Lys Arg Asn Ile Leu Pro Asp Asp Ala Leu Ala Lys
50 55 60

Val Phe Gly Ser Lys Asn Pro Ile Asp Met Phe Gln Met Thr Lys Ala
65 70 75 80

Leu Ser Ala His Ile Val Lys
85

<210> SEQ ID NO 69
<211> LENGTH: 264
<212> TYPE: DNA
<213> ORGANISM: Chlamydia pneumoniae

<400> SEQUENCE: 69
atgagtcaaa aaaataaaaa ctctgctttt atgcatcccg tgaatatttc cacagattta 60
gcagttatag ttggcaaggg acctatgccc agaaccgaaa ttgtaaagaa agtttgggaa 120
tacattaaaa aacacaactg tcaggatcaa aaaaataaac gtaatatcct tcccgatgcg 180
aatcttgcca aagtctttgg ctctagtgat cctatcgaca tgttccaaat gaccaaagcc 240
ctttccaaac atattgtaaa ataa 264

<210> SEQ ID NO 70
<211> LENGTH: 87
<212> TYPE: PRT
<213> ORGANISM: Chlamydia pneumoniae

<400> SEQUENCE: 70

Met Ser Gln Lys Asn Lys Asn Ser Ala Phe Met His Pro Val Asn Ile
1 5 10 15

Ser Thr Asp Leu Ala Val Ile Val Gly Lys Gly Pro Met Pro Arg Thr
20 25 30

Glu Ile Val Lys Lys Val Trp Glu Tyr Ile Lys Lys His Asn Cys Gln
35 40 45

Asp Gln Lys Asn Lys Arg Asn Ile Leu Pro Asp Ala Asn Leu Ala Lys
50 55 60

Val Phe Gly Ser Ser Asp Pro Ile Asp Met Phe Gln Met Thr Lys Ala
65 70 75 80

Leu Ser Lys His Ile Val Lys
85

<210> SEQ ID NO 71
<211> LENGTH: 1266
<212> TYPE: DNA
<213> ORGANISM: Chlamydia trachomatis

<400> SEQUENCE: 71

```
atgactgcat caggaggagc tggagggcta ggcagcaccc aaacagtaga cgttgcgcga      60
gcacaagctg ctgcagctac tcaagatgca caagaggtta tcggctctca ggaagcttct     120
gaggcaagta tgctcaaagg atgtgaggat ctcataaatc ctgcagctgc aacccgaatc     180
aaaaaaaaag gagagaagtt tgaatcatta gaagctcgtc gcaaaccaac agcggataaa     240
gcagaaaaga atccgagag cacagaggaa aaggcgata ctcctcttga gatcgtttc       300
acagaagatc tttccgaagt ctccggagaa gattttcgag gattgaaaaa ttcgttcgat     360
gatgattctt ctcctgacga aattctcgat gcgctcacaa gtaaattttc tgatcccaca     420
ataaaggatc tagctcttga ttatctaatt caaacagctc cctctgatgg gaaacttaag     480
tccactctca ttcaggcaaa gcatcaactg atgagccaga atcctcaggc gattgttgga     540
ggacgcaatg ttctgttagc ttcagaaacc tttgcttcca gagcaaatac atctccttca     600
tcgcttcgct cctatatttt ccaagtaacc tcatccccct ctaattgcgc taattacat     660
caaatgcttg cttcttactt gccatcagag aaaccgctg ttatggagtt tctagtaaat      720
ggcatggtag cagatttaaa atcggagggc ccttccattc ctcctgcaaa attgcaagta     780
tatatgacgg aactaagcaa tctccaagcc ttacactctg taaatagctt ttttgataga     840
aatattggga acttggaaaa tagcttaaag catgaaggac atgcccctat tccatcctta     900
acgacaggaa atttaactaa aaccttctta caattagtag aagataaatt cccttcctct     960
tccaaagctc aaaaggcatt aaatgaactg gtaggcccag atactggtcc tcaaactgaa    1020
gttttaaact tattcttccg cgctcttaat ggctgttcgc ctagaatatt ctctggagct    1080
gaaaaaaaac agcagctggc atcggttatc acaaatacgc tagatgcgat aaatgcggat    1140
aatgaggatt atcctaaacc aggtgacttc ccacgatctt ccttctctag tacgcctcct    1200
catgctccag tacctcaatc tgagattcca acgtcaccta cctcaacaca gcctccatca    1260
ccctaa                                                                1266
```

<210> SEQ ID NO 72
<211> LENGTH: 421
<212> TYPE: PRT
<213> ORGANISM: Chlamydia trachomatis

<400> SEQUENCE: 72

```
Met Thr Ala Ser Gly Gly Ala Gly Gly Leu Gly Ser Thr Gln Thr Val
1               5                   10                  15

Asp Val Ala Arg Ala Gln Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Thr Arg Ile Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Ser Ser Pro Asp Glu Ile
        115                 120                 125

Leu Asp Ala Leu Thr Ser Lys Phe Ser Asp Pro Thr Ile Lys Asp Leu
```

```
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420

<210> SEQ ID NO 73
<211> LENGTH: 1257
<212> TYPE: DNA
<213> ORGANISM: Chlamydia muridarum

<400> SEQUENCE: 73
atgactgcat ccggaggagc tggagggtta ggcggaaccc aaacagtaaa cgtagcacaa      60
gcgcaagctg cagcagctac tcaggatgca caagaaatca taggctctca ggaagcttct     120
gaagccagtt tgattaaagg aagtgaggat cttgctaatc ctgctgcagc gactagaatc     180
aaaaagaaag aagacaaatt tcagtcatta gaagctcgtc gaaaaacaac tagtaaatcc     240
gaaaaaaaat cagaaagtac agaagagaaa tcagactctt ctcttgaaga gcgcttcaca     300
gaaaatcttt cggatgtttc tggagaagat tttcgagggt taaaggattc tctgagtgaa     360
gattcctctc ctgaagagat tcttgagaag ctgtcaggca aattttcgga ccccacaatt     420
aaagatcttg ctctagactt tctgattcaa tcgagtcctc ctgatgggaa attaagagcc     480
```

-continued

```
tctcttattc aggcaaaaca gacgcttttt caacaaaatc ctcaagcagt caaggaggg       540
cgcaacgttc ttttagcatc agaagccttt gcttctaaag caaacacttc ccctgcatca      600
ttacgcgcat tgtataccca agtaacctca tctccggcta attgtgcttc tctaagtcag      660
atgctatcct cttattctcc tacagaaaaa gcagctgtta tagatttttt aacaaatggt      720
atggtgtctg atctcaaatc aggagggcct tccatccctg ctccacaatt gcaagtgtat      780
atgacggagc tcagcaatct acaagccctc aactctgtag acagtttttt tgacaaaaat      840
acaaaaggac tagaagacaa tttaaaagcc gaaggacata cccttccacc atccctaact      900
cccagtaatc ttgctcaaac tttttttaaag ttagtggaag ataagttccc gtcctcccaa     960
aaagctcaaa aattgttgga tggccttgtt ggttctgacg ttactcctca aactgaagtt     1020
ttaaatctct tttaccgagc gctcaatggt tgttccccac gaatattcgg caatgctgag     1080
aaaaaacagc agctagcaac agtaattact aacacattag ataccgtgaa tgccgataac     1140
gaagattatc ctaaacctag cgatttcccc aaaccttcct tccatggcac tcctcctcat     1200
gctccagtgt ctctatctga tattccatca gcaacaacaa actctgcaga ccaataa       1257
```

<210> SEQ ID NO 74
<211> LENGTH: 418
<212> TYPE: PRT
<213> ORGANISM: Chlamydia muridarum

<400> SEQUENCE: 74

```
Met Thr Ala Ser Gly Gly Ala Gly Gly Leu Gly Gly Thr Gln Thr Val
1               5                  10                   15

Asn Val Ala Gln Ala Gln Ala Ala Ala Ala Thr Gln Asp Ala Gln Glu
            20                  25                   30

Ile Ile Gly Ser Gln Glu Ala Ser Glu Ala Ser Leu Ile Lys Gly Ser
        35                  40                  45

Glu Asp Leu Ala Asn Pro Ala Ala Ala Thr Arg Ile Lys Lys Lys Glu
    50                  55                  60

Asp Lys Phe Gln Ser Leu Glu Ala Arg Arg Lys Thr Thr Ser Lys Ser
65                  70                  75                  80

Glu Lys Lys Ser Glu Ser Thr Glu Glu Lys Ser Asp Ser Ser Leu Glu
                85                  90                  95

Glu Arg Phe Thr Glu Asn Leu Ser Asp Val Ser Gly Glu Asp Phe Arg
            100                 105                 110

Gly Leu Lys Asp Ser Leu Ser Glu Asp Ser Pro Glu Glu Ile Leu
        115                 120                 125

Glu Lys Leu Ser Gly Lys Phe Ser Asp Pro Thr Ile Lys Asp Leu Ala
    130                 135                 140

Leu Asp Phe Leu Ile Gln Ser Ser Pro Pro Asp Gly Lys Leu Arg Ala
145                 150                 155                 160

Ser Leu Ile Gln Ala Lys Gln Thr Leu Phe Gln Gln Asn Pro Gln Ala
                165                 170                 175

Val Lys Gly Gly Arg Asn Val Leu Leu Ala Ser Glu Ala Phe Ala Ser
            180                 185                 190

Lys Ala Asn Thr Ser Pro Ala Ser Leu Arg Ala Leu Tyr Thr Gln Val
        195                 200                 205

Thr Ser Ser Pro Ala Asn Cys Ala Ser Leu Ser Gln Met Leu Ser Ser
    210                 215                 220

Tyr Ser Pro Thr Glu Lys Ala Ala Val Ile Asp Phe Leu Thr Asn Gly
225                 230                 235                 240

Met Val Ser Asp Leu Lys Ser Gly Gly Pro Ser Ile Pro Ala Pro Gln
```

```
                245                 250                 255
Leu Gln Val Tyr Met Thr Glu Leu Ser Asn Leu Gln Ala Leu Asn Ser
                260                 265                 270

Val Asp Ser Phe Phe Asp Lys Asn Thr Lys Gly Leu Glu Asp Asn Leu
            275                 280                 285

Lys Ala Glu Gly His Thr Leu Pro Pro Ser Leu Thr Pro Ser Asn Leu
        290                 295                 300

Ala Gln Thr Phe Leu Lys Leu Val Glu Asp Lys Phe Pro Ser Ser Gln
305                 310                 315                 320

Lys Ala Gln Lys Leu Leu Asp Gly Leu Val Gly Ser Asp Val Thr Pro
                325                 330                 335

Gln Thr Glu Val Leu Asn Leu Phe Tyr Arg Ala Leu Asn Gly Cys Ser
            340                 345                 350

Pro Arg Ile Phe Gly Asn Ala Glu Lys Lys Gln Gln Leu Ala Thr Val
        355                 360                 365

Ile Thr Asn Thr Leu Asp Thr Val Asn Ala Asp Asn Glu Asp Tyr Pro
    370                 375                 380

Lys Pro Ser Asp Phe Pro Lys Pro Ser Phe His Gly Thr Pro Pro His
385                 390                 395                 400

Ala Pro Val Ser Leu Ser Asp Ile Pro Ser Ala Thr Thr Asn Ser Ala
                405                 410                 415

Asp Gln

<210> SEQ ID NO 75
<211> LENGTH: 1194
<212> TYPE: DNA
<213> ORGANISM: Chlamydia psitacci

<400> SEQUENCE: 75
atggctgcat ctggaggagc tggtggctta ggcggttcac aagctgttga cgttgcgcaa      60
gtgcaagctg cagctgcgaa agctgatgcc caagaagtta tcgctagcca agagcaatcc     120
gacatcagta tgattaagga ttctcaggat ttatcaaatc ctcaggctgc gacacgtaca     180
aagaaaaaag aagaaaaatt ccaaactcta gaatctagaa ggaaaggcgc gactcaagca     240
gagaaaaagt ctgaaagcac gggagataaa tccgacgcgg atcttgcgga taagtataca     300
gaaaataatg ctgaaatctc aggtcaagat ttacgcagta ccgagattc tttgcatgat     360 ggttcttccg aagaagatgt tttagatctt gtaaaatcta agttctctga tcctgcgctt     420
caaagtgttg ccctagatta tttagtccag acaacaccag cttctaaagg agctttaaaa     480
gacaccttaa tcagggcaca acaaaaccac atgcaacaaa atcgacaagc tgttgttggt     540
ggtaaaaata ttctatttgc ctctcaagag tatgcatctt tattaaatac ctctgctcca     600
ggattacgtg ctctttatct tgaggtaacg tctgatttcc attcttgtga gcaattacta     660
acatctctcc agtcacgtta tagttacgaa gaaatgggca ctgtttcctc tttcatactt     720
aaggggatgg ctgctgattt aaaatctgaa ggatcttcaa ttccagctcc gaaactacag     780
gtgatgatga cagaaactcg taaccttcaa gctgtgctta ctggttatca tttctttgag     840
acaaagctac aacacttac cgcatcttta aaagccgatg gggtaacagt tccggatctt     900
aaatttgata agtagccga tactttcttt aagttaatca atgataaatt ccctacgget     960 tcaaaaatgg agcgcggtgt ccgtgacctt attggcgacg atacagaagc tgttacaggg    1020
atgctcaacc tcttctttgt tgcttttaagg gggacatcc caagattatt tgcttcagca    1080
gaaaagcgtc agcaattagg cacaatgatg gctaatgctt tagatgctgt gaatattaac    1140
```
aacgaagatt acccaaaatc tacagacttc cccaaacctt atccctggtc ttaa                1194

<210> SEQ ID NO 76
<211> LENGTH: 397
<212> TYPE: PRT
<213> ORGANISM: Chlamydia psitacci

<400> SEQUENCE: 76

Met Ala Ala Ser Gly Gly Ala Gly Gly Leu Gly Gly Ser Gln Ala Val
1 5 10 15

Asp Val Ala Gln Val Gln Ala Ala Ala Ala Lys Ala Asp Ala Gln Glu
20 25 30

Val Ile Ala Ser Gln Glu Gln Ser Asp Ile Ser Met Ile Lys Asp Ser
35 40 45

Gln Asp Leu Ser Asn Pro Gln Ala Ala Thr Arg Thr Lys Lys Lys Glu
50 55 60

Glu Lys Phe Gln Thr Leu Glu Ser Arg Arg Lys Gly Ala Thr Gln Ala
65 70 75 80

Glu Lys Lys Ser Glu Ser Thr Gly Asp Lys Ser Asp Ala Asp Leu Ala
85 90 95

Asp Lys Tyr Thr Glu Asn Asn Ala Glu Ile Ser Gly Gln Asp Leu Arg
100 105 110

Ser Ile Arg Asp Ser Leu His Asp Gly Ser Ser Glu Glu Asp Val Leu
115 120 125

Asp Leu Val Lys Ser Lys Phe Ser Asp Pro Ala Leu Gln Ser Val Ala
130 135 140

Leu Asp Tyr Leu Val Gln Thr Thr Pro Ala Ser Lys Gly Ala Leu Lys
145 150 155 160

Asp Thr Leu Ile Arg Ala Gln Gln Asn His Met Gln Gln Asn Arg Gln
165 170 175

Ala Val Val Gly Gly Lys Asn Ile Leu Phe Ala Ser Gln Glu Tyr Ala
180 185 190

Ser Leu Leu Asn Thr Ser Ala Pro Gly Leu Arg Ala Leu Tyr Leu Glu
195 200 205

Val Thr Ser Asp Phe His Ser Cys Glu Gln Leu Leu Thr Ser Leu Gln
210 215 220

Ser Arg Tyr Ser Tyr Glu Glu Met Gly Thr Val Ser Ser Phe Ile Leu
225 230 235 240

Lys Gly Met Ala Ala Asp Leu Lys Ser Glu Gly Ser Ser Ile Pro Ala
245 250 255

Pro Lys Leu Gln Val Met Met Thr Glu Thr Arg Asn Leu Gln Ala Val
260 265 270

Leu Thr Gly Tyr His Phe Phe Glu Thr Lys Leu Pro Thr Leu Thr Ala
275 280 285

Ser Leu Lys Ala Asp Gly Val Thr Val Pro Asp Leu Lys Phe Asp Lys
290 295 300

Val Ala Asp Thr Phe Phe Lys Leu Ile Asn Asp Lys Phe Pro Thr Ala
305 310 315 320

Ser Lys Met Glu Arg Gly Val Arg Asp Leu Ile Gly Asp Asp Thr Glu
325 330 335

Ala Val Thr Gly Met Leu Asn Leu Phe Phe Val Ala Leu Arg Gly Thr
340 345 350

Ser Pro Arg Leu Phe Ala Ser Ala Glu Lys Arg Gln Gln Leu Gly Thr
355 360 365

Met Met Ala Asn Ala Leu Asp Ala Val Asn Ile Asn Asn Glu Asp Tyr 370          375          380
Pro Lys Ser Thr Asp Phe Pro Lys Pro Tyr Pro Trp Ser
385                   390                  395

<210> SEQ ID NO 77
<211> LENGTH: 1200
<212> TYPE: DNA
<213> ORGANISM: Chlamydia pneumoniae

<400> SEQUENCE: 77

```
atggcagcat caggaggcac aggtggttta ggaggcactc agggtgtcaa ccttgcagct     60
gtagaagctg cagctgcaaa agcagatgca gcagaagttg tagccagcca agaaggttct    120
gagatgaaca tgattcaaca atctcaggac ctgacaaatc ccgcagcagc aacacgcacg    180
aaaaaaaagg aagagaagtt tcaaactcta gaatctcgga aaaaggaga agctggaaag     240
gctgagaaaa atctgaatc tacagaagag aagcctgaca cagatcttgc tgataagtat    300
gcttctggga attctgaaat ctctggtcaa gaacttcgcg gcctgcgtga tgcaatagga    360
gacgatgctt ctccagaaga cattcttgct cttgtacaag agaaaattaa agacccagct    420
ctgcaatcca cagctttgga ctacctggtt caaacgactc cacctcccca ggtaaaatta    480
aaagaagcgc ttatccaagc aaggaatact catacggagc aattcggacg aactgctatt    540
ggtgcgaaaa acatcttatt tgcctctcaa gaatatgcag accaactgaa tgtttctcct    600
tcagggcttc gctctttgta cttagaagtg actggagaca cacatacctg tgatcagcta    660
cttctctatgc ttcaagaccg ctatacctac caagatatgg ctattgtcag ctccttttcta    720
atgaaaggaa tggcaacaga attaaaaagg cagggtccct acgtacccag tgcgcaacta    780
caagttctca tgacagaaac tcgtaacctg caagcagttc ttacctcgta cgattacttt    840
gaaagtcgcg ttcctatttt actcgatagc ttaaaagctg agggaatcca aactccttct    900
gatctaaact tgtgaaggt agctgagtcc taccataaaa tcattaacga taagttccca    960
acagcatcta agtagaacg agaagtccgc aatctcatag gagacgatgt tgattctgtg   1020
accggtgtct tgaacttatt cttttctgct ttacgtcaaa cgtcgtcacg ccttttctct   1080
tcagcagaca aacgtcagca attaggagct atgattgcta atgctttaga tgctgtaaat   1140
ataaacaatg aagattatcc caaagcatca gacttcccta accctatacc ttggtcatga   1200
```

<210> SEQ ID NO 78
<211> LENGTH: 399
<212> TYPE: PRT
<213> ORGANISM: Chlamydia pneumoniae

<400> SEQUENCE: 78

Met Ala Ala Ser Gly Gly Thr Gly Gly Leu Gly Gly Thr Gln Gly Val
1               5                   10                  15

Asn Leu Ala Ala Val Glu Ala Ala Ala Ala Lys Ala Asp Ala Ala Glu
            20                  25                  30

Val Val Ala Ser Gln Glu Gly Ser Glu Met Asn Met Ile Gln Gln Ser
        35                  40                  45

Gln Asp Leu Thr Asn Pro Ala Ala Ala Thr Arg Thr Lys Lys Lys Glu
    50                  55                  60

Glu Lys Phe Gln Thr Leu Glu Ser Arg Lys Lys Gly Glu Ala Gly Lys
65                  70                  75                  80

Ala Glu Lys Lys Ser Glu Ser Thr Glu Glu Lys Pro Asp Thr Asp Leu
                85                  90                  95

Ala Asp Lys Tyr Ala Ser Gly Asn Ser Glu Ile Ser Gly Gln Glu Leu

```
                        100                 105                 110
Arg Gly Leu Arg Asp Ala Ile Gly Asp Asp Ala Ser Pro Glu Asp Ile
            115                 120                 125

Leu Ala Leu Val Gln Glu Lys Ile Lys Asp Pro Ala Leu Gln Ser Thr
130                 135                 140

Ala Leu Asp Tyr Leu Val Gln Thr Thr Pro Ser Gln Gly Lys Leu
145                 150                 155                 160

Lys Glu Ala Leu Ile Gln Ala Arg Asn Thr His Thr Glu Gln Phe Gly
                165                 170                 175

Arg Thr Ala Ile Gly Ala Lys Asn Ile Leu Phe Ala Ser Gln Glu Tyr
            180                 185                 190

Ala Asp Gln Leu Asn Val Ser Pro Ser Gly Leu Arg Ser Leu Tyr Leu
            195                 200                 205

Glu Val Thr Gly Asp Thr His Thr Cys Asp Gln Leu Leu Ser Met Leu
            210                 215                 220

Gln Asp Arg Tyr Thr Tyr Gln Asp Met Ala Ile Val Ser Ser Phe Leu
225                 230                 235                 240

Met Lys Gly Met Ala Thr Glu Leu Lys Arg Gln Gly Pro Tyr Val Pro
                245                 250                 255

Ser Ala Gln Leu Gln Val Leu Met Thr Glu Thr Arg Asn Leu Gln Ala
            260                 265                 270

Val Leu Thr Ser Tyr Asp Tyr Phe Glu Ser Arg Val Pro Ile Leu Leu
            275                 280                 285

Asp Ser Leu Lys Ala Glu Gly Ile Gln Thr Pro Ser Asp Leu Asn Phe
            290                 295                 300

Val Lys Val Ala Glu Ser Tyr His Lys Ile Ile Asn Asp Lys Phe Pro
305                 310                 315                 320

Thr Ala Ser Lys Val Glu Arg Glu Val Arg Asn Leu Ile Gly Asp Asp
                325                 330                 335

Val Asp Ser Val Thr Gly Val Leu Asn Leu Phe Phe Ser Ala Leu Arg
            340                 345                 350

Gln Thr Ser Ser Arg Leu Phe Ser Ser Ala Asp Lys Arg Gln Gln Leu
            355                 360                 365

Gly Ala Met Ile Ala Asn Ala Leu Asp Ala Val Asn Ile Asn Asn Glu
            370                 375                 380

Asp Tyr Pro Lys Ala Ser Asp Phe Pro Lys Pro Tyr Pro Trp Ser
385                 390                 395

<210> SEQ ID NO 79
<211> LENGTH: 1266
<212> TYPE: DNA
<213> ORGANISM: Chlamydia trachomatis

<400> SEQUENCE: 79
atgactgcat caggaggagc tggagggcta ggcagcaccc aaacagtaga cgttgcgcga    60
gcacaagctg ctgcagctac tcaagatgca caagaggtta tcggctctca ggaagcttct   120
gaggcaagta tgctcaaagg atgtgaggat ctcataaatc ctgcagctgc aacccgaatc   180
aaaaaaaaag aagagaagtt tgaatcatta gaagctcgtc gcaaaccaac agcggataaa   240
gcagaaaaga aatccgagag cacagaggaa aaggcgata ctcctcttga agatcgtttc   300
acagaagatc tttccgaagt ctccggagaa gattttcgag gattgaaaaa ttcgttcgat   360
gatgattctt ctcctgaaga aattctcgat gcgctcacaa gtaaattttc tgatcccaca   420 ataaggatc tagctcttga ttatctaatt caaacagctc cctctgatag gaaacttaag   480
```

```
tccgctctca ttcaggcaaa gcatcaactg atgagccaga atcctcaggc gattgttgga     540
ggacgcaatg ttctgttagc ttcagaaacc tttgcttcca gagcaaatac atctccttca     600
tcgcttcgct ccttatattt ccaagtaacc tcatcccct ctaattgtga taatttacgt     660
caaatgcttg cttcttactc gccatcagag aaaaccgctg ttatggagtt tctagtaaat     720
ggcatggtag cagatttaaa atcggagggc ccttccattc ctcctgcaaa attgcaagta     780
tatatgacgg aactaagcaa tctccaagcc ttacactctg tagatagctt ttttgataga     840
aatattggga acttggaaaa tagcttaaag catgaaggac atgcccctat tccatcctta     900
acgacaggaa atttaactaa aaccttctta caattagtag aagataaatt cccttcctct     960
tccaaagctc aaaaggcatt aaatgaactg gtaggcccag atactggtcc tcaaactgaa    1020 gtttaaact tattcttccg cgctcttaat ggctgttcgc ctagaatatt ctctggagct    1080
gaaaaaaaac agcagctggc atcggttatc acaaatacgc tagatgcgat aaatgcggat    1140
aatgaggatt atcctaaacc aggtgacttc ccacgatctt ccttctctag tacgcctcct    1200
catgctccag tacctcaatc tgagattcca acgtcaccta cctcaacaca gcctccatca    1260
ccctaa                                                               1266
```

<210> SEQ ID NO 80
<211> LENGTH: 421
<212> TYPE: PRT
<213> ORGANISM: Chlamydia trachomatis

<400> SEQUENCE: 80

```
Met Thr Ala Ser Gly Gly Ala Gly Gly Leu Gly Ser Thr Gln Thr Val
1               5                   10                  15

Asp Val Ala Arg Ala Gln Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Ser Pro Glu Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Arg Lys Leu Lys
145                 150                 155                 160

Ser Ala Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Asp Asn Leu Arg Gln Met Leu Ala
    210                 215                 220

Ser Tyr Ser Pro Ser Glu Lys Thr Ala Val Met Glu Phe Leu Val Asn
225                 230                 235                 240
```

| | | | | | | | | | | | |
|---|---|---|---|---|---|---|---|---|---|---|---|
| Gly | Met | Val | Ala | Asp | Leu | Lys | Ser | Glu | Gly | Pro | Ser | Ile | Pro | Pro | Ala |
| | | | | 245 | | | | | 250 | | | | | 255 | |

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
                260                 265                 270

Ser Val Asp Ser Phe Phe Asp Arg Asn Ile Gly Asn Leu Glu Asn Ser
            275                 280                 285

Leu Lys His Glu Gly His Ala Pro Ile Pro Ser Leu Thr Thr Gly Asn
        290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
                340                 345                 350

Ser Pro Arg Ile Phe Ser Gly Ala Glu Lys Lys Gln Gln Leu Ala Ser
            355                 360                 365

Val Ile Thr Asn Thr Leu Asp Ala Ile Asn Ala Asp Asn Glu Asp Tyr
        370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420

<210> SEQ ID NO 81
<211> LENGTH: 1266
<212> TYPE: DNA
<213> ORGANISM: Chlamydia trachomatis

<400> SEQUENCE: 81

```
atgactgcat caggaggagc tggagggcta ggcagcaccc aaacagtaga cgttgcgcga    60
gcacaagctg ctgcagctac tcaagatgca caagaggtta tcggctctca ggaagcttct   120
gaggcaagta tgctcaaagg atgtgaggat ctcataaatc ctgcagctgc aacccgaatc   180
aaaaaaaaag aagagaagtt tgaatcatta gaagctcgtc gcaaaccaac agcggataaa   240
gcagaaaaga atccgagag cacagaggaa aaaggcgata ctcctcttga agatcgtttc   300
acagaagatc tttccgaagt ctccggagaa gattttcgag gattgaaaaa ttcgttcgat   360
gatgattctt ctcctgaaga aattctcgat gcgctcacaa gtaaattttc tgatcccaca   420
ataaggatc tagctcttga ttatctaatt caaacagctc cctctgatag gaaacttaag   480
tccgctctca ttcaggcaaa gcatcaactg atgagccaga tcctcaggc gattgttgga   540
ggacgcaatg ttctgttagc ttcagaaacc tttgcttcca gagcaaatac atctccttca   600
tcgcttcgct ccttatatct ccaagtaacc tcatccccct ctaattgtga aatttacgt    660
caaatgcttg cttcttactc gccatcagag aaaaccgctg ttatggagtt tctagtaaat   720
ggcatggtag cagatttaaa atcggagggc ccttccattc ctcctgcaaa attgcaagta   780
tatatgacgg aactaagcaa tctccaagcc ttacactctg tagatagctt ttttgataga   840
aatattggga acttggaaaa tagcttaaag catgaaggac atgccctat tccatccta    900
acgacaggaa atttaactaa aaccttctta caattagtag aagataaatt cccttcctct   960
tccaaagctc aaaaggcatt aaatgaactg gtaggcccag atactggtcc tcaaactgaa  1020
gttttaaact tattcttccg cgctcttaat ggctgttcgc ctagaatatt ctctggagct  1080
```

```
gaaaaaaaac agcagctggc atcggttatc acaaatacgc tagatgcgat aaatgcggat    1140
aatgaggatt atcctaaacc aggtgacttc ccacgatctt ccttctctag tacgcctcct    1200
catgctccag tacctcaatc tgagattcca acgtcaccta cctcaacaca gcctccatca    1260
ccctaa                                                                1266
```

<210> SEQ ID NO 82
<211> LENGTH: 421
<212> TYPE: PRT
<213> ORGANISM: Chlamydia trachomatis

<400> SEQUENCE: 82

```
Met Thr Ala Ser Gly Gly Ala Gly Gly Leu Gly Ser Thr Gln Thr Val
1               5                   10                  15

Asp Val Ala Arg Ala Gln Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Ser Ser Pro Glu Glu Ile
        115                 120                 125

Leu Asp Ala Leu Thr Ser Lys Phe Ser Asp Pro Thr Ile Lys Asp Leu
130                 135                 140

Ala Leu Asp Tyr Leu Ile Gln Thr Ala Pro Ser Asp Arg Lys Leu Lys
145                 150                 155                 160

Ser Ala Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Leu Gln
        195                 200                 205

Val Thr Ser Ser Pro Ser Asn Cys Asp Asn Leu Arg Gln Met Leu Ala
210                 215                 220

Ser Tyr Ser Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asp Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335
```

```
Pro Gln Thr Glu Val Leu Asn Leu Phe Phe Arg Ala Leu Asn Gly Cys
        340                 345                 350

Ser Pro Arg Ile Phe Ser Gly Ala Glu Lys Lys Gln Gln Leu Ala Ser
            355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420

<210> SEQ ID NO 83
<211> LENGTH: 1266
<212> TYPE: DNA
<213> ORGANISM: Chlamydia trachomatis

<400> SEQUENCE: 83
atgactgcat caggaggagc tggagggcta ggcagcaccc aaacagtaga cgttgcgcga      60
gcacaagctg ctgcagctac tcaagatgca caagaggtta tcggctctca ggaagcttct    120
gaggcaagta tgctcaaagg atgtgaggat ctcataaatc ctgcagctgc aacccgaatc    180
aaaaaaaaag gagagaagtt tgaatcatta gaagctcgtc gcaaaccaac agcggataaa    240
gcagaaaaga atccgagag cacagaggaa aaggcgata ctcctcttga agatcgtttc      300
acagaagatc tttccgaagt ctccggagaa gattttcgag gattgaaaaa ttcgttcgat    360
gatgattctt ctcctgacga aattctcgat gcgctcacaa gtaaattttc tgatcccaca    420 ataaggatc tagctcttga ttatctaatt caaacagctc cctctgatgg gaaacttaag    480
tccactctca ttcaggcaaa gcatcaactg atgagccaga tcctcaggc gattgttgga    540 ggacgcaatg ttctgttagc ttcagaaacc tttgcttcca gagcaaatac atctccttca    600
tcgcttcgct ccttatattt ccaagtaacc tcatcccct ctaattgcgc taatttacat    660
caaatgcttg cttcttactt gccatcagag aaaaccgctg ttatggagtt tctagtaaat    720
ggcatggtag cagatttaaa atcggagggc ccttccattc ctcctgcaaa attgcaagta    780
tatatgacgg aactaagcaa tctccaagcc ttacactctg taaatagctt ttttgataga    840
aatattggga acttggaaaa tagcttaaag catgaaggac atgcccctat tccatcctta    900
acgacaggaa atttaactaa aaccttctta caattagtag aagataaatt cccttcctct    960
tccaaagctc aaaaggcatt aaatgaactg gtaggcccag atactggtcc tcaaactgaa   1020
gttttaaact tattcttccg cgctcttaat ggctgttcgc ctagaatatt ctctggagct   1080
gaaaaaaaac agcagctggc atcggttatc acaaatacgc tagatgcgat aaatgcggat   1140
aatgaggatt atcctaaacc aggtgacttc ccacgatctt ccttctctag tacgcctcct   1200
catgctccag tacctcaatc tgagattcca acgtcaccta cctcaacaca gcctccatca   1260
ccctaa                                                              1266

<210> SEQ ID NO 84
<211> LENGTH: 421
<212> TYPE: PRT
<213> ORGANISM: Chlamydia trachomatis

<400> SEQUENCE: 84

Met Thr Ala Ser Gly Gly Ala Gly Gly Leu Gly Ser Thr Gln Thr Val
1               5                   10                  15
```

Asp Val Ala Arg Ala Gln Ala Ala Ala Thr Gln Asp Ala Gln Glu
             20                  25                  30

Val Ile Gly Ser Gln Glu Ala Ser Glu Ala Ser Met Leu Lys Gly Cys
         35                  40                  45

Glu Asp Leu Ile Asn Pro Ala Ala Thr Arg Ile Lys Lys Lys Gly
 50                  55                  60

Glu Lys Phe Glu Ser Leu Glu Ala Arg Arg Lys Pro Thr Ala Asp Lys
 65                  70                  75                  80

Ala Glu Lys Lys Ser Glu Ser Thr Glu Lys Gly Asp Thr Pro Leu
                 85                  90                  95

Glu Asp Arg Phe Thr Glu Asp Leu Ser Glu Val Ser Gly Glu Asp Phe
             100                 105                 110

Arg Gly Leu Lys Asn Ser Phe Asp Asp Ser Ser Pro Asp Glu Ile
             115                 120                 125

Leu Asp Ala Leu Thr Ser Lys Phe Ser Asp Pro Thr Ile Lys Asp Leu
 130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                 165                 170                 175

Ala Ile Val Gly Gly Arg Asn Val Leu Leu Ala Ser Glu Thr Phe Ala
             180                 185                 190

Ser Arg Ala Asn Thr Ser Pro Ser Ser Leu Arg Ser Leu Tyr Phe Gln
             195                 200                 205

Val Thr Ser Ser Pro Ser Asn Cys Ala Asn Leu His Gln Met Leu Ala
210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
             245                 250                 255

Lys Leu Gln Val Tyr Met Thr Glu Leu Ser Asn Leu Gln Ala Leu His
             260                 265                 270

Ser Val Asn Ser Phe Phe Asp Arg Asn Ile Gly Asn Leu Glu Asn Ser
             275                 280                 285

Leu Lys His Glu Gly His Ala Pro Ile Pro Ser Leu Thr Thr Gly Asn
 290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
             325                 330                 335

Pro Gln Thr Glu Val Leu Asn Leu Phe Phe Arg Ala Leu Asn Gly Cys
             340                 345                 350

Ser Pro Arg Ile Phe Ser Gly Ala Glu Lys Lys Gln Gln Leu Ala Ser
             355                 360                 365

Val Ile Thr Asn Thr Leu Asp Ala Ile Asn Ala Asp Asn Glu Asp Tyr
 370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Thr Ser Thr
             405                 410                 415

Gln Pro Pro Ser Pro
             420

<210> SEQ ID NO 85
<211> LENGTH: 1266
<212> TYPE: DNA
<213> ORGANISM: Chlamydia trachomatis

<400> SEQUENCE: 85

```
atgactgcat caggaggagc tggagggcta ggcagcaccc aaacagtaga cgttgcgcga      60
gcacaagctg ctgcagctac tcaagatgca caagaggtta tcggctctca ggaagcttct     120
gaggcaagta tgctcaaagg atgtgaggat ctcataaatc ctgcagctgc aacccgaatc     180
aaaaaaaaag aagagaagtt tgaatcatta gaagctcgtc gcaaaccaac agcggataaa     240
gcagaaaaga atccgagag cacagaggaa aaggcgata ctcctcttga agatcgtttc       300
acagaagatc tttccgaagt ctccggagaa gattttcgag gattgaaaaa ttcgttcgat     360
gatgattctt ctcctgacga aattctcgat gcgctcacaa gtaaattttc tgatcccaca     420
ataaaggatc tagctcttga ttatctaatt caaacagctc cctctgatgg gaaacttaag     480
tccgctctca ttcaggcaaa gcatcaactg atgagccaga tcctcaggc gattgttgga     540
ggacgcaatg ttctgttagc ttcagaaacc tttgcttcca gagcaaatac atctccttca    600
tcgcttcgct cctatatttt ccaagtaacc tcatccccct ctaattgcgc taatttacat     660
caaatgcttg cttcttactt gccatcagag aaaaccgctg ttatggagtt tctagtaaat    720
ggcatggtag cagatttaaa atcggagggc ccttccattc ctcctgcaaa attgcaagta    780
tatatgacgg aactaagcaa tctccaagcc ttacactctg taaatagctt ttttgataga   840
aatattggga acttggaaaa tagcttaaag catgaaggac atgcccctat tccatcctta   900
acgacaggaa atttaactaa aaccttctta caattagtag aagataaatt cccttcctct   960
tccaaagctc aaaaggcatt aaatgaactg gtaggcccag atactggtcc tcaaactgaa  1020
gttttaaact tattcttccg cgctcttaat ggctgttcgc ctagaatatt ctctggagct   1080
gaaaaaaaac agcagctggc atcggttatc acaaatacgc tagatgcgat aaatgcggat  1140
aatgaggatt atcctaaacc aggtgacttc ccacgatctt ccttctctag tacgcctcct  1200
catgctccag tacctcaatc tgagattcca acgtcaccta cctcaacaca gcctccatca  1260
ccctaa                                                             1266
```

<210> SEQ ID NO 86
<211> LENGTH: 421
<212> TYPE: PRT
<213> ORGANISM: Chlamydia trachomatis

<400> SEQUENCE: 86

```
Met Thr Ala Ser Gly Gly Ala Gly Gly Leu Gly Ser Thr Gln Thr Val
1               5                   10                  15

Asp Val Ala Arg Ala Gln Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110
```

```
Arg Gly Leu Lys Asn Ser Phe Asp Asp Asp Ser Ser Pro Asp Glu Ile
        115                 120                 125
Leu Asp Ala Leu Thr Ser Lys Phe Ser Asp Pro Thr Ile Lys Asp Leu
    130                 135                 140
Ala Leu Asp Tyr Leu Ile Gln Thr Ala Pro Ser Asp Gly Lys Leu Lys
145                 150                 155                 160
Ser Ala Leu Ile Gln Ala Lys His Gln Leu Met Ser Gln Asn Pro Gln
                165                 170                 175
Ala Ile Val Gly Gly Arg Asn Val Leu Leu Ala Ser Glu Thr Phe Ala
            180                 185                 190
Ser Arg Ala Asn Thr Ser Pro Ser Ser Leu Arg Ser Leu Tyr Phe Gln
        195                 200                 205
Val Thr Ser Ser Pro Ser Asn Cys Ala Asn Leu His Gln Met Leu Ala
    210                 215                 220
Ser Tyr Leu Pro Ser Glu Lys Thr Ala Val Met Glu Phe Leu Val Asn
225                 230                 235                 240
Gly Met Val Ala Asp Leu Lys Ser Glu Gly Pro Ser Ile Pro Pro Ala
                245                 250                 255
Lys Leu Gln Val Tyr Met Thr Glu Leu Ser Asn Leu Gln Ala Leu His
            260                 265                 270
Ser Val Asn Ser Phe Phe Asp Arg Asn Ile Gly Asn Leu Glu Asn Ser
        275                 280                 285
Leu Lys His Glu Gly His Ala Pro Ile Pro Ser Leu Thr Thr Gly Asn
    290                 295                 300
Leu Thr Lys Thr Phe Leu Gln Leu Val Glu Asp Lys Phe Pro Ser Ser
305                 310                 315                 320
Ser Lys Ala Gln Lys Ala Leu Asn Glu Leu Val Gly Pro Asp Thr Gly
                325                 330                 335
Pro Gln Thr Glu Val Leu Asn Leu Phe Phe Arg Ala Leu Asn Gly Cys
            340                 345                 350
Ser Pro Arg Ile Phe Ser Gly Ala Glu Lys Lys Gln Gln Leu Ala Ser
        355                 360                 365
Val Ile Thr Asn Thr Leu Asp Ala Ile Asn Ala Asp Asn Glu Asp Tyr
    370                 375                 380
Pro Lys Pro Gly Asp Phe Pro Arg Ser Ser Phe Ser Ser Thr Pro Pro
385                 390                 395                 400
His Ala Pro Val Pro Gln Ser Glu Ile Pro Thr Ser Pro Thr Ser Thr
                405                 410                 415
Gln Pro Pro Ser Pro
            420

<210> SEQ ID NO 87
<211> LENGTH: 1266
<212> TYPE: DNA
<213> ORGANISM: Chlamydia trachomatis

<400> SEQUENCE: 87
atgactgcat caggaggagc tggagggcta ggcagcaccc aaacagtaga cgttgcgcga    60
gcacaagctg ctgcagctac tcaagatgca caagaggtta tcggctctca ggaagcttct   120
gaggcaagta tgctcaaagg atgtgaggat ctcataaatc ctgcagctgc aacccgaatc   180
aaaaaaaaag gagagaagtt tgaatcatta gaagctcgtc gcaaaccaac agcggataaa   240
gcagaaaaga aatccgagag cacagaggaa aaggcgata ctcctcttga agatcgtttc   300
acagaagatc tttccgaagt ctccggagaa gattttcgag gattgaaaaa ttcgttcgat   360
```

-continued

```
gatgattctt ctcctgacga aattctcgat gcgctcacaa gtaaattttc tgatcccaca    420
ataaaggatc tagctcttga ttatctaatt caaacagctc cctctgatgg gaaacttaag    480
tccactctca ttcaggcaaa gcatcaactg atgagccaga atcctcaggc gattgttgga    540
ggacgcaatg ttctgttagc ttcagaaacc tttgcttcca gagcaaatac atctccttca    600
tcgcttcgct ccttatattt ccaagtaacc tcatccccct ctaattgcgc taatttacat    660
caaatgcttg cttcttactt gccatcagag aaaaccgctg ttatggagtt tctagtaaat    720
ggcatggtag cagatttaaa atcggagggc ccttccattc ctcctgcaaa attgcaagta    780
tatatgacgg aactaagcaa tctccaagcc ttacactctg taaatagctt ttttgataga    840
aatattggga acttggaaaa tagcttaaag catgaaggac atgcccctat tccatcctta    900
acgacaggaa atttaactaa aaccttctta caattagtag aagataaatt cccttcctct    960
tccaaagctc aaaaggcatt aaatgaactg gtaggcccag atactggtcc tcaaactgaa   1020
gttttaaact tattcttccg cgctcttaat ggctgttcgc ctagaatatt ctctggagct   1080
gaaaaaaaac agcagctggc atcggttatc acaaatacgc tagatgcgat aaatgcggat   1140
aatgaggatt atcctaaacc aggtgacttc ccacgatctt ccttctctag tacgcctcct   1200
catgctccag tacctcaatc tgagattcca acgtcaccta cctcaacaca gcctccatca   1260
ccctaa                                                              1266
```

<210> SEQ ID NO 88
<211> LENGTH: 421
<212> TYPE: PRT
<213> ORGANISM: Chlamydia trachomatis

<400> SEQUENCE: 88

Met Thr Ala Ser Gly Gly Ala Gly Gly Leu Gly Ser Thr Gln Thr Val
1               5                   10                  15

Asp Val Ala Arg Ala Gln Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala

```
                210                 215                 220
Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
                260                 265                 270

Ser Val Asn Ser Phe Phe Asp Arg Asn Ile Gly Asn Leu Glu Asn Ser
                275                 280                 285

Leu Lys His Glu Gly His Ala Pro Ile Pro Ser Leu Thr Thr Gly Asn
290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
                340                 345                 350

Ser Pro Arg Ile Phe Ser Gly Ala Glu Lys Lys Gln Gln Leu Ala Ser
                355                 360                 365

Val Ile Thr Asn Thr Leu Asp Ala Ile Asn Ala Asp Asn Glu Asp Tyr
370                 375                 380

Pro Lys Pro Gly Asp Phe Pro Arg Ser Ser Phe Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
                420

<210> SEQ ID NO 89
<211> LENGTH: 1266
<212> TYPE: DNA
<213> ORGANISM: Chlamydia trachomatis

<400> SEQUENCE: 89
atgactgcat caggaggagc tggagggcta ggcagcaccc aaacagtaga cgttgcgcga      60
gcacaagctg ctgcagctac tcaagatgca caagaggtta tcggctctca ggaagcttct     120
gaggcaagta tgctcaaaga atgtgcggat ctcataaatc ctgcagctgc aacccgaatc     180
aaaaaaaaaa aagagaagtt tgaatcatta gaagctcgtc gcaaaccaac agcggataaa     240
gcagaaaaga atccgagag cacagaggaa aaaggcgata ctcctcttga agatcgtttc     300
acagaagatc tttccgaagt ctctggagaa gattttcgag gattgaaaaa ttcgttcgat     360
gatgattctt cttctgacga aattctcgat gcgctcacaa gtaaattttc tgatcccaca     420
ataaaggatc tagctcttga ttatctaatt caaatagctc cctctgatgg gaaacttaag     480
tccactctca ttcaggcaaa gcatcaactg atgagccaga tcctcaggc gattgttgga     540 ggacgcaatg ttctgttagc ttcagaaacc tttgcttcca gagcaaatac atctccttca     600
tcgcttcgct cctatatctc caagtaacc tcatccccct taattgcgc taatttacat      660 caaatgcttg cttcttactc gccatcagag aaaccgctg ttatggagtt tctagtgaat     720
ggcatggtag cagatttaaa atcggagggc ccttccattc ctcctgcaaa attgcaagta     780
tatatgacgg aactaagcaa tctccaagcc ttacactctg tagatagctt ttttgataga     840
aatattggga acttggaaaa tagcttaaag catgaaggac atgcccctat tccatcctta     900
acgacaggaa atttaactaa aaccttctta caattagtag aagataaatt cccttcctct     960
```

-continued

```
tccaaagctc aaaaggcatt aaatgaactg gtaggcccag atactggtcc tcaaactgaa    1020
gttttaaact tattcttccg cgctcttaat ggctgttcgc ctagaatatt ctctggagct    1080
gaaaaaaaac agcagctggc atcggttatc acaaatacgc tagatgcgat aaatgcggat    1140
aatgaggatt atcctaaacc aggtgacttc ccacgatctt ccttctctag tacgcctcct    1200
catgctccag tacctcaatc tgagattcca acgtcaccta cctcaacaca gcctccatca    1260
ccctaa                                                              1266
```

<210> SEQ ID NO 90
<211> LENGTH: 421
<212> TYPE: PRT
<213> ORGANISM: Chlamydia trachomatis

<400> SEQUENCE: 90

```
Met Thr Ala Ser Gly Gly Ala Gly Gly Leu Gly Ser Thr Gln Thr Val
1               5                   10                  15

Asp Val Ala Arg Ala Gln Ala Ala Ala Thr Gln Asp Ala Gln Glu
            20                  25                  30

Val Ile Gly Ser Gln Glu Ala Ser Glu Ala Ser Met Leu Lys Glu Cys
        35                  40                  45

Ala Asp Leu Ile Asn Pro Ala Ala Ala Thr Arg Ile Lys Lys Lys
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Ser Ser Ser Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Ile Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Leu Gln
        195                 200                 205

Val Thr Ser Ser Pro Ser Asn Cys Ala Asn Leu His Gln Met Leu Ala
    210                 215                 220

Ser Tyr Ser Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asp Ser Phe Phe Asp Arg Asn Ile Gly Asn Leu Glu Asn Ser
        275                 280                 285

Leu Lys His Glu Gly His Ala Pro Ile Pro Leu Thr Thr Gly Asn
    290                 295                 300

Leu Thr Lys Thr Phe Leu Gln Leu Val Glu Asp Lys Phe Pro Ser Ser
305                 310                 315                 320
```

Ser Lys Ala Gln Lys Ala Leu Asn Glu Leu Val Gly Pro Asp Thr Gly
            325                 330                 335

Pro Gln Thr Glu Val Leu Asn Leu Phe Phe Arg Ala Leu Asn Gly Cys
        340                 345                 350

Ser Pro Arg Ile Phe Ser Gly Ala Glu Lys Lys Gln Gln Leu Ala Ser
            355                 360                 365

Val Ile Thr Asn Thr Leu Asp Ala Ile Asn Ala Asp Asn Glu Asp Tyr
370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
            405                 410                 415

Gln Pro Pro Ser Pro
            420

<210> SEQ ID NO 91
<211> LENGTH: 1266
<212> TYPE: DNA
<213> ORGANISM: Chlamydia trachomatis

<400> SEQUENCE: 91
atgactgcat caggaggagc tgagggcta  ggcagcaccc aaacagtaga cgttgcgcga       60
gcacaagctg ctgcagctac tcaagatgca caagaggtta tcggctctca ggaagcttct      120
gaggcaagta tgctcaaagg atgtgaggat ctcataaatc ctgcagctgc aacccgaatc      180
aaaaaaaaag gagagaagtt tgaatcatta gaagctcgtc gcaaaccaac agcggataaa      240
gcagaaaaga atccgagag  cacagaggaa aaggcgata  ctcctcttga agatcgtttc      300
acagaagatc tttccgaagt ctccggagaa gattttcgag gattgaaaaa ttcgttcgat      360
gatgattctt ctcctgacga aattctcgat gcgctcacaa gtaaattttc tgatcccaca      420
ataaaggatc tagctcttga ttatctaatt caaacagctc cctctgatgg gaaacttaag      480
tccactctca ttcaggcaaa gcatcaactg atgagccaga tcctcaggc  gattgttgga      540 ggacgcaatg ttctgttagc ttcagaaacc tttgcttcca gagcaaatac atctccttca      600
tcgcttcgct ccttatattt ccaagtaacc tcatcccccct ctaattgcgc taatttacat      660
caaatgcttg cttcttactt gccatcagag aaaaccgctg ttatggagtt tctagtaaat      720
ggcatggtag cagatttaaa atcggagggc ccttccattc ctcctgcaaa attgcaagta      780
tatatgacgg aactaagcaa tctccaagcc ttacactctg taaatagctt ttttgataga      840
aatattggga acttggaaaa tagcttaaag catgaaggac atgcccctat tccatcctta      900
acgacaggaa atttaactaa aaccttctta caattagtag aagataaatt cccttcctct      960
tccaaagctc aaaaggcatt aaatgaactg gtaggcccag atactggtcc tcaaactgaa     1020
gttttaaact tattcttccg cgctcttaat ggctgttcgc ctagaatatt ctctggagct     1080
gaaaaaaaac agcagctggc atcggttatc acaaatacgc tagatgcgat aaatgcggat     1140
aatgaggatt atcctaaacc aggtgacttc ccacgatctt ccttctctag tacgcctcct     1200
catgctccag tacctcaatc tgagattcca acgtcaccta cctcaacaca gcctccatca     1260
ccctaa                                                                1266

<210> SEQ ID NO 92
<211> LENGTH: 421
<212> TYPE: PRT
<213> ORGANISM: Chlamydia trachomatis -continued

<400> SEQUENCE: 92

```
Met Thr Ala Ser Gly Gly Ala Gly Gly Leu Gly Ser Thr Gln Thr Val
1               5                   10                  15

Asp Val Ala Arg Ala Gln Ala Ala Ala Thr Gln Asp Ala Gln Glu
            20                  25                  30

Val Ile Gly Ser Gln Glu Ala Ser Glu Ala Ser Met Leu Lys Gly Cys
            35                  40                  45

Glu Asp Leu Ile Asn Pro Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Lys Gly Asp Thr Pro Leu
                85                  90                  95

Glu Asp Arg Phe Thr Glu Asp Leu Ser Glu Val Ser Gly Glu Asp Phe
                100                 105                 110

Arg Gly Leu Lys Asn Ser Phe Asp Asp Ser Ser Pro Asp Glu Ile
            115                 120                 125

Leu Asp Ala Leu Thr Ser Lys Phe Ser Asp Pro Thr Ile Lys Asp Leu
130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
                180                 185                 190

Ser Arg Ala Asn Thr Ser Pro Ser Ser Leu Arg Ser Leu Tyr Phe Gln
            195                 200                 205

Val Thr Ser Ser Pro Ser Asn Cys Ala Asn Leu His Gln Met Leu Ala
210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Thr Pro Pro
385                 390                 395                 400

His Ala Pro Val Pro Gln Ser Glu Ile Pro Thr Ser Pro Thr Ser Thr
                405                 410                 415
```

Gln Pro Pro Ser Pro
            420

<210> SEQ ID NO 93
<211> LENGTH: 1266
<212> TYPE: DNA
<213> ORGANISM: Chlamydia trachomatis

<400> SEQUENCE: 93

| | | |
|---|---|---|
| atgactgcat caggaggagc tggagggcta ggcagcaccc aaacagtaga cgttgcgcga | 60 |
| gcacaagctg ctgcagctac tcaagatgca caagaggtta tcggctctca ggaagcttct | 120 |
| gaggcaagta tgctcaaaga atgtgaggat ctcataaatc ctgcagctgc aacccgaatc | 180 |
| aaaaaaaaag aagagaagtt tgaatcatta gaagctcgtc gcaaaccaac agcggataaa | 240 |
| gcagaaaaga atccgagag cacagaggaa aaggcgata ctcctcttga agatcgtttc | 300 |
| acagaagatc tttccgaagt ctctggagaa gattttcgag gattgaaaaa ttcgttcgat | 360 |
| gatgattctt cttctgacga aattctcgat gcgctcacaa gtaaattttc tgatcccaca | 420 |
| ataaaggatc tagctcttga ttatctaatt caaatagctc cctctgatgg gaaacttaag | 480 |
| tccgctctca ttcaggcaaa gcatcaactg atgagccaga tcctcaggc gattgttgga | 540 |
| ggacgcaatg ttctgttagc ttcagaaacc tttgcttcca gagcaaatac atctccttca | 600 |
| tcgcttcgct cctatatttt ccaagtaacc tcatccccct ctaattgcgc taatttacat | 660 |
| caaatgcttg cttcttactc gccatcagag aaaaccgctg ttatggagtt tctagtgaat | 720 |
| ggcatggtag cagatttaaa atcggagggc ccttccattc ctcctgcaaa attgcaagta | 780 |
| tatatgacgg aactaagcaa tctccaagcc ttacactctg tagatagctt ttttgataga | 840 |
| aatattggga acttggaaaa tagcttaaag catgaaggac atgcccctat tccatcctta | 900 |
| acgacaggaa atttaactaa aaccttctta caattagtag aagataaatt cccttcctct | 960 |
| tccaaagctc aaaaggcatt aaatgaactg gtaggcccgg atactggtcc tcaaactgaa | 1020 |
| gttttaaact tattcttccg cgctcttaat ggctgttcgc ctagaatatt ctctggagct | 1080 |
| gaaaaaaaac agcagctggc atcggttatc acaaatacgc tagatgcgat aaatgcggat | 1140 |
| aatgaggatt atcctaaacc aggtgacttc ccacgatctt ccttctctag tacgcctcct | 1200 |
| catgctccag tacctcaatc tgagattcca acgtcaccta cctcaacaca gcctccatca | 1260 |
| ccctaa | 1266 |

<210> SEQ ID NO 94
<211> LENGTH: 421
<212> TYPE: PRT
<213> ORGANISM: Chlamydia trachomatis

<400> SEQUENCE: 94

Met Thr Ala Ser Gly Gly Ala Gly Gly Leu Gly Ser Thr Gln Thr Val
1               5                   10                  15

Asp Val Ala Arg Ala Gln Ala Ala Ala Thr Gln Asp Ala Gln Glu
            20                  25                  30

Val Ile Gly Ser Gln Glu Ala Ser Glu Ala Ser Met Leu Lys Glu Cys
        35                  40                  45

Glu Asp Leu Ile Asn Pro Ala Ala Ala Thr Arg Ile Lys Lys Lys Glu
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Ser Ser Asp Glu Ile
        115                 120                 125

Leu Asp Ala Leu Thr Ser Lys Phe Ser Asp Pro Thr Ile Lys Asp Leu
130                 135                 140

Ala Leu Asp Tyr Leu Ile Gln Ile Ala Pro Ser Asp Gly Lys Leu Lys
145                 150                 155                 160

Ser Ala Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
                180                 185                 190

Ser Arg Ala Asn Thr Ser Pro Ser Ser Leu Arg Ser Leu Tyr Phe Gln
                195                 200                 205

Val Thr Ser Ser Pro Ser Asn Cys Ala Asn Leu His Gln Met Leu Ala
        210                 215                 220

Ser Tyr Ser Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
                260                 265                 270

Ser Val Asp Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
        290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
            355                 360                 365

Val Ile Thr Asn Thr Leu Asp Ala Ile Asn Ala Asp Asn Glu Asp Tyr
            370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420

<210> SEQ ID NO 95
<211> LENGTH: 1749
<212> TYPE: DNA
<213> ORGANISM: Chlamydia trachomatis

<400> SEQUENCE: 95
atggtacaag gagaaagctt ggtttgcaag aatgctcttc aagatttgag ttttttagag     60
catttattac aggttaaata tgctcctaaa acatggaaag agcaatactt aggatgggat    120
cttgttcaaa gctccgtttc tgcacagcag aagcttcgta cacaagaaaa tccatcaaca    180 agttttgcc agcaggtcct tgctgatttt atcggaggat taaatgactt tcacgctgga    240

-continued

```
gtaactttct tgcgataga aagtgcttac cttccttata ccgtacaaaa aagtagtgac    300
ggccgtttct actttgtaga tatcatgact ttttcttcag agatccgtgt tggagatgag    360
ttgctagagg tggatggggc gcctgtccaa gatgtactcg ctactctata tggaagcaat    420
cacaaaggga ctgcagctga agagtcggct gctttaagaa cactattttc tcgcatggcc    480
tctttagggc acaaagtacc ttctgggcgc actactttaa agattcgtcg tccttttggt    540
actacgagag aagttcgtgt gaaatggcgt tatgttcctg aaggtgtagg agatttggct    600
accatagctc cttctatcag ggctccacag ttacagaaat cgatgagaag ctttttcctt    660
aagaaagatg atgcgtttca tcggtctagt tcgctattct actctccaat ggttccgcat    720
ttttgggcag agcttcgcaa tcattatgca acgagtggtt tgaaaagcgg gtacaatatt    780
gggagtaccg atgggtttct ccctgtcatt gggcctgtta tatgggagtc ggagggtctt    840
ttccgcgctt atatttcttc ggtgactgat ggggatggta agagccataa agtaggattt    900
ctaagaattc ctacatatag ttggcaggac atggaagatt tgatccttc aggaccgcct    960
ccttgggaag aatttgctaa gattattcaa gtattttctt ctaatacaga agctttgatt   1020
atcgaccaaa cgaacaaccc aggtggtagt gtcctttatc tttatgcact gctttccatg   1080
ttgacagacc gtcctttaga acttcctaaa catagaatga ttctgactca ggatgaagtg   1140
gttgatgctt tagattggtt aaccctgttg gaaaacgtag acacaaacgt ggartctcgc   1200
cttgctctgg gagacaacat ggaaggatat actgtggatc tacaggttgc cgagtattta   1260
aaaagctttg gacgtcaagt attgaattgt tggagtaaag gggatattga gttatcaacg   1320
cctattcctc ttttttggttt tgagaagatt catccacatc ctcgagttca atactctaaa   1380
ccgatttgtg ttttgatcaa tgagcaagac ttttcttgtg ctgacttctt ccctgtagtt   1440
ttgaaagaca atgatcgagc tcttattgtt ggtactcgaa cagctggagc tggaggattt   1500
gtctttaatg tgcagttccc aaatagaact ggaataaaaa cttgttcttt aacaggatca   1560
ttagctgtta gagagcatgg tgccttcatt gagaacatcg gagtcgaacc gcatatcgat   1620
ctgccttta cagcgaatga tattcgctat aaaggctatt ccgagtatct tgataaggtc   1680
aaaaaattgg tttgtcagct gatcaataac gacggtacca ttattcttgc ggaagatggt   1740
agttttag                                                            1749
```

<210> SEQ ID NO 96
<211> LENGTH: 582
<212> TYPE: PRT
<213> ORGANISM: Chlamydia trachomatis

<400> SEQUENCE: 96

```
Met Val Gln Gly Glu Ser Leu Val Cys Lys Asn Ala Leu Gln Asp Leu
 1               5                  10                  15

Ser Phe Leu Glu His Leu Leu Gln Val Lys Tyr Ala Pro Lys Thr Trp
            20                  25                  30

Lys Glu Gln Tyr Leu Gly Trp Asp Leu Val Gln Ser Val Ser Ala
        35                  40                  45

Gln Gln Lys Leu Arg Thr Gln Glu Asn Pro Ser Thr Ser Phe Cys Gln
    50                  55                  60

Gln Val Leu Ala Asp Phe Ile Gly Gly Leu Asn Asp Phe His Ala Gly
65                  70                  75                  80

Val Thr Phe Phe Ala Ile Glu Ser Ala Tyr Leu Pro Tyr Thr Val Gln
                85                  90                  95

Lys Ser Ser Asp Gly Arg Phe Tyr Phe Val Asp Ile Met Thr Phe Ser
            100                 105                 110
```

```
Ser Glu Ile Arg Val Gly Asp Glu Leu Leu Glu Val Asp Gly Ala Pro
            115                 120                 125

Val Gln Asp Val Leu Ala Thr Leu Tyr Gly Ser Asn His Lys Gly Thr
        130                 135                 140

Ala Ala Glu Glu Ser Ala Ala Leu Arg Thr Leu Phe Ser Arg Met Ala
145                 150                 155                 160

Ser Leu Gly His Lys Val Pro Ser Gly Arg Thr Thr Leu Lys Ile Arg
                165                 170                 175

Arg Pro Phe Gly Thr Thr Arg Glu Val Arg Val Lys Trp Arg Tyr Val
            180                 185                 190

Pro Glu Gly Val Gly Asp Leu Ala Thr Ile Ala Pro Ser Ile Arg Ala
        195                 200                 205

Pro Gln Leu Gln Lys Ser Met Arg Ser Phe Phe Leu Lys Lys Asp Asp
        210                 215                 220

Ala Phe His Arg Ser Ser Ser Leu Phe Tyr Ser Pro Met Val Pro His
225                 230                 235                 240

Phe Trp Ala Glu Leu Arg Asn His Tyr Ala Thr Ser Gly Leu Lys Ser
                245                 250                 255

Gly Tyr Asn Ile Gly Ser Thr Asp Gly Phe Leu Pro Val Ile Gly Pro
            260                 265                 270

Val Ile Trp Glu Ser Glu Gly Leu Phe Arg Ala Tyr Ile Ser Ser Val
        275                 280                 285

Thr Asp Gly Asp Gly Lys Ser His Lys Val Gly Phe Leu Arg Ile Pro
        290                 295                 300

Thr Tyr Ser Trp Gln Asp Met Glu Asp Phe Asp Pro Ser Gly Pro Pro
305                 310                 315                 320

Pro Trp Glu Glu Phe Ala Lys Ile Ile Gln Val Phe Ser Ser Asn Thr
                325                 330                 335

Glu Ala Leu Ile Ile Asp Gln Thr Asn Asn Pro Gly Gly Ser Val Leu
            340                 345                 350

Tyr Leu Tyr Ala Leu Leu Ser Met Leu Thr Asp Arg Pro Leu Glu Leu
            355                 360                 365

Pro Lys His Arg Met Ile Leu Thr Gln Asp Glu Val Val Asp Ala Leu
        370                 375                 380

Asp Trp Leu Thr Leu Leu Glu Asn Val Asp Thr Asn Val Glu Ser Arg
385                 390                 395                 400

Leu Ala Leu Gly Asp Asn Met Glu Gly Tyr Thr Val Asp Leu Gln Val
                405                 410                 415

Ala Glu Tyr Leu Lys Ser Phe Gly Arg Gln Val Leu Asn Cys Trp Ser
            420                 425                 430

Lys Gly Asp Ile Glu Leu Ser Thr Pro Ile Pro Leu Phe Gly Phe Glu
        435                 440                 445

Lys Ile His Pro His Pro Arg Val Gln Tyr Ser Lys Pro Ile Cys Val
        450                 455                 460

Leu Ile Asn Glu Gln Asp Phe Ser Cys Ala Asp Phe Phe Pro Val Val
465                 470                 475                 480

Leu Lys Asp Asn Asp Arg Ala Leu Ile Val Gly Thr Arg Thr Ala Gly
                485                 490                 495

Ala Gly Gly Phe Val Phe Asn Val Gln Phe Pro Asn Arg Thr Gly Ile
            500                 505                 510

Lys Thr Cys Ser Leu Thr Gly Ser Leu Ala Val Arg Glu His Gly Ala
            515                 520                 525

Phe Ile Glu Asn Ile Gly Val Glu Pro His Ile Asp Leu Pro Phe Thr
```

```
            530              535              540
Ala Asn Asp Ile Arg Tyr Lys Gly Tyr Ser Glu Tyr Leu Asp Lys Val
545                  550              555              560

Lys Lys Leu Val Cys Gln Leu Ile Asn Asn Asp Gly Thr Ile Ile Leu
                565              570              575

Ala Glu Asp Gly Ser Phe
            580

<210> SEQ ID NO 97
<211> LENGTH: 1749
<212> TYPE: DNA
<213> ORGANISM: Chlamydia trachomatis

<400> SEQUENCE: 97
```

| | | | | | |
|---|---|---|---|---|---|
| atggtacaag | gagaaagctt | ggtttgcaag | aatgctcttc | aagatttgag | ttttttagag | 60 |
| catttattac | aggttaaata | tgctcctaaa | acatggaaag | agcaatactt | aggatgggat | 120 |
| cttgttcaaa | gctccgtttc | tgcacagcag | aagcttcgta | cacaagaaaa | tccatcaaca | 180 |
| agttttgcc | agcaggtcct | tgctgatttt | atcggaggat | taaatgactt | tcacgctgga | 240 |
| gtaactttct | ttgcgataga | aagtgcttac | cttcctata | ccgtacaaaa | aagtagtgac | 300 |
| ggccgtttct | actttgtaga | tatcatgact | ttttcttcag | atccgtgt | tggagatgag | 360 |
| ttgctagagg | tggatggggc | gcctgtccaa | gatgtactcg | ctactctata | tggaagcaat | 420 |
| cacaaaggga | ctgcagctga | agagtcggct | gctttaagaa | cactatttc | tcgcatggcc | 480 |
| tctttagggc | acaaagtacc | ttctgggcgc | actactttaa | agattcgtcg | tccttttggt | 540 |
| actacgagag | aagttcgtgt | gaaatggcgt | tatgttcctg | aaggtgtagg | agatttggct | 600 |
| accatagctc | cttctatcag | ggctccacag | ttacagaaat | cgatgagaag | ctttttccct | 660 |
| aagaaagatg | atgcgtttca | tcggtctagt | tcgctattct | actctccaat | ggttccgcat | 720 |
| ttttgggcag | agcttcgcaa | tcattatgca | acgagtggt | tgaaaagcgg | gtacaatatt | 780 |
| gggagtaccg | atgggtttct | ccctgtcatt | gggcctgtta | tatgggagtc | ggagggtctt | 840 |
| ttccgcgctt | atatttcttc | ggtgactgat | ggggatggta | agagccataa | agtaggattt | 900 |
| ctaagaattc | ctacatatag | ttggcaggac | atggaagatt | ttgatccttc | aggaccgcct | 960 |
| ccttgggaag | aatttgctaa | gattattcaa | gtattttctt | ctaatacaga | agctttgatt | 1020 |
| atcgaccaaa | cgaacaaccc | aggtggtagt | gtcctttatc | tttatgcact | gctttccatg | 1080 |
| ttgacagacc | gtcctttaga | acttcctaaa | catagaatga | ttctgactca | ggatgaagtg | 1140 |
| gttgatgctt | tagattggtt | aaccctgttg | gaaaacgtag | acacaaacgt | ggaatctcgc | 1200 |
| cttgctctgg | gagacaacat | ggaaggatat | actgtggatc | tacaggttgc | cgagtattta | 1260 |
| aaaagctttg | gacgtcaagt | attgaattgt | tggagtaaag | gggatatcga | gttatcaacg | 1320 |
| cctattcctc | tttttggttt | tgagaagatt | catccacatc | ctcgagttca | atactctaaa | 1380 |
| ccgatttgtg | ttttgatcaa | tgagcaagac | ttttcttgtg | ctgacttctt | ccctgtagtt | 1440 |
| ttgaaagaca | atgatcgagc | tcttattgtt | ggtactcgaa | cagctggagc | tggaggattt | 1500 |
| gtctttaatg | tgcagttccc | aaatagaact | ggaataaaaa | cttgttcttt | aacaggatca | 1560 |
| ttagctgtta | gagagcatgg | tgccttcatt | gagaacatcg | gagtcgaacc | gcatatcgat | 1620 |
| ctgccttta | cagcgaatga | tattcgctat | aaaggctatt | ccgagtatct | tgataaggtc | 1680 |
| aaaaaattgg | tttgtcagct | gatcaataac | gacggtacca | ttattcttgc | ggaagatggt | 1740 |
| agttttag | | | | | | 1749 |

```
<210> SEQ ID NO 98
<211> LENGTH: 582
<212> TYPE: PRT
<213> ORGANISM: Chlamydia trachomatis

<400> SEQUENCE: 98

Met Val Gln Gly Glu Ser Leu Val Cys Lys Asn Ala Leu Gln Asp Leu
1               5                   10                  15

Ser Phe Leu Glu His Leu Leu Gln Val Lys Tyr Ala Pro Lys Thr Trp
            20                  25                  30

Lys Glu Gln Tyr Leu Gly Trp Asp Leu Val Gln Ser Ser Val Ser Ala
        35                  40                  45

Gln Gln Lys Leu Arg Thr Gln Glu Asn Pro Ser Thr Ser Phe Cys Gln
    50                  55                  60

Gln Val Leu Ala Asp Phe Ile Gly Gly Leu Asn Asp Phe His Ala Gly
65                  70                  75                  80

Val Thr Phe Phe Ala Ile Glu Ser Ala Tyr Leu Pro Tyr Thr Val Gln
                85                  90                  95

Lys Ser Ser Asp Gly Arg Phe Tyr Phe Val Asp Ile Met Thr Phe Ser
            100                 105                 110

Ser Glu Ile Arg Val Gly Asp Glu Leu Leu Glu Val Asp Gly Ala Pro
        115                 120                 125

Val Gln Asp Val Leu Ala Thr Leu Tyr Gly Ser Asn His Lys Gly Thr
    130                 135                 140

Ala Ala Glu Glu Ser Ala Ala Leu Arg Thr Leu Phe Ser Arg Met Ala
145                 150                 155                 160

Ser Leu Gly His Lys Val Pro Ser Gly Arg Thr Thr Leu Lys Ile Arg
                165                 170                 175

Arg Pro Phe Gly Thr Thr Arg Glu Val Arg Val Lys Trp Arg Tyr Val
            180                 185                 190

Pro Glu Gly Val Gly Asp Leu Ala Thr Ile Ala Pro Ser Ile Arg Ala
        195                 200                 205

Pro Gln Leu Gln Lys Ser Met Arg Ser Phe Pro Lys Lys Asp Asp
    210                 215                 220

Ala Phe His Arg Ser Ser Ser Leu Phe Tyr Ser Pro Met Val Pro His
225                 230                 235                 240

Phe Trp Ala Glu Leu Arg Asn His Tyr Ala Thr Ser Gly Leu Lys Ser
                245                 250                 255

Gly Tyr Asn Ile Gly Ser Thr Asp Gly Phe Leu Pro Val Ile Gly Pro
            260                 265                 270

Val Ile Trp Glu Ser Glu Gly Leu Phe Arg Ala Tyr Ile Ser Ser Val
        275                 280                 285

Thr Asp Gly Asp Gly Lys Ser His Lys Val Gly Phe Leu Arg Ile Pro
    290                 295                 300

Thr Tyr Ser Trp Gln Asp Met Glu Asp Phe Asp Pro Ser Gly Pro Pro
305                 310                 315                 320

Pro Trp Glu Glu Phe Ala Lys Ile Ile Gln Val Phe Ser Ser Asn Thr
                325                 330                 335

Glu Ala Leu Ile Ile Asp Gln Thr Asn Asn Pro Gly Gly Ser Val Leu
            340                 345                 350

Tyr Leu Tyr Ala Leu Leu Ser Met Leu Thr Asp Arg Pro Leu Glu Leu
        355                 360                 365

Pro Lys His Arg Met Ile Leu Thr Gln Asp Glu Val Val Asp Ala Leu
    370                 375                 380

Asp Trp Leu Thr Leu Leu Glu Asn Val Asp Thr Asn Val Glu Ser Arg
```

```
                385                 390                 395                 400
Leu Ala Leu Gly Asp Asn Met Glu Gly Tyr Thr Val Asp Leu Gln Val
                    405                 410                 415
Ala Glu Tyr Leu Lys Ser Phe Gly Arg Gln Val Leu Asn Cys Trp Ser
                420                 425                 430
Lys Gly Asp Ile Glu Leu Ser Thr Pro Ile Pro Leu Phe Gly Phe Glu
            435                 440                 445
Lys Ile His Pro His Pro Arg Val Gln Tyr Ser Lys Pro Ile Cys Val
        450                 455                 460
Leu Ile Asn Glu Gln Asp Phe Ser Cys Ala Asp Phe Phe Pro Val Val
465                 470                 475                 480
Leu Lys Asp Asn Asp Arg Ala Leu Ile Val Gly Thr Arg Thr Ala Gly
                485                 490                 495
Ala Gly Gly Phe Val Phe Asn Val Gln Phe Pro Asn Arg Thr Gly Ile
                500                 505                 510
Lys Thr Cys Ser Leu Thr Gly Ser Leu Ala Val Arg Glu His Gly Ala
            515                 520                 525
Phe Ile Glu Asn Ile Gly Val Glu Pro His Ile Asp Leu Pro Phe Thr
        530                 535                 540
Ala Asn Asp Ile Arg Tyr Lys Gly Tyr Ser Glu Tyr Leu Asp Lys Val
545                 550                 555                 560
Lys Lys Leu Val Cys Gln Leu Ile Asn Asn Asp Gly Thr Ile Ile Leu
                565                 570                 575
Ala Glu Asp Gly Ser Phe
            580

<210> SEQ ID NO 99
<211> LENGTH: 1749
<212> TYPE: DNA
<213> ORGANISM: Chlamydia trachomatis

<400> SEQUENCE: 99
atggtacaag gagaaagctt ggtttgcaag aatgctcttc aagatttgag ttttttagag    60
catttattac aggttaaata tgctcctaaa acatggaaag agcaatactt aggatgggat   120
cttgttcaaa gctccgtttc tgcacagcag aagcttcgta cacaagaaaa tccatcaaca   180
agttttgcc agcaggtcct tgctgatttt atcggaggat taaatgactt tcacgctgga   240
gtaactttct ttgcgataga aagtgcttac cttccttata ccgtacaaaa aagtagtgac   300
ggccgttct actttgtaga tatcatgact ttttcttcag atccgtgt tggagatgag     360
ttgctagagg tggatggggc gcctgtccaa gatgtactcg ctactctata tggaagcaat   420
cacaaaggga ctgcagctga gagtcggct gctttaagaa cactattttc tcgcatggcc   480
tctttagggc acaaagtacc ttctgggcgc actactttaa agattcgtcg tccttttggt   540
actacgagag aagttcgtgt gaaatggcgt tatgttcctg aaggtgtagg agatttggct   600
accatagctc cttctatcag ggctccacag ttacagaaat cgatgagaag cttttttccct   660
aagaaagatg atgcgtttca tcggtctagt tcgctattct actctccaat ggttccgcat   720
ttttgggcag agcttcgcaa tcattatgca acgagtggtt tgaaaagcgg gtacaatatt   780
gggagtaccg atgggtttct ccctgtcatt gggcctgtta tatgggagtc ggagggtctt   840
ttccgcgctt atatttcttc ggtgactgat ggggatggta gagccataa agtaggattt   900
ctaagaattc ctacatatag ttggcaggac atggaagatt tgatccttc aggaccgcct   960
ccttgggaag aatttgctaa gattattcaa gtattttctt ctaatacaga agctttgatt   1020
```

-continued

```
atcgaccaaa cgaacaaccc aggtggtagt gtcctttatc tttatgcact gctttccatg    1080
ttgacagacc gtcctttaga acttcctaaa catagaatga ttctgactca ggatgaagtg    1140
gttgatgctt tagattggtt aaccctgttg gaaaacgtag acacaaacgt ggagtctcgc    1200
cttgctctgg gagacaacat ggaaggatat actgtggatc tacaggttgc cgagtattta    1260
aaaagctttg gacgtcaagt attgaattgt tggagtaaag gggatatcga gttatcaacg    1320
cctattcctc tttttggttt tgagaagatt catccacatc ctcgagttca atactctaaa    1380
ccgatttgtg ttttgatcaa tgagcaagac ttttcttgtg ctgacttctt ccctgtagtt    1440
ttgaaagaca atgatcgagc tcttattgtt ggtactcgaa cagctggagc tggaggattt    1500
gtctttaatg tgcagttccc aaatagaact ggaataaaaa cttgttcttt aacaggatca    1560
ttagctgtta gagagcatgg tgccttcatt gagaacatcg gagtcgaacc gcatatcgat    1620 ctgccttta cagcgaatga tattcgctat aaaggctatt ccgagtatct tgataaggtc    1680
aaaaaattgg tttgtcagct gatcaataac gacggtacca ttattcttgc ggaagatggt    1740
agttttag                                                              1749
```

<210> SEQ ID NO 100
<211> LENGTH: 582
<212> TYPE: PRT
<213> ORGANISM: Chlamydia trachomatis

<400> SEQUENCE: 100

```
Met Val Gln Gly Glu Ser Leu Val Cys Lys Asn Ala Leu Gln Asp Leu
1               5                   10                  15

Ser Phe Leu Glu His Leu Leu Gln Val Lys Tyr Ala Pro Lys Thr Trp
            20                  25                  30

Lys Glu Gln Tyr Leu Gly Trp Asp Leu Val Gln Ser Ser Val Ser Ala
        35                  40                  45

Gln Gln Lys Leu Arg Thr Gln Glu Asn Pro Ser Thr Ser Phe Cys Gln
    50                  55                  60

Gln Val Leu Ala Asp Phe Ile Gly Gly Leu Asn Asp Phe His Ala Gly
65                  70                  75                  80

Val Thr Phe Phe Ala Ile Glu Ser Ala Tyr Leu Pro Tyr Thr Val Gln
                85                  90                  95

Lys Ser Asp Gly Arg Phe Tyr Phe Val Asp Ile Met Thr Phe Ser
            100                 105                 110

Ser Glu Ile Arg Val Gly Asp Glu Leu Leu Glu Val Asp Gly Ala Pro
        115                 120                 125

Val Gln Asp Val Leu Ala Thr Leu Tyr Gly Ser Asn His Lys Gly Thr
    130                 135                 140

Ala Ala Glu Glu Ser Ala Ala Leu Arg Thr Leu Phe Ser Arg Met Ala
145                 150                 155                 160

Ser Leu Gly His Lys Val Pro Ser Gly Arg Thr Thr Leu Lys Ile Arg
                165                 170                 175

Arg Pro Phe Gly Thr Thr Arg Glu Val Arg Val Lys Trp Arg Tyr Val
            180                 185                 190

Pro Glu Gly Val Gly Asp Leu Ala Thr Ile Ala Pro Ser Ile Arg Ala
        195                 200                 205

Pro Gln Leu Gln Lys Ser Met Arg Ser Phe Pro Lys Lys Asp Asp
    210                 215                 220

Ala Phe His Arg Ser Ser Ser Leu Phe Tyr Ser Pro Met Val Pro His
225                 230                 235                 240

Phe Trp Ala Glu Leu Arg Asn His Tyr Ala Thr Ser Gly Leu Lys Ser
```

-continued

```
                245                 250                 255
Gly Tyr Asn Ile Gly Ser Thr Asp Gly Phe Leu Pro Val Ile Gly Pro
            260                 265                 270

Val Ile Trp Glu Ser Glu Gly Leu Phe Arg Ala Tyr Ile Ser Ser Val
        275                 280                 285

Thr Asp Gly Asp Gly Lys Ser His Lys Val Gly Phe Leu Arg Ile Pro
    290                 295                 300

Thr Tyr Ser Trp Gln Asp Met Glu Asp Phe Asp Pro Ser Gly Pro Pro
305                 310                 315                 320

Pro Trp Glu Glu Phe Ala Lys Ile Ile Gln Val Phe Ser Ser Asn Thr
                325                 330                 335

Glu Ala Leu Ile Ile Asp Gln Thr Asn Asn Pro Gly Gly Ser Val Leu
            340                 345                 350

Tyr Leu Tyr Ala Leu Leu Ser Met Leu Thr Asp Arg Pro Leu Glu Leu
        355                 360                 365

Pro Lys His Arg Met Ile Leu Thr Gln Asp Glu Val Val Asp Ala Leu
    370                 375                 380

Asp Trp Leu Thr Leu Leu Glu Asn Val Asp Thr Asn Val Glu Ser Arg
385                 390                 395                 400

Leu Ala Leu Gly Asp Asn Met Glu Gly Tyr Thr Val Asp Leu Gln Val
                405                 410                 415

Ala Glu Tyr Leu Lys Ser Phe Gly Arg Gln Val Leu Asn Cys Trp Ser
            420                 425                 430

Lys Gly Asp Ile Glu Leu Ser Thr Pro Ile Pro Leu Phe Gly Phe Glu
        435                 440                 445

Lys Ile His Pro His Pro Arg Val Gln Tyr Ser Lys Pro Ile Cys Val
    450                 455                 460

Leu Ile Asn Glu Gln Asp Phe Ser Cys Ala Asp Phe Phe Pro Val Val
465                 470                 475                 480

Leu Lys Asp Asn Asp Arg Ala Leu Ile Val Gly Thr Arg Thr Ala Gly
                485                 490                 495

Ala Gly Gly Phe Val Phe Asn Val Gln Phe Pro Asn Arg Thr Gly Ile
            500                 505                 510

Lys Thr Cys Ser Leu Thr Gly Ser Leu Ala Val Arg Glu His Gly Ala
        515                 520                 525

Phe Ile Glu Asn Ile Gly Val Glu Pro His Ile Asp Leu Pro Phe Thr
    530                 535                 540

Ala Asn Asp Ile Arg Tyr Lys Gly Tyr Ser Glu Tyr Leu Asp Lys Val
545                 550                 555                 560

Lys Lys Leu Val Cys Gln Leu Ile Asn Asn Asp Gly Thr Ile Ile Leu
                565                 570                 575

Ala Glu Asp Gly Ser Phe
            580

<210> SEQ ID NO 101
<211> LENGTH: 1749
<212> TYPE: DNA
<213> ORGANISM: Chlamydia trachomatis

<400> SEQUENCE: 101
atggtacaag gagaaagctt ggtttgcaag aatgctcttc aagatttgag ttttttagag    60
catttattac aggttaaata tgctcctaaa acatggaaag agcaatactt aggatgggat   120
cttgttcaaa gctccgtttc tgcacagcag aagcttcgta cacaagaaaa tccatcaaca   180 agttttttgcc agcaggtcct tgctgatttt atcggaggat taaatgactt tcacgctgga   240
```

```
gtaactttct tgcgataga aagtgcttac cttccttata ccgtacaaaa aagtagtgac      300
ggccgtttct actttgtaga tatcatgact ttttcttcag agatccgtgt tggagatgag      360
ttgctagagg tggatggggc gcctgtccaa gatgtactcg ctactctata tggaagcaat      420
cacaaaggga ctgcagctga agagtcggct gctttaagaa cactatttc tcgcatggcc      480
tctttagggc acaaagtacc ttctgggcgc actactttaa agattcgtcg tccttttggt      540
actacgagag aagttcgtgt gaaatggcgt tatgttcctg aaggtgtagg agatttggct      600
accatagctc cttctatcag ggctccacag ttacagaaat cgatgagaag cttttttccct     660
aagaaagatg atgcgtttca tcggtctagt tcgctattct actctccaat ggttccgcat      720
ttttgggcag agcttcgcaa tcattatgca acgagtggtt tgaaaagcgg gtacaatatt      780
gggagtaccg atgggtttct ccctgtcatt gggcctgtta tatgggagtc ggagggtctt      840
ttccgcgctt atatttcttc ggtgactgat ggggatggta agagccataa agtaggattt      900
ctaagaattc ctacatatag ttggcaggac atggaagatt tgatccttc aggaccgcct      960
ccttgggaag aatttgctaa gattattcaa gtattttctt ctaatacaga agctttgatt     1020
atcgaccaaa cgaacaaccc aggtggtagt gtcctttatc tttatgcact gctttccatg     1080
ttgacagacc gtcctttaga acttcctaaa catagaatga ttctgactca ggatgaagtg     1140
gttgatgctt tagattggtt aaccctgttg gaaaacgtag acacaaacgt ggagtctcgc     1200
cttgctctgg gagacaacat ggaaggatat actgtggatc tacaggttgc cgagtattta     1260
aaaagctttg gacgtcaagt attgaattgt tggagtaaag gggatatcga gttatcaacg     1320
cctattcctc ttttttggttt tgagaagatt catccacatc ctcgagttca atactctaaa     1380
ccgatttgtg ttttgatcaa tgagcaagac ttttcttgtg ctgacttctt ccctgtagtt     1440
ttgaaagaca atgatcgagc tcttattgtt ggtactcgaa cagctggagc tggaggattt     1500
gtctttaatg tgcagttccc aaatagaact ggaataaaaa cttgttcttt aacaggatca     1560
ttagctgtta gagagcatgg tgccttcatt gagaacatcg gagtcgaacc gcatatcgat     1620
ctgccttttta cagcgaatga tattcgctat aaaggctatt ccgagtatct tgataaggtc     1680
aaaaaattgg tttgtcagct gatcaataac gacggtacca ttattcttgc ggaagatggt     1740
agttttag                                                              1749
```

<210> SEQ ID NO 102
<211> LENGTH: 582
<212> TYPE: PRT
<213> ORGANISM: Chlamydia trachomatis

<400> SEQUENCE: 102

```
Met Val Gln Gly Glu Ser Leu Val Cys Lys Asn Ala Leu Gln Asp Leu
1               5                   10                  15

Ser Phe Leu Glu His Leu Leu Gln Val Lys Tyr Ala Pro Lys Thr Trp
            20                  25                  30

Lys Glu Gln Tyr Leu Gly Trp Asp Leu Val Gln Ser Val Ser Ala
        35                  40                  45

Gln Gln Lys Leu Arg Thr Gln Glu Asn Pro Ser Thr Ser Phe Cys Gln
    50                  55                  60

Gln Val Leu Ala Asp Phe Ile Gly Gly Leu Asn Asp Phe His Ala Gly
65                  70                  75                  80

Val Thr Phe Phe Ala Ile Glu Ser Ala Tyr Leu Pro Tyr Thr Val Gln
                85                  90                  95

Lys Ser Ser Asp Gly Arg Phe Tyr Phe Val Asp Ile Met Thr Phe Ser
```

```
                    100                 105                 110
Ser Glu Ile Arg Val Gly Asp Glu Leu Leu Glu Val Asp Gly Ala Pro
            115                 120                 125
Val Gln Asp Val Leu Ala Thr Leu Tyr Gly Ser Asn His Lys Gly Thr
        130                 135                 140
Ala Ala Glu Glu Ser Ala Leu Arg Thr Leu Phe Ser Arg Met Ala
145                 150                 155                 160
Ser Leu Gly His Lys Val Pro Ser Gly Arg Thr Thr Leu Lys Ile Arg
                165                 170                 175
Arg Pro Phe Gly Thr Thr Arg Glu Val Arg Val Lys Trp Arg Tyr Val
            180                 185                 190
Pro Glu Gly Val Gly Asp Leu Ala Thr Ile Ala Pro Ser Ile Arg Ala
        195                 200                 205
Pro Gln Leu Gln Lys Ser Met Arg Ser Phe Phe Pro Lys Lys Asp Asp
        210                 215                 220
Ala Phe His Arg Ser Ser Leu Phe Tyr Ser Pro Met Val Pro His
225                 230                 235                 240
Phe Trp Ala Glu Leu Arg Asn His Tyr Ala Thr Ser Gly Leu Lys Ser
                245                 250                 255
Gly Tyr Asn Ile Gly Ser Thr Asp Gly Phe Leu Pro Val Ile Gly Pro
            260                 265                 270
Val Ile Trp Glu Ser Glu Gly Leu Phe Arg Ala Tyr Ile Ser Ser Val
        275                 280                 285
Thr Asp Gly Asp Gly Lys Ser His Lys Val Gly Phe Leu Arg Ile Pro
        290                 295                 300
Thr Tyr Ser Trp Gln Asp Met Glu Asp Phe Asp Pro Ser Gly Pro Pro
305                 310                 315                 320
Pro Trp Glu Glu Phe Ala Lys Ile Ile Gln Val Phe Ser Ser Asn Thr
                325                 330                 335
Glu Ala Leu Ile Ile Asp Gln Thr Asn Asn Pro Gly Gly Ser Val Leu
            340                 345                 350
Tyr Leu Tyr Ala Leu Leu Ser Met Leu Thr Asp Arg Pro Leu Glu Leu
        355                 360                 365
Pro Lys His Arg Met Ile Leu Thr Gln Asp Glu Val Val Asp Ala Leu
        370                 375                 380
Asp Trp Leu Thr Leu Leu Glu Asn Val Asp Thr Asn Val Glu Ser Arg
385                 390                 395                 400
Leu Ala Leu Gly Asp Asn Met Glu Gly Tyr Thr Val Asp Leu Gln Val
                405                 410                 415
Ala Glu Tyr Leu Lys Ser Phe Gly Arg Gln Val Leu Asn Cys Trp Ser
            420                 425                 430
Lys Gly Asp Ile Glu Leu Ser Thr Pro Ile Pro Leu Phe Gly Phe Glu
        435                 440                 445
Lys Ile His Pro His Pro Arg Val Gln Tyr Ser Lys Pro Ile Cys Val
        450                 455                 460
Leu Ile Asn Glu Gln Asp Phe Ser Cys Ala Asp Phe Pro Val Val
465                 470                 475                 480
Leu Lys Asp Asn Asp Arg Ala Leu Ile Val Gly Thr Arg Thr Ala Gly
                485                 490                 495
Ala Gly Gly Phe Val Phe Asn Val Gln Phe Pro Asn Arg Thr Gly Ile
            500                 505                 510
Lys Thr Cys Ser Leu Thr Gly Ser Leu Ala Val Arg Glu His Gly Ala
        515                 520                 525
```

```
Phe Ile Glu Asn Ile Gly Val Glu Pro His Ile Asp Leu Pro Phe Thr
        530                 535                 540
Ala Asn Asp Ile Arg Tyr Lys Gly Tyr Ser Glu Tyr Leu Asp Lys Val
545                 550                 555                 560
Lys Lys Leu Val Cys Gln Leu Ile Asn Asn Asp Gly Thr Ile Ile Leu
                565                 570                 575
Ala Glu Asp Gly Ser Phe
            580

<210> SEQ ID NO 103
<211> LENGTH: 1749
<212> TYPE: DNA
<213> ORGANISM: Chlamydia trachomatis

<400> SEQUENCE: 103
```

| | | |
|---|---|---|
| atggtacaag gagaaagctt ggtttgcaag aatgctcttc aagatttgag ttttttagag | 60 |
| catttattac aggttaaata tgctcctaaa acatggaaag agcaatactt aggatgggat | 120 |
| cttgttcaaa gctccgtttc tgcacagcag aagcttcgta cacagaaaaa tccatcaaca | 180 |
| agttttgcc agcaggtcct tgctgatttt atcggaggat aaatgacttt cacgctgga | 240 |
| gtaactttct ttgcgataga aagtgcttac cttccttata ccgtacaaaa aagtagtgac | 300 |
| ggccgtttct actttgtaga tatcatgact ttttcttcag atccgtgt tggagatgag | 360 |
| ttgctagagg tggatggggc gcctgtccaa gatgtactcg ctactctata tggaagcaat | 420 |
| cacaaaggga ctgcagctga agagtcggct gctttaagaa cactatttc tcgcatggcc | 480 |
| tctttagggc acaaagtacc ttctgggcgc actactttaa agattcgtcg tcctttggt | 540 |
| actacgagag aagttcgtgt gaaatggcgt tatgttcctg aaggtgtagg agatttggct | 600 |
| accatagctc cttctatcag ggctccacag ttacagaaat cgatgagaag cttttttccct | 660 |
| aagaaagatg atgcgtttca tcggtctagt tcgctattct actctccaat ggttccgcat | 720 |
| ttttgggcag agcttcgcaa tcattatgca acgagtggtt tgaaaagcgg gtacaatatt | 780 |
| gggagtaccg atgggttct ccctgtcatt gggcctgtta tatggagtc ggagggtctt | 840 |
| ttccgcgctt atatttcttc ggtgactgat ggggatggta gagccataa agtaggattt | 900 |
| ctaagaattc ctacatatag ttggcaggac atggaagatt tgatccttc aggaccgcct | 960 |
| ccttgggaag aatttgctaa gattattcaa gtattttctt ctaatacaga agctttgatt | 1020 |
| atcgaccaaa cgaacaaccc aggtggtagt gtcctttatc tttatgcact gctttccatg | 1080 |
| ttgacagacc gtcctttaga acttcctaaa catagaatga ttctgactca ggatgaagtg | 1140 |
| gttgatgctt tagattggtt aaccctgttg gaaaacgtag acacaaacgt ggagtctcgc | 1200 |
| cttgctctgg gagacaacat ggaaggatat actgtggatc tacaggttgc cgagtattta | 1260 |
| aaaagctttg gacgtcaagt attgaattgt tggagtaaag gggatatcga ttatcaacg | 1320 |
| cctattcctc ttttttggttt tgagaagatt catccacatc ctcgagttca atactctaaa | 1380 |
| ccgatttgtg ttttgatcaa tgagcaagac ttttcttgtg ctgacttctt ccctgtagtt | 1440 |
| ttgaaagaca atgatcgagc tcttattgtt ggtactcgaa cagctggagc tggaggattt | 1500 |
| gtctttaatg tgcagttccc aaatagaact ggaataaaaa cttgttcttt aacaggatca | 1560 |
| ttagctgtta gagagcatgg tgccttcatt gagaacatcg gagtcgaacc gcatatcgat | 1620 |
| ctgccttta cagcgaatga tattcgctat aaaggctatt ccgagtatct tgataaggtc | 1680 |
| aaaaaattgg tttgtcagct gatcaataac gacggtacca ttattcttgc ggaagatggt | 1740 |
| agttttag | 1749 |

<210> SEQ ID NO 104
<211> LENGTH: 582
<212> TYPE: PRT
<213> ORGANISM: Chlamydia trachomatis

<400> SEQUENCE: 104

| | | | | | | | | | | | | | | |
|---|---|---|---|---|---|---|---|---|---|---|---|---|---|---|
| Met | Val | Gln | Gly | Glu | Ser | Leu | Val | Cys | Lys | Asn | Ala | Leu | Gln | Asp | Leu |
| 1 | | | | 5 | | | | | 10 | | | | | 15 | |

| Ser | Phe | Leu | Glu | His | Leu | Leu | Gln | Val | Lys | Tyr | Ala | Pro | Lys | Thr | Trp |
| 20 | | | | | 25 | | | | | 30 | | | | | |

| Lys | Glu | Gln | Tyr | Leu | Gly | Trp | Asp | Leu | Val | Gln | Ser | Ser | Val | Ser | Ala |
| | | 35 | | | | | 40 | | | | | 45 | | | |

| Gln | Gln | Lys | Leu | Arg | Thr | Gln | Glu | Asn | Pro | Ser | Thr | Ser | Phe | Cys | Gln |
| 50 | | | | | 55 | | | | | 60 | | | | | |

| Gln | Val | Leu | Ala | Asp | Phe | Ile | Gly | Gly | Leu | Asn | Asp | Phe | His | Ala | Gly |
| 65 | | | | | 70 | | | | | 75 | | | | | 80 |

| Val | Thr | Phe | Phe | Ala | Ile | Glu | Ser | Ala | Tyr | Leu | Pro | Tyr | Thr | Val | Gln |
| | | | | 85 | | | | | 90 | | | | | 95 | |

| Lys | Ser | Ser | Asp | Gly | Arg | Phe | Tyr | Phe | Val | Asp | Ile | Met | Thr | Phe | Ser |
| | | | 100 | | | | | 105 | | | | | 110 | | |

| Ser | Glu | Ile | Arg | Val | Gly | Asp | Glu | Leu | Leu | Glu | Val | Asp | Gly | Ala | Pro |
| | | 115 | | | | | 120 | | | | | 125 | | | |

| Val | Gln | Asp | Val | Leu | Ala | Thr | Leu | Tyr | Gly | Ser | Asn | His | Lys | Gly | Thr |
| 130 | | | | | 135 | | | | | 140 | | | | | |

| Ala | Ala | Glu | Glu | Ser | Ala | Ala | Leu | Arg | Thr | Leu | Phe | Ser | Arg | Met | Ala |
| 145 | | | | | 150 | | | | | 155 | | | | | 160 |

| Ser | Leu | Gly | His | Lys | Val | Pro | Ser | Gly | Arg | Thr | Thr | Leu | Lys | Ile | Arg |
| | | | | 165 | | | | | 170 | | | | | 175 | |

| Arg | Pro | Phe | Gly | Thr | Thr | Arg | Glu | Val | Arg | Val | Lys | Trp | Arg | Tyr | Val |
| | | | 180 | | | | | 185 | | | | | 190 | | |

| Pro | Glu | Gly | Val | Gly | Asp | Leu | Ala | Thr | Ile | Ala | Pro | Ser | Ile | Arg | Ala |
| | | 195 | | | | | 200 | | | | | 205 | | | |

| Pro | Gln | Leu | Gln | Lys | Ser | Met | Arg | Ser | Phe | Phe | Pro | Lys | Lys | Asp | Asp |
| 210 | | | | | 215 | | | | | 220 | | | | | |

| Ala | Phe | His | Arg | Ser | Ser | Ser | Leu | Phe | Tyr | Ser | Pro | Met | Val | Pro | His |
| 225 | | | | | 230 | | | | | 235 | | | | | 240 |

| Phe | Trp | Ala | Glu | Leu | Arg | Asn | His | Tyr | Ala | Thr | Ser | Gly | Leu | Lys | Ser |
| | | | | 245 | | | | | 250 | | | | | 255 | |

| Gly | Tyr | Asn | Ile | Gly | Ser | Thr | Asp | Gly | Phe | Leu | Pro | Ile | Gly | Pro |
| | | | 260 | | | | | 265 | | | | | 270 | | |

| Val | Ile | Trp | Glu | Ser | Glu | Gly | Leu | Phe | Arg | Ala | Tyr | Ile | Ser | Ser | Val |
| | | 275 | | | | | 280 | | | | | 285 | | | |

| Thr | Asp | Gly | Asp | Gly | Lys | Ser | His | Lys | Val | Gly | Phe | Leu | Arg | Ile | Pro |
| 290 | | | | | 295 | | | | | 300 | | | | | |

| Thr | Tyr | Ser | Trp | Gln | Asp | Met | Glu | Asp | Phe | Asp | Pro | Ser | Gly | Pro | Pro |
| 305 | | | | | 310 | | | | | 315 | | | | | 320 |

| Pro | Trp | Glu | Glu | Phe | Ala | Lys | Ile | Ile | Gln | Val | Phe | Ser | Ser | Asn | Thr |
| | | | | 325 | | | | | 330 | | | | | 335 | |

| Glu | Ala | Leu | Ile | Ile | Asp | Gln | Thr | Asn | Asn | Pro | Gly | Gly | Ser | Val | Leu |
| | | | 340 | | | | | 345 | | | | | 350 | | |

| Tyr | Leu | Tyr | Ala | Leu | Leu | Ser | Met | Leu | Thr | Asp | Arg | Pro | Leu | Glu | Leu |
| | | 355 | | | | | 360 | | | | | 365 | | | |

| Pro | Lys | His | Arg | Met | Ile | Leu | Thr | Gln | Asp | Glu | Val | Val | Asp | Ala | Leu |
| | 370 | | | | | 375 | | | | | 380 | | | | |

```
Asp Trp Leu Thr Leu Leu Glu Asn Val Asp Thr Asn Val Glu Ser Arg
385                 390                 395                 400

Leu Ala Leu Gly Asp Asn Met Glu Gly Tyr Thr Val Asp Leu Gln Val
            405                 410                 415

Ala Glu Tyr Leu Lys Ser Phe Gly Arg Gln Val Leu Asn Cys Trp Ser
            420                 425                 430

Lys Gly Asp Ile Glu Leu Ser Thr Pro Ile Pro Leu Phe Gly Phe Glu
            435                 440                 445

Lys Ile His Pro His Pro Arg Val Gln Tyr Ser Lys Pro Ile Cys Val
        450                 455                 460

Leu Ile Asn Glu Gln Asp Phe Ser Cys Ala Asp Phe Phe Pro Val Val
465                 470                 475                 480

Leu Lys Asp Asn Asp Arg Ala Leu Ile Val Gly Thr Arg Thr Ala Gly
                485                 490                 495

Ala Gly Gly Phe Val Phe Asn Val Gln Phe Pro Asn Arg Thr Gly Ile
            500                 505                 510

Lys Thr Cys Ser Leu Thr Gly Ser Leu Ala Val Arg Glu His Gly Ala
        515                 520                 525

Phe Ile Glu Asn Ile Gly Val Glu Pro His Ile Asp Leu Pro Phe Thr
530                 535                 540

Ala Asn Asp Ile Arg Tyr Lys Gly Tyr Ser Glu Tyr Leu Asp Lys Val
545                 550                 555                 560

Lys Lys Leu Val Cys Gln Leu Ile Asn Asn Asp Gly Thr Ile Ile Leu
                565                 570                 575

Ala Glu Asp Gly Ser Phe
            580

<210> SEQ ID NO 105
<211> LENGTH: 1749
<212> TYPE: DNA
<213> ORGANISM: Chlamydia trachomatis

<400> SEQUENCE: 105
atggtacgag agaaaagctt ggtttgcaag aatgctcttc aagatttgag tttttagag        60 catttattac aggttaaata tgctcctaaa acatggaaag agcaatactt aggatgggat      120
cttgttcaaa gctccgtttc tgcacagcag aagcttcgta cacaagaaaa tccatcaaca      180 agttttgcc agcaggtcct tgctgatttt atcggaggat taaatgactt tcacgctgga      240
gtaactttct ttgcgataga aagtgcttac cttccttata ccgtacaaaa agtagtgac       300 ggccgtttct actttgtaga tatcatgact ttttcttcag agatccgtgt tggagatgag      360
ttgctagagg tggatggggc gcctgtccaa gatgtgctcg ctactctata tggaagcaat      420
cacaaaggga ctgcagctga gagtcggct gctttaagaa cactattttc tcgcatggcc      480
tctttagggc acaaagtacc ttctgggcgc actactttaa agattcgtcg tccttttggt      540
actacgagag aagttcgtgt gaaatggcgt tatgttcctg aaggtgtagg agatttggct      600
accatagctc cttctatcag ggctccacag ttacagaaat cgatgagaag cttttttcct      660
aagaaagatg atgcgtttca tcggtctagt tcgctattct actctccaat ggttccgcat      720
ttttgggcag agcttcgcaa tcattatgca acgagtggtt tgaaaagcgg gtacaatatt      780
gggagtaccg atgggtttct ccctgtcatt gggcctgtta tatgggagtc ggagggtctt      840
ttccgcgctt atattcttc ggtgactgat ggggatggta agagccataa agtaggattt      900
ctaagaattc ctacatatag ttggcaggac atggaagatt tgatccttc aggaccgcct       960 ccttgggaag aatttgctaa gattattcaa gtattttctt ctaatacaga agctttgatt     1020
```

```
atcgaccaaa cgaacaaccc aggtggtagt gtcctttatc tttatgcact gctttccatg    1080
ttgacagacc gtcctttaga acttcctaaa catagaatga ttctgactca ggatgaagtg    1140
gttgatgctt tagattggtt aaccctgttg gaaaacgtag acacaaacgt ggagtctcgc    1200
cttgctctgg gagacaacat ggaaggatat actgtggatc tacaggttgc cgagtattta    1260
aaaagctttg gacgtcaagt attgaattgt tggagtaaag gggatatcga gttatcaaca    1320
cctattcctc tttttggttt tgagaagatt catccacatc ctcgagttca atactctaaa    1380
ccgatttgtg ttttgatcaa tgagcaagac ttttcttgtg ctgacttctt ccctgtagtt    1440
ttgaaagaca atgatcgagc tcttattgtt ggtactcgaa cagctggagc tggaggattt    1500
gtctttaatg tgcagttccc aaatagaact ggaataaaaa cttgttcttt aacaggatca    1560
ttagctgtta gagagcatgg tgccttcatt gagaacatcg gagtcgaacc gcatatcgat    1620 ctgccttttta cagcgaatga tattcgctat aaaggctatt ccgagtatct tgataaggtc    1680
aaaaaattgg tttgtcagct gatcaataac gacggtacca ttattcttgc ggaagatggt    1740
agttttttag                                                            1749
```

<210> SEQ ID NO 106
<211> LENGTH: 582
<212> TYPE: PRT
<213> ORGANISM: Chlamydia trachomatis

<400> SEQUENCE: 106

```
Met Val Arg Gly Glu Ser Leu Val Cys Lys Asn Ala Leu Gln Asp Leu
1               5                   10                  15

Ser Phe Leu Glu His Leu Leu Gln Val Lys Tyr Ala Pro Lys Thr Trp
                20                  25                  30

Lys Glu Gln Tyr Leu Gly Trp Asp Leu Val Gln Ser Ser Val Ser Ala
            35                  40                  45

Gln Gln Lys Leu Arg Thr Gln Glu Asn Pro Ser Thr Ser Phe Cys Gln
        50                  55                  60

Gln Val Leu Ala Asp Phe Ile Gly Gly Leu Asn Asp Phe His Ala Gly
65                  70                  75                  80

Val Thr Phe Phe Ala Ile Glu Ser Ala Tyr Leu Pro Tyr Thr Val Gln
                85                  90                  95

Lys Ser Ser Asp Gly Arg Phe Tyr Phe Val Asp Ile Met Thr Phe Ser
                100                 105                 110

Ser Glu Ile Arg Val Gly Asp Glu Leu Leu Glu Val Asp Gly Ala Pro
            115                 120                 125

Val Gln Asp Val Leu Ala Thr Leu Tyr Gly Ser Asn His Lys Gly Thr
        130                 135                 140

Ala Ala Glu Glu Ser Ala Ala Leu Arg Thr Leu Phe Ser Arg Met Ala
145                 150                 155                 160

Ser Leu Gly His Lys Val Pro Ser Gly Arg Thr Thr Leu Lys Ile Arg
                165                 170                 175

Arg Pro Phe Gly Thr Thr Arg Glu Val Arg Val Lys Trp Arg Tyr Val
            180                 185                 190

Pro Glu Gly Val Gly Asp Leu Ala Thr Ile Ala Pro Ser Ile Arg Ala
        195                 200                 205

Pro Gln Leu Gln Lys Ser Met Arg Ser Phe Phe Leu Lys Lys Asp Asp
    210                 215                 220

Ala Phe His Arg Ser Ser Ser Leu Phe Tyr Ser Pro Met Val Pro His
225                 230                 235                 240
```

```
Phe Trp Ala Glu Leu Arg Asn His Tyr Ala Thr Ser Gly Leu Lys Ser
                245                 250                 255
Gly Tyr Asn Ile Gly Ser Thr Asp Gly Phe Leu Pro Val Ile Gly Pro
            260                 265                 270
Val Ile Trp Glu Ser Glu Gly Leu Phe Arg Ala Tyr Ile Ser Ser Val
        275                 280                 285
Thr Asp Gly Asp Gly Lys Ser His Lys Val Gly Phe Leu Arg Ile Pro
    290                 295                 300
Thr Tyr Ser Trp Gln Asp Met Glu Asp Phe Asp Pro Ser Gly Pro Pro
305                 310                 315                 320
Pro Trp Glu Glu Phe Ala Lys Ile Ile Gln Val Phe Ser Asn Thr
                325                 330                 335
Glu Ala Leu Ile Ile Asp Gln Thr Asn Asn Pro Gly Gly Ser Val Leu
                340                 345                 350
Tyr Leu Tyr Ala Leu Leu Ser Met Leu Thr Asp Arg Pro Leu Glu Leu
                355                 360                 365
Pro Lys His Arg Met Ile Leu Thr Gln Asp Glu Val Val Asp Ala Leu
                370                 375                 380
Asp Trp Leu Thr Leu Leu Glu Asn Val Asp Thr Asn Val Glu Ser Arg
385                 390                 395                 400
Leu Ala Leu Gly Asp Asn Met Glu Gly Tyr Thr Val Asp Leu Gln Val
                405                 410                 415
Ala Glu Tyr Leu Lys Ser Phe Gly Arg Gln Val Leu Asn Cys Trp Ser
                420                 425                 430
Lys Gly Asp Ile Glu Leu Ser Thr Pro Ile Pro Leu Phe Gly Phe Glu
                435                 440                 445
Lys Ile His Pro His Pro Arg Val Gln Tyr Ser Lys Pro Ile Cys Val
                450                 455                 460
Leu Ile Asn Glu Gln Asp Phe Ser Cys Ala Asp Phe Phe Pro Val Val
465                 470                 475                 480
Leu Lys Asp Asn Asp Arg Ala Leu Ile Val Gly Thr Arg Thr Ala Gly
                485                 490                 495
Ala Gly Gly Phe Val Phe Asn Val Gln Phe Pro Asn Arg Thr Gly Ile
                500                 505                 510
Lys Thr Cys Ser Leu Thr Gly Ser Leu Ala Val Arg Glu His Gly Ala
                515                 520                 525
Phe Ile Glu Asn Ile Gly Val Glu Pro His Ile Asp Leu Pro Phe Thr
                530                 535                 540
Ala Asn Asp Ile Arg Tyr Lys Gly Tyr Ser Glu Tyr Leu Asp Lys Val
545                 550                 555                 560
Lys Lys Leu Val Cys Gln Leu Ile Asn Asn Asp Gly Thr Ile Ile Leu
                565                 570                 575
Ala Glu Asp Gly Ser Phe
                580

<210> SEQ ID NO 107
<211> LENGTH: 1749
<212> TYPE: DNA
<213> ORGANISM: Chlamydia trachomatis

<400> SEQUENCE: 107
atggtacaag gagaaagctt ggtttgcaag aatgctcttc aagatttgag ttttttagag      60
catttattac aggttaaata tgctcctaaa acatggaaag agcaatactt aggatgggat     120
cttgttcaaa gctccgtttc tgcacagcag aagcttcgta cacaagaaaa tccatcaaca     180
```

```
agtttttgcc agcaggtcct tgctgatttt atcggaggat taaatgactt tcacgctgga    240
gtaactttct ttgcgataga aagtgcttac cttccttata ccgtacaaaa aagtagtgac    300
ggccgtttct actttgtaga tatcatgact ttttcttcag agatccgtgt tggagatgag    360
ttgctagagg tggatggggc gcctgtccaa gatgtactcg ctactctata tggaagcaat    420
cacaaaggga ctgcagctga agagtcggct gctttaagaa cactattttc tcgcatggcc    480
tctttagggc acaaagtacc ttctgggcgc actactttaa agattcgtcg tccttttggt    540
actacgagag aagttcgtgt gaaatggcgt tatgttcctg aaggtgtagg agatttggct    600
accatagctc cttctatcag ggctccacag ttacagaaat cgatgagaag cttttttcct    660
aagaaagatg atgcgtttca tcggtctagt tcgctattct actctccaat ggttccgcat    720
tttgggcag agcttcgcaa tcattatgca acgagtggt tgaaaagcgg gtacaatatt    780
gggagtaccg atgggtttct ccctgtcatt gggcctgtta tatgggagtc ggagggtctt    840
ttccgcgctt atatttcttc ggtgactgat ggggatggta agagccataa agtaggattt    900
ctaagaattc ctacatatag ttggcaggac atggaagatt ttgatccttc aggaccgcct    960
ccttgggaag aatttgctaa gattattcaa gtattttctt ctaatacaga agctttgatt   1020
atcgaccaaa cgaacaaccc aggtggtagt gtcctttatc tttatgcact gctttccatg   1080
ttgacagacc gtccttttaga acttcctaaa catagaatga ttctgactca ggatgaagtg   1140
gttgatgctt tagattggtt aaccctgttg gaaaacgtag acacaaacgt ggagtctcgc   1200
cttgctctgg gagacaacat ggaaggatat actgtggatc tacaggttgc cgagtattta   1260
aaaagctttg gacgtcaagt attgaattgt tggagtaaag gggatatcga gttatcaacg   1320
cctattcctc ttttttggttt tgagaagatt catccacatc ctcgagttca atactctaaa   1380
ccgatttgtg ttttgatcaa tgagcaagac ttttcttgtg ctgacttctt ccctgtagtt   1440
ttgaaagaca atgatcgagc tcttattgtt ggtactcgaa cagctggagc tggaggattt   1500
gtctttaatg tgcagttccc aaatagaact ggaataaaaa cttgttcttt aacaggatca   1560
ttagctgtta gagagcatgg tgccttcatt gagaacatcg gagtcgaacc gcatatcgat   1620
ctgccttttta cagcgaatga tattcgctat aaaggctatt ccgagtatct tgataaggtc   1680
aaaaaattgg tttgtcagct gatcaataac gacggtacca ttattcttgc ggaagatggt   1740
agttttag                                                            1749
```

<210> SEQ ID NO 108
<211> LENGTH: 582
<212> TYPE: PRT
<213> ORGANISM: Chlamydia trachomatis

<400> SEQUENCE: 108

```
Met Val Gln Gly Glu Ser Leu Val Cys Lys Asn Ala Leu Gln Asp Leu
1               5                   10                  15

Ser Phe Leu Glu His Leu Leu Gln Val Lys Tyr Ala Pro Lys Thr Trp
            20                  25                  30

Lys Glu Gln Tyr Leu Gly Trp Asp Leu Val Gln Ser Ser Val Ser Ala
        35                  40                  45

Gln Gln Lys Leu Arg Thr Gln Glu Asn Pro Ser Thr Ser Phe Cys Gln
    50                  55                  60

Gln Val Leu Ala Asp Phe Ile Gly Gly Leu Asn Asp Phe His Ala Gly
65                  70                  75                  80

Val Thr Phe Phe Ala Ile Glu Ser Ala Tyr Leu Pro Tyr Thr Val Gln
                85                  90                  95
```

-continued

Lys Ser Ser Asp Gly Arg Phe Tyr Phe Val Asp Ile Met Thr Phe Ser
            100                 105                 110

Ser Glu Ile Arg Val Gly Asp Glu Leu Leu Glu Val Asp Gly Ala Pro
            115                 120                 125

Val Gln Asp Val Leu Ala Thr Leu Tyr Gly Ser Asn His Lys Gly Thr
130                 135                 140

Ala Ala Glu Glu Ser Ala Ala Leu Arg Thr Leu Phe Ser Arg Met Ala
145                 150                 155                 160

Ser Leu Gly His Lys Val Pro Ser Gly Arg Thr Thr Leu Lys Ile Arg
                165                 170                 175

Arg Pro Phe Gly Thr Thr Arg Glu Val Arg Val Lys Trp Arg Tyr Val
            180                 185                 190

Pro Glu Gly Val Gly Asp Leu Ala Thr Ile Ala Pro Ser Ile Arg Ala
            195                 200                 205

Pro Gln Leu Gln Lys Ser Met Arg Ser Phe Leu Lys Lys Asp Asp
210                 215                 220

Ala Phe His Arg Ser Ser Leu Phe Tyr Ser Pro Met Val Pro His
225                 230                 235                 240

Phe Trp Ala Glu Leu Arg Asn His Tyr Ala Thr Ser Gly Leu Lys Ser
            245                 250                 255

Gly Tyr Asn Ile Gly Ser Thr Asp Gly Phe Leu Pro Val Ile Gly Pro
            260                 265                 270

Val Ile Trp Glu Ser Glu Gly Leu Phe Arg Ala Tyr Ile Ser Ser Val
            275                 280                 285

Thr Asp Gly Asp Gly Lys Ser His Lys Val Gly Phe Leu Arg Ile Pro
290                 295                 300

Thr Tyr Ser Trp Gln Asp Met Glu Asp Phe Asp Pro Ser Gly Pro Pro
305                 310                 315                 320

Pro Trp Glu Glu Phe Ala Lys Ile Ile Gln Val Phe Ser Ser Asn Thr
            325                 330                 335

Glu Ala Leu Ile Ile Asp Gln Thr Asn Asn Pro Gly Gly Ser Val Leu
            340                 345                 350

Tyr Leu Tyr Ala Leu Leu Ser Met Leu Thr Asp Arg Pro Leu Glu Leu
            355                 360                 365

Pro Lys His Arg Met Ile Leu Thr Gln Asp Glu Val Val Asp Ala Leu
            370                 375                 380

Asp Trp Leu Thr Leu Leu Glu Asn Val Asp Thr Asn Val Glu Ser Arg
385                 390                 395                 400

Leu Ala Leu Gly Asp Asn Met Glu Gly Tyr Thr Val Asp Leu Gln Val
                405                 410                 415

Ala Glu Tyr Leu Lys Ser Phe Gly Arg Gln Val Leu Asn Cys Trp Ser
            420                 425                 430

Lys Gly Asp Ile Glu Leu Ser Thr Pro Ile Pro Leu Phe Gly Phe Glu
            435                 440                 445

Lys Ile His Pro His Pro Arg Val Gln Tyr Ser Lys Pro Ile Cys Val
            450                 455                 460

Leu Ile Asn Glu Gln Asp Phe Ser Cys Ala Asp Phe Phe Pro Val Val
465                 470                 475                 480

Leu Lys Asp Asn Asp Arg Ala Leu Ile Val Gly Thr Arg Thr Ala Gly
                485                 490                 495

Ala Gly Gly Phe Val Phe Asn Val Gln Phe Pro Asn Arg Thr Gly Ile
            500                 505                 510

Lys Thr Cys Ser Leu Thr Gly Ser Leu Ala Val Arg Glu His Gly Ala
            515                 520                 525

```
Phe Ile Glu Asn Ile Gly Val Glu Pro His Ile Asp Leu Pro Phe Thr
    530                 535                 540

Ala Asn Asp Ile Arg Tyr Lys Gly Tyr Ser Glu Tyr Leu Asp Lys Val
545                 550                 555                 560

Lys Lys Leu Val Cys Gln Leu Ile Asn Asn Asp Gly Thr Ile Ile Leu
                565                 570                 575

Ala Glu Asp Gly Ser Phe
            580

<210> SEQ ID NO 109
<211> LENGTH: 1749
<212> TYPE: DNA
<213> ORGANISM: Chlamydia trachomatis

<400> SEQUENCE: 109
```

| | | |
|---|---|---|
| atggtacgag gagaaagctt ggtttgcaag aatgctcttc aagatttgag ttttttagag | 60 |
| catttattac aggttaaata tgctcctaaa acatggaaag agcaatactt aggatgggat | 120 |
| cttgttcaaa gctccgtttc tgcacagcag aagcttcgta cacaagaaaa tccatcaaca | 180 |
| agttttgcc agcaggtcct tgctgatttt atcggaggat aaatgactt tcacgctgga | 240 |
| gtaactttct ttgcgataga aagtgcttac cttccttata ccgtacaaaa agtagtgac | 300 |
| ggccgtttct actttgtaga tatcatgact ttttcttcag atccgtgt tggagatgag | 360 |
| ttgctagagg tggatggggc gcctgtccaa gatgtgctcg ctactctata tggaagcaat | 420 |
| cacaaaggga ctgcagctga agagtcggct gctttaagaa cactatttc tcgcatggcc | 480 |
| tctttagggc acaaagtacc ttctgggcgc actactttaa agattcgtcg tccttttggt | 540 |
| actacgagag aagttcgtgt gaaatggcgt tatgttcctg aaggtgtagg agatttggct | 600 |
| accatagctc cttctatcag ggctccacag ttacagaaat cgatgagaag cttttttccct | 660 |
| aagaaagatg atgcgtttca tcggtctagt tcgctattct actctccaat ggttccgcat | 720 |
| ttttgggcag agcttcgcaa tcattatgca acgagtggtt tgaaaagcgg gtacaatatt | 780 |
| gggagtaccg atgggtttct ccctgtcatt gggcctgtta tgggagtc ggagggtctt | 840 |
| ttccgcgctt atatttcttc ggtgactgat ggggatggta agagccataa agtaggattt | 900 |
| ctaagaattc ctacatatag ttggcaggac atggaagatt tgatcccttc aggaccgcct | 960 |
| ccttgggaag aatttgctaa gattattcaa gtatttctt ctaatacaga agctttgatt | 1020 |
| atcgaccaaa cgaacaaccc aggtggtagt gtccttttatc tttatgcact gctttccatg | 1080 |
| ttgacagacc gtcctttaga acttcctaaa catagaatga ttctgactca ggatgaagtg | 1140 |
| gttgatgctt tagattggtt aaccctgttg gaaaacgtag acacaaacgt ggagtctcgc | 1200 |
| cttgctctgg gagacaacat ggaaggatat actgtggatc tacaggttgc cgagtattta | 1260 |
| aaaagctttg gacgtcaagt attgaattgt tggagtaaag gggatatcga gttatcaaca | 1320 |
| cctattcctc ttttttggttt tgagaagatt catccacatc ctcgagttca atactctaaa | 1380 |
| ccgatttgtg ttttgatcaa tgagcaagac ttttcttgtg ctgacttctt ccctgtagtt | 1440 |
| ttgaaagaca atgatcgagc tcttattgtt ggtactcgaa cagctggagc tggaggattt | 1500 |
| gtctttaatg tgcagttccc aaatagaact ggaataaaaa cttgttcttt aacaggatca | 1560 |
| ttagctgtta gagagcatgg tgccttcatt gagaacatcg gagtcgaacc gcatatcgat | 1620 |
| ctgccttta cagcgaatga tattcgctat aaaggctatt ccgagtatct tgataaggtc | 1680 |
| aaaaaattgg tttgtcagct gatcaataac gacggtacca ttattcttgc ggaagatggt | 1740 |
| agttttag | 1749 |

-continued

```
<210> SEQ ID NO 110
<211> LENGTH: 582
<212> TYPE: PRT
<213> ORGANISM: Chlamydia trachomatis

<400> SEQUENCE: 110
```

| | | | | | | | | | | | | | | | |
|---|---|---|---|---|---|---|---|---|---|---|---|---|---|---|---|
| Met | Val | Arg | Gly | Glu | Ser | Leu | Val | Cys | Lys | Asn | Ala | Leu | Gln | Asp | Leu |
| 1 | | | | 5 | | | | | 10 | | | | | 15 | |
| Ser | Phe | Leu | Glu | His | Leu | Leu | Gln | Val | Lys | Tyr | Ala | Pro | Lys | Thr | Trp |
| | | | 20 | | | | | 25 | | | | | 30 | | |
| Lys | Glu | Gln | Tyr | Leu | Gly | Trp | Asp | Leu | Val | Gln | Ser | Ser | Val | Ser | Ala |
| | | | 35 | | | | 40 | | | | | 45 | | | |
| Gln | Gln | Lys | Leu | Arg | Thr | Gln | Glu | Asn | Pro | Ser | Thr | Ser | Phe | Cys | Gln |
| | 50 | | | | | 55 | | | | | 60 | | | | |
| Gln | Val | Leu | Ala | Asp | Phe | Ile | Gly | Gly | Leu | Asn | Asp | Phe | His | Ala | Gly |
| 65 | | | | | 70 | | | | | 75 | | | | | 80 |
| Val | Thr | Phe | Phe | Ala | Ile | Glu | Ser | Ala | Tyr | Leu | Pro | Tyr | Thr | Val | Gln |
| | | | | 85 | | | | | 90 | | | | | 95 | |
| Lys | Ser | Ser | Asp | Gly | Arg | Phe | Tyr | Phe | Val | Asp | Ile | Met | Thr | Phe | Ser |
| | | | 100 | | | | | 105 | | | | | 110 | | |
| Ser | Glu | Ile | Arg | Val | Gly | Asp | Glu | Leu | Leu | Glu | Val | Asp | Gly | Ala | Pro |
| | | | 115 | | | | | 120 | | | | | 125 | | |
| Val | Gln | Asp | Val | Leu | Ala | Thr | Leu | Tyr | Gly | Ser | Asn | His | Lys | Gly | Thr |
| | 130 | | | | | 135 | | | | | 140 | | | | |
| Ala | Ala | Glu | Glu | Ser | Ala | Ala | Leu | Arg | Thr | Leu | Phe | Ser | Arg | Met | Ala |
| 145 | | | | | 150 | | | | | 155 | | | | | 160 |
| Ser | Leu | Gly | His | Lys | Val | Pro | Ser | Gly | Arg | Thr | Thr | Leu | Lys | Ile | Arg |
| | | | | 165 | | | | | 170 | | | | | 175 | |
| Arg | Pro | Phe | Gly | Thr | Thr | Arg | Glu | Val | Arg | Val | Lys | Trp | Arg | Tyr | Val |
| | | | 180 | | | | | 185 | | | | | 190 | | |
| Pro | Glu | Gly | Val | Gly | Asp | Leu | Ala | Thr | Ile | Ala | Pro | Ser | Ile | Arg | Ala |
| | | | 195 | | | | | 200 | | | | | 205 | | |
| Pro | Gln | Leu | Gln | Lys | Ser | Met | Arg | Ser | Phe | Phe | Leu | Lys | Lys | Asp | Asp |
| | 210 | | | | | 215 | | | | | 220 | | | | |
| Ala | Phe | His | Arg | Ser | Ser | Ser | Leu | Phe | Tyr | Ser | Pro | Met | Val | Pro | His |
| 225 | | | | | 230 | | | | | 235 | | | | | 240 |
| Phe | Trp | Ala | Glu | Leu | Arg | Asn | His | Tyr | Ala | Thr | Ser | Gly | Leu | Lys | Ser |
| | | | | 245 | | | | | 250 | | | | | 255 | |
| Gly | Tyr | Asn | Ile | Gly | Ser | Thr | Asp | Gly | Phe | Leu | Pro | Val | Ile | Gly | Pro |
| | | | 260 | | | | | 265 | | | | | 270 | | |
| Val | Ile | Trp | Glu | Ser | Glu | Gly | Leu | Phe | Arg | Ala | Tyr | Ile | Ser | Ser | Val |
| | | | 275 | | | | | 280 | | | | | 285 | | |
| Thr | Asp | Gly | Asp | Gly | Lys | Ser | His | Lys | Val | Gly | Phe | Leu | Arg | Ile | Pro |
| | 290 | | | | | 295 | | | | | 300 | | | | |
| Thr | Tyr | Ser | Trp | Gln | Asp | Met | Glu | Asp | Phe | Asp | Pro | Ser | Gly | Pro | Pro |
| 305 | | | | | 310 | | | | | 315 | | | | | 320 |
| Pro | Trp | Glu | Glu | Phe | Ala | Lys | Ile | Ile | Gln | Val | Phe | Ser | Ser | Asn | Thr |
| | | | | 325 | | | | | 330 | | | | | 335 | |
| Glu | Ala | Leu | Ile | Ile | Asp | Gln | Thr | Asn | Asn | Pro | Gly | Gly | Ser | Val | Leu |
| | | | 340 | | | | | 345 | | | | | 350 | | |
| Tyr | Leu | Tyr | Ala | Leu | Leu | Ser | Met | Leu | Thr | Asp | Arg | Pro | Leu | Glu | Leu |
| | | | 355 | | | | | 360 | | | | | 365 | | |
| Pro | Lys | His | Arg | Met | Ile | Leu | Thr | Gln | Asp | Glu | Val | Val | Asp | Ala | Leu |
| | 370 | | | | | 375 | | | | | 380 | | | | |

```
Asp Trp Leu Thr Leu Leu Glu Asn Val Asp Thr Asn Val Glu Ser Arg
385                 390                 395                 400

Leu Ala Leu Gly Asp Asn Met Glu Gly Tyr Thr Val Asp Leu Gln Val
            405                 410                 415

Ala Glu Tyr Leu Lys Ser Phe Gly Arg Gln Val Leu Asn Cys Trp Ser
                420                 425                 430

Lys Gly Asp Ile Glu Leu Ser Thr Pro Ile Pro Leu Phe Gly Phe Glu
            435                 440                 445

Lys Ile His Pro His Pro Arg Val Gln Tyr Ser Lys Pro Ile Cys Val
        450                 455                 460

Leu Ile Asn Glu Gln Asp Phe Ser Cys Ala Asp Phe Phe Pro Val Val
465                 470                 475                 480

Leu Lys Asp Asn Asp Arg Ala Leu Ile Val Gly Thr Arg Thr Ala Gly
                485                 490                 495

Ala Gly Gly Phe Val Phe Asn Val Gln Phe Pro Asn Arg Thr Gly Ile
                500                 505                 510

Lys Thr Cys Ser Leu Thr Gly Ser Leu Ala Val Arg Glu His Gly Ala
            515                 520                 525

Phe Ile Glu Asn Ile Gly Val Glu Pro His Ile Asp Leu Pro Phe Thr
        530                 535                 540

Ala Asn Asp Ile Arg Tyr Lys Gly Tyr Ser Glu Tyr Leu Asp Lys Val
545                 550                 555                 560

Lys Lys Leu Val Cys Gln Leu Ile Asn Asn Asp Gly Thr Ile Ile Leu
                565                 570                 575

Ala Glu Asp Gly Ser Phe
                580

<210> SEQ ID NO 111
<211> LENGTH: 1770
<212> TYPE: DNA
<213> ORGANISM: Chlamydia trachomatis

<400> SEQUENCE: 111
atgagcatca ggggagtagg aggcaacggg aatagtcgaa tcccttctca taatggggat      60
ggatcgaatc gcagaagtca aaatacgaag aataaagttg aagatcgagt tcgttctcta     120
tattcatctc gtagtaacga aaatagagaa tctccttatg cagtagtaga cgtcagctct     180
atgatcgaga gcaccccaac gagtggagag acgacaagag cttcgcgtgg agtattcagt     240
cgtttccaaa gaggtttagg acgagtagct gacaaagtaa gacgagctgt tcagcgtgcg     300
tggagttcag tctctataag aagatcgtct gcaacaagag ccacagaatc cagatcaagt     360
agtcgtactc tcgtggtgc aagttctggg tataaggagt attctccttc agcagctaga     420
gggctgcgtc ttatgttcac agatttctgg agaactcggg ttttacgcca gacctctcct     480
atggctggag tttttgggaa tcttgatgtg aacgaggctc gtttgatggc tgcgtacaca     540
agtgagtgcg cggatcattt agaagcgaag gagttggctg ccctgacgg ggtagcggcc     600 gcccgggaaa ttgctaaaag atgggagaaa agagttagag atctacaaga taaaggtgct     660
gcacgaaaat tattaaatga tcctttaggc cgacgaacac ctaattatca gagcaaaaat     720
ccaggtgagt atactgtagg gaattccatg ttttacgatg gtcctcaggt agcgaatctc     780
cagaacgtcg acactggttt ttggctggac atgagcaatc tctcagacgt tgtattatcc     840
agagagattc aaacaggact tcgagcacga gctactttgg aagaatccat gccgatgtta     900
gagaatttag aagagcgttt tagacgtttg caagaaactt gtgatgcggc tcgtactgag     960
```

-continued

```
atagaagaat cgggatggac tcgagagtcc gcatcaagaa tggaaggcga tgaggcgcaa    1020
ggaccttcta gagcacaaca agcttttcag agctttgtaa atgaatgtaa cagcatcgag    1080
ttctcatttg ggagctttgg agagcatgtg cgagttctct gcgctagagt atcacgagga    1140
ttagctgccg caggagaggc gattcgccgt tgcttctctt gttgtaaagg atcgacgcat    1200
cgctacgctc ctcgcgatga cctatctcct gaaggtgcat cgttagcaga gactttggct    1260
agattcgcag atgatatggg aatagagcga ggtgctgatg aacctacga tattcctttg     1320
gtagatgatt ggagaagagg ggttcctagt attgaaggag aaggatctga ctcgatctat    1380
gaaatcatga tgcctatcta tgaagttatg aatatggatc tagaaacacg aagatctttt    1440
gcggtacagc aagggcacta tcaggaccca agagcttcag attatgacct cccacgtgct    1500
agcgactatg atttgcctag aagcccatat cctactccac ctttgcctcc tagatatcag    1560
ctacagaata tggatgtaga agcagggttc cgtgaggcag tttatgcttc ttttgtagca    1620
ggaatgtaca attatgtagt gacacagccg caagagcgta ttcccaatag tcagcaggtg    1680
gaagggattc tgcgtgatat gcttaccaac gggtcacaga catttagaga cctgatgaag    1740
cgttggaata gagaagtcga tagggaataa                                     1770
```

<210> SEQ ID NO 112
<211> LENGTH: 589
<212> TYPE: PRT
<213> ORGANISM: Chlamydia trachomatis

<400> SEQUENCE: 112

```
Met Ser Ile Arg Gly Val Gly Gly Asn Gly Asn Ser Arg Ile Pro Ser
1               5                   10                  15

His Asn Gly Asp Gly Ser Asn Arg Arg Ser Gln Asn Thr Lys Asn Lys
            20                  25                  30

Val Glu Asp Arg Val Arg Ser Leu Tyr Ser Ser Arg Ser Asn Glu Asn
        35                  40                  45

Arg Glu Ser Pro Tyr Ala Val Val Asp Val Ser Ser Met Ile Glu Ser
    50                  55                  60

Thr Pro Thr Ser Gly Glu Thr Thr Arg Ala Ser Arg Gly Val Phe Ser
65                  70                  75                  80

Arg Phe Gln Arg Gly Leu Gly Arg Val Ala Asp Lys Val Arg Arg Ala
                85                  90                  95

Val Gln Arg Ala Trp Ser Ser Val Ser Ile Arg Arg Ser Ser Ala Thr
            100                 105                 110

Arg Ala Thr Glu Ser Arg Ser Ser Ser Arg Thr Ala Arg Gly Ala Ser
        115                 120                 125

Ser Gly Tyr Lys Glu Tyr Ser Pro Ser Ala Ala Arg Gly Leu Arg Leu
    130                 135                 140

Met Phe Thr Asp Phe Trp Arg Thr Arg Val Leu Arg Gln Thr Ser Pro
145                 150                 155                 160

Met Ala Gly Val Phe Gly Asn Leu Asp Val Asn Glu Ala Arg Leu Met
                165                 170                 175

Ala Ala Tyr Thr Ser Glu Cys Ala Asp His Leu Glu Ala Lys Glu Leu
            180                 185                 190

Ala Gly Pro Asp Gly Val Ala Ala Arg Glu Ile Ala Lys Arg Trp
        195                 200                 205

Glu Lys Arg Val Arg Asp Leu Gln Asp Lys Gly Ala Ala Arg Lys Leu
    210                 215                 220

Leu Asn Asp Pro Leu Gly Arg Arg Thr Pro Asn Tyr Gln Ser Lys Asn
225                 230                 235                 240
```

Pro Gly Glu Tyr Thr Val Gly Asn Ser Met Phe Tyr Asp Gly Pro Gln
            245                 250                 255

Val Ala Asn Leu Gln Asn Val Asp Thr Gly Phe Trp Leu Asp Met Ser
            260                 265                 270

Asn Leu Ser Asp Val Val Leu Ser Arg Glu Ile Gln Thr Gly Leu Arg
            275                 280                 285

Ala Arg Ala Thr Leu Glu Glu Ser Met Pro Met Leu Glu Asn Leu Glu
        290                 295                 300

Glu Arg Phe Arg Arg Leu Gln Glu Thr Cys Asp Ala Ala Arg Thr Glu
305                 310                 315                 320

Ile Glu Glu Ser Gly Trp Thr Arg Glu Ser Ala Ser Arg Met Glu Gly
                325                 330                 335

Asp Glu Ala Gln Gly Pro Ser Arg Ala Gln Gln Ala Phe Gln Ser Phe
            340                 345                 350

Val Asn Glu Cys Asn Ser Ile Glu Phe Ser Phe Gly Ser Phe Gly Glu
            355                 360                 365

His Val Arg Val Leu Cys Ala Arg Val Ser Arg Gly Leu Ala Ala Ala
        370                 375                 380

Gly Glu Ala Ile Arg Arg Cys Phe Ser Cys Cys Lys Gly Ser Thr His
385                 390                 395                 400

Arg Tyr Ala Pro Arg Asp Asp Leu Ser Pro Glu Gly Ala Ser Leu Ala
                405                 410                 415

Glu Thr Leu Ala Arg Phe Ala Asp Met Gly Ile Glu Arg Gly Ala
            420                 425                 430

Asp Gly Thr Tyr Asp Ile Pro Leu Val Asp Asp Trp Arg Arg Gly Val
            435                 440                 445

Pro Ser Ile Glu Gly Gly Ser Asp Ser Ile Tyr Glu Ile Met Met
450                 455                 460

Pro Ile Tyr Glu Val Met Asn Met Asp Leu Glu Thr Arg Arg Ser Phe
465                 470                 475                 480

Ala Val Gln Gln Gly His Tyr Gln Asp Pro Arg Ala Ser Asp Tyr Asp
                485                 490                 495

Leu Pro Arg Ala Ser Asp Tyr Asp Leu Pro Arg Ser Pro Tyr Pro Thr
            500                 505                 510

Pro Pro Leu Pro Pro Arg Tyr Gln Leu Gln Asn Met Asp Val Glu Ala
            515                 520                 525

Gly Phe Arg Glu Ala Val Tyr Ala Ser Phe Val Ala Gly Met Tyr Asn
530                 535                 540

Tyr Val Val Thr Gln Pro Gln Glu Arg Ile Pro Asn Ser Gln Gln Val
545                 550                 555                 560

Glu Gly Ile Leu Arg Asp Met Leu Thr Asn Gly Ser Gln Thr Phe Arg
                565                 570                 575

Asp Leu Met Lys Arg Trp Asn Arg Glu Val Asp Arg Glu
            580                 585

<210> SEQ ID NO 113
<211> LENGTH: 1770
<212> TYPE: DNA
<213> ORGANISM: Chlamydia trachomatis

<400> SEQUENCE: 113
atgagcatca ggggagtagg aggcaacggg aatagtcgaa tcccttctca taatggggat    60
ggatcgaatc gcagaagtca aaatacgaag aataaagttg aagatcgagt tcgttctcta   120
tattcatctc gtagtaacga aaatagagaa tctccttatg cagtagtaga cgtcagctct   180

```
atgatcgaga gcaccccaac gagtggagag acgacaagag cttcgcgtgg agtattcagt    240
cgtttccaaa gaggtttagg acgagtagct gacaaagtaa gacgagctgt tcagcgtgcg    300
tggagttcag tctctataag aagatcgtct gcaacaagag ccgcagaatc cagatcaagt    360
agtcgtactg ctcgtggtgc aagttctggg tatagggagt attctccttc agcagctaga    420
gggctgcgtc ttatgttcac agatttctgg agaactcggg ttttacgcca gacctctcct    480
atggctggag tttttgggaa tcttgatgtg aacgaggctc gtttgatggc tgcgtacaca    540
agtgagtgcg cggatcattt agaagcgaag gagttggctg ccctgacgg ggtagcggcc     600 gcccgggaaa ttgctaaaag atgggagaaa agagttagag atctacaaga taaaggtgct    660
gcacgaaaat tattaaatga tcctttaggc cgacgaacac ctaattatca gagcaaaaat    720
ccaggtgagt atactgtagg gaattccatg ttttacgatg gtcctcaggt agcgaatctc    780
cagaacgtcg acactggttt ttggctggac atgagcaatc tctcagacgt tgtattatcc    840
agagagattc aaacaggact tcgagcacga gctactttgg aagaatccat gccgatgtta    900
gagaatttag aagagcgttt tagacgtttg caagaaactt gtgatgcggc tcgtactgag    960
atagaagaat cgggatggac tcgagagtcc gcatcaagaa tggaaggcga tgaggcgcaa   1020
ggaccttcta gagcacaaca agcttttcag agctttgtaa atgaatgtaa cagcatcgag   1080
ttctcatttg ggagctttgg agagcatgtg cgagttctct gcgctagagt atcacgagga   1140
ttagctgccg caggagaggc gattcgccgt tgcttctctt gttgtaaagg atcgacgcat   1200
cgctacgctc ctcgcgatga cctatctcct gaaggtgcat cgttagcaga gactttggct   1260
agattcgcag atgatatggg aatagagcga ggtgctgatg gaacctacga tattcctttg   1320
gtagatgatt ggagaagagg ggttcctagt attgaaggag aaggatctga ctcgatctat   1380
gaaatcatga tgcctatcta tgaagttatg aatatggatc tagaaacacg aagatctttt   1440
gcggtacagc aagggcacta tcaggaccca agagcttcag attatgacct cccacgtgct   1500
agcgactatg atttgcctag aagcccatat cctactccac ctttgcctcc tagatatcag   1560
ctacagaata tggatgtaga agcagggttc cgtgaggcag tttatgcttc ttttgtagca   1620
ggaatgtaca attatgtagt gacacagccg caagagcgta ttcccaatag tcagcaggtg   1680
gaagagattc tgcgtgatat gcttaccaac gggtcacaga catttagaga cctgatgaag   1740
cgttggaata gagaagtcga tagggaataa                                    1770
```

<210> SEQ ID NO 114
<211> LENGTH: 589
<212> TYPE: PRT
<213> ORGANISM: Chlamydia trachomatis

<400> SEQUENCE: 114

Met Ser Ile Arg Gly Val Gly Gly Asn Gly Asn Ser Arg Ile Pro Ser
1               5                   10                  15

His Asn Gly Asp Gly Ser Asn Arg Arg Ser Gln Asn Thr Lys Asn Lys
            20                  25                  30

Val Glu Asp Arg Val Arg Ser Leu Tyr Ser Ser Arg Ser Asn Glu Asn
        35                  40                  45

Arg Glu Ser Pro Tyr Ala Val Val Asp Val Ser Met Ile Glu Ser
    50                  55                  60

Thr Pro Thr Ser Gly Glu Thr Thr Arg Ala Ser Arg Gly Val Phe Ser
65                  70                  75                  80

Arg Phe Gln Arg Gly Leu Gly Arg Val Ala Asp Lys Val Arg Arg Ala
                85                  90                  95

```
Val Gln Arg Ala Trp Ser Ser Val Ser Ile Arg Arg Ser Ser Ala Thr
            100                 105                 110
Arg Ala Ala Glu Ser Arg Ser Ser Ser Arg Thr Ala Arg Gly Ala Ser
        115                 120                 125
Ser Gly Tyr Arg Glu Tyr Ser Pro Ser Ala Ala Arg Gly Leu Arg Leu
    130                 135                 140
Met Phe Thr Asp Phe Trp Arg Thr Arg Val Leu Arg Gln Thr Ser Pro
145                 150                 155                 160
Met Ala Gly Val Phe Gly Asn Leu Asp Val Asn Glu Ala Arg Leu Met
                165                 170                 175
Ala Ala Tyr Thr Ser Glu Cys Ala Asp His Leu Glu Ala Lys Glu Leu
            180                 185                 190
Ala Gly Pro Asp Gly Val Ala Ala Arg Glu Ile Ala Lys Arg Trp
        195                 200                 205
Glu Lys Arg Val Arg Asp Leu Gln Asp Lys Gly Ala Ala Arg Lys Leu
    210                 215                 220
Leu Asn Asp Pro Leu Gly Arg Arg Thr Pro Asn Tyr Gln Ser Lys Asn
225                 230                 235                 240
Pro Gly Glu Tyr Thr Val Gly Asn Ser Met Phe Tyr Asp Gly Pro Gln
                245                 250                 255
Val Ala Asn Leu Gln Asn Val Asp Thr Gly Phe Trp Leu Asp Met Ser
            260                 265                 270
Asn Leu Ser Asp Val Val Leu Ser Arg Glu Ile Gln Thr Gly Leu Arg
        275                 280                 285
Ala Arg Ala Thr Leu Glu Glu Ser Met Pro Met Leu Glu Asn Leu Glu
    290                 295                 300
Glu Arg Phe Arg Arg Leu Gln Glu Thr Cys Asp Ala Ala Arg Thr Glu
305                 310                 315                 320
Ile Glu Glu Ser Gly Trp Thr Arg Glu Ser Ala Ser Arg Met Glu Gly
                325                 330                 335
Asp Glu Ala Gln Gly Pro Ser Arg Ala Gln Gln Ala Phe Gln Ser Phe
            340                 345                 350
Val Asn Glu Cys Asn Ser Ile Glu Phe Ser Phe Gly Ser Phe Gly Glu
        355                 360                 365
His Val Arg Val Leu Cys Ala Arg Val Ser Arg Gly Leu Ala Ala Ala
    370                 375                 380
Gly Glu Ala Ile Arg Arg Cys Phe Ser Cys Cys Lys Gly Ser Thr His
385                 390                 395                 400
Arg Tyr Ala Pro Arg Asp Asp Leu Ser Pro Glu Gly Ala Ser Leu Ala
                405                 410                 415
Glu Thr Leu Ala Arg Phe Ala Asp Asp Met Gly Ile Glu Arg Gly Ala
            420                 425                 430
Asp Gly Thr Tyr Asp Ile Pro Leu Val Asp Asp Trp Arg Arg Gly Val
        435                 440                 445
Pro Ser Ile Glu Gly Glu Gly Ser Asp Ser Ile Tyr Glu Ile Met Met
    450                 455                 460
Pro Ile Tyr Glu Val Met Asn Met Asp Leu Glu Thr Arg Arg Ser Phe
465                 470                 475                 480
Ala Val Gln Gln Gly His Tyr Gln Asp Pro Arg Ala Ser Asp Tyr Asp
                485                 490                 495
Leu Pro Arg Ala Ser Asp Tyr Asp Leu Pro Arg Ser Pro Tyr Pro Thr
            500                 505                 510
Pro Pro Leu Pro Pro Arg Tyr Gln Leu Gln Asn Met Asp Val Glu Ala
```

```
              515                 520                 525
Gly Phe Arg Glu Ala Val Tyr Ala Ser Phe Val Ala Gly Met Tyr Asn
            530                 535                 540

Tyr Val Val Thr Gln Pro Gln Glu Arg Ile Pro Asn Ser Gln Gln Val
545                 550                 555                 560

Glu Glu Ile Leu Arg Asp Met Leu Thr Asn Gly Ser Gln Thr Phe Arg
                565                 570                 575

Asp Leu Met Lys Arg Trp Asn Arg Glu Val Asp Arg Glu
            580                 585

<210> SEQ ID NO 115
<211> LENGTH: 1776
<212> TYPE: DNA
<213> ORGANISM: Chlamydia trachomatis

<400> SEQUENCE: 115
atgagcatca gggagtagg aggcaacggg aatagtcgaa tcccttctca taatggggat      60
ggatcgaatc gcagaagtca aaatacgaag gtaataata aagttgaaga tcgagtttgt    120
tctctatatt catctcgtag taacgaaaat agagaatctc cttatgcagt agtgagcgtc    180
agctctatga tcgagagcac cccaacgagt ggagagacga caagagcttc gcgtggagtg    240
ttcagtcgtt ccaaagagg tttagtacga gtagctgaca aagtaagacg agctgttcag    300
tgtgcgtgga gttcagtctc tacaagaaga tcgtctgcaa caagagccgc agaatccgga    360
tcaagtagtc gtactgctcg tggtgcaagt tctgggtata gggagtattc tccttcagca    420
gctagagggc tgcgtcttat gttcacagat ttctggagaa ctcgggtttt acgccagacc    480
tctcctatgg ctggagtttt tgggaatctt gatgtgaacg aggctcgttt gatggctgcg    540
tacacaagtg agtgcgcgga tcatttagaa gcgaacaagt tggctggccc tgacgggta    600 gcggccgccc gggaaattgc taaaagatgg gagcaaagag ttagagatct acaagataaa    660
ggtgctgcac gaaaattatt aaatgatcct ttaggccgac gaacacctaa ttatcagagc    720
aaaaatccag gtgagtatac tgtagggaat tccatgtttt acgatggtcc tcaggtagcg    780
aatctccaga acgtcgacac tggtttttgg ctggacatga gcaatctctc agacgttgta    840
ttatccagag agattcaaac aggacttcga gcacgagcta ctttggaaga atccatgccg    900
atgttagaga atttagaaga gcgttttaga cgtttgcaag aaacttgtga tgcggctcgt    960
actgagatag aagaatcggg atggactcga gagtccgcat caagaatgga aggcgatgag   1020
gcgcaaggac cttctagagc acaacaagct tttcagagct ttgtaaatga atgtaacagc   1080
atcgagttct catttgggag ctttggagag catgtgcgag ttctctgcgc tagagtatca   1140
cgaggattag ctgccgcagg agaggcgatt cgccgttgct tctcttgttg taaaggatcg   1200
acgcatcgct acgctcctcg cgatgaccta tctcctgaag gtgcatcgtt agcagagact   1260
ttggctagat tcgcagatga tatgggaata gagcgaggtg ctgatggaac ctacgatatt   1320
cctttggtag atgattggag aagaggggtt cctagtattg aaggagaagg atctgactcg   1380
atctatgaaa tcatgatgcc tatctatgaa gttatggata tggatctaga aacacgaaga   1440
tcttttgcgg tacagcaagg gcactatcag gacccaagag cttcagatta tgacctccca   1500
cgtgctagcg actatgattt gcctagaagc ccatatccta ctccaccttt gcctcctaga   1560
tatcagctac agaatatgga tgtagaagca gggttccgtg aggcagttta tgcttctttt   1620
gtagcaggaa tgtacaatta tgtagtgaca cagccgcaag agcgtattcc caatagtcag   1680
caggtggaag ggattctgcg tgatatgctt accaacgggt cacagacatt tagagacctg   1740
```

```
atgaggcgtt ggaatagaga agtcgatagg gaataa                                    1776
```

<210> SEQ ID NO 116
<211> LENGTH: 591
<212> TYPE: PRT
<213> ORGANISM: Chlamydia trachomatis

<400> SEQUENCE: 116

```
Met Ser Ile Arg Gly Val Gly Gly Asn Gly Asn Ser Arg Ile Pro Ser
1               5                   10                  15

His Asn Gly Asp Gly Ser Asn Arg Arg Ser Gln Asn Thr Lys Gly Asn
            20                  25                  30

Asn Lys Val Glu Asp Arg Val Cys Ser Leu Tyr Ser Ser Arg Ser Asn
        35                  40                  45

Glu Asn Arg Glu Ser Pro Tyr Ala Val Val Asp Val Ser Ser Met Ile
    50                  55                  60

Glu Ser Thr Pro Thr Ser Gly Glu Thr Thr Arg Ala Ser Arg Gly Val
65                  70                  75                  80

Phe Ser Arg Phe Gln Arg Gly Leu Val Arg Val Ala Asp Lys Val Arg
                85                  90                  95

Arg Ala Val Gln Cys Ala Trp Ser Val Ser Thr Arg Arg Ser Ser
            100                 105                 110

Ala Thr Arg Ala Ala Glu Ser Gly Ser Ser Ser Arg Thr Ala Arg Gly
        115                 120                 125

Ala Ser Ser Gly Tyr Arg Glu Tyr Ser Pro Ser Ala Ala Arg Gly Leu
    130                 135                 140

Arg Leu Met Phe Thr Asp Phe Trp Arg Thr Arg Val Leu Arg Gln Thr
145                 150                 155                 160

Ser Pro Met Ala Gly Val Phe Gly Asn Leu Asp Val Asn Glu Ala Arg
                165                 170                 175

Leu Met Ala Ala Tyr Thr Ser Glu Cys Ala Asp His Leu Glu Ala Asn
            180                 185                 190

Lys Leu Ala Gly Pro Asp Gly Val Ala Ala Arg Glu Ile Ala Lys
        195                 200                 205

Arg Trp Glu Gln Arg Val Arg Asp Leu Gln Asp Lys Gly Ala Ala Arg
    210                 215                 220

Lys Leu Leu Asn Asp Pro Leu Gly Arg Arg Thr Pro Asn Tyr Gln Ser
225                 230                 235                 240

Lys Asn Pro Gly Glu Tyr Thr Val Gly Asn Ser Met Phe Tyr Asp Gly
                245                 250                 255

Pro Gln Val Ala Asn Leu Gln Asn Val Asp Thr Gly Phe Trp Leu Asp
            260                 265                 270

Met Ser Asn Leu Ser Asp Val Val Leu Ser Arg Glu Ile Gln Thr Gly
        275                 280                 285

Leu Arg Ala Arg Ala Thr Leu Glu Glu Ser Met Pro Met Leu Glu Asn
    290                 295                 300

Leu Glu Glu Arg Phe Arg Arg Leu Gln Glu Thr Cys Asp Ala Ala Arg
305                 310                 315                 320

Thr Glu Ile Glu Glu Ser Gly Trp Thr Arg Glu Ser Ala Ser Arg Met
                325                 330                 335

Glu Gly Asp Glu Ala Gln Gly Pro Ser Arg Ala Gln Gln Ala Phe Gln
            340                 345                 350

Ser Phe Val Asn Glu Cys Asn Ser Ile Glu Phe Ser Phe Gly Ser Phe
        355                 360                 365

Gly Glu His Val Arg Val Leu Cys Ala Arg Val Ser Arg Gly Leu Ala
```

```
                370             375             380
Ala Ala Gly Glu Ala Ile Arg Arg Cys Phe Ser Cys Cys Lys Gly Ser
385             390             395             400

Thr His Arg Tyr Ala Pro Arg Asp Asp Leu Ser Pro Glu Gly Ala Ser
            405             410             415

Leu Ala Glu Thr Leu Ala Arg Phe Ala Asp Asp Met Gly Ile Glu Arg
            420             425             430

Gly Ala Asp Gly Thr Tyr Asp Ile Pro Leu Val Asp Asp Trp Arg Arg
            435             440             445

Gly Val Pro Ser Ile Glu Gly Glu Ser Asp Ser Ile Tyr Glu Ile
450             455             460

Met Met Pro Ile Tyr Glu Val Met Asp Met Asp Leu Glu Thr Arg Arg
465             470             475             480

Ser Phe Ala Val Gln Gln Gly His Tyr Gln Asp Pro Arg Ala Ser Asp
            485             490             495

Tyr Asp Leu Pro Arg Ala Ser Asp Tyr Asp Leu Pro Arg Ser Pro Tyr
            500             505             510

Pro Thr Pro Pro Leu Pro Pro Arg Tyr Gln Leu Gln Asn Met Asp Val
            515             520             525

Glu Ala Gly Phe Arg Glu Ala Val Tyr Ala Ser Phe Val Ala Gly Met
            530             535             540

Tyr Asn Tyr Val Val Thr Gln Pro Gln Glu Arg Ile Pro Asn Ser Gln
545             550             555             560

Gln Val Glu Gly Ile Leu Arg Asp Met Leu Thr Asn Gly Ser Gln Thr
            565             570             575

Phe Arg Asp Leu Met Arg Arg Trp Asn Arg Glu Val Asp Arg Glu
            580             585             590

<210> SEQ ID NO 117
<211> LENGTH: 1776
<212> TYPE: DNA
<213> ORGANISM: Chlamydia trachomatis

<400> SEQUENCE: 117
atgagcatca ggggagtagg aggcaacggg aatagtcgaa tcccttctca taatggggat      60
ggatcgaatc gcagaagtca aaatacgaag ggtaataata agttgaagat cgagtttgt     120 tctctatatt catctcgtag taacgaaaat agagaatctc cttatgcagt agtagacgtc    180
agctctatga tcgagagcac cccaacgagt ggagagacga caagagcttc gcgtggagtg    240
ttcagtcgtt tccaaagagg tttagtacga gtagctgaca agtaagacg agctgttcag     300 tgtgcgtgga gttcagtctc tacaagaaga tcgtctgcaa caagagccgc agaatccgga    360
tcaagtagtc gtactgctcg tggtgcaagt tctgggtata gggagtattc tccttcagca    420
gctagagggc tgcgtcttat gttcacagat ttctggagaa ctcgggtttt acgccagacc    480
tctcctatgg ctggagtttt tgggaatctt gatgtgaacg aggctcgttt gatggctgcg    540
tacacaagtg agtgcgcgga tcatttagaa gcgaacaagt tggctggccc tgacggggta    600
gcggccgccc gggaaattgc taaaagatgg gagcaaagag ttagagatct acaagataaa    660
ggtgctgcac gaaaattatt aaatgatcct ttaggccgac gaacacctaa ttatcagagc    720
aaaaatccag gtgagtatac tgtagggaat tccatgtttt acgatggtcc tcaggtagcg    780
aatctccaga cgtcgacact ggttttttgg ctggacatga gcaatctctc agacgttgta    840
ttatccagag agattcaaac aggacttcga gcacgagcta ctttggaaga atccatgccg    900
atgttagaga atttagaaga gcgttttaga cgtttgcaag aaacttgtga tgcggctcgt    960
```

```
actgagatag aagaatcggg atggactcga gagtccgcat caagaatgga aggcgatgag    1020
gcgcaaggac cttctagagc acaacaagct tttcagagct ttgtaaatga atgtaacagc    1080
atcgagttct catttgggag ctttggagag catgtgcgag ttctctgcgc tagagtatca    1140
cgaggattag ctgccgcagg agaggcgatt cgccgttgct tctcttgttg taaaggatcg    1200
acgcatcgct acgctcctcg cgatgaccta tctcctgaag gtgcatcgtt agcagagact    1260
ttggctagat tcgcagatga tatgggaata gagcgaggtg ctgatggaac ctacgatatt    1320
cctttggtag atgattggag aagagggggt cctagtattg aaggagaagg atctgactcg    1380
atctatgaaa tcatgatgcc tatctatgaa gttatggata tggatctaga aacacgaaga    1440
tcttttgcgg tacagcaagg gcactatcag gacccaagag cttcagatta tgacctccca    1500
cgtgctagcg actatgattt gcctagaagc ccatatccta ctccacccttt gcctcctaga   1560 tatcagctac agaatatgga tgtagaagca gggttccgtg aggcagttta tgcttctttt    1620
gtagcaggaa tgtataatta tgtagtgaca cagccgcaag agcgtattcc caatagtcag    1680
caggtggaag ggattctgcg tgatatgctt accaacgggt cacagacatt tagagacctg    1740
atgaagcgtt ggaatagaga agtcgatagg gaataa                              1776

<210> SEQ ID NO 118
<211> LENGTH: 591
<212> TYPE: PRT
<213> ORGANISM: Chlamydia trachomatis

<400> SEQUENCE: 118

Met Ser Ile Arg Gly Val Gly Gly Asn Gly Asn Ser Arg Ile Pro Ser
1               5                   10                  15

His Asn Gly Asp Gly Ser Asn Arg Arg Ser Gln Asn Thr Lys Gly Asn
            20                  25                  30

Asn Lys Val Glu Asp Arg Val Cys Ser Leu Tyr Ser Ser Arg Ser Asn
        35                  40                  45

Glu Asn Arg Glu Ser Pro Tyr Ala Val Val Asp Val Ser Ser Met Ile
    50                  55                  60

Glu Ser Thr Pro Thr Ser Gly Glu Thr Thr Arg Ala Ser Arg Gly Val
65                  70                  75                  80

Phe Ser Arg Phe Gln Arg Gly Leu Val Arg Val Ala Asp Lys Val Arg
                85                  90                  95

Arg Ala Val Gln Cys Ala Trp Ser Ser Val Ser Thr Arg Arg Ser Ser
            100                 105                 110

Ala Thr Arg Ala Ala Glu Ser Gly Ser Ser Ser Arg Thr Ala Arg Gly
        115                 120                 125

Ala Ser Ser Gly Tyr Arg Glu Tyr Ser Pro Ser Ala Ala Arg Gly Leu
    130                 135                 140

Arg Leu Met Phe Thr Asp Phe Trp Arg Thr Arg Val Leu Arg Gln Thr
145                 150                 155                 160

Ser Pro Met Ala Gly Val Phe Gly Asn Leu Asp Val Asn Glu Ala Arg
                165                 170                 175

Leu Met Ala Ala Tyr Thr Ser Glu Cys Ala Asp His Leu Glu Ala Asn
            180                 185                 190

Lys Leu Ala Gly Pro Asp Gly Val Ala Ala Arg Glu Ile Ala Lys
        195                 200                 205

Arg Trp Glu Gln Arg Val Arg Asp Leu Gln Asp Lys Gly Ala Ala Arg
    210                 215                 220

Lys Leu Leu Asn Asp Pro Leu Gly Arg Arg Thr Pro Asn Tyr Gln Ser
```

```
                    225                 230                 235                 240
Lys Asn Pro Gly Glu Tyr Thr Val Gly Asn Ser Met Phe Tyr Asp Gly
                245                 250                 255

Pro Gln Val Ala Asn Leu Gln Asn Val Asp Thr Gly Phe Trp Leu Asp
            260                 265                 270

Met Ser Asn Leu Ser Asp Val Val Leu Ser Arg Glu Ile Gln Thr Gly
        275                 280                 285

Leu Arg Ala Arg Ala Thr Leu Glu Glu Ser Met Pro Met Leu Glu Asn
    290                 295                 300

Leu Glu Glu Arg Phe Arg Arg Leu Gln Glu Thr Cys Asp Ala Ala Arg
305                 310                 315                 320

Thr Glu Ile Glu Glu Ser Gly Trp Thr Arg Glu Ser Ala Ser Arg Met
                325                 330                 335

Glu Gly Asp Glu Ala Gln Gly Pro Ser Arg Ala Gln Gln Ala Phe Gln
            340                 345                 350

Ser Phe Val Asn Glu Cys Asn Ser Ile Glu Phe Ser Phe Gly Ser Phe
        355                 360                 365

Gly Glu His Val Arg Val Leu Cys Ala Arg Val Ser Arg Gly Leu Ala
    370                 375                 380

Ala Ala Gly Glu Ala Ile Arg Arg Cys Phe Ser Cys Cys Lys Gly Ser
385                 390                 395                 400

Thr His Arg Tyr Ala Pro Arg Asp Leu Ser Pro Glu Gly Ala Ser
                405                 410                 415

Leu Ala Glu Thr Leu Ala Arg Phe Ala Asp Asp Met Gly Ile Glu Arg
            420                 425                 430

Gly Ala Asp Gly Thr Tyr Asp Ile Pro Leu Val Asp Asp Trp Arg Arg
        435                 440                 445

Gly Val Pro Ser Ile Glu Gly Glu Gly Ser Asp Ser Ile Tyr Glu Ile
    450                 455                 460

Met Met Pro Ile Tyr Glu Val Met Asp Met Asp Leu Glu Thr Arg Arg
465                 470                 475                 480

Ser Phe Ala Val Gln Gln Gly His Tyr Gln Asp Pro Arg Ala Ser Asp
                485                 490                 495

Tyr Asp Leu Pro Arg Ala Ser Asp Tyr Asp Leu Pro Arg Ser Pro Tyr
            500                 505                 510

Pro Thr Pro Pro Leu Pro Pro Arg Tyr Gln Leu Gln Asn Met Asp Val
        515                 520                 525

Glu Ala Gly Phe Arg Glu Ala Val Tyr Ala Ser Phe Val Ala Gly Met
    530                 535                 540

Tyr Asn Tyr Val Val Thr Gln Pro Gln Glu Arg Ile Pro Asn Ser Gln
545                 550                 555                 560

Gln Val Glu Gly Ile Leu Arg Asp Met Leu Thr Asn Gly Ser Gln Thr
                565                 570                 575

Phe Arg Asp Leu Met Lys Arg Trp Asn Arg Glu Val Asp Arg Glu
            580                 585                 590

<210> SEQ ID NO 119
<211> LENGTH: 1776
<212> TYPE: DNA
<213> ORGANISM: Chlamydia trachomatis

<400> SEQUENCE: 119
atgagcatca ggggagtagg aggcaacggg aatagtcgaa tcccttctca taatggggat    60
ggatcgaatc gcagaagtca aaatacgaag ggtaataata aagttgaaga tcgagtttgt   120
```

```
tctctatatt catctcgtag taacgaaaat agagaatctc cttatgcagt agtagacgtc    180
agctctatga tcgagagcac cccaacgagt ggagagacga caagagcttc gcgtggagtg    240
ttcagtcgtt tccaaagagg tttagtacga gtagctgaca agtaagacg agctgttcag     300 tgtgcgtgga gttcagtctc tacaagaaga tcgtctgcaa caagagccgc agaatccgga   360
tcaagtagtc gtactgctcg tggtgcaagt tctgggtata gggagtattc tccttcagca   420
gctagagggc tgcgtcttat gttcacagat ttctggagaa ctcgggtttt acgccagacc   480
tctcctatgg ctggagtttt tgggaatctt gatgtgaacg aggctcgttt gatggctgcg   540
tacacaagtg agtgcgcgga tcatttagaa gcgaacaagt tggctggccc tgacggggta   600
gcggccgccc gggaaattgc taaagatgg gagcaaagag ttagagatct acaagataaa    660
ggtgctgcac gaaaattatt aaatgatcct ttaggccgac gaacacctaa ttatcagagc   720
aaaaatccag gtgagtatac tgtagggaat tccatgtttt acgatggtcc tcaggtagcg   780
aatctccaga acgtcgacac tggttttttgg ctggacatga gcaatctctc agacgttgta   840
ttatccagag agattcaaac aggacttcga gcacgagcta ctttggaaga atccatgccg   900
atgttagaga atttagaaga gcgttttaga cgtttgcaag aaacttgtga tgcggctcgt   960
actgagatag aagaatcggg atggactcga gagtccgcat caagaatgga aggcgatgag  1020
gcgcaaggac cttctagagc acaacaagct tttcagagct ttgtaaatga atgtaacagc  1080
atcgagttct catttgggag ctttggagag catgtgcgag ttctctgcgc tagagtatca  1140
cgaggattag ctgccgcagg agaggcgatt cgccgttgct tctcttgttg taaaggatcg  1200
acgcatcgct acgtcctcg cgatgaccta tctcctgaag gtgcatcgtt agcagagact   1260
ttggctagat tcgcagatga tatgggaata gagcgaggtg ctgatggaac ctacgatatt  1320
cctttggtag atgattggag aagaggggtt cctagtattg aaggagaagg atctgactcg  1380
atctatgaaa tcatgatgcc tatctatgaa gttatggata tggatctaga aacacgaaga  1440
tcttttgcgg tacagcaagg gcactatcag gacccaagag cttcagatta tgacctccca  1500
cgtgctagcg actatgattt gcctagaagc ccatatccta ctccaccttt gcctcctaga   1560
tatcagctac agaatatgga tgtagaagca gggttccgtg aggcagttta tgcttctttt  1620
gtagcaggaa tgtacaatta tgtagtgaca cagccgcaag agcgtattcc caatagtcag  1680
caggtggaag ggattctgcg tgatatgctt accaacgggt cacagacatt tagagacctg  1740
atgaggcgtt ggaatagaga agtcgatagg gaataa                            1776
```

<210> SEQ ID NO 120
<211> LENGTH: 591
<212> TYPE: PRT
<213> ORGANISM: Chlamydia trachomatis

<400> SEQUENCE: 120

Met Ser Ile Arg Gly Val Gly Gly Asn Gly Asn Ser Arg Ile Pro Ser
1               5                   10                  15

His Asn Gly Asp Gly Ser Asn Arg Arg Ser Gln Asn Thr Lys Gly Asn
            20                  25                  30

Asn Lys Val Glu Asp Arg Val Cys Ser Leu Tyr Ser Ser Arg Ser Asn
        35                  40                  45

Glu Asn Arg Glu Ser Pro Tyr Ala Val Val Asp Val Ser Ser Met Ile
    50                  55                  60

Glu Ser Thr Pro Thr Ser Gly Glu Thr Thr Arg Ala Ser Arg Gly Val
65                  70                  75                  80

Phe Ser Arg Phe Gln Arg Gly Leu Val Arg Val Ala Asp Lys Val Arg

```
                    85                  90                  95
Arg Ala Val Gln Cys Ala Trp Ser Ser Val Ser Thr Arg Arg Ser Ser
                100                 105                 110
Ala Thr Arg Ala Ala Glu Ser Gly Ser Ser Ser Arg Thr Ala Arg Gly
                115                 120                 125
Ala Ser Ser Gly Tyr Arg Glu Tyr Ser Pro Ser Ala Ala Arg Gly Leu
                130                 135                 140
Arg Leu Met Phe Thr Asp Phe Trp Arg Thr Arg Val Leu Arg Gln Thr
145                 150                 155                 160
Ser Pro Met Ala Gly Val Phe Gly Asn Leu Asp Val Asn Glu Ala Arg
                165                 170                 175
Leu Met Ala Ala Tyr Thr Ser Glu Cys Ala Asp His Leu Glu Ala Asn
                180                 185                 190
Lys Leu Ala Gly Pro Asp Gly Val Ala Ala Arg Glu Ile Ala Lys
                195                 200                 205
Arg Trp Glu Gln Arg Val Arg Asp Leu Gln Asp Lys Gly Ala Ala Arg
                210                 215                 220
Lys Leu Leu Asn Asp Pro Leu Gly Arg Arg Thr Pro Asn Tyr Gln Ser
225                 230                 235                 240
Lys Asn Pro Gly Glu Tyr Thr Val Gly Asn Ser Met Phe Tyr Asp Gly
                245                 250                 255
Pro Gln Val Ala Asn Leu Gln Asn Val Asp Thr Gly Phe Trp Leu Asp
                260                 265                 270
Met Ser Asn Leu Ser Asp Val Val Leu Ser Arg Glu Ile Gln Thr Gly
                275                 280                 285
Leu Arg Ala Arg Ala Thr Leu Glu Glu Ser Met Pro Met Leu Glu Asn
                290                 295                 300
Leu Glu Glu Arg Phe Arg Arg Leu Gln Glu Thr Cys Asp Ala Ala Arg
305                 310                 315                 320
Thr Glu Ile Glu Glu Ser Gly Trp Thr Arg Glu Ser Ala Ser Arg Met
                325                 330                 335
Glu Gly Asp Glu Ala Gln Gly Pro Ser Arg Ala Gln Gln Ala Phe Gln
                340                 345                 350
Ser Phe Val Asn Glu Cys Asn Ser Ile Glu Phe Ser Phe Gly Ser Phe
                355                 360                 365
Gly Glu His Val Arg Val Leu Cys Ala Arg Val Ser Arg Gly Leu Ala
                370                 375                 380
Ala Ala Gly Glu Ala Ile Arg Arg Cys Phe Ser Cys Cys Lys Gly Ser
385                 390                 395                 400
Thr His Arg Tyr Ala Pro Arg Asp Asp Leu Ser Pro Glu Gly Ala Ser
                405                 410                 415
Leu Ala Glu Thr Leu Ala Arg Phe Ala Asp Asp Met Gly Ile Glu Arg
                420                 425                 430
Gly Ala Asp Gly Thr Tyr Asp Ile Pro Leu Val Asp Asp Trp Arg Arg
                435                 440                 445
Gly Val Pro Ser Ile Glu Gly Glu Gly Ser Asp Ser Ile Tyr Glu Ile
                450                 455                 460
Met Met Pro Ile Tyr Glu Val Met Asp Met Asp Leu Glu Thr Arg Arg
465                 470                 475                 480
Ser Phe Ala Val Gln Gln Gly His Tyr Gln Asp Pro Arg Ala Ser Asp
                485                 490                 495
Tyr Asp Leu Pro Arg Ala Ser Asp Tyr Asp Leu Pro Arg Ser Pro Tyr
                500                 505                 510
```

```
        Pro Thr Pro Pro Leu Pro Pro Arg Tyr Gln Leu Gln Asn Met Asp Val
            515                 520                 525

Glu Ala Gly Phe Arg Glu Ala Val Tyr Ala Ser Phe Val Ala Gly Met
            530                 535                 540

Tyr Asn Tyr Val Val Thr Gln Pro Gln Glu Arg Ile Pro Asn Ser Gln
        545                 550                 555                 560

Gln Val Glu Gly Ile Leu Arg Asp Met Leu Thr Asn Gly Ser Gln Thr
                        565                 570                 575

Phe Arg Asp Leu Met Arg Arg Trp Asn Arg Glu Val Asp Arg Glu
            580                 585                 590

<210> SEQ ID NO 121
<211> LENGTH: 1773
<212> TYPE: DNA
<213> ORGANISM: Chlamydia trachomatis

<400> SEQUENCE: 121
atgagcatca ggggagtagg aggcaacggg aatagtcgaa tcccttctca taatggggat      60
ggatcgaatc gcagaagtca aaatacgaag ggtaataata aagttgaaga tcgagttcat     120
tctctatatt catctcttag taacgaaaat agagaatctc cttatccagt agtagacgtc     180
agctctatga tcgagagcac cccaacgagt ggagagacgc caagagcttc gcgtggagtg     240
ttcagtcgtt tccaaagagg tttaggacga gtagctgaca agtaagacg agctgttcag      300 tgtgcgtggg gttcagtctc tacaagaaga tcgtctgcaa caagagccgt agaatccgga     360
tcaagtagtc gtactgctcg tggtgcaagt tctggggagggg agtattctcc ttcagcagct   420
agagggctgc gtcttatgtt cacagatttc tggagaactc gggttttacg ccagacctct     480
cctatggatg tagttttttgg gaatcttgat gtgaacgagg ctcgtttgat ggctgcttac    540
acaagtgagt gcgcggatta tttagaagcg cacgatttgg ctggccctga cggggtagcg    600
gccgcccggg aaattgctca agatgggag aaaagagtta gagatctaca agataaaggt     660
gctgcacaaa aattattaaa tgatccttta ggccgacgaa cacctaatta tcagagcaaa     720
aatccaggtg agtatactgt agggaattcc atgttttacg atggtcctca ggtagcgaat     780
ctccagaacg tcgacactgg ttttttggctg acatgagca atttctcaga cgttgtatta    840
tccagagaga ttcaaacagg gcttcgagca cgagctactt tggaagaatc catgccgatg    900
ttagagaatt tagaagagcg ttttagacgt ttgcaagaaa cttgtgatgc ggctcgtact   960
gagatagaag aatcgggatg gactcgagag tccgcatcaa gaatgggagg cgatgagacg   1020
caaggacctt ctagagcaca acaagctttt cagagctttg taaatgaatg taatagcatc   1080
gagttctcat ttgggagctt tggagagcat gtgcgagttc tctgcgctag agtatcacga   1140
ggattagttg ccgcaggaga ggcgattcgc cgttgcttct cttgttgtaa aggatcgacg   1200
catcgctacg ctcctcgcga tgacctatct cctgaaggtg catcgttagc agagactttg   1260
gctagattcg cagatgatat gggaatagag caaggtgctg atggaaccta cgatattcct   1320
tgggtagatg attggagaag aggggttcct agtattgaag gagaaggatc tgactcgatc   1380
tatgaaatca tgatgcctat ctatgaagtt atgaatatgg atctagaaac acgaagatct   1440
tttgcggtac agcaagggca ctatcaggac ccaagagctt cagattatga cctcccacgt   1500
gctagcgact atgatttgcc tagaagccca tatcctactc caccttttgcc ttctagatat   1560 cagctacaga atatggatgt agaagcaggg ttccgtgagg cagtttatgc ttcttttgta   1620
gcaggaatgt acaattatgt agtgacacag ccgcaagagc gtattcccaa tagtcagcag   1680
gtggaaggga ttctgcgtga tatgcttacc aacgggtcac agacatttag cgacctgatg   1740
```

```
aagcgttggg atagagaagt cgatagggaa taa                                    1773
```

<210> SEQ ID NO 122
<211> LENGTH: 590
<212> TYPE: PRT
<213> ORGANISM: Chlamydia trachomatis

<400> SEQUENCE: 122

| Met | Ser | Ile | Arg | Gly | Val | Gly | Gly | Asn | Gly | Asn | Ser | Arg | Ile | Pro | Ser |
|---|---|---|---|---|---|---|---|---|---|---|---|---|---|---|---|
| 1 | | | | 5 | | | | | 10 | | | | | 15 | |

| His | Asn | Gly | Asp | Gly | Ser | Asn | Arg | Arg | Ser | Gln | Asn | Thr | Lys | Gly | Asn |
|---|---|---|---|---|---|---|---|---|---|---|---|---|---|---|---|
| | | | 20 | | | | | 25 | | | | | 30 | | |

| Asn | Lys | Val | Glu | Asp | Arg | Val | His | Ser | Leu | Tyr | Ser | Ser | Leu | Ser | Asn |
|---|---|---|---|---|---|---|---|---|---|---|---|---|---|---|---|
| | | | 35 | | | | | 40 | | | | | 45 | | |

| Glu | Asn | Arg | Glu | Ser | Pro | Tyr | Pro | Val | Val | Asp | Val | Ser | Ser | Met | Ile |
|---|---|---|---|---|---|---|---|---|---|---|---|---|---|---|---|
| | 50 | | | | | 55 | | | | | 60 | | | | |

| Glu | Ser | Thr | Pro | Thr | Ser | Gly | Glu | Thr | Pro | Arg | Ala | Ser | Arg | Gly | Val |
|---|---|---|---|---|---|---|---|---|---|---|---|---|---|---|---|
| 65 | | | | | 70 | | | | | 75 | | | | | 80 |

| Phe | Ser | Arg | Phe | Gln | Arg | Gly | Leu | Gly | Arg | Val | Ala | Asp | Lys | Val | Arg |
|---|---|---|---|---|---|---|---|---|---|---|---|---|---|---|---|
| | | | | 85 | | | | | 90 | | | | | 95 | |

| Arg | Ala | Val | Gln | Cys | Ala | Trp | Gly | Ser | Val | Ser | Thr | Arg | Arg | Ser | Ser |
|---|---|---|---|---|---|---|---|---|---|---|---|---|---|---|---|
| | | | 100 | | | | | 105 | | | | | 110 | | |

| Ala | Thr | Arg | Ala | Val | Glu | Ser | Gly | Ser | Ser | Ser | Arg | Thr | Ala | Arg | Gly |
|---|---|---|---|---|---|---|---|---|---|---|---|---|---|---|---|
| | | | 115 | | | | | 120 | | | | | 125 | | |

| Ala | Ser | Ser | Gly | Arg | Glu | Tyr | Ser | Pro | Ser | Ala | Ala | Arg | Gly | Leu | Arg |
|---|---|---|---|---|---|---|---|---|---|---|---|---|---|---|---|
| | 130 | | | | | 135 | | | | | 140 | | | | |

| Leu | Met | Phe | Thr | Asp | Phe | Trp | Arg | Thr | Arg | Val | Leu | Arg | Gln | Thr | Ser |
|---|---|---|---|---|---|---|---|---|---|---|---|---|---|---|---|
| 145 | | | | | 150 | | | | | 155 | | | | | 160 |

| Pro | Met | Asp | Val | Val | Phe | Gly | Asn | Leu | Asp | Val | Asn | Glu | Ala | Arg | Leu |
|---|---|---|---|---|---|---|---|---|---|---|---|---|---|---|---|
| | | | | 165 | | | | | 170 | | | | | 175 | |

| Met | Ala | Ala | Tyr | Thr | Ser | Glu | Cys | Ala | Asp | Tyr | Leu | Glu | Ala | His | Asp |
|---|---|---|---|---|---|---|---|---|---|---|---|---|---|---|---|
| | | | 180 | | | | | 185 | | | | | 190 | | |

| Leu | Ala | Gly | Pro | Asp | Gly | Val | Ala | Ala | Ala | Arg | Glu | Ile | Ala | Gln | Arg |
|---|---|---|---|---|---|---|---|---|---|---|---|---|---|---|---|
| | | | 195 | | | | | 200 | | | | | 205 | | |

| Trp | Glu | Lys | Arg | Val | Arg | Asp | Leu | Gln | Asp | Lys | Gly | Ala | Ala | Gln | Lys |
|---|---|---|---|---|---|---|---|---|---|---|---|---|---|---|---|
| | 210 | | | | | 215 | | | | | 220 | | | | |

| Leu | Leu | Asn | Asp | Pro | Leu | Gly | Arg | Arg | Thr | Pro | Asn | Tyr | Gln | Ser | Lys |
|---|---|---|---|---|---|---|---|---|---|---|---|---|---|---|---|
| 225 | | | | | 230 | | | | | 235 | | | | | 240 |

| Asn | Pro | Gly | Glu | Tyr | Thr | Val | Gly | Asn | Ser | Met | Phe | Tyr | Asp | Gly | Pro |
|---|---|---|---|---|---|---|---|---|---|---|---|---|---|---|---|
| | | | | 245 | | | | | 250 | | | | | 255 | |

| Gln | Val | Ala | Asn | Leu | Gln | Asn | Val | Asp | Thr | Gly | Phe | Trp | Leu | Asp | Met |
|---|---|---|---|---|---|---|---|---|---|---|---|---|---|---|---|
| | | | 260 | | | | | 265 | | | | | 270 | | |

| Ser | Asn | Phe | Ser | Asp | Val | Val | Leu | Ser | Arg | Glu | Ile | Gln | Thr | Gly | Leu |
|---|---|---|---|---|---|---|---|---|---|---|---|---|---|---|---|
| | 275 | | | | | 280 | | | | | 285 | | | | |

| Arg | Ala | Arg | Ala | Thr | Leu | Glu | Glu | Ser | Met | Pro | Met | Leu | Glu | Asn | Leu |
|---|---|---|---|---|---|---|---|---|---|---|---|---|---|---|---|
| | | | 290 | | | | | 295 | | | | | 300 | | |

| Glu | Glu | Arg | Phe | Arg | Arg | Leu | Gln | Glu | Thr | Cys | Asp | Ala | Ala | Arg | Thr |
|---|---|---|---|---|---|---|---|---|---|---|---|---|---|---|---|
| 305 | | | | | 310 | | | | | 315 | | | | | 320 |

| Glu | Ile | Glu | Glu | Ser | Gly | Trp | Thr | Arg | Glu | Ser | Ala | Ser | Arg | Met | Gly |
|---|---|---|---|---|---|---|---|---|---|---|---|---|---|---|---|
| | | | | 325 | | | | | 330 | | | | | 335 | |

| Gly | Asp | Glu | Thr | Gln | Gly | Pro | Ser | Arg | Ala | Gln | Gly | Ala | Phe | Gln | Ser |
|---|---|---|---|---|---|---|---|---|---|---|---|---|---|---|---|
| | | | 340 | | | | | 345 | | | | | 350 | | |

| Phe | Val | Asn | Glu | Cys | Asn | Ser | Ile | Glu | Phe | Ser | Phe | Gly | Ser | Phe | Gly |
|---|---|---|---|---|---|---|---|---|---|---|---|---|---|---|---|
| | | | 355 | | | | | 360 | | | | | 365 | | |

```
Glu His Val Arg Val Leu Cys Ala Arg Val Ser Arg Gly Leu Val Ala
        370                 375                 380

Ala Gly Glu Ala Ile Arg Arg Cys Phe Ser Cys Cys Lys Gly Ser Thr
385                 390                 395                 400

His Arg Tyr Ala Pro Arg Asp Asp Leu Ser Pro Glu Gly Ala Ser Leu
                405                 410                 415

Ala Glu Thr Leu Ala Arg Phe Ala Asp Asp Met Gly Ile Glu Gln Gly
            420                 425                 430

Ala Asp Gly Thr Tyr Asp Ile Pro Trp Val Asp Trp Arg Arg Gly
            435                 440                 445

Val Pro Ser Ile Glu Gly Glu Gly Ser Asp Ser Ile Tyr Glu Ile Met
        450                 455                 460

Met Pro Ile Tyr Glu Val Met Asn Met Asp Leu Glu Thr Arg Arg Ser
465                 470                 475                 480

Phe Ala Val Gln Gln Gly His Tyr Gln Asp Pro Arg Ala Ser Asp Tyr
                485                 490                 495

Asp Leu Pro Arg Ala Ser Asp Tyr Asp Leu Pro Arg Ser Pro Tyr Pro
                500                 505                 510

Thr Pro Pro Leu Pro Ser Arg Tyr Gln Leu Gln Asn Met Asp Val Glu
            515                 520                 525

Ala Gly Phe Arg Glu Ala Val Tyr Ala Ser Phe Val Ala Gly Met Tyr
        530                 535                 540

Asn Tyr Val Val Thr Gln Pro Gln Glu Arg Ile Pro Asn Ser Gln Gln
545                 550                 555                 560

Val Glu Gly Ile Leu Arg Asp Met Leu Thr Asn Gly Ser Gln Thr Phe
                565                 570                 575

Ser Asp Leu Met Lys Arg Trp Asp Arg Glu Val Asp Arg Glu
            580                 585                 590

<210> SEQ ID NO 123
<211> LENGTH: 1776
<212> TYPE: DNA
<213> ORGANISM: Chlamydia trachomatis

<400> SEQUENCE: 123
atgagcatca ggggagtagg aggcaacggg aatagtcgaa tcccttctca taatggggat    60
ggatcgaatc gcagaagtca aaatacgaag ggtaataata aagttgaaga tcgagtttgt   120
tctctatatt catctcgtag taacgaaaat agagaatctc cttatgcagt agtagacgtc   180
agctctatga tcgagagcac cccaacgagt ggagagacga caagagcttc gcgtggagtg   240
ttcagtcgtt tccaaagagg tttagtacga gtagctgaca aagtaagacg agctgttcag   300
tgtgcgtgga gttcagtctc tacaagaaga tcgtctgcaa caagagccgc agaatccgga   360
tcaagtagtc gtactgctcg tggtgcaagt tctgggtata gggagtattc tccttcagca   420
gctagagggc tgcgtcttat gttcacagat ttctggagaa ctcgggtttt acgccagacc   480
tctcctatgg ctggagtttt tgggaatctt gatgtgaacg aggctcgttt gatggctgcg   540
tacacaagtg agtgcgcgga tcatttagaa gcgaacaagt tggctggccc tgacggggta   600
gcggccgccc gggaaattgc taaaagatgg gagcaaagag ttagagatct acaagataaa   660
ggtgctgcac gaaaattatt aaatgatcct ttaggccgac gaacacctaa ttatcagagc   720
aaaaatccag gtgagtatac tgtagggaat tccatgtttt acgatggtcc tcaggtagcg   780
aatctccaga acgtcgacac tggttttttgg ctggacatga gcaatctctc agacgttgta   840
ttatccagag agattcaaac aggacttcga gcacgagcta ctttggaaga atccatgccg   900
```

-continued

```
atgttagaga atttagaaga gcgttttaga cgtttgcaag aaacttgtga tgcggctcgt    960
actgagatag aagaatcggg atggactcga gagtccgcat caagaatgga aggcgatgag   1020
gcgcaaggac cttctagagc acaacaagct tttcagagct ttgtaaatga atgtaacagc   1080
atcgagttct catttgggag ctttggagag catgtgcgag ttctctgcgc tagagtatca   1140
cgaggattag ctgccgcagg agaggcgatt cgccgttgct tctcttgttg taaaggatcg   1200
acgcatcgct acgctcctcg cgatgaccta tctcctgaag gtgcatcgtt agcagagact   1260
ttggctagat tcgcagatga tatgggaata gagcgaggtg ctgatggaac ctacgatatt   1320
cctttggtag atgattggag aagagggggtt cctagtattg aaggagaagg atctgactcg   1380
atctatgaaa tcatgatgcc tatctatgaa gttatggata tggatctaga aacacgaaga   1440
tcttttgcgg tacagcaagg gcactatcag gacccaagag cttcagatta tgacctccca   1500
cgtgctagcg actatgattt gcctagaagc ccatatccta ctccacctttt gcctcctaga   1560
tatcagctac agaatatgga tgtagaagca gggttccgtg aggcagttta tgcttctttt   1620
gtagcaggaa tgtacaatta tgtagtgaca cagccgcaag agcgtattcc caatagtcag   1680
caggtggaag ggattctgcg tgatatgctt accaacgggt cacagacatt tagagacctg   1740
atgaggcgtt ggaatagaga agtcgatagg gaataa                              1776
```

<210> SEQ ID NO 124
<211> LENGTH: 591
<212> TYPE: PRT
<213> ORGANISM: Chlamydia trachomatis

<400> SEQUENCE: 124

```
Met Ser Ile Arg Gly Val Gly Gly Asn Gly Asn Ser Arg Ile Pro Ser
1               5                   10                  15

His Asn Gly Asp Gly Ser Asn Arg Arg Ser Gln Asn Thr Lys Gly Asn
            20                  25                  30

Asn Lys Val Glu Asp Arg Val Cys Ser Leu Tyr Ser Ser Arg Ser Asn
        35                  40                  45

Glu Asn Arg Glu Ser Pro Tyr Ala Val Val Asp Val Ser Ser Met Ile
    50                  55                  60

Glu Ser Thr Pro Thr Ser Gly Glu Thr Thr Arg Ala Ser Arg Gly Val
65                  70                  75                  80

Phe Ser Arg Phe Gln Arg Gly Leu Val Arg Val Ala Asp Lys Val Arg
                85                  90                  95

Arg Ala Val Gln Cys Ala Trp Ser Ser Val Ser Thr Arg Ser Ser
            100                 105                 110

Ala Thr Arg Ala Ala Glu Ser Gly Ser Ser Arg Thr Ala Arg Gly
        115                 120                 125

Ala Ser Ser Gly Tyr Arg Glu Tyr Ser Pro Ser Ala Ala Arg Gly Leu
    130                 135                 140

Arg Leu Met Phe Thr Asp Phe Trp Arg Thr Arg Val Leu Arg Gln Thr
145                 150                 155                 160

Ser Pro Met Ala Gly Val Phe Gly Asn Leu Asp Val Asn Glu Ala Arg
                165                 170                 175

Leu Met Ala Ala Tyr Thr Ser Glu Cys Ala Asp His Leu Glu Ala Asn
            180                 185                 190

Lys Leu Ala Gly Pro Asp Gly Val Ala Ala Arg Glu Ile Ala Lys
        195                 200                 205

Arg Trp Glu Gln Arg Val Arg Asp Leu Gln Asp Lys Gly Ala Ala Arg
    210                 215                 220
```

| | | | | | | | | | | | | |
|---|---|---|---|---|---|---|---|---|---|---|---|---|
| Lys | Leu | Leu | Asn | Asp | Pro | Leu | Gly | Arg | Arg | Thr | Pro | Asn | Tyr | Gln | Ser |
| 225 | | | | 230 | | | | | 235 | | | | | 240 | |

Lys Leu Leu Asn Asp Pro Leu Gly Arg Arg Thr Pro Asn Tyr Gln Ser
225                 230                 235                 240

Lys Asn Pro Gly Glu Tyr Thr Val Gly Asn Ser Met Phe Tyr Asp Gly
                245                 250                 255

Pro Gln Val Ala Asn Leu Gln Asn Val Asp Thr Gly Phe Trp Leu Asp
            260                 265                 270

Met Ser Asn Leu Ser Asp Val Val Leu Ser Arg Glu Ile Gln Thr Gly
        275                 280                 285

Leu Arg Ala Arg Ala Thr Leu Glu Glu Ser Met Pro Met Leu Glu Asn
    290                 295                 300

Leu Glu Glu Arg Phe Arg Arg Leu Gln Glu Thr Cys Asp Ala Ala Arg
305                 310                 315                 320

Thr Glu Ile Glu Glu Ser Gly Trp Thr Arg Glu Ser Ala Ser Arg Met
                325                 330                 335

Glu Gly Asp Glu Ala Gln Gly Pro Ser Arg Ala Gln Asn Ala Phe Gln
            340                 345                 350

Ser Phe Val Asn Glu Cys Asn Ser Ile Glu Phe Ser Phe Gly Ser Phe
        355                 360                 365

Gly Glu His Val Arg Val Leu Cys Ala Arg Val Ser Arg Gly Leu Ala
    370                 375                 380

Ala Ala Gly Glu Ala Ile Arg Arg Cys Phe Ser Cys Cys Lys Gly Ser
385                 390                 395                 400

Thr His Arg Tyr Ala Pro Arg Asp Asp Leu Ser Pro Glu Gly Ala Ser
                405                 410                 415

Leu Ala Glu Thr Leu Ala Arg Phe Ala Asp Met Gly Ile Glu Arg
            420                 425                 430

Gly Ala Asp Gly Thr Tyr Asp Ile Pro Leu Val Asp Asp Trp Arg Arg
        435                 440                 445

Gly Val Pro Ser Ile Glu Gly Glu Gly Ser Asp Ser Ile Tyr Glu Ile
    450                 455                 460

Met Met Pro Ile Tyr Glu Val Met Asp Met Asp Leu Glu Thr Arg Arg
465                 470                 475                 480

Ser Phe Ala Val Gln Gln Gly His Tyr Gln Asp Pro Arg Ala Ser Asp
                485                 490                 495

Tyr Asp Leu Pro Arg Ala Ser Asp Tyr Asp Leu Pro Arg Ser Pro Tyr
            500                 505                 510

Pro Thr Pro Pro Leu Pro Pro Arg Tyr Gln Leu Gln Asn Met Asp Val
        515                 520                 525

Glu Ala Gly Phe Arg Glu Ala Val Tyr Ala Ser Phe Val Ala Gly Met
    530                 535                 540

Tyr Asn Tyr Val Val Thr Gln Pro Gln Glu Arg Ile Pro Asn Ser Gln
545                 550                 555                 560

Gln Val Glu Gly Ile Leu Arg Asp Met Leu Thr Asn Gly Ser Gln Thr
                565                 570                 575

Phe Arg Asp Leu Met Arg Arg Trp Asn Arg Glu Val Asp Arg Glu
            580                 585                 590

<210> SEQ ID NO 125
<211> LENGTH: 1773
<212> TYPE: DNA
<213> ORGANISM: Chlamydia trachomatis

<400> SEQUENCE: 125
atgagcatca gggagtagg aggcaacggg aatagtcgaa tcccttctca taatggggat        60
ggatcgaatc gcagaagtca aaatacgaag ggtaataata aagttgaaga tcgagttcat       120

```
tctctatatt catctcttag taacgaaaat agagaatctc cttatccagt agtagacgtc      180
agctctatga tcgagagcac cccaacgagt ggagagacgc caagagcttc gcgtggagtg      240
ttcagtcgtt tccaaagagg tttaggacga gtagctgaca agtaagacg agctgttcag       300 tgtgcgtggg gttcagtctc tacaagaaga tcgtctgcaa caagagccgt agaatccgga     360
tcaagtagtc gtactgctcg tggtgcaagt tctgggaggg agtattctcc ttcagcagct     420
agagggctgc gtcttatgtt cacagatttc tggagaactc gggttttacg ccagacctct    480
cctatggatg tagttttttgg gaatcttgat gtgaacgagg ctcgtttgat ggctgcttac  540
acaagtgagt gcgcggatta tttagaagcg cacgatttgg ctggccctga cggggtagcg  600
gccgcccggg aaattgctca agatgggat aaaagagtta gagatctaca agataaaggt    660
gctgcacaaa aattattaaa tgatccttta ggccgacgaa cacctaatta tcagagcaaa  720
aatccaggtg agtatactgt agggaattcc atgttttacg atggtcctca ggtagcgaat  780
ctccagaacg tcgacactgg tttttggctg gacatgagca atttctcaga cgttgtatta  840
tccagagaga ttcaaacagg gcttcgagca cgagctactt tggaagaatc catgccgatg  900
ttagagaatt tagaagagcg ttttagacgt ttgcaagaaa cttgtgatgc ggctcgtact  960
gagatagaag aatcgggatg gactcgagag tccgcatcaa gaatgggagg cgatgagacg 1020 caaggaccctt ctagagcaca caagctttt cagagctttg taaatgaatg taatagcatc 1080
gagttctcat ttgggagctt tggagagcat gtgcgagttc tctgcgctag agtatcacga 1140
ggattagttg ccgcaggaga ggcgattcgc cgttgcttct cttgttgtaa aggatcgacg 1200
catcgctacg ctcctcgcga tgacctatct cctgaaggtg catcgttagc agagactttg 1260
gctagattcg cagatgatat gggaatagag caaggtgctg atggaaccta cgatattcct 1320
tgggtagatg attggagaag aggggttcct agtattgaag gagaaggatc tgactcgatc 1380
tatgaaatca tgatgcctat ctatgaagtt atgaatatgg atctagaaac acgaagatct 1440
tttgcggtac agcaagggca ctatcaggac ccaagagctt cagattatga cctcccacgt 1500
gctagcgact atgatttgcc tagaagccca tatcctactc caccttttgcc ttctagatat 1560 cagctacaga atatggatgt agaagcaggg ttccgtgagg cagtttatgc ttcttttgta  1620
gcaggaatgt acaattatgt agtgacacag ccgcaagagc gtattcccaa tagtcagcag 1680
gtggaaggga ttctgcgtga tatgcttacc aacgggtcac agacatttag caacctgatg 1740
cagcgttggg atagagaagt cgatagggaa taa                                      1773
```

<210> SEQ ID NO 126
<211> LENGTH: 590
<212> TYPE: PRT
<213> ORGANISM: Chlamydia trachomatis

<400> SEQUENCE: 126

Met Ser Ile Arg Gly Val Gly Gly Asn Gly Asn Ser Arg Ile Pro Ser
1               5                   10                  15

His Asn Gly Asp Gly Ser Asn Arg Arg Ser Gln Asn Thr Lys Gly Asn
            20                  25                  30

Asn Lys Val Glu Asp Arg Val His Ser Leu Tyr Ser Ser Leu Ser Asn
        35                  40                  45

Glu Asn Arg Glu Ser Pro Tyr Pro Val Val Asp Val Ser Ser Met Ile
    50                  55                  60

Glu Ser Thr Pro Thr Ser Gly Glu Thr Pro Arg Ala Ser Arg Gly Val
65                  70                  75                  80

-continued

```
Phe Ser Arg Phe Gln Arg Gly Leu Gly Arg Val Ala Asp Lys Val Arg
                85                  90                  95

Arg Ala Val Gln Cys Ala Trp Gly Val Ser Thr Arg Arg Ser Ser
            100                 105                 110

Ala Thr Arg Ala Val Glu Ser Gly Ser Ser Ser Arg Thr Ala Arg Gly
            115                 120                 125

Ala Ser Ser Gly Arg Glu Tyr Ser Pro Ser Ala Ala Arg Gly Leu Arg
        130                 135                 140

Leu Met Phe Thr Asp Phe Trp Arg Thr Arg Val Leu Arg Gln Thr Ser
145                 150                 155                 160

Pro Met Asp Val Val Phe Gly Asn Leu Asp Val Asn Glu Ala Arg Leu
                165                 170                 175

Met Ala Ala Tyr Thr Ser Glu Cys Ala Asp Tyr Leu Glu Ala His Asp
            180                 185                 190

Leu Ala Gly Pro Asp Gly Val Ala Ala Arg Glu Ile Ala Gln Arg
        195                 200                 205

Trp Asp Lys Arg Val Arg Asp Leu Gln Asp Lys Gly Ala Ala Gln Lys
    210                 215                 220

Leu Leu Asn Asp Pro Leu Gly Arg Arg Thr Pro Asn Tyr Gln Ser Lys
225                 230                 235                 240

Asn Pro Gly Glu Tyr Thr Val Gly Asn Ser Met Phe Tyr Asp Gly Pro
                245                 250                 255

Gln Val Ala Asn Leu Gln Asn Val Asp Thr Gly Phe Trp Leu Asp Met
            260                 265                 270

Ser Asn Phe Ser Asp Val Val Leu Ser Arg Glu Ile Gln Thr Gly Leu
        275                 280                 285

Arg Ala Arg Ala Thr Leu Glu Glu Ser Met Pro Met Leu Glu Asn Leu
    290                 295                 300

Glu Glu Arg Phe Arg Arg Leu Gln Glu Thr Cys Asp Ala Ala Arg Thr
305                 310                 315                 320

Glu Ile Glu Glu Ser Gly Trp Thr Arg Glu Ser Ala Ser Arg Met Gly
                325                 330                 335

Gly Asp Glu Thr Gln Gly Pro Ser Arg Ala Gln Gln Ala Phe Gln Ser
            340                 345                 350

Phe Val Asn Glu Cys Asn Ser Ile Glu Phe Ser Phe Gly Ser Phe Gly
        355                 360                 365

Glu His Val Arg Val Leu Cys Ala Arg Val Ser Arg Gly Leu Val Ala
    370                 375                 380

Ala Gly Glu Ala Ile Arg Arg Cys Phe Ser Cys Cys Lys Gly Ser Thr
385                 390                 395                 400

His Arg Tyr Ala Pro Arg Asp Asp Leu Ser Pro Glu Gly Ala Ser Leu
                405                 410                 415

Ala Glu Thr Leu Ala Arg Phe Ala Asp Asp Met Gly Ile Glu Gln Gly
            420                 425                 430

Ala Asp Gly Thr Tyr Asp Ile Pro Trp Val Asp Asp Trp Arg Arg Gly
        435                 440                 445

Val Pro Ser Ile Glu Gly Glu Gly Ser Asp Ser Ile Tyr Glu Ile Met
    450                 455                 460

Met Pro Ile Tyr Glu Val Met Asn Met Asp Leu Glu Thr Arg Arg Ser
465                 470                 475                 480

Phe Ala Val Gln Gln Gly His Tyr Gln Asp Pro Arg Ala Ser Asp Tyr
                485                 490                 495

Asp Leu Pro Arg Ala Ser Asp Tyr Asp Leu Pro Arg Ser Pro Tyr Pro
            500                 505                 510
```

-continued

```
Thr Pro Pro Leu Pro Ser Arg Tyr Gln Leu Gln Asn Met Asp Val Glu
        515                 520                 525

Ala Gly Phe Arg Glu Ala Val Tyr Ala Ser Phe Val Ala Gly Met Tyr
        530                 535                 540

Asn Tyr Val Val Thr Gln Pro Gln Glu Arg Ile Pro Asn Ser Gln Gln
545                 550                 555                 560

Val Glu Gly Ile Leu Arg Asp Met Leu Thr Asn Gly Ser Gln Thr Phe
                565                 570                 575

Ser Asn Leu Met Gln Arg Trp Asp Arg Glu Val Asp Arg Glu
                580                 585                 590
```